(12) United States Patent
Fujita et al.

(10) Patent No.: US 10,125,104 B2
(45) Date of Patent: Nov. 13, 2018

(54) CAROTENOID DERIVATIVE, PHARMACEUTICALLY ACCEPTABLE SALT THEREOF, OR PHARMACEUTICALLY ACCEPTABLE ESTER OR AMIDE THEREOF

(71) Applicant: Asta Pharmaceuticals Co., Ltd., Nakaniikawa-gun (JP)

(72) Inventors: Takashi Fujita, Nakaniikawa-gun (JP); Satoshi Kobayashi, Nakaniikawa-gun (JP); Ryoma Shinohara, Nakaniikawa-gun (JP); Yasuhiro Nishida, Nakaniikawa-gun (JP); Jiro Takahashi, Nakaniikawa-gun (JP)

(73) Assignee: Asta Pharmaceuticals Co., Ltd., Nakaniikawa-gun (JP)

( * ) Notice: Subject to any disclaimer, the term of this patent is extended or adjusted under 35 U.S.C. 154(b) by 0 days.

(21) Appl. No.: 15/312,111

(22) PCT Filed: May 20, 2015

(86) PCT No.: PCT/JP2015/064408
§ 371 (c)(1),
(2) Date: Nov. 17, 2016

(87) PCT Pub. No.: WO2015/178404
PCT Pub. Date: Nov. 26, 2015

(65) Prior Publication Data
US 2017/0081289 A1    Mar. 23, 2017

(30) Foreign Application Priority Data

May 20, 2014  (JP) ................... 2014-104480
Dec. 8, 2014  (JP) ................... 2014-247549

(51) Int. Cl.
| C07D 233/61 | (2006.01) |
| A61K 31/22 | (2006.01) |
| A61K 31/27 | (2006.01) |
| A61K 31/4178 | (2006.01) |
| C07C 403/24 | (2006.01) |

(52) U.S. Cl.
CPC ............ *C07D 233/61* (2013.01); *A61K 31/22* (2013.01); *A61K 31/27* (2013.01); *A61K 31/4178* (2013.01); *C07C 403/24* (2013.01)

(58) Field of Classification Search
CPC ...... C07D 233/61; A61K 31/22; A61K 31/27; A61K 31/4178; C07C 403/24
See application file for complete search history.

(56) References Cited

U.S. PATENT DOCUMENTS

| 7,317,008 | B2 | 1/2008 | Lockwood et al. |
| 2004/0162329 | A1 | 8/2004 | Lockwood et al. |
| 2005/0004235 | A1 | 1/2005 | Lockwood et al. |
| 2005/0009758 | A1 | 1/2005 | Lockwood et al. |
| 2005/0009788 | A1 | 1/2005 | Lockwood et al. |
| 2005/0009930 | A1 | 1/2005 | Lockwood et al. |

(Continued)

FOREIGN PATENT DOCUMENTS

| CN | 1628097 A | 6/2005 |
| CN | 1708480 A | 12/2005 |

(Continued)

OTHER PUBLICATIONS

Alex et al, 2010, Chapter 1, pp. 1-60.*

(Continued)

*Primary Examiner* — Sudhakar Katakam
(74) *Attorney, Agent, or Firm* — Oblon, McClelland, Maier & Neustadt, L.L.P.

(57) ABSTRACT

The object of the present invention is to find a carotenoid compound that is excellent in water solubility.

A carotenoid derivative having a formula (I):

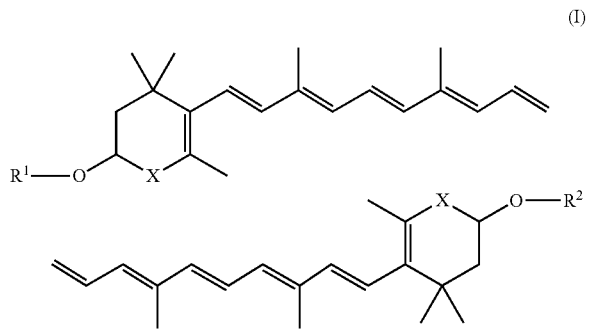

wherein
X represents a carbonyl group or a methylene group, one of $R^1$ and $R^2$ represents (a) or (b) and the other represents (a), (b), (c) or a hydrogen atom:

(a): —CO-A-B-D wherein A represents an alkylene group an alkenylene group, etc., B represents a formula of —S(O)$_n$— or a formula of —NR$^4$CONR$^5$— and D represents a hydrogen atom, a carboxy group, etc., (b): —CO-E-F wherein E represents an alkylene group or a formula of —NR$^3$— wherein R$^3$ represents (a1) a hydrogen atom, (b1) an alkyl group etc., and F represents a sulfo group and (c): —CO-G wherein G represents a hydrogen atom, an alkyl group, etc., a pharmaceutically acceptable salt thereof, or a pharmaceutically acceptable ester or amide thereof.

11 Claims, 4 Drawing Sheets

(56) References Cited

U.S. PATENT DOCUMENTS

| | | |
|---|---|---|
| 2005/0026874 A1 | 2/2005 | Lockwood et al. |
| 2005/0049248 A1 | 3/2005 | Lockwood et al. |
| 2005/0059635 A1 | 3/2005 | Lockwood et al. |
| 2005/0059659 A1 | 3/2005 | Lockwood et al. |
| 2005/0065096 A1 | 3/2005 | Lockwood et al. |
| 2005/0075316 A1 | 4/2005 | Lockwood et al. |
| 2005/0090469 A1 | 4/2005 | Lockwood et al. |
| 2005/0096477 A1 | 5/2005 | Gloor et al. |
| 2005/0113372 A1 | 5/2005 | Lockwood et al. |
| 2005/0143475 A1 | 6/2005 | Lockwood et al. |
| 2005/0148517 A1 | 7/2005 | Lockwood et al. |
| 2008/0008798 A1 | 1/2008 | Gloor et al. |
| 2009/0099061 A1 | 4/2009 | Foss et al. |

FOREIGN PATENT DOCUMENTS

| | | |
|---|---|---|
| CN | 102741224 A | 10/2012 |
| EP | 1 952 845 A1 | 8/2008 |
| JP | 2005-517010 A | 6/2005 |
| JP | 2006-517197 A | 7/2006 |
| JP | 2007-176814 A | 7/2007 |
| JP | 2007-238564 A | 9/2007 |
| JP | 2010-248243 A | 11/2010 |
| JP | 2013-518856 A | 5/2013 |
| WO | 03/066583 A1 | 8/2003 |
| WO | WO 03/093229 A1 | 11/2003 |
| WO | 2004/011423 A2 | 2/2004 |
| WO | WO 2005/102356 A1 | 11/2005 |
| WO | WO 2006/099015 A2 | 9/2006 |
| WO | WO 2006/105214 A2 | 10/2006 |
| WO | WO 2006/119168 A2 | 11/2006 |
| WO | WO 2008/023283 A2 | 2/2008 |
| WO | WO 2008/118862 A2 | 2/2008 |
| WO | WO 2008/106606 A2 | 9/2008 |
| WO | WO 2009/027499 A2 | 3/2009 |
| WO | WO 2010/100226 A1 | 9/2010 |
| WO | WO 2010/100227 A1 | 9/2010 |
| WO | WO 2010/100228 A1 | 9/2010 |
| WO | WO 2010/100229 A1 | 9/2010 |
| WO | WO 2010/100232 A2 | 9/2010 |
| WO | WO 2010/100233 A1 | 9/2010 |
| WO | 2011/095571 A2 | 8/2011 |
| WO | WO 2016/037785 A1 | 3/2016 |

OTHER PUBLICATIONS

International Search Report dated Aug. 11, 2015 in PCT/JP2015/064408 filed May 20, 2015.

Parris Kidd, "Astaxanthin, Cell Membrane Nutrient with Diverse Clinical Benefits and Anti-Aging Potential", Alternative Medicine Review, 2011, vol. 16, No. 4, pp. 355-364.

Martin Guerin et al., "Haematococcus astaxanthin: applications for human health and nutrition", TRENDS in Biotechnology, May 2003, vol. 21, No. 5, pp. 210-216.

Yuri Ohi et al., "Pharmacokinetic of Astaxanthin after oral administration of a soft gel capsule preparation", Clinical Medicine, 2011, vol. 27, No. 4, pp. 297-303 (with English abstract).

Partial Supplementary European Search Report dated Oct. 16, 2017 in Patent Application No. 15795815.8.

Kim Hong Pyo, et al.,"Zeaxanthin dipalmitate from *Lycium chinense* fruit reduces experimentally induced hepatic fibrosis in rats", Biological and Pharmaceutical Bulletin, vol. 25 No. 3, XP002411762, 2002, pp. 390-392.

Combined Office Action and Search Report dated Aug. 2, 2017 in Chinese Patent Application No. 201580026006.9 (with English translation of Office Action and English translation of categories of cited documents).

\* cited by examiner

CAROTENOID DERIVATIVE, PHARMACEUTICALLY ACCEPTABLE SALT THEREOF, OR PHARMACEUTICALLY ACCEPTABLE ESTER OR AMIDE THEREOF

CROSS-REFERENCE TO RELATED APPLICATIONS

This application is a National Stage of PCT/JP2015/064408, which was filed on May 20, 2015. This application is based upon and the claims the benefit of priority to Japanese Application No. 2014-104480, which was filed on May 20, 2014, and to Japanese Application No. 2014-247549, which was filed on Dec. 8, 2014.

TECHNICAL FIELD

The present invention relates to a carotenoid derivative that has excellent water solubility, and is useful as a medicine.

BACKGROUND ART

In a living body producing energy by aerobic respiration, a variety of an active oxygen is generated in the process. An active oxygen is a chemical species having higher reactivity than oxygen in the atmosphere. For example, a superoxide anion, a hydroxy radical, a singlet oxygen, hydrogen peroxide, a hydroperoxy radical and so on are known. It is known that excessive active oxygens generated in a cell non-specifically react with molecules in a living body such as a nucleic acid, a protein and a lipid to damage the cell and that they are involved with various diseases including metabolic syndrome such as diabetes, high blood pressure, hyperlipidemia and arteriosclerosis, a liver disease, a digestive system disease, a brain dysfunction disease, a cardiovascular system disease, cardiac hypofunction, a cancer, atopic dermatitis and so on. For this reason, it is indispensable to remove excessive active oxygens for maintaining the life of an aerobic organism, and there is an oxidation defense mechanism using antioxidant enzymes or antioxidant substances. The antioxidant enzymes are enzymes that remove specific active oxygens. For example, superoxide dismutase (SOD), peroxidase, catalase and so on are known. Antioxidant substances are substances that detoxify active oxygens by its own oxidization (elimination of singlet oxygen is partly caused by energy transfer) and, for example, carotenoids such as astaxanthin, zeaxanthin, canthaxanthin, lutein and β-carotene, vitamins such as vitamin C and vitamin E, α-lipoic acid, and glutathione are known.

Among carotenoids, it is known that astaxanthin, which has particularly excellent anti-oxidation activity, is useful in, for example, fields of a photolesion disease, an ophthalmic disease, a dermatologic disease, an inflammation disease, an immune disease, a cardiac disease, a malignant tumor disease, a liver disease, a kidney disease, a neurodegenerative disease, an addictive disease, an allergic disease, an insulin-resistant disease, a diabetic disease, a hyperlipidemia disease, a cardiac function disease, a vascular system disease and so on (Non Patent Literatures 1 and 2). It is useful as a therapeutic agent, a preventive agent and so on in various diseases in which an active oxygen participates, for example, ocular diseases such as retinopathy (including diabetic retinopathy), (age-related) macular degeneration, cataract and dry eye, metabolic syndromes such as diabetes, high blood pressure, hyperlipidemia and arteriosclerosis, liver diseases such as alcoholic liver disease, non-alcoholic steatohepatitis (NASH), a viral or drug-induced liver disease and steatohepatitis, kidney diseases such as glomerulonephritis, kidney failure and diabetic nephropathy, digestive system diseases such as reflux esophagitis, stomach ulcer, duodenal ulcer and an inflammatory bowel disease, brain dysfunction diseases such as a cerebrovascular disorder and dementia, cardiovascular system diseases such as myocardial infarction, angina pectoris, heart failure, arrhythmia and myocarditis, cardiac hypofunction, cancer, skin diseases such as atopic dermatitis, wound and bedsore, neurodegenerative diseases such as amyotrophic lateral sclerosis, Alzheimer's disease, Parkinson's syndrome and diabetic neuropathy, sarcopenia and so on.

Meanwhile, it is known that digestive absorption of astaxanthin is very low, and the biological availability is around several percent. For example, when astaxanthin originated from Haematococcus algae (containing esters of fatty acids as a main component) is administered in 9 mg/day (as a conversion to a free form of astaxanthin) to a human, Cmax in the blood plasma is 77.15 ng/mL, and AUC (0-72 h) is 1683 ng·h/mL (Non Patent Literature 3). One factor conceivable for this is that carotenoids such as astaxanthin has extremely high hydrophobicity and lacks water solubility. This is also a cause for a limited administration form of astaxanthin to a warm-blooded animal (particularly, human). For that reason, astaxanthin derivatives having further water solubility are considered to be useful and a preparation method therefor has been reported (Patent Literatures 1 and 2).

CITATION LIST

Patent Literature

Patent Literature 1: WO 2004/011423 A
Patent Literature 2: WO 2003/066583 A

Non Patent Literature

Non Patent Literature 1: Alternative Medicine Review, 2011, 16(4), 355-364
Non Patent Literature 2: Trends in Biotechnology, 2003, 21(5), 210-216
Non Patent Literature 3: Clinical Medicine, 2011, 27(4), 297-303

SUMMARY OF INVENTION

Technical Problem To Be Solved By Invention

However, water solubility and oral absorbability of the above astaxanthin derivatives were not satisfactory enough.

Accordingly, an object of the present invention is to provide astaxanthin derivatives that have further improved water solubility and oral absorbability and that have an excellent pharmacological activity such as an anti-inflammatory action; a composition containing the same; and preparation methods thereof.

Means to Solve Technical Problem

The present inventors have investigated synthesis of a series of carotenoid derivatives, and as the result, they have found that carotenoid derivatives having a novel side chain structure have excellent water solubility and oral absorbability and that they can be applied in broad administration methods including, in addition to oral administration, for example, liquid preparations such as an injection and an eye drop, external preparations such as an ointment, and they have completed the present invention.

The present invention provides a carotenoid derivative of formula (I):

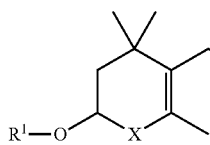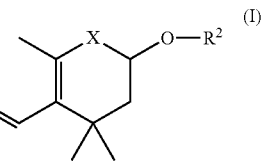

(I)

wherein X represents a carbonyl group or a methylene group, at least one of $R^1$ and $R^2$ represents a group selected from the group consisting of following general formulae (a) and (b) and the other represents a group selected from the group consisting of the following general formulae (a), (b) and (c), and a hydrogen atom:

—CO-A-B-D  (a):

wherein A represents a divalent group consisting of 1 to 10 groups of one or more kinds selected from the group consisting of (i) to (xi) described below, provided that the oxygen atom does not bind to another adjacent oxygen atom: (i) a $C_1$-$C_{10}$ alkylene group wherein the alkylene group is linear or branched, optionally includes a cyclic alkylene moiety in the chain and optionally has substituent α(s) described below, (ii) a $C_2$-$C_{10}$ alkenylene group wherein the alkenylene group is linear or branched and optionally has substituent α(s) described below, (iii) a $C_2$-$C_{10}$ alkynylene group wherein the alkynylene group is linear or branched and optionally has substituent α(s) described below, (iv) —$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described below or (d1) a $C_6$-$C_{10}$ aryl-$C_1$-$C_6$ alkyl group optionally having 1 to 5 substituent β(s) described below in the aryl moiety, (v) an oxygen atom, (vi) a carbonyl group, (viia) a formula of —$S(O)_n$— wherein n represents an integer of 0 or 2, (viii) a $C_6$-$C_{10}$ divalent arylene group optionally having 1 to 4 substituent β(s) described below, (ix) a $C_5$-$C_{10}$ divalent and saturated cyclic hydrocarbon group optionally having 1 to 4 substituent α(s) described below, (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described below and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described below, B represents (viib) a formula of —$S(O)_n$— wherein n represents an integer of 0 to 2 or (xii) a formula of —$NR^4CONR^5$— wherein $R^4$ and $R^5$ are the same or different and each represents (a1) a hydrogen atom, (b1) a $C_1$-$C_6$ alkyl group, (c1) a $C_6$-$C_{10}$ aryl group optionally having 1 to 5 substituent β(s) described below or (d1) a $C_6$-$C_{10}$ aryl-$C_1$-$C_6$ alkyl group optionally having 1 to 5 substituent β(s) described below in the aryl moiety, or $R^4$ and $R^5$ together represent an ethylene group, a propylene group or a group —$COCH_2$—, provided that when B is (viib) a formula of —$S(O)_n$— wherein n represents an integer of 0 to 2, mentioned above, the binding site of A to B is a carbon atom; and D represents a monovalent group consisting of 0 to 10 groups of one or more kinds selected from the group consisting of following (i) to (xi); and a group selected from the group consisting of (xiii) to (xxiv) described below:
(i) a $C_1$-$C_{10}$ alkylene group wherein the alkylene group is linear or branched, optionally includes a cyclic alkylene moiety in the chain and optionally has substituent α(s) described below, (ii) a $C_2$-$C_{10}$ alkenylene group wherein the alkenylene group is linear or branched and optionally has substituent α(s) described below, (iii) a $C_2$-$C_{10}$ alkynylene group wherein the alkynylene group is linear or branched and optionally has substituent α(s) described below, (iv) a group having a formula of —$N(R^{a3})$— wherein $R^{a3}$ represents (a1) a hydrogen atom, (b1) a $C_1$-$C_6$ alkyl group, (c1) a $C_6$-$C_{10}$ aryl group optionally having 1 to 5 substituent β(s) described below or (d1) a $C_6$-$C_{10}$ aryl-$C_1$-$C_6$ alkyl group optionally having 1 to 5 substituent β(s) described below in the aryl moiety, (v) an oxygen atom, (vi) a carbonyl group, (viib) a group having a formula of —$S(O)_n$— wherein n represents an integer of 0 to 2, (viii) a $C_6$-$C_{10}$ divalent arylene group optionally having 1 to 4 substituent β(s) described below, (ix) a $C_5$-$C_{10}$ divalent and saturated cyclic hydrocarbon group optionally having 1 to 4 substituent α(s) described below, (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described below, (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described below, (xiii) a hydrogen atom, (xiv) a $C_1$-$C_6$ alkyl group wherein the alkyl group is linear or branched and optionally has substituent α(s) described below, (xv) a $C_1$-$C_6$ halogenoalkyl group wherein the alkyl group is linear or branched and optionally has substituent α(s) described below, (xvi) a $C_3$-$C_{10}$ cycloalkyl group, (xviia) a $C_6$-$C_{10}$ aryl group optionally having 1 to 5 substituent β(s) described below, (xviii) a 5- to 7-membered ring heteroaryl group containing 1 to 3 hetero atoms selected from the group consisting of an oxygen atom, a nitrogen atom and a sulfur atom and optionally having 1 to 2 substituent γ(s) described below, (xix) a group having a formula of —$N(R^{a1})(R^{a2})$ wherein $R^{a1}$ represents (a1) a hydrogen atom, (b1) a $C_1$-$C_6$ alkyl group, (c1) a $C_6$-$C_{10}$ aryl group optionally having 1 to 5 substituent β(s) described below or (d1) a $C_6$-$C_{10}$ aryl-$C_1$-$C_6$ alkyl group optionally having 1 to 5 substituent β(s) described below in the aryl moiety and $R^{a2}$ represents a hydrogen atom or a $C_1$-$C_6$ alkyl group, (xx) a hydroxy group, (xxi) a formyl group, (xxii) a carboxy group, (xxiii)

a sulfo group and (xxiv) a phospho group, and D, together with —NR$^5$— in B, optionally form a heterocyclic ring containing a nitrogen atom;

—CO-E-F    (b):

wherein E represents a divalent group consisting of 1 to 10 groups of one or more kinds selected from the group consisting of (i) to (xi) described below, provided that the oxygen atom does not bind to another adjacent oxygen atom: (i) a $C_1$-$C_{10}$ alkylene group wherein the alkylene group is linear or branched, optionally includes a cyclic alkylene moiety in the chain and optionally has substituent α(s) described below, (ii) a $C_2$-$C_{10}$ alkenylene group wherein the alkenylene group is linear or branched and optionally has substituent α(s) described below, (iii) a $C_2$-$C_{10}$ alkynylene group wherein the alkynylene group is linear or branched and optionally has substituent α(s) described below, (iv) —NR$^3$— wherein R$^3$ represents (a1) a hydrogen atom, (b1) a $C_1$-$C_6$ alkyl group, (c1) a $C_6$-$C_{10}$ aryl group optionally having 1 to 5 substituent β(s) described below or (d1) a $C_6$-$C_{10}$ aryl-$C_1$-$C_6$ alkyl group optionally having 1 to 5 substituent β(s) described below in the aryl moiety, (v) an oxygen atom, (vi) a carbonyl group, (viia) a formula of —S(O)$_n$— wherein n represents an integer of 0 or 2, (viii) a $C_6$-$C_{10}$ divalent arylene group optionally having 1 to 4 substituent β(s) described below, (ix) a $C_5$-$C_{10}$ divalent and saturated cyclic hydrocarbon group optionally having 1 to 4 substituent α(s) described below, (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described below and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described below; and F represents (xxiii) a sulfa group; and —CO-G    (c):

wherein G represents a monovalent group consisting of 0 to 10 groups of one or more kinds selected from the group consisting of (i) to (xi) described below; and a group selected from the group consisting of (xiii) to (xxiv) described below, provided that the oxygen atom does not bind to another adjacent oxygen atom:
(i) a $C_1$-$C_{10}$ alkylene group wherein the alkylene group is linear or branched, optionally includes a cyclic alkylene moiety in the chain and optionally has substituent α(s) described below, (ii) a $C_2$-$C_{10}$ alkenylene group wherein the alkenylene group is linear or branched and optionally has substituent α(s) described below, (iii) a $C_2$-$C_{10}$ alkynylene group wherein the alkynylene group is linear or branched and optionally has substituent α(s) described below, (iv) a group having a formula of —N(R$^{a3}$)— wherein R$^{a3}$ represents (a1) a hydrogen atom, (b1) a $C_1$-$C_6$ alkyl group, (c1) a $C_6$-$C_{10}$ aryl group optionally having 1 to 5 substituent β(s) described below, (d1) a $C_6$-$C_{10}$ aryl-$C_1$-$C_6$ alkyl group optionally having 1 to 5 substituent β(s) described below in the aryl moiety, (v) an oxygen atom, (vi) a carbonyl group, (viia) a group having a formula of —S(O)$_n$— wherein n represents an integer of 0 or 2, (viii) a $C_6$-$C_{10}$ divalent arylene group optionally having 1 to 4 substituent β(s) described below, (ix) a $C_5$-$C_{10}$ divalent and saturated cyclic hydrocarbon group optionally having 1 to 4 substituent α(s) described below, (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described below, (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described below, (xiii) a hydrogen atom, (xiv) a $C_1$-$C_6$ alkyl group wherein the alkyl group is linear or branched and optionally has substituent α(s) described below, (xv) a $C_1$-$C_6$ halogenoalkyl group wherein the alkyl group is linear or branched and optionally has substituent α(s) described below, (xvi) a $C_3$-$C_{10}$ cycloalkyl group, (xviia) a $C_6$-$C_{10}$ aryl group optionally having 1 to 5 substituent β (s) described below, (xviii) a 5- to 7-membered ring heteroaryl group containing 1 to 3 hetero atoms selected from the group consisting of an oxygen atom, a nitrogen atom and a sulfur atom and optionally having 1 to 2 substituent γ(s) described below, (xix) a group having a formula of —N(R$^{a1}$)(R$^{a2}$) wherein R$^{a1}$ represents (a1) a hydrogen atom, (b1) a $C_1$-$C_6$ alkyl group, (c1) a $C_6$-$C_{10}$ aryl group optionally having 1 to 5 substituent β(s) described below or (d1) a $C_6$-$C_{10}$ aryl-$C_1$-$C_6$ alkyl group optionally having 1 to 5 substituent β(s) described below in the aryl moiety and R$^{a2}$ represents a hydrogen atom or a $C_1$-$C_6$ alkyl group, (xx) a hydroxy group, (xxi) a formyl group, (xxii) a carboxy group, (xxiii) a sulfa group and (xxiv) a phospho group;

wherein a substituent α represents following (xviib) to (xxx):
(xviib) a $C_6$-$C_{10}$ aryl group optionally having 1 to 5 substituent β(s) described below, a $C_3$-$C_{10}$ monocyclo or bicycloalkyl group (and/) or a $C_3$-$C_{10}$ monocyclo or bicycloalkenyl group, (xviii) a divalent and 5- to 10-membered ring heteroaryl group containing 1 to 3 hetero atoms selected from the group consisting of an oxygen atom, a nitrogen atom and a sulfur atom and optionally having 1 to 2 substituent β(s) described below, (xix) a group having a formula of —N(R$^{a1}$)(R$^{a2}$) wherein R$^{a1}$ represents (a1) a hydrogen atom, (b1) a $C_1$-$C_6$ alkyl group, (c1) a $C_6$-$C_{10}$ aryl group optionally having 1 to 5 substituent β(s) described below or (d1) a $C_6$-$C_{10}$ aryl-$C_1$-$C_6$ alkyl group optionally having 1 to 5 substituent β(s) described below in the aryl moiety and R$^{a2}$ represents a hydrogen atom or a $C_1$-$C_6$ alkyl group, (xx) a hydroxy group, (xxi) a formyl group, (xxii) a carboxy group, (xxiii) a sulfo group, (xxiv) a phospho group, (xxv) a $C_1$-$C_6$ alkoxy group, (xxvi) a $C_6$-$C_{10}$ aryloxy group optionally having 1 to 5 substituent β(s) described below, (xxvii) a $C_1$-$C_6$ alkylthio group, (xxviii) a $C_6$-$C_{10}$ arylthio group optionally having 1 to 5 substituent β(s) described below, (xxix) a carbamoyl group or (xxx) a guanidyl group;

a substituent β represents following (xiv), (xv), (xviia), (xx) to (xxii), (xxv), (xxvi), (xxix), or (xxxi) to (xxxvii):
(xiv) a $C_1$-$C_6$ alkyl group, (xv) a $C_1$-$C_6$ halogenoalkyl group, (xviia) a $C_6$-$C_{10}$ aryl group optionally having 1 to 5 substituent γ(s) described below, (xx) a hydroxy group, (xxi) a formyl group, (xxii) a carboxy group, (xxv) a $C_1$-$C_6$ alkoxy group, (xxvi) a $C_6$-$C_{10}$ aryloxy group optionally having 1 to 5 substituent γ(s) described below, (xxix) a carbamoyl group, (xxxi) a halogen atom, (xxxii) a cyano group, (xxviii) a nitro group, (xxxiv) a $C_6$-$C_{10}$ aryl-$C_1$-$C_6$ alkyl group optionally having 1 to 5 substituent γ(s) described below in the aryl moiety, (xxxv) an amino group, (xxxvi) a $C_6$-$C_{10}$ aryl-$C_1$-$C_6$ alkoxy group optionally having 1 to 5 substituent γ(s) described below in the aryl moiety or (xxxvii) a $C_1$-$C_6$ alkoxycarbonyl group; and a substituent γ represents following (xiv), (xv), (xx) to (xxii), (xxv), (xxxi) or (xxxv):

(xiv) a $C_1$-$C_6$ alkyl group, (xv) a $C_1$-$C_6$ halogenoalkyl group, (xx) a hydroxy group, (xxi) a formyl group, (xxii) a carboxy group, (xxv) a $C_1$-$C_6$ alkoxy group, (xxxi) a halogen atom or (xxxv) an amino group;

a pharmaceutically acceptable salt thereof; or a pharmaceutically acceptable ester or amide thereof.

In addition, the present invention provides a pharmaceutical composition comprising a carotenoid derivative represented by the general formula (I), a pharmaceutically acceptable salt thereof, or a pharmaceutically acceptable ester or amide thereof as an active ingredient; use of a carotenoid derivative having the general formula (I), a pharmaceutically acceptable salt thereof, or a pharmaceutically acceptable ester or amide thereof for producing a pharmaceutical composition; use of a carotenoid derivative having the general formula (I), a pharmaceutically acceptable salt thereof, or a pharmaceutically acceptable ester or amide thereof as a pharmaceutical composition; a carotenoid derivative having the general formula (I), a pharmaceutically acceptable salt thereof, or a pharmaceutically acceptable ester or amide thereof for treating a disease involved in active oxygens; and a method for treating or preventing a disease involved in active oxygens, comprising administering an effective amount of a carotenoid derivative having the general formula (I), a pharmaceutically acceptable salt thereof, or a pharmaceutically acceptable ester or amide thereof to a warm-blooded animal (particularly, human).

Effects of Invention

The carotenoid derivative, a pharmaceutically acceptable salt thereof, or a pharmaceutically acceptable ester or amide thereof of the present invention has a unique chemical structure and it has excellent water solubility and oral absorbability. For that reason, the carotenoid derivative, a pharmaceutically acceptable salt thereof, or a pharmaceutically acceptable ester or amide thereof of the present invention is suitable for a pharmaceutical composition in a dosage form of a water-soluble active ingredient such as an injection, an eye drop and an external preparation in addition to an oral preparation.

DESCRIPTION OF EMBODIMENTS

Figure 1:
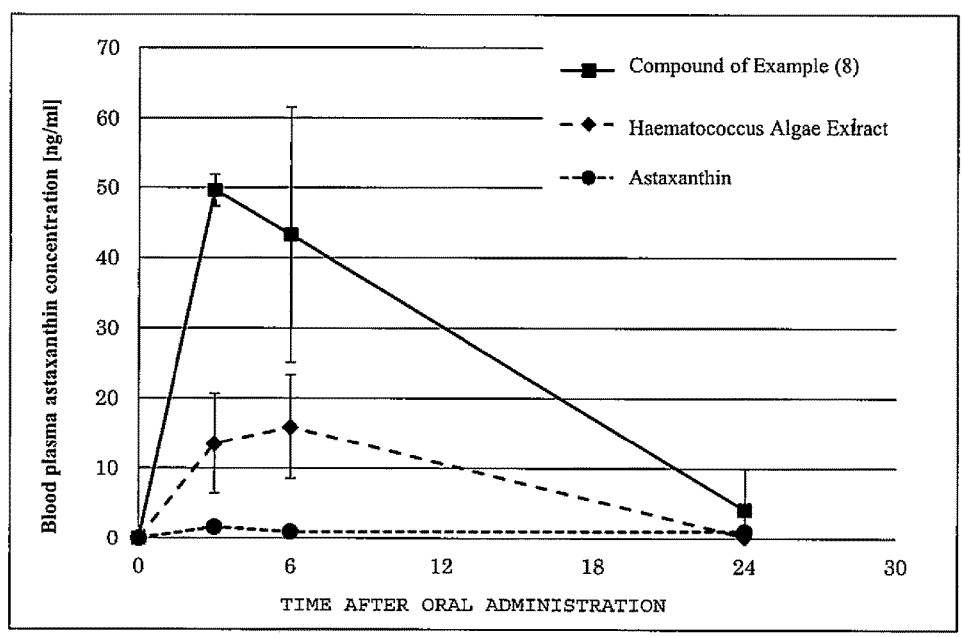
FIG. 1 shows the change of the blood concentration of astaxanthin when the compound was orally administered to a rat in Test example (2).

The carotenoid derivative in the present invention includes a carotenoid derivative, a pharmaceutically acceptable salt thereof, or a pharmaceutically acceptable ester or amide thereof, unless otherwise stated.

The "$C_1$-$C_{10}$ alkylene group" in A, D, E and G in the present invention is a linear or branched alkylene group having 1 to 10 carbon atoms and optionally includes a cyclic alkylene moiety in the chain, and may be, for example, —$CH_2$—, —$CH(CH_3)$—, —$CH(C_2H_5)$—, —CH(n-$C_3H_7$)—, —CH(i-$C_3H_7$)—, —CH(n-$C_4H_9$)—, —CH(i-$C_4H_9$)—, —CH(s-$C_4H_9$)—, —$CH_2CH_2$—, —$CH_2CH_2CH_2$—, —$CH_2CH(CH_3)$—, —$CH_2CH_2CH_2CH_2$—, —$CH(CH_3)CH_2CH_2$—, —$CH_2CH(CH_3)CH_2$—, —$CH(CH_3)CH_2$—, —$CH_2CH(i-C_4H_9)CH_2$—, —$CH_2C(CH_2CH_2CH_2CH_2CH_2)CH_2$—, —$CH_2CH_2CH_2CH_2CH_2$—, —$CH(CH_3)CH_2CH_2CH_2$—, —$CH_2CH(CH_3)CH_2CH_2$—, —$CH_2CH(CH_3)CH(CH_3)$—, —$CH_2CH_2CH_2CH_2CH_2CH_2$—, —$CH(CH_3)CH_2CH_2CH_2CH_2$—, —$CH(C_2H_5)CH_2CH_2CH_2$—, —CH($CH_3$)CH($CH_3$)$CH_2CH_2$—, —CH($CH_3$)CH($CH_3$)CH($CH_3$)—, —$CH_2CH_2CH_2CH_2CH_2CH_2CH_2$—, —$CH_2CH_2CH_2CH_2CH_2CH_2CH_2CH_2$—, —$CH_2CH_2CH_2CH_2CH_2CH_2CH_2CH_2CH_2$—, —$CH_2CH_2CH_2CH_2CH_2CH_2CH_2CH_2CH_2CH_2$—, —CH(i-$C_3H_7$)$CH_2CH_2CH_2CH_2CH_2CH_2$—, -6-$CH_2$-3-methylbicyclo[3,2,0]hepta-3-en-6-yl-$CH_2$— or -6-$CH_2$-3-ethylbicyclo[3,2,0]hepta-3-en-6-yl-$CH_2$— and it is preferably a $C_1$-$C_8$ alkylene group, further more preferably a $C_1$-$C_7$ alkylene group, more preferably —$CH_2$—, —$CH(CH_3)$—, —CH($C_2H_5$)—, —CH(n-$C_3H_7$)—, —CH(i-$C_3H_7$)—, —CH(n-$C_4H_9$)—, —CH(i-$C_4H_9$)—, —CH(s-$C_4H_9$)—, —$CH_2CH_2$—, —$CH_2CH_2CH_2$—, —$CH_2CH(i-C_4H_9)CH_2$—, —$CH_2CH(CH_3)$—, —$CH_2C(CH_2CH_2CH_2CH_2)CH_2$— or —$CH_2CH_2CH_2CH_2CH_2$— and most preferably —$CH_2$—, —$CH(CH_3)$—, —CH($C_2H_5$)—, —CH(i-$C_3H_7$)—, —CH(n-$C_4H_9$)—, —CH(i-$C_4H_9$)—, —$CH_2CH_2$—, —$CH_2CH_2CH_2$—, —$CH_2CH(i-C_4H_9)CH_2$— or —$CH_2C(CH_2CH_2CH_2CH_2CH_2)CH_2$—.

The "$C_1$-$C_{10}$ alkylene group having the substituent α(s)" is a group wherein the above-mentioned "$C_1$-$C_{10}$ alkylene group" has 1 to 3 substituents selected from the group of the above-mentioned substituent α(s) and may be, for example, —CH($CH_2$SMe)-, —CH($CH_2CH_2$SMe)-, —CH($CH_2$Phenyl)-, —CH[$CH_2$(4-hydroxyphenyl)]-, —CH[$CH_2$(4-imidazolyl)]-, —CH($CH_2$CONH$_2$)—, —CH($CH_2CH_2$CONH$_2$)—, —CH($CH_2$OH)—, —CH[CHOH($CH_3$)]—, —CH($CH_2CH_2CH_2$NH$_2$)—, —CH($CH_2CH_2CH_2CH_2$NH$_2$)—, —CH[$CH_2CH_2CH_2$(NHC(=NH)NH$_2$)]—, —CH($CH_2$CO$_2$H)—, —CH($CH_2CH_2$CO$_2$H)—, —$CH_2CH_2CH_2$CH(COOH)—, —$CH_2CH_2CH_2CH_2$(COOH)—, —$CH_2$CH($CH_2$OCH$_3$)—, —$CH_2$CH[O-(4-trifluoromethylphenyl)]$CH_2$—, —$CH_2$CH(CHO)—, —$CH_2$CH(3-chlorophenyl)$CH_2CH_2CH_2$— or —CH(OH)$CH_2$CH(OH)—, and it is preferably —CH($CH_2$SMe)-, —CH($CH_2CH_2$SMe)-, —CH($CH_2$Phenyl)-, —CH[$CH_2$(4-hydroxyphenyl)]-, —CH[$CH_2$(4-imidazolyl)]-, —CH($CH_2$CONH$_2$)—, —CH($CH_2CH_2$CONH$_2$)—, —CH($CH_2$OH)—, —CH[CHOH($CH_3$)]—, —CH($CH_2CH_2CH_2$NH$_2$)—, —CH($CH_2CH_2CH_2CH_2$NH$_2$)—, —CH[$CH_2CH_2CH_2$NHC(=NH)NH$_2$]—, —CH($CH_2$CO$_2$H)— or —CH($CH_2CH_2$CO$_2$H)—.

The "$C_2$-$C_{10}$ alkenylene group" in A, D, E, G and so on is a linear or branched alkenylene group having 2 to 10 carbon atoms and may be, for example, —CH═CH—, —CH═CHCH$_2$—, —CH═C(CH$_3$)—, —CH═CHCH$_2$CH$_2$—, —CH$_2$CH═CHCH$_2$—, —CH═CHCH═CH—, —C(CH$_3$)═CHCH$_2$—, —CH═C(CH$_3$)CH$_2$—, —CH$_2$CH═CHCH$_2$CH$_2$—, —CH(CH$_3$)CH$_2$CH═CH—, —CH$_2$C(CH$_3$)═CHCH$_2$—, —CH$_2$C(CH$_3$)═C(CH$_3$)—, —CH═CHCH$_2$CH$_2$CH$_2$CH$_2$—, —CH(CH$_3$)CH═CHCH$_2$CH$_2$—, —CH(C$_2$H$_5$)CH═CHCH$_2$—, —CH(CH$_3$)C(CH$_3$)═CHCH$_2$—, —C(CH$_3$)═C(CH$_3$)CH(CH$_3$)—, —CH$_2$CH═CHCH═CHCH$_2$—, —CH$_2$CH$_2$CH$_2$CH═CHCH$_2$CH$_2$CH$_2$—, —CH$_2$CH═CHCH$_2$CH$_2$CH$_2$CH$_2$CH$_2$—, —CH═CHCH═CHCH$_2$CH$_2$CH$_2$CH$_2$CH$_2$— or —CH(CH(CH$_3$)$_2$)—CH$_2$CH$_2$CH$_2$CH═CHCH$_2$—, and it is preferably a C$_2$-C$_5$ alkenylene group, more preferably a C$_2$-C$_4$ alkenylene group, even more preferably —CH═CH—, —CH═CHCH$_2$—, —CH═C(CH$_3$)— or —CH$_2$CH═CH$_2$CH$_2$— and most preferably —CH═CH— or —CH═CHCH$_2$—.

The "C$_2$-C$_{10}$ alkenylene group having the substituent α(s)" is a group wherein the above-mentioned "C$_1$-C$_{10}$ alkenylene group" has 1 to 3 substituents selected from the group of the above-mentioned substituent α(s), and it is, for example, —CH═C(CH$_2$COOH)—, —CH═CHCH(CH$_2$COOH)—, —C(CH$_2$COOH)═C(CH$_3$)—, —CH═CHCH$_2$CH(CH$_2$COOH)—, —CH$_2$CH═CHCH(NH$_2$)—, —CH═CHC(CH$_2$COOH)═CH—, —C(CH$_3$)═CHCH(CH$_2$OH)—, —CH═C(CH$_2$OCH$_3$)CH$_2$—, —CH$_2$CH═CHCH(Cl)CH$_2$—, —CH(CH$_2$Ph)CH$_2$CH═CH—, —CH$_2$C(CH$_2$Ph)═CHCH$_2$—, —CH$_2$C(CH$_2$NHCH$_3$)═C(CH$_3$)—, —CH═CHCH═CHCH$_2$CH$_2$CH$_2$CH(CH$_2$COOH)—, —CH═CHCH(CH$_2$NMe$_2$)-, —CH═CHCH [CH$_2$NMe(CH$_2$Ph)]-, —CH═C(Ph)-, —CH═CHCH(3-pyridyl)-, —CH═CHCH(SPh)-, —CH═CHCH(OPh)- and so on.

The "C$_2$-C$_{10}$ alkynylene group" in A, D, E, G and so on is a linear or branched alkynylene group having 2 to 10 carbon atoms, and may be, for example, —C≡C—, —C≡CCH$_2$—, —C≡CCH$_2$CH$_2$—, —CH$_2$C≡CCH$_2$—, —C≡CC≡C—, —CH$_2$C≡CCH$_2$CH$_2$—, —CH(CH$_3$)CH$_2$C≡C—, —C≡CCH$_2$CH$_2$CH$_2$CH$_2$—, —CH(CH$_3$)C≡CCH$_2$CH$_2$—, —CH(C$_2$H$_5$)C≡CCH$_2$—, —CH(CH$_3$)C≡CCH$_2$—, —CH(CH$_3$)C≡CCH(CH$_3$)—, —CH$_2$C≡CCH═CHCH$_2$CH$_2$—, —CH$_2$CH$_2$CH$_2$C≡CCH$_2$CH$_2$CH$_2$—, —CH$_2$C≡CCH$_2$CH$_2$CH$_2$CH$_2$CH$_2$—, —C≡CCH═CHCH$_2$CH$_2$CH$_2$CH$_2$CH$_2$— or —CH(CH(CH$_3$)$_2$)CH$_2$CH$_2$CH$_2$C≡CCH$_2$—, and it is preferably a C$_2$-C$_5$ alkynylene group, more preferably a C$_2$-C$_4$ alkynylene group, even more preferably —C≡C—, —C≡CCH$_2$— or —CH$_2$C≡CCH$_2$— and most preferably —C≡C— or —C≡CCH$_2$—.

The "C$_2$-C$_{10}$ alkynylene group having the substituent α(s)" is a group wherein the above-mentioned "C$_2$-C$_{10}$ alkynylene group" has 1 to 3 substituents selected from the group of the above-mentioned substituent α(s), and it is, for example, —C≡CCH(Ph)-, —C≡CCH(OMe)CH$_2$—, —CH$_2$C≡CCH(CH$_2$COOH)—, —CH$_2$C≡CCH$_2$CH(CH$_2$COOH)—, —CH(CH$_2$OH)CH$_2$C≡C—, —C≡CCH$_2$CH$_2$CH$_2$CH(CH$_2$OH)—, —C≡CCH$_2$CH$_2$CH$_2$CH(CH$_2$NHPh)- and so on.

The "C$_1$-C$_6$ alkyl" moiety in the "C$_1$-C$_6$ alkyl group", the "C$_1$-C$_6$ alkoxy group", the "C$_1$-C$_6$ alkylthio group", the "C$_1$-C$_6$ halogenoalkyl group", the "C$_6$-C$_{10}$ aryl C$_1$-C$_6$ alkyl group optionally having 1 to 5 substituent β(s)", the "C$_6$-C$_{10}$ aryl-C$_1$-C$_6$ alkoxy group optionally having 1 to 5 substituent γ(s)", or the "C$_1$-C$_6$ alkoxycarbonyl group" and so on in R$^3$, R$^4$, R$^5$, D, R$^{a1}$, R$^{a2}$, R$^{a3}$, G, the substituent α, the substituent β, the substituent γ and so on, is a linear or branched alkyl group having 1 to 6 carbon atoms, and may be, for example, a methyl, ethyl, propyl, isopropyl, butyl, isobutyl, s-butyl, t-butyl, pentyl, s-pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, and it is preferably a C$_1$-C$_5$ alkyl group, more preferably a C$_1$-C$_4$ alkyl group, even more preferably a methyl group, an ethyl group, a propyl group, an isopropyl group, a butyl group or an isobutyl group and most preferably a methyl group, an ethyl group or a propyl group.

The moiety of the "C$_6$-C$_{10}$ aryl optionally having 1 to 5 substituent β(s) or γ(s)" in the "C$_6$-C$_{10}$ aryl group optionally having 1 to 5 substituent β(s)" in R$^3$, R$^4$, R$^5$, D, R$^{a1}$, R$^{a3}$, G, the substituent α(s) and so on, in the "C$_6$-C$_{10}$ aryl group optionally having 1 to 5 substituent γ(s)" in the substituent β(s) and so on or in the "C$_6$-C$_{10}$ aryl-C$_1$-C$_6$ alkyl group optionally having 1 to 5 the substituent β(s)" in R$^3$, R$^4$, R$^5$, R$^{a1}$, R$^{a3}$ and so on, is an aromatic hydrocarbon group having 6 to 10 carbon atoms and optionally having 1 to 5 substituent β(s) or γ(s), and may be, for example, a phenyl, indenyl, or 1- or 2-naphthyl group, optionally having 1 to 5 substituent β(s) or γ(s), and it is preferably a phenyl group, or a 1- or 2-naphthyl group, optionally having 1 to 3 substituent β(s) or γ(s) and most preferably a phenyl group optionally having the substituent β(s) or γ(s).

The "C$_1$-C$_6$ halogenoalkyl group" in D, G, the substituent β, the substituent γ and so on is a group in which the above-mentioned "C$_1$-C$_6$ alkyl group" is substituted by halogen atom(s), and may be, for example, a fluoromethyl, difluoromethyl, trifluoromethyl, chloromethyl, dichloromethyl, trichloromethyl, bromomethyl, iodomethyl, 2-fluoroethyl, 2,2,2-trifluoroethyl, 2-chloroethyl, 2,2,2-trichloroethyl, 2-bromoethyl, 2,2-dibromoethyl, 2-iodoethyl, 3-chloropropyl, 4-fluorobutyl or 6-iodohexyl group, and it is preferably a fluoromethyl, difluoromethyl, trifluoromethyl, dichloromethyl, 2-fluoroethyl, 2,2,2-trifluoroethyl, 2-chloroethyl, 2,2,2-trichloroethyl, 3-chloropropyl, 4-fluorobutyl or 6-iodohexyl group, more preferably a fluoromethyl, difluoromethyl, trifluoromethyl, 2-fluoroethyl, 2,2,2-trifluoroethyl, 3-chloropropyl or 4-fluorobutyl group and most preferably a trifluoromethyl group.

The "C$_3$-C$_{10}$ cycloalkyl group" in D, G and so on is a 3- to 10-membered saturated cyclic hydrocarbon group optionally being condensed, and may be, for example, a cyclopropyl, cyclobutyl, cyclopentyl, cyclohexyl, cycloheptyl, norbornyl or adamantyl group, and it is preferably a cyclopropyl, cyclobutyl, cyclopentyl, cyclohexyl or norbornyl group, more preferably a cyclopropyl, cyclobutyl, cyclopentyl or cyclohexyl group and most preferably a cyclopropyl, cyclobutyl or cyclohexyl group.

The moiety of the "halogen" in the "halogen atom" in the substituent β, the substituent γ and so on or in the "C$_1$-C$_6$ halogenoalkyl group" in D, G, the substituent β, the substituent γ and so on, may be, for example, a fluorine atom, a chlorine atom, a bromine atom or an iodine atom, and it is preferably a fluorine atom, a chlorine atom or a bromine atom and more preferably a fluorine atom or a chlorine atom.

The ring in the "C$_5$-C$_{10}$ divalent and saturated cyclic hydrocarbon group optionally having 1 to 4 substituent α(s)" contained in A, D, E and G is, for example, cyclopentane, cyclohexane, cycloheptane, cyclooctane, cyclononane, cyclodecane, bicyclo[4,4,0]decane or bicyclo[2,2,1]heptane and preferably cyclopentane, cyclohexane or cycloheptane.

The ring in the "C$_6$-C$_{10}$ divalent arylene group optionally having 1 to 4 substituent β(s)" contained in A, D, E and G is, for example, benzene or naphthalene and preferably benzene.

The heterocyclic ring in the "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s)" contained in A, D, E and G is, for example, furan, pyrrole, thiophene, imidazole, pyridine, pyrimidine, pyrazine, preferably pyrrole, imidazole, pyridine, pyrimidine or pyrazine and most preferably imidazole, pyridine or pyrazine.

The heterocyclic ring in the "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)" contained in A, D, E and G may be, for example tetrahydrofuran, tetrahydropyran, hexamethylene oxide, pyrrolidine, piperidine, hexamethylene imine, tetrahydrothiophene, tetrahydrothiopyran, hexamethylene sulfide, morpholine, 1,2-oxathiolane, 1,4-dioxane or piperazine, preferably may be tetrahydrofuran, tetrahydropyran, pyrrolidine, piperidine, hexamethylene imine, tetrahydrothiophene, morpholine, 1,4-dioxane or piperazine and more preferably may be tetrahydrofuran, pyrrolidine, piperidine, morpholine, 1,4-dioxane or piperazine, and most preferably pyrrolidine, piperidine or piperazine.

The heterocyclic ring in the "5- to 7-membered ring heteroaryl group containing 1 to 3 hetero atoms selected from the group consisting of an oxygen atom, a nitrogen atom and a sulfur atom and optionally having 1 to 2 substituent γ(s)" contained in D, G and the substituent α is, for example, furan, pyrrole, thiophene, imidazole, pyridine, pyrimidine or pyrazine, preferably furan, pyrrole, imidazole, pyridine, pyrimidine or pyrazine, more preferably pyrrole, imidazole, pyridine, pyrimidine or pyrazine and most preferably imidazole, pyridine or pyrazine.

The "group having a formula of —N($R^{a1}$)($R^{a2}$) wherein $R^{a1}$ represents (a1) a hydrogen atom, (b1) a $C_1$-$C_6$ alkyl group, (c1) a $C_6$-$C_{10}$ aryl group optionally having 1 to 5 substituent β(s) or (d1) a $C_6$-$C_{10}$ aryl-$C_1$-$C_6$ alkyl group optionally having 1 to 5 substituent β(s) in the aryl moiety and $R^{a2}$ represents a hydrogen atom or a $C_1$-$C_6$ alkyl group" contained in D, G and the substituent α is, for example, —$NH_2$, —$NHCH_3$, —$NHC_2H_5$, —NH(n-$C_3H_7$), —NH(i-$C_3H_7$), —NH(n-$C_4H_9$), —NH(i-$C_4H_9$), —NH(s-$C_4H_9$), —NH(n-$C_5H_{11}$), —NH(n-$C_6H_{13}$), —N($C_2H_5$)$_2$. —NH(Ph), —$NCH_3$(Ph), —$NC_2H_5$($CH_2$Ph), —NH(3,5-di-Methyl-4-hydroxyphenyl), —NH(3-Chlorophenyl) and so on.

The heterocyclic group wherein "D may, together with —$NR^5$— in B, form a heterocyclic ring containing a nitrogen atom" contained in D is an unsaturated or saturated heterocyclic group, and it is, for example, an imidazolyl group, a pyrrole group, a pyrrolidinyl group, a piperidinyl group or a morpholinyl group and preferably an imidazolyl group, a pyrrolidinyl group, a piperidinyl group or a morpholinyl group.

One of the features in the carotenoid derivative (I) of the present invention is to have any one or more of —S(O)$_n$— wherein n represents an integer of 0 or 2, —$NR^4CONR^5$— wherein $R^4$ and $R^5$ are as described above and a —$SO_3H$ group on either one or both in $R^1$ and $R^2$. The location of these group is specifically in B and/or D of "(a) —CO-A-B-D", F of "(b) —CO-E-F", G of "(c) —CO-G" and so on, provided that G may or may not contain any one of these groups.

The paragraph that "at least one of $R^1$ and $R^2$ represents a group selected from the group consisting of (a) and (b) and the other represents a group selected from the group consisting of (a), (b), (c) and a hydrogen atom" in the present invention means that $R^1$ and $R^2$ does not include a combination of (c) and (c), (c) and H, or H and H, respectively and specifically $R^1$ and $R^2$ consist of a combination of (a) and (a), (a) and (b), (a) and (c), (a) and H, (b) and (b), (b) and (c) or (b) and H, respectively.

(R-1): At least one of $R^1$ and $R^2$ is (a): —CO-A-B-D or (b): —CO-E-F and the other is (a): —CO-A-B-D, (b): —CO-E-F, (c): —CO-G or a hydrogen atom.

(R-2): Preferably, at least one of $R^1$ and $R^2$ is (a): —CO-A-B-D or (b): —CO-E-F and the other is a hydrogen atom.

(R-3): More preferably, $R^1$ and $R^2$ are the same or different and each is (a): —CO-A-B-D or (b): —CO-E-F.

(R-4): Most preferably, $R^1$ and $R^2$ are the same and each is (a): —CO-A-B-D or (b): —CO-E-F.

(X-1): X is a carbonyl group or a methylene group and (X-2): preferably, X is a carbonyl group.

The "divalent group consisting of 1 to 10 groups of one or more kinds selected from the group consisting of (i) to (xi)" in A of "(a): —CO-A-B-D" means a divalent group consisting of one (, two) or more groups selected from the group consisting of divalent (i) to (xi) in which the total number of the (i) to (xi) groups is 1 to 10 and the (i) to (xi) groups bind linearly.

(A-1): A contained in "(a): —CO-A-B-D" is a divalent group that consists of 1 to 6 groups of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s) described above", (ii) a "$C_2$-$C_{10}$ alkenylene group wherein the alkenylene group is linear or branched and optionally has the substituent α(s) described above", (iii) a "$C_2$-$C_{10}$ alkynylene group wherein the alkynylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 of the substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2", (viii) a "$C_6$-$C_{10}$ divalent arylene group optionally having 1 to 4 substituent β(s) described above", (ix) a "$C_5$-$C_{10}$ divalent and saturated cyclic hydrocarbon group optionally having 1 to 4 substituent α(s) described above", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(A-2): Preferably, A contained in "(a): —CO-A-B-D" is a divalent group that consists of 1 to 6 groups of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s) described above", (ii) a "$C_2$-$C_{10}$ alkenylene group wherein the alkenylene group is linear or branched and optionally has the substituent α(s) described above, (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2", (viii) a "$C_6$-$C_{10}$ divalent arylene group optionally having 1 to 4 substituent β(s) described above", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(A-3): More preferably, A contained in "(a): —CO-A-B-D" is a divalent group that consists of 1 to 6 of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s) described above", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(A-4): More preferably, A contained in "(a): —CO-A-B-D" is a divalent group consisting of 1 to 6 of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(A-5): Most preferably, A contained in "(a): —CO-A-B-D" is a divalent group consisting of 1 to 6 of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

A is, for example,
—$CH_2$—, —$CH(CH_3)$—, —$CH(C_2H_5)$—, —$CH$(n-$C_3H_7$)—, —$CH$(i-$C_3H_7$)—, —$CH$(n-$C_4H_9$)—, —$CH$(i-$C_4H_9$)—, —$CH$(s-$C_4H_9$)—, —$CH_2CH_2$—, —$CH_2CH_2CH_2$—, —$CH_2CH(CH_3)$—, —$CH_2CH_2CH_2CH_2$—, —$CH(CH_3)CH_2CH_2$—, —$CH_2CH(CH_3)CH_2$—, —$CH_2C(CH_2CH_2CH_2CH_2)CH_2$—, —$CH_2CH_2CH_2CH_2$—, —$CH(CH_3)CH_2CH_2CH_2$—, —$CH_2CH(CH_3)CH_2CH_2$—, —$CH_2CH(CH_3)CH(CH_3)$—, —$CH_2CH_2CH_2CH_2CH_2CH_2$—, —$CH(CH_3)CH_2CH_2CH_2CH_2$—, —$CH(C_2H_5)CH_2CH_2CH_2$—, —$CH(CH_3)CH(CH_3)CH_2CH_2$—, —$CH(CH_3)CH(CH_3)CH(CH_3)$—, —$CH_2CH_2CH_2CH_2CH_2CH_2CH_2$—, —$CH_2CH_2CH_2CH_2CH_2CH_2CH_2CH_2$—, —$CH_2CH_2CH_2CH_2CH_2CH_2CH_2CH_2CH_2$—, —$CH_2CH_2CH_2CH_2CH_2CH_2CH_2CH_2CH_2CH_2$—, —$CH(CH(CH_3)_2)CH_2CH_2CH_2CH_2CH_2$—, -6-$CH_2$-3-ethyl-bicyclo[3, 2, 0]hepta-3-ene-6-yl-$CH_2$—, —$CH(CH_2SCH_3)$—, —$CH(CH_2CH_2SCH_3)$—, —$CH(CH_2Phenyl)$-, —$CH[CH_2$(4-hydroxyphenyl)]-, —$CH[CH_2$(4-imidazolyl)]-, —$CH(CH_2CONH_2)$—, —$CH(CH_2CH_2CONH_2)$—, —$CH(CH_2OH)$—, —$CH[CHOH(CH_3)]$—, —$CH(CH_2CH_2NH_2)$—, —$CH(CH_2CH_2CH_2NH_2)$—, —$CH[CH_2CH_2CH_2NHC(=NH)NH_2]$—, —$CH(CH_2CO_2H)$—, —$CH(CH_2CO_2Bu^t)$-, —$CH(CH_2CH_2CO_2H)$—, —$CH(CH_2CH_2CO_2Bu^t)$-, —$CH(NH_2)CH_2$—, —$CH(COOH)$—, —$CH(COOH)CH_2$—, —$CH(CH_2SCH_3)CH_2$—, —$CH(CH_2S$-n-hexyl)-, —$CH(CH_2$-2-imidazolyl)-, —$CH_2NHCH_2$—, —$CH_2CH_2NHCH_2CH_2$—, —$CH_2CH_2N(CH_3)CH_2CH_2$—, —$CH_2CH_2N$(i-$C_3H_7$)$CH_2CH_2$—, —$CH_2CH_2N$(4-Methoxyphenyl)$CH_2CH_2$—, —$CH_2CH_2N(CH_2Ph)CH_2CH_2$—, —$CH_2CH_2N$(n-$C_4H_9$)$CH_2CH_2CH_2$—, —$CH_2CH_2N$(n-$C_4H_9$)$CH_2CH_2CH_2CH_2$—, —$CH_2CH(OH)CH_2NHCH_2CH_2$—, —$CH_2NHCH_2CH_2$—, —$CH_2CH_2NHCH_2CH_2CH_2$—, —$CH_2CH_2NHCH_2CH_2CH_2CH_2CH_2$—, —$CH_2N(CH_3)CH_2CH_2$—, —$CH_2CH_2N(CH_3)CH_2CH_2$—, —$CH_2N(C_2H_5)CH_2CH_2$—, —$CH_2CH_2N(C_2H_5)CH_2CH_2$—, —$CH_2CH_2N(C_2H_5)CH_2CH_2CH_2$—, —$CH_2N(C_2H_5)CH_2CH_2CH_2CH_2$—, $CH_2N$(—$C_3H_7$)$CH_2CH_2CH_2$—, —$CH_2N(CH_3)CH_2NHCH_2$—, —$CH_2N(Ph)CH_2CH_2$—, —$CH_2N$(4-Cl-Ph)$CH_2CH_2$—, —$CH_2N$(4-Cl-3-$CH_3$-Ph)$CH_2CH_2$—, —$CH_2N(CH_2Ph)CH_2CH_2$—, —$CH_2CH_2N(CH_2Ph)CH_2CH_2$—, —$CH_2CH_2SCH_2CH_2$—, —$CH_2CH_2SCH_2$—, —$CH_2CH(OH)CH_2SCH_2CH_2$—, —$CH_2CH_2S(O)_2CH_2CH_2$—, —$CH_2COCH_2$—, —$CH_2CH_2COCH_2CH_2$—, —NH—, —$N(CH_3)$—, —$N(CH_2CH_3)$—, —$N(CH_2CH_2CH_3)$—, —$N(CH_2CH_2Ph)$-, —$N$(—$C_3H_7$)—, —$N(CH_2CH_2CH_2CH_3)$—, —$N$(i-$C_4H_9$)—, —$N$(s-$C_4H_9$)—, —N(Ph)-, —N(3-Bromo-Ph)-, —N(3-Nitro-Ph)-, —N(4-Ethyl-Ph)-, —N(4-Butyl-Ph)-, —N(4-Chloro-Ph)-, —N(3-Chloro-Ph)-, —N(2-Chloro-Ph)-, —N(4-Fluoro-Ph)-, —N(4-Benzyl-Ph)-, —N(2, 4-Dichloro-Ph)-, —N(4-Trifluoromethyl-Ph)-, —N(4-Hydroxy-Ph)-, —N(4-Cyano-Ph)-, —N(4-Ph-Ph)-, —N(4—CHO-Ph)-, —N(4-Carbamoyl-Ph)-, —N(4-Amino-Ph)-, —N(3-(N,N-Dimethylamino)-Ph)-, —N(4-Me-Ph-Ph)-, —N(4-Benzyloxy-Ph)-, —N(4-Ethoxycarbonyl-Ph)-, —N(4-Carboxy-Ph)-, —N(3-Carboxy-Ph)-, —N(2-Carboxy-Ph)-, —N($CH_2Ph$)-, —N(4-Carboxyphenylmethyl)-,

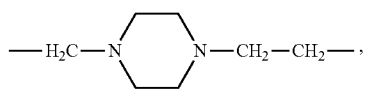

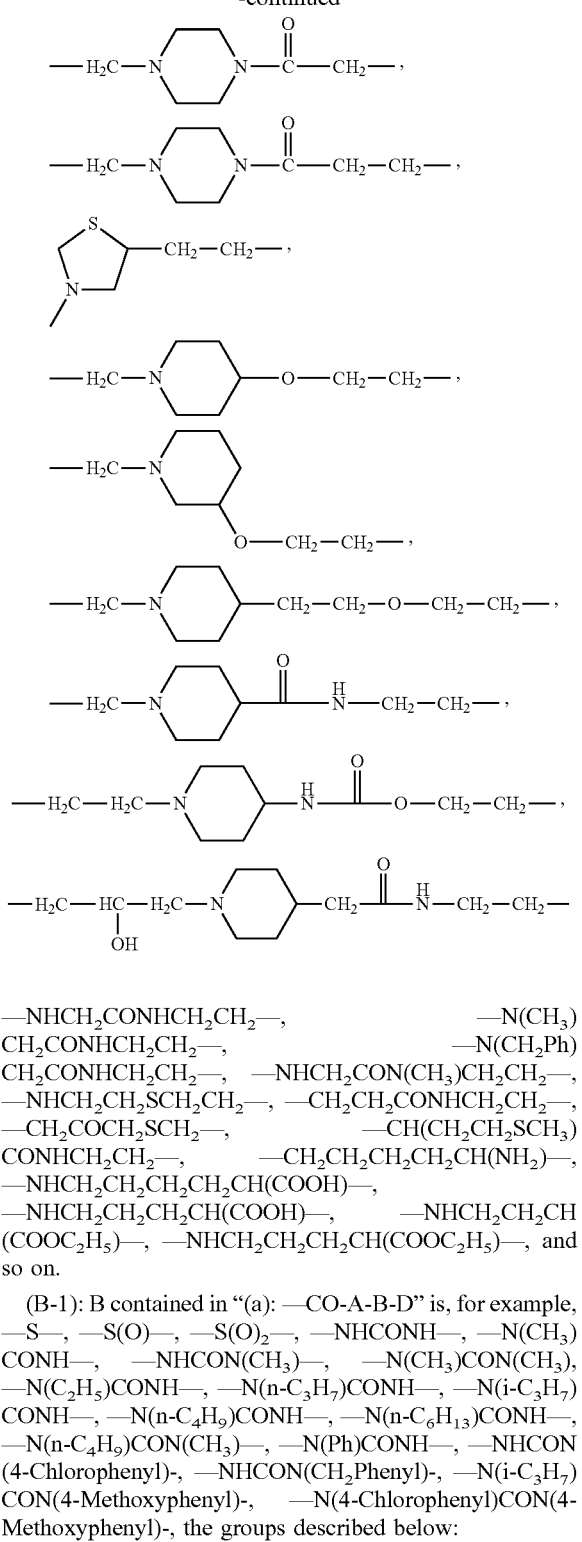

—NHCH$_2$CONHCH$_2$CH$_2$—, —N(CH$_3$)CH$_2$CONHCH$_2$CH$_2$—, —N(CH$_2$Ph)CH$_2$CONHCH$_2$CH$_2$—, —NHCH$_2$CON(CH$_3$)CH$_2$CH$_2$—, —NHCH$_2$CH$_2$SCH$_2$CH$_2$—, —CH$_2$CH$_2$CONHCH$_2$CH$_2$—, —CH$_2$COCH$_2$SCH$_2$—, —CH(CH$_2$CH$_2$SCH$_3$)CONHCH$_2$CH$_2$—, —CH$_2$CH$_2$CH$_2$CH$_2$CH(NH$_2$)—, —NHCH$_2$CH$_2$CH$_2$CH$_2$CH(COOH)—, —NHCH$_2$CH$_2$CH$_2$CH(COOH)—, —NHCH$_2$CH$_2$CH(COOC$_2$H$_5$)—, —NHCH$_2$CH$_2$CH$_2$CH(COOC$_2$H$_5$)—, and so on.

(B-1): B contained in "(a): —CO-A-B-D" is, for example, —S—, —S(O)—, —S(O)$_2$—, —NHCONH—, —N(CH$_3$)CONH—, —NHCON(CH$_3$)—, —N(CH$_3$)CON(CH$_3$), —N(C$_2$H$_5$)CONH—, —N(n-C$_3$H$_7$)CONH—, —N(i-C$_3$H$_7$)CONH—, —N(n-C$_4$H$_9$)CONH—, —N(n-C$_6$H$_{13}$)CONH—, —N(n-C$_4$H$_9$)CON(CH$_3$)—, —N(Ph)CONH—, —NHCON(4-Chlorophenyl)-, —NHCON(CH$_2$Phenyl)-, —N(i-C$_3$H$_7$)CON(4-Methoxyphenyl)-, —N(4-Chlorophenyl)CON(4-Methoxyphenyl)-, the groups described below:

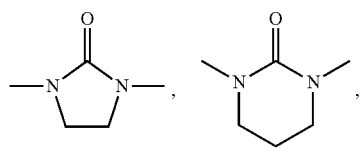

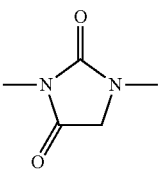

and so on.

(B-2): Preferably, B contained in "(a): —CO-A-B-D" is —S—, —S(O)—, —S(O)$_2$—, —NHCONH—, —N(CH$_3$)CONH—, —NHCON(CH$_3$)—, —N(CH$_3$)CON(CH$_3$)—, —N(C$_2$H$_5$)CONH—, —N(n-C$_3$H$_7$)CONH—, —N(i-C$_3$H$_7$)CONH—, —N(n-C$_4$H$_9$)CONH—, —N(n-C$_6$H$_{13}$)CONH—, —N(n-C$_4$H$_9$)CON(CH$_3$)—, the groups described below:

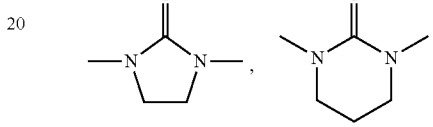

and so on.

(B-3): More preferably, B contained in "(a): —CO-A-B-D" is —S—, —S(O)—, —S(O)$_2$—, —NHCONH—, —N(CH$_3$)CONH—, —NHCON(CH$_3$)—, —N(C$_2$H$_5$)CONH—, —N(n-C$_3$H$_7$)CONH—, —N(i-C$_3$H$_7$)CONH— and so on.

(B-4): Most preferably, B contained in "(a): —CO-A-B-D" is —S—, —S(O)—, —S(O)$_2$—, —NHCONH—, —N(CH$_3$)CONH—, —NHCON(CH$_3$)—, —N(C$_2$H$_5$)CONH— and so on.

The "monovalent group consisting of 0 to 10 groups of one or more kinds selected from the group consisting of (i) to (xi) and a group selected from the group consisting of (xiii) to (xxiv)" in D in "(a): —CO-A-B-D" means a monovalent group (of which the bond is) selected from the group consisting of (xiii) to (xxiv) or a monovalent group constituted by binding the terminal of the divalent group consisting of one (, two) or more groups selected from the group consisting of divalent (i) to (xi) in which the total number of the (i) to (xi) groups is 1 to 10 and the (i) to (xi) groups bind linearly to a group selected from monovalent (xiii) to (xxiv).

(D-1): D contained in "(a): —CO-A-B-D" is a monovalent group consisting of a divalent group consisting of 10 to 6 groups of one or more kinds selected from the group consisting of (i) a "C$_1$-C$_{10}$ alkylene group", (ii) a "C$_2$-C$_{10}$ alkynylene group", (iii) a "C$_2$-C$_{10}$ alkynylene group", (iv) a "formula of —NR$^3$—" (v) an "oxygen atom", (vi) a "carbonyl group", (viib) a "formula of —S(O)$_n$— wherein n represents an integer of 0 to 2", (viii) a "C$_6$-C$_{10}$ divalent arylene group optionally having 1 to 4 substituent β(s)", (ix) a "C$_5$-C$_{10}$ divalent and saturated cyclic hydrocarbon group optionally having 1 to 4 substituent α(s)", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s)" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)"; and a group selected from the group consisting of
(xiii) a hydrogen atom, (xiv) the alkyl group described in the "$C_1$-$C_6$ alkyl group", (xv) the halogenoalkyl group described in the "$C_1$-$C_6$ halogenoalkyl group", (xvi) the cycloalkyl group described in the "$C_3$-$C_{10}$ cycloalkyl group", (xviia) the aryl group described in the "$C_6$-$C_{10}$ aryl group optionally having 1 to 5 substituent β(s)", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —N($R^{a1}$)($R^{a2}$)", (xx) a hydroxy group, (xxi) a formyl group, (xxii) a carboxy group, (xxiii) a sulfo group and (xxiv) a phospho group,
and includes, for example, a monovalent group constituted by binding one group selected from the group consisting of (xiii) a hydrogen atom, (xiv) the alkyl group described in the "$C_1$-$C_6$ alkyl group", (xv) the halogenoalkyl group described in the "$C_1$-$C_6$ halogenoalkyl group", (xvi) the cycloalkyl group described in the "$C_3$-$C_{10}$ cycloalkyl group", (xviia) the aryl group described in the "$C_6$-$C_{10}$ aryl group optionally having 1 to 5 substituent β(s)", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —N($R^{a1}$)($R^{a2}$)", (xx) a hydroxy group, provided that when the present hydroxy group binds to a carbon atom, the carbon atom is not a unsaturated carbon atom, (xxi) a formyl group, (xxii) a carboxy group, (xxiii) a sulfo group and (xxiv) a phospho group, to the terminal of the divalent group shown in A (A-1).

(D-2): Preferably, D contained in "(a): —CO-A-B-D" is a monovalent group consisting of a divalent group consisting of 0 to 6 groups of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2", (viii) a "$C_6$-$C_{10}$ divalent arylene group optionally having 1 to 4 substituent β(s) described above", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above";
and a group selected from the group consisting of
(xiii) a hydrogen atom, (xiv) the alkyl group described in the "$C_1$-$C_6$ alkyl group", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —N($R^{a1}$)($R^{a2}$)", (xx) a hydroxy group, provided that when the present hydroxy group binds to a carbon atom, the carbon atom is not a unsaturated carbon atom, (xxi) a formyl group, (xxii) a carboxy group, (xxiii) a sulfo group and (xxiv) a phospho group.

(D-3): More preferably, D contained in "(a): —CO-A-B-D" is a monovalent group consisting of a divalent group consisting of 0 to 6 groups of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above, (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above";
and a group selected from the group consisting of
(xiii) a hydrogen atom, (xiv) the alkyl group described in the "$C_1$-$C_6$ alkyl group", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —N($R^{a1}$)($R^{a2}$)", (xx) a hydroxy group, provided that when the present hydroxy group binds to a carbon atom, the carbon atom is not a unsaturated carbon atom, (xxii) a carboxy group, (xxiii) a sulfa group and (xxiv) a phospho group.

(D-4): Further more preferably, D contained in "(a): —CO-A-B-D" is a monovalent group consisting of a divalent group consisting of 0 to 6 groups of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s)", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above";
and a group selected from the group consisting of
(xiii) a hydrogen atom, (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ"(s) described above, (xix) the amino group described in the "group having a formula of —N(R$^{a1}$)(R$^{a2}$)", (xx) a hydroxy group, provided that when the present hydroxy group binds to a carbon atom, the carbon atom is not a unsaturated carbon atom, (xxii) a carboxy group, (xxiii) a sulfo group and (xxiv) a phospho group.

(D-5): Most preferably, D contained in "(a): —CO-A-B-D" is a monovalent group consisting of a divalent group consisting of 0 to 6 groups of one or more kinds selected from the group consisting of
(i) a "$C_1$-$C_{10}$ alkylene group wherein the alkylene group is linear or branched, optionally includes a cyclic alkylene moiety in the chain and optionally has the substituent α(s)", (iv) "—NR$^3$— wherein R$^3$ represents (a1) a hydrogen atom, (b1) a $C_1$-$C_6$ alkyl group, (c1) a $C_6$-$C_{10}$ aryl group optionally having 1 to 5 substituent β(s) described above, or (d1) a $C_6$-$C_{10}$ aryl-$C_1$-$C_6$ alkyl group optionally having 1 to 5 substituent β(s) described above in the aryl moiety", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above"; and a group selected from the group consisting of
(xiii) a hydrogen atom, (xix) the amino group described in the "group having a formula —N(R$^{a1}$)(R$^{a2}$)", (xx) a hydroxy group, provided that when the present hydroxy group binds to a carbon atom, the carbon atom is not a unsaturated carbon atom, (xxii) a carboxy group, (xxiii) a sulfo group, and (xxiv) a phospho group.

D is, for example, a hydrogen atom, —CH$_2$COOH, —CH$_2$CH$_2$COOH, —CH$_2$CH$_2$CH$_2$COOH, —CH$_2$CH(i-C$_4$H$_9$)CH$_2$COOH, —CH$_2$CH(i-C$_4$H$_9$)CH$_2$CONHCH$_2$CH(i-C$_4$H$_9$)CH$_2$COOH, —CH$_2$C(CH$_2$CH$_2$CH$_2$CH$_2$CH$_2$)CH$_2$COOH, —CH$_2$C(CH$_2$CH$_2$CH$_2$CH$_2$CH$_2$)CH$_2$CONHCH$_2$C(CH$_2$CH$_2$CH$_2$CH$_2$)CH$_2$COOH, —CH(CH$_2$SCH$_3$)COOH, —CH(CH$_2$CH$_2$SCH$_3$)COOH, —CH(CH$_2$Phenyl)COOH, —CH[CH$_2$(4-hydroxyphenyl)]COOH, —CH[CH$_2$(4-imidazolyl)]COOH, —CH(CH$_2$CONH$_2$)COOH, —CH(CH$_2$CH$_2$CONH$_2$)COOH, —CH(CH$_2$OH)COOH, —CH[CHOH(CH$_3$)]COOH, —CH(CH$_2$CH$_2$CH$_2$NH$_2$)COOH, —CH(CH$_2$CH$_2$CH$_2$CH$_2$NH$_2$)COOH, —CH[CH$_2$CH$_2$NHC(=NH) NH$_2$]COOH, —CH(CH$_2$CO$_2$H)COOH, —CH(CH$_2$CO$_2$Bu$^t$)COOH, —CH(CH$_2$CH$_2$CO$_2$H)COOH, —CH(CH$_2$CH$_2$CO$_2$Bu$^t$)COOH, —CH$_2$CH$_2$CH$_2$CH(NH$_2$)COOH, —CH$_2$CH$_2$CH$_2$CH$_2$CH(NH$_2$)COOH, —CH(COOH)CH$_3$, —CH$_2$CH$_2$SO$_3$H, —CH$_2$CH$_2$CH$_2$SO$_3$H, —CH$_2$CH$_2$NH$_2$— CH$_2$CH$_2$CH$_2$NH$_2$, —CH$_2$CH$_2$CH$_2$CH$_2$NH$_2$, —CH$_2$CH$_2$CH$_2$CH(NH$_2$)COOH, —CH$_2$CH$_2$CH$_2$CH$_2$CH (NH$_2$)COOH, —CH$_2$CH$_2$OH, —CH$_2$CH$_2$CH$_2$OH, —CH$_2$CH$_2$CH$_2$CH$_2$OH, —CH$_2$PO$_3$H, —CH$_2$CONHCH$_2$COOH, —CH$_2$CONHCH (CH$_2$CH$_2$SCH$_3$)COOH, —CH$_2$CONHCH[CH$_2$(4-imidazolyl)]COOH, —CH$_2$CONHCH(CH$_2$CONH$_2$)COOH, —CH$_2$CONHCH(CH$_2$CH$_2$CONH$_2$)COOH, —CH$_2$CH$_2$CONHCH$_2$COOH, —CH$_2$CH$_2$CONHCH (CH$_2$CH$_2$SCH$_3$)COOH, —CH$_2$CH$_2$CONHCH[CH$_2$(4-imidazolyl)]COOH, —CH$_2$CH$_2$CONHCH(CH$_2$CONH$_2$) COOH, —CH$_2$CH$_2$CONHCH(CH$_2$CH$_2$CONH$_2$)COOH, —CH$_2$CH$_2$CH$_2$CONHCH$_2$COOH, —CH$_2$CH$_2$CH$_2$CONHCH(CH$_2$CH$_2$SCH$_3$)COOH, —CH$_2$CH$_2$CH$_2$CONHCH[CH$_2$(4-imidazolyl)]COOH, —CH$_2$CH$_2$CH$_2$CONHCH(CH$_2$CONH$_2$)COOH, —CH$_2$CH$_2$CH$_2$CONHCH(CH$_2$CH$_2$CONH$_2$)COOH, -6-CH$_2$-3-ethylbicyclo-[3,2,0]hepta-3-en-6-yl-CH$_2$COOH and the groups described below, formed together with —NR$^5$— in B:

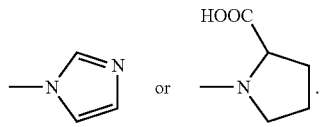

The "divalent group consisting of 1 to 10 groups of one or more kinds selected from the group consisting of (i) to (xi)" in E of "(b): —CO-E-F" means a divalent group which consists of one (, two) or more groups selected from the group consisting of divalent (i) to (xi) in which the total number of the groups (i) to (xi) is 1 to 10 and the groups (i) to (xi) bind non-branchedly and linearly.

(E-1): E contained in "(b): —CO-E-F" is divalent group consisting of 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iii) a "$C_2$-$C_{10}$ alkynylene group wherein the alkynylene group is linear or branched and optionally has the substituent α(s) described above", (iv) "—NR$^3$— wherein R$^3$ represents (a1) a hydrogen atom, (b1) a $C_1$-$C_6$ alkyl group, (c1) a $C_6$-$C_{10}$ aryl-group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2", (viii) a "$C_6$-$C_{10}$ divalent arylene group optionally having 1 to 4 substituent β(s) described above", (ix) a "$C_5$-$C_{10}$ divalent and saturated cyclic hydrocarbon group optionally having 1 to 4 substituent α(s) described above", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above", and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(E-2): Preferably, E contained in "(b): —CO-E-F" is a divalent group consisting of 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—NR$^3$— wherein R$^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2", (viii) a "$C_6$-$C_{10}$ divalent arylene group optionally having 1 to 4 substituent β(s) described above", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above", and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(E-3): More preferably, E contained in "(b): —CO-E-F" is a divalent group consisting of 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(E-4): Further more preferably, E contained in "(b): —CO-E-F" is a divalent group consisting of 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", an "oxygen atom", (vi) a "carbonyl group", (viia) a "formula of —S(O)$_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

(E-5): Most preferably, E contained in "(b): —CO-E-F" is a divalent group consisting of 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (iv) "—$NR^3$— wherein $R^3$ represents (a1)) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (vi) a "carbonyl group" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above".

E is, for example, —CH($CH_3$)—, —CH($C_2H_5$)—, —CH(n-$C_3H_7$)—, —CH(i-$C_3H_7$)—, —CH(n-$C_4H_9$)—, —CH(i-$C_4H_9$)—, —$CH_2CH_2$—, —$CH_2CH_2CH_2$—, —$CH_2CH$($CH_3$)—, —$CH_2CH_2CH_2CH_2$—, —CH($CH_3$)$CH_2CH_2$—, —$CH_2CH$($CH_3$)$CH_2$—, —$CH_2CH$(i-$C_4H_9$)$CH_2$—, —$CH_2CH_2CH_2CH_2CH_2$—, —CH($CH_3$)$CH_2CH_2CH_2$—, —$CH_2CH$($CH_3$)$CH_2CH_2$—, —$CH_2CH$($CH_3$)CH($CH_3$)—, —$CH_2CH_2CH_2CH_2CH_2CH_2$—, —CH($CH_3$)$CH_2CH_2CH_2CH_2$—, —CH($C_2H_5$)$CH_2CH_2CH_2$—, —CH($CH_3$)CH($CH_3$)$CH_2CH_2$—, —CH($CH_3$)CH($CH_3$)CH($CH_3$)—, —$CH_2CH_2CH_2CH_2CH_2CH_2CH_2$—, —$CH_2CH_2CH_2CH_2CH_2CH_2CH_2CH_2$—, —$CH_2C$($CH_2CH_2CH_2CH_2CH_2$)$CH_2$—, —$CH_2CH_2CH_2CH_2CH_2CH_2CH_2CH_2CH_2$—, —$CH_2CH_2CH_2CH_2CH_2CH_2CH_2CH_2CH_2CH_2$—, —CH($CH($CH_3)_2$)$CH_2CH_2CH_2CH_2CH_2CH_2$—, -6-$CH_2$-3-ethyl-bicyclo[3,2,0]hepta-3-ene-6-yl-$CH_2$—, —CH($CH_2CH_2SCH_3$)—, —CH($CH_2$Phenyl)-, —CH[$CH_2$(4-hydroxyphenyl)]-, —CH[$CH_2$(4-imidazolyl)]-, —CH($CH_2CONH_2$)—, —CH($CH_2CH_2CONH_2$)—, —CH($CH_2OH$)—, —CH[CHOH($CH_3$)]—, —CH($CH_2CO_2H$)—, —CH(COOH)$CH_2$—, —CH($CH_2SCH_3$)—, —CH($CH_2$S-n-hexyl)-, —$CH_2CH_2NHCH_2CH_2$—, —$CH_2CH_2N$($CH_3$)$CH_2CH_2$—, —$CH_2CH_2N$(1-$C_3H_7$)$CH_2CH_2$—, —$CH_2CH_2N$(4-Methoxyphenyl)$CH_2CH_2$—, —$CH_2CH_2N$($CH_2$Ph)$CH_2CH_2$—, —$CH_2N$($CH_3$)$CH_2CH_2$—, —$CH_2CH_2N$($CH_3$)$CH_2CH_2CH_2$—, —$CH_2N$($C_2H_5$)$CH_2CH_2$—, —$CH_2CH_2N$($C_2H_5$)$CH_2CH_2$—, —$CH_2CH_2N$($C_2H_5$)$CH_2CH_2CH_2$—, —$CH_2N$($C_2H_5$)$CH_2CH_2CH_2CH_2$—, —$CH_2N$(i-$C_3H_7$)$CH_2CH_2CH_2CH_2$—, —$CH_2N$($CH_3$)S(O)$_2CH_2CH_2$—, —$CH_2N$(Ph)$CH_2CH_2$—, —$CH_2N$(4-Cl-Ph)$CH_2CH_2$—, —$CH_2N$(4-Cl-3-$CH_3$-Ph)$CH_2CH_2$—, —$CH_2N$($CH_2$Ph)$CH_2CH_2$—, —$CH_2CH_2N$($CH_2$Ph)$COCH_2CH_2$—, —$CH_2CH_2SCH_2CH_2$—, —$CH_2CH_2SCH_2$—, —$CH_2CH$(OH)$CH_2SCH_2CH_2$—, —$CH_2CH_2S$(O)$_2CH_2CH_2$—, —$CH_2CH_2S$(O)$_2CH_2$—, —$CH_2COCH_2$—, —$CH_2CH_2COCH_2CH_2$—,

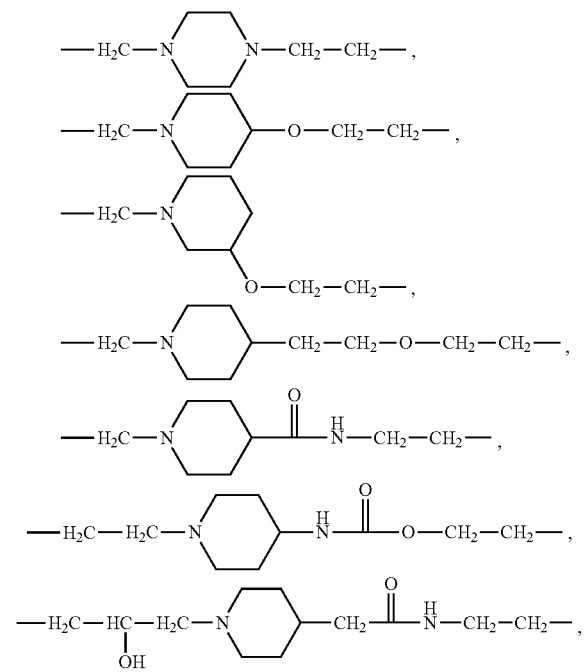

—NHCH$_2$CONHCH$_2$CH$_2$—, —N(CH$_3$)CH$_2$CONHCH$_2$CH$_2$—, —N(CH$_2$Ph)CH$_2$CONHCH$_2$CH$_2$—, —NHCH$_2$CON(CH$_3$)CH$_2$CH$_2$—, —NHCH$_2$CH$_2$SCH$_2$CH$_2$—, —CH$_2$CH$_2$CONHCH$_2$CH$_2$—, —CH(CH$_2$CH$_2$SCH$_3$)CONHCH$_2$CH$_2$— and so on.

The "monovalent group consisting of 0 to 10 groups of one or more kinds selected from the group consisting of (i)

to (xi); and a group selected from the group consisting of (xiii) to (xxiv)" in G of "(c): —CO-G" means a monovalent group (of which the bond is) selected from the group consisting of (xiii) to (xxiv), or a monovalent group constituted by binding the terminal of a divalent group consisting of one (, two) or more groups selected from the group consisting of divalent (i) to (xi) in which the total number of the groups (i) to (xi) is 1 to 10 and the groups (i) to (xi) bind linearly, to a monovalent group selected from the group consisting of monovalent (xiii) to (xxiv).

(G-1): G contained in "(c): —CO-G" is a monovalent group consisting of a divalent group consisting of 0 to 6 groups of one or more kinds selected from the group consisting of (i) a "$C_1$-$C_{10}$ alkylene group", (ii) a "$C_2$-$C_{10}$ alkenylene group", (iii) a "$C_2$-$C_{10}$ alkynylene group", (iv) a "formula of —$NR^3$—", (v) an "oxygen atom", (vi) a "carbonyl group", (viia) a "formula of —$S(O)_n$— wherein n represents an integer of 0 or 2", (viii) a "$C_6$-$C_{10}$ divalent arylene group optionally having 1 to 4 substituent β(s)", (ix) a "$C_5$-$C_{10}$ divalent and saturated cyclic hydrocarbon group optionally having 1 to 4 substituent α(s)", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s)" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)"; and a group selected from the group consisting of (xiii) a hydrogen atom, (xiv) the alkyl group described in the "$C_1$-$C_6$ alkyl group", (xv) the halogenoalkyl group described in the "$C_1$-$C_6$ halogenoalkyl group", (xvi) the cycloalkyl group described in the "$C_3$-$C_{10}$ cycloalkyl group", (xviia) the aryl group described in the "$C_6$-$C_{10}$ aryl group optionally having 1 to 5 substituent β(s)", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —$N(R^{a1})(R^{a2})$", (xx) a hydroxy group, (xxi) a formyl group, (xxii) a carboxy group, (xxiii) a sulfo group and (xxiv) a phospho group.

(G-2): Preferably, G contained in "(c): —CO-G" is a monovalent group consisting of a divalent group consisting of 0 to 6 groups of one or more kinds selected from the group consisting of (i) a "$C_1$-$C_{10}$ alkylene group" described above, (ii) a "$C_2$-$C_{10}$ alkenylene group", (iii) a "$C_2$-$C_{10}$ alkynylene group", (iv) a "formula of —$NR^3$—", (v) an "oxygen atom", (vi) a "carbonyl group", (viia) a "formula of —$S(O)_n$— wherein n represents an integer of 0 or 2", (viii) a "$C_6$-$C_{10}$ divalent arylene group optionally having 1 to 4 substituent β(s)", (ix) a "$C_5$-$C_{10}$ divalent and saturated cyclic hydrocarbon group optionally having 1 to 4 substituent α(s)", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s)" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)"; and a group selected from the group consisting of (xiii) a hydrogen atom, (xiv) the alkyl group described in the "$C_1$-$C_6$ alkyl group", (xvi) the cycloalkyl group described in the "$C_3$-$C_{10}$ cycloalkyl group", (xviia) the aryl group described in the "$C_6$-$C_{10}$ aryl group optionally having 1 to 5 substituent β(s)", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —$N(R^{a1})(R^{a2})$", (xx) a hydroxy group, (xxi) a formyl group, (xxii) a carboxy group, (xxiii) a sulfo group and (xxiv) a phospho group.

(G-3): More preferably, G contained in "(c): —CO-G" is a monovalent group consisting of a divalent group consisting of 0 to 6 groups of one or more kinds selected from the group consisting of (i) a "$C_1$-$C_{10}$ alkylene group" described above, (ii) a "$C_2$-$C_{10}$ alkenylene group", (iv) a "formula of —$NR^3$—", (v) an "oxygen atom", (vi) a "carbonyl group", (viia) a "formula of —$S(O)_n$— wherein n represents an integer of 0 or 2", (viii) a "$C_6$-$C_{10}$ divalent arylene group optionally having 1 to 4 substituent β(s)" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)"; and a group selected from the group consisting of (xiii) a hydrogen atom, (xiv) the alkyl group described in the "$C_1$-$C_6$ alkyl group", (xviia) the aryl group described in the "$C_6$-$C_{10}$ aryl group optionally having 1 to 5 substituent β(s)", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula —$N(R^{a1})(R^{a2})$", (xx) a hydroxy group, (xxi) a formyl group, (xxii) a carboxy group, (xxiii) a sulfo group and (xxiv) a phospho group.

(G-4): Further more preferably, G contained in "(c): —CO-G" is a monovalent group consisting of a divalent group consisting of 0 to 6 groups of one or more kinds selected from the group consisting of (i) a "$C_1$-$C_{10}$ alkylene group" described above, (iv) a "formula of —$NR^3$—", (v) an "oxygen atom", (vi) a "carbonyl group", (viia) a "formula of —$S(O)_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)"; and a group selected from the group consisting of (xiii) a hydrogen atom, (xiv) the alkyl group described in the "$C_1$-$C_6$ alkyl group", (xviia) the aryl group described in the "$C_6$-$C_{10}$ aryl group optionally having 1 to 5 substituent β(s)", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —$N(R^{a1})(R^{a2})$", (xx) a hydroxy group, (xxi) a formyl group, (xxii) a carboxy group, (xxiii) a sulfo group and (xxiv) a phospho group.

(G-5): Further even more preferably, G contained in "(c): —CO-G" is a monovalent group consisting of a divalent group consisting of 0 to 6 groups of one or more kinds selected from the group consisting of (i) a "$C_1$-$C_{10}$ alkylene group" described above, (iv) a "formula of —$NR^3$—", (vi) a "carbonyl group", (viia) a "formula of —$S(O)_n$— wherein n represents an integer of 0 or 2", (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)";
and a group selected from the group consisting of (xiii) a hydrogen atom, (xiv) the alkyl group described in the "$C_1$-$C_6$ alkyl group", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —N($R^{a1}$)($R^{a2}$)", (xx) a hydroxy group, (xxi) a formyl group, (xxii) a carboxy group, (xxiii) a sulfo group and (xxiv) a phospho group.

(G-6): Most preferably, G contained in "(c): —CO-G" is a monovalent group consisting of a divalent group consisting of 0 to 6 groups of one or more kinds selected from the group consisting of (i) a "$C_1$-$C_{10}$ alkylene group" described above, (iv) a "formula of —$NR^3$—", (vi) a "carbonyl group", (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)";
and a group selected from the group consisting of (xiii) a hydrogen atom, (xiv) the alkyl group described in the "$C_1$-$C_6$ alkyl group", (xix) the amino group described in the "group having a formula of —N($R^{a1}$)($R^{a2}$)", (xx) a hydroxy group, (xxi) a formyl group, (xxii) a carboxy group, (xxiii) a sulfo group and (xxiv) a phospho group.

When the carotenoid derivative (I) of the present invention has acidic group(s) (for example, a carboxy group, a sulfo group or a phospho group) and/or basic group(s) (for example, an amino group, a guanidyl group or a ureido group) in the molecule, it can be made to a pharmaceutically acceptable salt by acting an acid and/or base in accordance with an ordinary method. Such salt may be, for example, an alkali metal salt such as a sodium salt, a potassium salt and a lithium salt; an alkali earth metal salt such as a calcium salt and a magnesium salt; a metal salt such as an aluminum salt, an iron salt, a zinc salt, a copper salt, a nickel salt, a cobalt salt and so on; an amine salt such as an ammonium salt, a t-octylamine salt, a dibenzylamine salt, a morpholine salt, a glucosamine salt, a phenyl glycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-N-phenethylamine salt, a piperazine salt, a tetramethylammonium salt and a tris(hydroxymethyl)-aminomethane salt; an amino acid salt such as a lysine salt, an ornithine salt and an arginine salt; a halide acid salt such as a hydrofluoric acid salt, a hydrochloric acid salt, a hydrobromic acid salt and a hydroiodic acid salt; a nitric acid salt; a perchloric acid salt; a sulfuric acid salt; a phosphoric acid salt; a sulfonic acid salt such as a methanesulfonic acid salt, a trifluoromethanesulfonic acid salt, an ethanesulfonic acid salt, a benzenesulfonic acid salt and a p-toluenesulfonic acid salt; a carboxylic acid salt such as an acetic acid salt, a malic acid salt, a fumaric acid salt, a succinic acid salt, a citric acid salt, a tartaric acid salt, an oxalic acid salt and a maleic acid salt; or an amino acid salt such as a glutamic acid salt and an aspartic acid salt, and it is preferably an alkali metal salt, an alkali earth metal salt, a amine salt, a halide acid salt, a nitric acid salt, a sulfuric acid salt, a phosphoric acid salt, a sulfonic acid salt, a carboxylic acid salt or an amino acid salt, and more preferably a sodium salt, a potassium salt, a lithium salt, a calcium salt, a magnesium salt, an ammonium salt, a morpholine salt, a glucosamine salt, a phenylglycine alkyl ester salt, an ethylenediamine salt, an N-methylglucamine salt, a guanidine salt, a chloroprocaine salt, a procaine salt, a tetramethylammonium salt, a lysine salt, a hydrochloric acid salt, a hydrobromic acid salt, a nitric acid salt, a sulfuric acid salt, a phosphoric acid salt, a methanesulfonic acid salt, a p-toluenesulfonic acid salt, an acetic acid salt, a malic acid salt, a fumaric acid salt, a succinic acid salt, a citric acid salt, a tartaric acid salt, an oxalic acid salt, a maleic acid salt, an ornithine acid salt, a glutamic acid salt or an aspartic acid salt. In addition, when an amino group is present in the molecule, it can be made to a quaternary ammonium salt by alkylation in accordance with an ordinary method, and such quaternary ammonium salt is also included in the carotenoid derivative (I) of the present invention.

When the carotenoid derivative (I) of the present invention has a carboxy group, it can be made to a pharmaceutically acceptable ester or amide in accordance with an ordinary method (condensation reaction of an carboxylic acid with an alcohol or an amine), by reacting the compound (I) or an active derivative thereof (for example, an acid chloride, a mixed acid anhydride and so on) with a corresponding alcohol (for example, $C_1$-$C_6$ alcohol and so on), an active derivative thereof (for example, a (5-methyl-2-oxo-1,3-dioxolen-4-yl)methyl body, a (pivaloyloxy)methyl body, a phthalidyl body, an (isopropoxycarbonyl)oxymethyl body and so on), ammonia or a corresponding amine (for example, a mono- or di-$C_1$-$C_6$ alkyl amine and so on); by reacting an ester body of the compound (I) with a corresponding alcohol (for example, a $C_1$-$C_6$ alcohol and so on) (ester exchange reaction), or ammonia or a corresponding amine (for example, a mono- or di-$C_1$-$C_6$ alkyl amine and so on) (amidation reaction); or by reacting an alkali metal salt of the compound (I) with a corresponding halide body (for example, $C_1$-$C_6$ alkyl chloride or bromide, (5-methyl-2-oxo-1,3-dioxolen-4-yl)methyl chloride or bromide, (pivaloyloxy)methyl chloride or bromide, phthalidyl chloride or bromide, [(isopropoxycarbonyl)oxy]methyl chloride or bromide and so on).

The ester of the carotenoid compound of the present invention may be, for example, a $C_1$-$C_6$ alkyl ester such as methyl ester, ethyl ester, propyl ester, isopropyl ester, butyl ester, s-butyl ester, t-butyl ester, pentyl ester and hexyl ester; a $C_3$-$C_6$ cycloalkyl ester such as cyclopentyl ester and cyclohexyl ester; a $C_6$-$C_{10}$ aryl ester such as phenyl ester and naphthyl ester; a $C_6$-$C_{10}$ aryl-$C_1$-$C_6$ alkyl ester such as benzyl ester, phenethyl ester, α-methylbenzyl ester, 3-phenylpropyl ester, 4-phenylbutyl ester, 6-phenyl-hexyl ester, diphenylmethyl ester and triphenylmethyl ester; or an ester that is hydrolyzed in a living body such as (5-methyl-2-oxo-1,3-dioxolen-4-yl)methyl ester, (pivaloyloxy)methyl ester, phthalidyl ester, [(isopropoxycarbonyl)oxy]methyl ester, [(cyclo-hexyloxycarbonyl)oxy]methyl ester and 1-[(cyclo-hexyloxycarbonyl)oxy]ethyl ester.

Preferably, the ester of the carotenoid compound of the present invention is methyl ester, ethyl ester, propyl ester, isopropyl ester, butyl ester, hexyl ester, cyclopentyl ester, cyclohexyl ester, diphenylmethyl ester, (5-methyl-2-oxo-1,3-dioxolen-4-yl)methyl ester, (pivaloyloxy)methyl ester, phthalidyl ester, [(iso-propoxycarbonyl)oxy]methyl ester, [(cyclo-hexyloxycarbonyl)oxy]methyl ester or 1-[(cyclo-hexyloxy-carbonyl)oxy]ethyl ester.

More preferably, the ester of the carotenoid compound of the present invention is methyl ester, ethyl ester, propyl ester, (5-methyl-2-oxo-1,3-dioxolen-4-yl)methyl ester, (pivaloyloxy)methyl ester, phthalidyl ester, [(isopropoxycarbonyl)oxy]methyl ester, [(cyclohexyloxy-carbonyl)oxy]methyl ester or 1-[(cyclohexyloxy-carbonyl)oxy]ethyl ester.

Further more preferably, the ester of the carotenoid compound of the present invention is methyl ester, ethyl ester, (5-methyl-2-oxo-1,3-dioxolen-4-yl)methyl ester, [(cyclohexyloxycarbonyl)oxy]methyl ester or 1-[(cyclo-hexyloxy-carbonyl)oxy]ethyl ester.

Most preferably, the ester of the carotenoid compound of the present invention is methyl ester, ethyl ester, (5-methyl-2-oxo-1,3-dioxolen-4-yl)methyl ester or 1-[(cyclo-hexyloxycarbonyl)oxy]ethyl ester.

The amide of the carotenoid compound of the present invention may be, for example, amide (—CONH$_2$); a mono-$C_1$-$C_6$ alkyl amide or mono-$C_3$-$C_6$ cycloalkyl amide such as N-methyl amide, N-ethyl amide, N-propyl amide, N-isopropyl amide, N-butyl amide, N-s-butyl amide, N-t-butyl amide, N-pentyl amide, N-hexyl amide, N-cyclopropyl amide, N-cyclopentyl amide and N-cyclohexyl amide; or a di-$C_1$-$C_6$ alkyl amide, N—$C_1$-$C_6$ alkyl-N—$C_3$-$C_6$ cycloalkyl amide or di-$C_3$-$C_6$ cycloalkyl amide such as N,N-dimethyl amide, N,N-diethyl amide, N,N-dipropyl amide, N,N-diiso- Further, a compound that is metabolized in a living body and converted to the compound (I) of the present invention or a pharmaceutically acceptable salt thereof, which is so called prodrug, is also all included in the present invention.

Furthermore, the compound (I) of the present invention has an optical isomer. That is, when the compound (I) of the present invention has a chiral carbon atom or a sulfoxide group, a steric isomer of R configuration or S configuration is present. In addition, a geometric isomer of a cis body or trans body is present based on a unsaturated double bond. Each of them or a compound composed of them in any ratio is also included in the present invention. When an optical isomer and/or steric isomer of the compound (I) of the present invention makes difference to the ligand action in a living body, they can be arbitrarily selected. Such steric isomer can be obtained by synthesizing the compound (I) using an optically-resolved raw material compound or if desired, optically resolving the synthesized compound (I) using an ordinary optical resolution or isolation.

Preferred compounds of the compound (I) of the present invention are shown below.

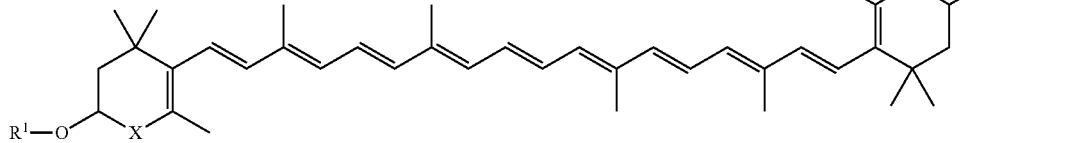

propyl amide, N-methyl-N-ethyl amide, N-methyl-N-propyl amide, N-methyl-N-butyl amide, N-ethyl-N-propyl amide, N-ethyl-N-butyl amide, N-butyl-N-cyclopentyl amide, N-ethyl-N-cyclopropyl amide and N,N-dicyclohexyl amide.

Preferably, the amide of the carotenoid compound of the present invention is amide (—CONH$_2$); N-methyl amide, N-ethyl amide, N-propyl amide, N-isopropyl amide, N-butyl amide, N-cyclopentyl amide; N,N-dimethyl amide, N,N-diethyl amide, N,N-dipropyl amide, N-methyl-N-ethyl amide or N-methyl-N-propyl amide.

More preferably, the amide of the carotenoid compound of the present invention is amide (—CONH$_2$), N-methyl amide, N-ethyl amide, N,N-dimethyl amide, N,N-diethyl amide, N-methyl-N-ethyl amide or N-methyl-N-propyl amide.

Most preferably, the amide of the carotenoid compound of the present invention is amide (—CONH$_2$), N-methyl amide, N-ethyl amide, N,N-dimethyl amide or N,N-diethyl amide.

A solvate, a solvent absorption substance and a solvent surface-attached substance of the compound (I) of the present invention are also included in the present invention. Such substance can be formed by, for example, leaving in the atmosphere, or dry and recrystallization from a solution. Examples of the solvent include an organic solvent such as alcohol, acetone, hexane and so on, and water.

In addition, when the compound (I) of the present invention exhibits various crystal forms by crystal precipitation, recrystallization and so on, such crystal form and noncrystalline form (amorphous) are also all included in the present invention. In addition, those partially containing a polymer or organic compound, usually used in a medicine in order to easily form a noncrystalline form are also included in the present invention.

The compound (I) of the present invention is preferably (T-1), wherein (X-1): X is a carbonyl group or a methylene group, (R-1): at least one of $R^1$ and $R^2$ is (a): —CO-A-B-D, (b): —CO-E-F or (c): —CO-G, and the other is (a), (b), (c) or a hydrogen atom (and the other is (a): —Z—CO-A-B—U, (b): —CO-E-F, (c): —CO-G or a hydrogen atom), (A-1): A is a divalent group obtained by combining 1 to 6 groups of one or more kinds selected from the group consisting of (i) a $C_1$-$C_{10}$ alkylene group wherein the alkylene group is linear or branched, optionally includes a cyclic alkylene moiety in the chain and optionally has the substituent α(s), (ii) a $C_2$-$C_{10}$ alkenylene group wherein the alkenylene group is linear or branched and optionally has the substituent α(s) described above, (iii) a $C_2$-$C_{10}$ alkynylene group wherein the alkynylene group is linear or branched and optionally has the substituent α(s) described above, (iv) —NR$^3$— wherein R$^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety, (v) an oxygen atom, (vi) a carbonyl group, (viia) a formula of —S(O)$_n$— wherein n represents an integer of 0 or 2, (viii) a $C_6$-$C_{10}$ divalent arylene group optionally having 1 to 4 substituent β(s) described above, (ix) a $C_5$-$C_{10}$ divalent and saturated cyclic hydrocarbon group optionally having 1 to 4 substituent α(s) described above, (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above, (B-1): B is —S—, —S(O)—, —S(O)$_2$—, —NHCONH—, —N(CH$_3$)CONH—, —NHCON(CH$_3$)—, —N(CH$_3$)CON(CH$_3$)—, —N(C$_2$H$_5$)CONH—, —N(n-C$_3$H$_7$)CONH—, —N(i-C$_3$H$_7$)CONH—, —N(n-C$_4$H$_9$)CONH—, —N(n-C$_6$H$_{13}$)CONH—, (n-C$_4$H$_9$)CON(CH$_3$)—, —N(Ph)CONH—, —NHCON(4-Chlorophenyl)-, —NHCON(CH$_2$Phenyl)-, —N(i-C$_3$H$_7$)CON(4-Methoxyphenyl)-, —N(4-Chlorophenyl)CON(4-Methoxyphenyl)- or a group selected from the groups described below:

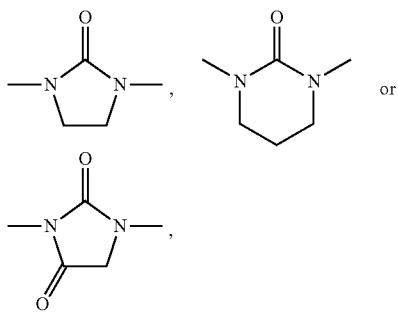

(D-1): D is a monovalent group obtained by combining a divalent group consisting of 10 to 6 groups of one or more kinds selected from the group consisting of (i) a C$_1$-C$_{10}$ alkylene group wherein the alkylene group is linear or branched, optionally includes a cyclic alkylene moiety in the chain and optionally has the substituent α(s), (ii) a C$_2$-C$_{10}$ alkenylene group wherein the alkenylene group is linear or branched and optionally has the substituent α(s), (iii) a C$_2$-C$_{10}$ alkynylene group wherein the alkynylene group is linear or branched and optionally has the substituent α(s), (iv) a group having a formula of —N(R$^{a3}$)— wherein R$^{a3}$ represents (a1) a hydrogen atom, (b1) a C$_1$-C$_6$ alkyl group, (c1) a C$_6$-C$_{10}$ aryl group optionally having 1 to 5 substituent β(s) or (d1) a C$_6$-C$_{10}$ aryl-C$_1$-C$_6$ alkyl group optionally having 1 to 5 substituent β(s) in the aryl moiety, an oxygen atom, (vi) a carbonyl group, (viib) a formula of —S(O)$_n$— wherein n represents an integer of 0 to 2, (viii) a C$_6$-C$_{10}$ divalent arylene group optionally having 1 to 4 substituent β(s), (ix) a C$_5$-C$_{10}$ divalent and saturated cyclic hydrocarbon group optionally having 1 to 4 substituent α(s), (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s), and (xi) a divalent and 5- to 7-membered saturated heterocyclic group containing 1 to 3 hetero atoms selected from the group consisting of an oxygen atom, a nitrogen atom and a sulfur atom and optionally having 1 to 2 substituent γ(s),
with a monovalent group selected from the group consisting of (xiii) a hydrogen atom, (xiv) a C$_1$-C$_6$ alkyl group wherein the alkyl group is linear or branched and optionally has the substituent α(s), (xv) a C$_1$-C$_6$ halogenoalkyl group wherein the alkyl group is linear or branched and optionally has the substituent α(s), (xvi) a C$_3$-C$_{10}$ cycloalkyl group, (xviia) a C$_6$-C$_{10}$ aryl group optionally having 1 to 5 substituent β(s), (xviii) a 5- to 7-membered ring heteroaryl group containing 1 to 3 hetero atoms selected from the group consisting of an oxygen atom, a nitrogen atom and a sulfur atom and optionally having 1 to 2 substituent γ(s), (xix) a group having a formula of —N(R$^{a1}$)(R$^{a2}$) wherein R$^{a1}$ represents (a1) a hydrogen atom, (b1) a C$_1$-C$_6$ alkyl group, (c1) a C$_6$-C$_{10}$ aryl group optionally having 1 to 5 substituent β(s) or (d1) a C$_6$-C$_{10}$ aryl-C$_1$-C$_6$ alkyl group optionally having 1 to 5 substituent β(s) in the aryl moiety and R$^{a2}$ represents a hydrogen atom or a C$_1$-C$_6$ alkyl group, (xx) a hydroxy group, (xxi) a formyl group, (xxii) a carboxy group, (xxiii) a sulfo group and (xxiv) a phospho group; and D may form, together with —NR$^5$— in B, a heterocyclic ring containing a nitrogen atom, (E-1): E is a divalent group obtained by combining 1 to 6 groups of one or more kinds selected from the group consisting of (i) a C$_1$-C$_{10}$ alkylene group wherein the alkylene group is a linear or branched, optionally includes cyclic alkylene moiety and optionally has the substituent α(s), (ii) a C$_2$-C$_{10}$ alkenylene group wherein the alkenylene group is linear or branched and optionally has the substituent α(s), (iii) a C$_2$-C$_{10}$ alkynylene group wherein the alkynylene group is linear or branched and optionally has the substituent α(s), (iv) —NR$^3$— wherein R$^3$ represents (a1) a hydrogen atom, (b1) a C$_1$-C$_6$ alkyl group, (c1) a C$_6$-C$_{10}$ aryl group optionally having 1 to 5 substituent β(s) or (d1) a C$_6$-C$_{10}$ aryl-C$_1$-C$_6$ alkyl group optionally having 1 to 5 substituent β(s) in the aryl moiety, (v) an oxygen atom, (vi) a carbonyl group, (viia) a formula of —S(O)$_n$— wherein n represents an integer of 0 or 2, (viii) a C$_6$-C$_{10}$ divalent and arylene group optionally having 1 to 4 substituent β(s), (ix) a C$_5$-C$_{10}$ divalent and saturated ring hydrocarbon group optionally having 1 to 4 substituent α(s), (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s), F is (xxiii) a sulfo group, and (G-1): G is a monovalent group obtained by combining a divalent group obtained by combining 0 to 6 groups of one or more kinds selected from the group consisting of (i) a C$_1$-C$_{10}$ alkylene group wherein the alkylene group is linear or branched, optionally includes a cyclic alkylene moiety in the chain, and optionally has the substituent α(s), (ii) a C$_2$-C$_{10}$ alkenylene group, wherein the alkenylene group is linear or branched and optionally has the substituent α(s), (iii) a C$_2$-C$_{10}$ alkynylene group wherein the alkynylene group is linear or branched and optionally has the substituent α(s), (iv) a group having a formula of —N(R$^{a3}$)— wherein R$^{a3}$ represents (a1) a hydrogen atom, (b1) a C$_1$-C$_6$ alkyl group, (c1) a C$_6$-C$_{10}$ aryl group optionally having 1 to 5 substituent β(s) or (d1) a C$_6$-C$_{10}$ aryl-C$_1$-C$_6$ alkyl group optionally having 1 to 5 substituent β(s) in the aryl moiety, (v) an oxygen atom, (vi) a carbonyl group, (viia) a group having of a formula —S(O)$_n$— wherein n represents an integer of 0 or 2, (viii) a C$_6$-C$_{10}$ divalent arylene group optionally having 1 to 4 substituent β(s), (ix) a C$_5$-C$_{10}$ divalent and saturated cyclic hydrocarbon group optionally having 1 to 4 substituent α(s), (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s), with a monovalent group selected from the group consisting of (xiii) a hydrogen atom, (xiv) a $C_1$-$C_6$ alkyl group wherein the alkyl group is linear or branched and optionally has the substituent α(s), (xv) a $C_1$-$C_6$ halogenoalkyl group wherein the alkyl group is linear or branched and optionally has the substituent α(s), (xvi) a $C_3$-$C_{10}$ cycloalkyl group, (xviia) a $C_6$-$C_{10}$ aryl group optionally having 1 to 5 substituent β(s), (xviii) a 5- to 7-membered ring heteroaryl group containing 1 to 3 hetero atoms selected from the group consisting of an oxygen atom, a nitrogen atom and a sulfur atom and optionally having 1 to 2 substituent γ(s), (xix) a group having a formula —N($R^{a1}$)($R^{a2}$) wherein $R^{a1}$ represents (a1) a hydrogen atom, (b1) a $C_1$-$C_6$ alkyl group, (c1) a $C_6$-$C_{10}$ aryl group optionally having 1 to 5 substituent β(s) or (d1) a $C_6$-$C_{10}$ aryl-$C_1$-$C_6$ alkyl group optionally having 1 to 5 substituent β(s) in the aryl moiety and $R^{a2}$ represents a hydrogen atom or a $C_1$-$C_6$ alkyl group, (xx) a hydroxy group, (xxi) a formyl group, (xxii) a carboxy group, (xxiii) a sulfo group and (xxiv) a phospho group.

More preferably, the compound (I) of the present invention is (T-2), wherein (X-2): X is a carbonyl group,
(R-1): at least one of $R^1$ and $R^2$ is (a): —CO-A-B-D or (b): —CO-E-F, and the other is (a): —CO-A-B-D, (b): —CO-E-F, (c): —CO-G or a hydrogen atom,
(A-2): A is a divalent group obtained by combining 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2", (viii) a "$C_6$-$C_{10}$ divalent arylene group optionally having 1 to 4 substituent β(s) described above", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above",
(B-1): B is —S—, —S(O)—, —S(O)$_2$—, —NHCONH—, —N(CH$_3$)CONH—, —NHCON(CH$_3$)—, —N(CH$_3$)CON(CH$_3$)—, —N(C$_2$H$_5$)CONH—, —N(n-C$_3$H$_7$)CONH—, —N(i-C$_3$H$_7$)CONH—, —N(n-C$_4$H$_9$)CONH—, —N(n-C$_6$H$_{13}$)CONH—, —N(n-C$_4$H$_9$)CON(CH$_3$)—, —N(Ph)CONH—, —NHCON(4-Chlorophenyl)-, —NHCON(CH$_2$Phenyl)-, —N(i-C$_3$H$_7$)CON(4-Methoxyphenyl)-, —N(4-Chlorophenyl)CON(4-Methoxyphenyl)- or, the group described below:

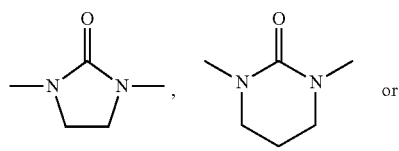

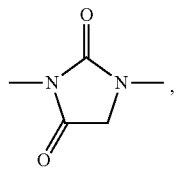

(D-2): D is a monovalent group obtained by combining a divalent group consisting of 10 to 6 groups of one or more kinds selected from the group consisting of (i) a $C_1$-$C_{10}$ alkylene group wherein the alkylene group is linear or branched, optionally includes a cyclic alkylene moiety in the chain and optionally has the substituent α(s), (ii) a $C_2$-$C_{10}$ alkenylene group wherein the alkenylene group is linear or branched and optionally has the substituent α(s), (iv) a group having a formula of —N($R^{a3}$)— wherein $R^{a3}$ represents (a1) a hydrogen atom, (b1) a $C_1$-$C_6$ alkyl group, (c1) a $C_6$-$C_{10}$ aryl group optionally having 1 to 5 substituent β(s) or (d1) a $C_6$-$C_{10}$ aryl-$C_1$-$C_6$ alkyl group optionally having 1 to 5 substituent β(s) in the aryl moiety, (v) an oxygen atom, (vi) a carbonyl group, (viib) a group having a formula of —S(O)$_n$— wherein n represents an integer of 0 to 2, (viii) a $C_6$-$C_{10}$ divalent arylene group optionally having 1 to 4 substituent β(s), (x) a divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s), with a group selected from the group consisting of (xiii) a hydrogen atom, (xiv) the alkyl group described in the "$C_1$-$C_6$ alkyl group", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —N($R^{a1}$)($R^{a2}$)", (xx) a hydroxy group, provided that when the present hydroxy group binds to a carbon atom, the carbon atom is not a unsaturated carbon atom, (xxi) a formyl group, (xxii) a carboxy group, (xxiii) a sulfo group and (xxiv) a phospho group (at the terminal of the divalent group shown in the above-mentioned -A(A-2)-B(B-1)-), (E-2): E is a divalent group obtained by combining 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —S(O)$_n$— wherein n represents an integer of 0 or 2", (viii) a "$C_6$-$C_{10}$ divalent arylene group optionally having 1 to 4 substituent β(s) described above", (x) a "divalent and 5- to 7-membered ring heteroarylene group containing 1 to 3 hetero atoms selected from the group consisting of an oxygen atom, a nitrogen atom and a sulfur atom and optionally having 1 to 2 substituent γ(s) described above" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above", F is (xxiii) a sulfo group, and (G-2): G is a monovalent group obtained by combining a divalent group consisting of 0 to 6 groups of one or more kinds selected from the group consisting of (i) a "$C_1$-$C_{10}$ alkylene group", (ii) a "$C_2$-$C_{10}$ alkenylene group", (iv) a "formula of —$NR^3$—" (v) an "oxygen atom", (vi) a "carbonyl group", (viia) a "formula of —$S(O)_n$—" (viii) a "$C_6$-$C_{10}$ divalent arylene group optionally having 1 to 4 substituent β(s)" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s)", with (xiii) a hydrogen atom, (xiv) the alkyl group described in the "$C_1$-$C_6$ alkyl group", (xviia) the aryl group described in the "$C_6$-$C_{10}$ aryl group optionally having 1 to 5 substituent β(s) described above", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s) described above", (xix) the amino group described in the "group having a formula of —$N(R^{a1})(R^{a2})$", (xx) a hydroxy group, (xxi) a formyl group, (xxii) a carboxy group, (xxiii) a sulfo group and (xxiv) a phospho group.

Further more preferably, the compound (I) of the present invention is (T-3), wherein (X-2): X is a carbonyl group, (R-2): at least one of $R^1$ and $R^2$ is (a): —CO-A-B-D, or (b): —CO-E-F, and the other is (a): —CO-A-B-D, (b): —CO-E-F or a hydrogen atom, (A-3); A is a divalent group obtained by combining 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —$S(O)_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above", (B-2): B is —S—, —S(O)—, —S(O)$_2$—, —NHCONH—, —N(CH$_3$)CONH—, —NHCON(CH$_3$)—, —N(CH$_3$)CON(CH$_3$)—, —N(C$_2$H$_5$)CONH—, —N(n-C$_3$H$_7$)CONH—, —N(i-C$_3$H$_7$)CONH—, —N(n-C$_4$H$_9$)CONH—, —N(n-C$_6$H$_{13}$)CONH—, —N(n-C$_4$H$_9$)CON(CH$_3$)— or the group described below:

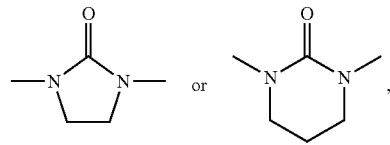

(D-3): D is a monovalent group obtained by combining a divalent group consisting of 0 to 6 groups of one or more kinds selected from the group consisting of (i) a $C_1$-$C_{10}$ alkylene group wherein the alkylene group is linear or branched, optionally includes a cyclic alkylene moiety in the chain and optionally has the substituent α(s), (ii) a $C_2$-$C_{10}$ alkenylene group wherein the alkenylene group is linear or branched and optionally has the substituent α(s), (iv) a group having a formula of —$N(R^{a3})$— wherein $R^{a3}$ represents (a1) a hydrogen atom, (b1) a $C_1$-$C_6$ alkyl group, (c1) a $C_6$-$C_{10}$ aryl group optionally having 1 to 5 substituent β(s) or (d1) a $C_6$-$C_{10}$ aryl-$C_1$-$C_6$ alkyl group optionally having 1 to 5 substituent β(s) in the aryl moiety, (v) an oxygen atom, (vi) a carbonyl group, (viib) a group having a formula of —$S(O)_n$— wherein n represents an integer of 0 to 2 and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s), with a group selected from the group consisting of (xiii) a hydrogen atom, (xiv) the alkyl group described in the "$C_1$-$C_6$ alkyl group", (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —N($R^{a1}$)($R^{a2}$)", (xx) a hydroxy group, provided that when the present hydroxy group binds to a carbon atom, the carbon atom is not a unsaturated carbon atom, (xxii) a carboxy group, (xxiii) a sulfa group and (xxiv) a phospho group (at the terminal of the divalent group constituted similarly to the above-mentioned A(A-3) and B(B-2)), (E-3); E is a divalent group obtained by combining 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (ii) a "$C_2$-$C_{10}$ alkenylene group wherein the alkenylene group is linear or branched and optionally has the substituent α(s) described above", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —$S(O)_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above", and F is (xxiii) a sulfo group.

Further even more preferably, the compound (I) of the present invention is (T-4), wherein (X-2): X is a carbonyl group, (R-3): $R^1$ and $R^2$ are the same or different and each is (a): —CO-A-B-D or (b): —CO-E-F, (A-4): A is a divalent group obtained by combining 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (v) an "oxygen atom", (vi) a "carbonyl group", (viia) a "formula of —$S(O)_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above", (B-3): B is —S—, —S(O)—, —$S(O)_2$—, —NHCONH—, —$N(CH_3)CONH$—, —$NHCON(CH_3)$—, —$N(C_2H_5)CONH$—, —$N(n-C_3H_7)CONH$— or —$N(i-C_3H_7)CONH$—, (D-4): D is a monovalent group obtained by combining a divalent group consisting of 0 to 6 groups of one or more kinds selected from the group consisting of (i) a $C_1$-$C_{10}$ alkylene group wherein the alkylene group is linear or branched, optionally includes a cyclic alkylene moiety in the chain and optionally has the substituent α(s), (iv) a group having a formula of —$N(R^{a3})$— wherein $R^{a3}$ represents (a1) a hydrogen atom, (b1) a $C_1$-$C_6$ alkyl group, (c1) a $C_6$-$C_{10}$ aryl group optionally having 1 to 5 substituent β(s) or (d1) a $C_6$-$C_{10}$ aryl-$C_1$-$C_6$ alkyl group optionally having 1 to 5 substituent β(s) in the aryl moiety, (v) an oxygen atom, (vi) a carbonyl group, (viib) a group having a formula of —$S(O)_n$— wherein n represents an integer of 0 to 2 and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s), with a group selected from the group consisting of (xiii) a hydrogen atom, (xviii) the heteroaryl group described in the "5- to 7-membered ring heteroaryl group containing 1 to 3 hetero atoms selected from the group consisting of an oxygen atom, a nitrogen atom and a sulfur atom and optionally having 1 to 2 substituent γ(s)", (xix) the amino group described in the "group having a formula of —$N(R^{a1})(R^{a2})$", (xx) a hydroxy group, provided that when the present hydroxy group binds to a carbon atom, the carbon atom is not an unsaturated carbon atom, (xxii) a carboxy group, (xxiii) a sulfo group and (xxiv) a phospho group (at the terminal of the divalent group shown in the above-mentioned -A(A-4)-B(B-3)-), and F is (xxiii) a sulfo group.

Most preferably, the compound (I) of the present invention is (T-5), wherein (X-2): X is a carbonyl group, (R-4): $R^1$ and $R^2$ are the same and each is (a): —CO-A-B-D or (b): —CO-E-F, (A-5): A is a divalent group obtained by combining 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (vi) a "carbonyl group", (viia) a "formula of —$S(O)_n$— wherein n represents an integer of 0 or 2" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above", (B-4): B is —S—, —S(O)—, —$S(O)_2$—, —NHCONH—, —$N(CH_3)CONH$—, —$NHCON(CH_3)$— or —$N(C_2H_5)CONH$—, (D-5): D is a monovalent group obtained by combining a divalent group consisting of 1 to 6 groups of one or more kinds selected from the group consisting of (i) a $C_1$-$C_{10}$ alkylene group wherein the alkylene group is linear or branched, optionally includes a cyclic alkylene moiety in the chain and optionally has the substituent α(s), (iv) a group having a formula of —$N(R^{a3})$— wherein $R^{a3}$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety, (vi) a carbonyl group, (viib) a group having a formula of —$S(O)_n$— wherein n represents an integer of 0 to 2 and (xi) a divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ(s) described above, with a group selected from (xiii) a hydrogen atom, (xix) the amino group described in the "group having a formula of —$N(R^{a1})(R^{a2})$", (xx) a hydroxy group, provided that when the present hydroxy group binds to a carbon atom, the carbon atom is not an unsaturated carbon atom, (xxii) a carboxy group, (xxiii) a sulfo group and (xxiv) a phospho group (at the terminal of the divalent group shown in the above-mentioned -A(A-5)-B(B-4)-), (E-5): E is a divalent group obtained by combining 1 to 6 groups of one or more kinds selected from the group consisting of (i) a "$C_1$-$C_{10}$ alkylene group wherein the alkylene group is linear or branched, optionally includes a cyclic alkylene moiety in the chain and optionally has the substituent α(s)", (iv) "—$NR^3$— wherein $R^3$ represents (a1) a hydrogen atom, (b1) a $C_1$-$C_6$ alkyl group, (c1) a $C_6$-$C_{10}$ aryl group optionally having 1 to 5 substituent β(s) described above or (d1) a $C_6$-$C_{10}$ aryl-$C_1$-$C_6$ alkyl group optionally having 1 to 5 substituent β(s) described above in the aryl moiety", (vi) a "carbonyl group" and (xi) a "divalent and 5- to 7-membered ring saturated heterocyclic group containing 1 to 3 hetero atoms selected from the group consisting of an oxygen atom, a nitrogen atom and a sulfur atom and optionally having 1 to 2 substituent γ"(s) described above, and F is (xxiii) a sulfo group.

Preferable specific compounds are shown in following (A) to (C).

(A) Compound of the formula described below wherein the $R^1$ and $R^2$ are shown in Tables 1 to 30.

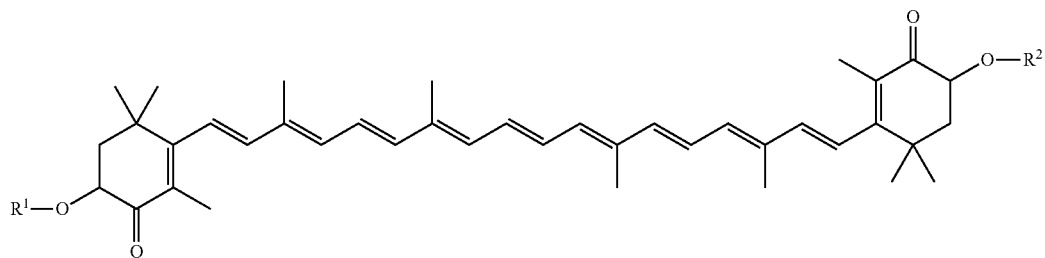

TABLE 1

| Exemplified Compound No. | R¹ | R² |
|---|---|---|
| 1-1 | —COCH₂—S—CH₂—COOH | —COCH₂—S—CH₂—COOH |
| 1-2 | —COCH₂—S(O)—CH₂—COOH | —COCH₂—S(O)—CH₂—COOH |
| 1-3 | —COCH₂—S(O)₂—CH₂—COOH | —COCH₂—S(O)₂—CH₂—COOH |
| 1-4 | —COCH₂CH₂—S—CH₂—COOH | —COCH₂CH₂—S—CH₂—COOH |
| 1-5 | —COCH₂CH₂—S—CH₂CH₂—COOH | —COCH₂CH₂—S—CH₂CH₂—COOH |
| 1-6 | —COCH₂CH₂CH₂—S—CH₂—COOH | —COCH₂CH₂CH₂—S—CH₂—COOH |
| 1-7 | —COCH(CH₃)—S—CH(CH₃)—COOH | —COCH(CH₃)—S—CH(CH₃)—COOH |
| 1-8 | —COCH(NH₂)CH₂—S—CH₂—COOH | —COCH(NH₂)CH₂—S—CH₂—COOH |
| 1-9 | —COCH(COOH)—S—CH₂—COOH | —COCH(COOH)—S—CH₂—COOH |
| 1-10 | —COCH₂OCH₂CH₂—S—CH₂—COOH | —COCH₂OCH₂CH₂—S—CH₂—COOH |
| 1-11 | —COCH₂NHCH₂CH₂—S—CH₂—COOH | —COCH₂NHCH₂CH₂—S—CH₂—COOH |
| 1-12 | —COCH₂—S—CH₂CH=CHCH₂—S—CH₂—COOH | —COCH₂—S—CH₂CH=CHCH₂—S—CH₂—COOH |
| 1-13 | —COCH₂CH₂CONHCH₂CH₂—S—CH₂—CONHCH₂CH₃ | —COCH₂CH₂CONHCH₂CH₂—S—CH₂—CONHCH₂CH₃ |
| 1-14 | —COCH₂—S—CH₂—CHO | —COCH₂—S—CH₂—CHO |
| 1-15 | —COCH₂—S—CH₂CH₂—NH₂ | —COCH₂—S—CH₂CH₂—NH₂ |

TABLE 2

| | | |
|---|---|---|
| 1-16 | [structure: —C(O)—CH₂—S—C₆H₄—S—CH₂—COOH (para)] | [structure: —C(O)—CH₂—S—C₆H₄—S—CH₂—COOH (para)] |
| 1-17 | [structure: —C(O)—CH₂—S—C₆H₄—O—CH₂—COOH (para)] | [structure: —C(O)—CH₂—S—C₆H₄—O—CH₂—COOH (para)] |
| 1-18 | [structure: —C(O)—CH₂—O—C₆H₄—S—CH₂—COOH (para)] | [structure: —C(O)—CH₂—O—C₆H₄—S—CH₂—COOH (para)] |
| 1-19 | [structure: —C(O)—CH₂—S—CH₂—C₆H₄—CH₂—S—CH₂—COOH (para)] | [structure: —C(O)—CH₂—S—CH₂—C₆H₄—CH₂—S—CH₂—COOH (para)] |
| 1-20 | [structure: —C(O)—CH₂—S—(3,5-di-t-Bu-4-OH-C₆H₂)] | [structure: —C(O)—CH₂—S—(3,5-di-t-Bu-4-OH-C₆H₂)] |
| 1-21 | —COCH₂—S—CH₂—COOH | H |
| 1-22 | —COCH₂—S(O)—CH₂—COOH | H |
| 1-23 | —COCH₂—S(O)₂—CH₂—COOH | H |
| 1-24 | —COCH₂CH₂—S—CH₂—COOH | H |

TABLE 2-continued

| | | |
|---|---|---|
| 1-25 | —COCH$_2$CH$_2$—S—CH$_2$CH$_2$—COOH | H |
| 1-26 | —COCH$_2$CH$_2$CH$_2$—S—CH$_2$—COOH | H |
| 1-27 | —COCH(CH$_3$)—S—CH(CH$_3$)—COOH | H |
| 1-28 | —COCH(NH$_2$)CH$_2$—S—CH$_2$—COOH | H |
| 1-29 | —COCH(COOH)—S—CH$_2$—COOH | H |
| 1-30 | —COCH$_2$OCH$_2$—S—CH$_2$—COOH | H |
| 1-31 | —COCH$_2$NHCH$_2$—S—CH$_2$CH$_2$—COOH | H |
| 1-32 | —COCH$_2$—S—CH$_2$CH=CHCH$_2$—S—CH$_2$—COOH | H |

TABLE 3

| | | |
|---|---|---|
| 1-33 | —COCH$_2$CH$_2$CONHCH$_2$CH$_2$—S—CH$_2$—CONHCH$_2$CH$_3$ | H |
| 1-34 | —COCH$_2$—S—CH$_2$—CHO | H |
| 1-35 | —COCH$_2$—S—CH$_2$CH(COOH)—NH$_2$ | —COCH$_2$—S—CH$_2$CH(COOH)—NH$_2$ |
| 1-36 | [structure: acetyl-CH$_2$-S-phenyl-S-CH$_2$-COOH] | H |
| 1-37 | [structure: acetyl-CH$_2$-S-phenyl-O-CH$_2$-COOH] | H |
| 1-38 | [structure: acetyl-CH$_2$-O-phenyl-S-CH$_2$-COOH] | H |
| 1-39 | [structure: acetyl-CH$_2$-S-CH$_2$-phenyl-CH$_2$-S-CH$_2$-COOH] | H |
| 1-40 | [structure: acetyl-CH$_2$-S-(3,5-di-t-Bu-4-OH-phenyl)] | H |
| 1-41 | —COCH$_2$—S—CH$_2$—COOH | —COCH$_3$ |
| 1-42 | —COCH$_2$—S(O)—CH$_2$—COOH | —COCH$_2$CH$_2$COOH |
| 1-43 | —COCH$_2$—S(O)$_2$—CH$_2$—COOH | —COCH$_2$NHCOCH$_3$ |
| 1-44 | —COCH$_2$CH$_2$—S—CH$_2$—COOH | —COCH$_2$NHCO$_2$t-Bu$^t$ |
| 1-45 | —COCH$_2$CH$_2$—S—CH$_2$CH$_2$—COOH | —COCH$_2$NH$_2$ |
| 1-46 | —COCH$_2$CH$_2$CH$_2$—S—CH$_2$—COOH | —COCH$_2$CH$_2$COOH |
| 1-47 | —COCH(CH$_3$)—S—CH(CH$_3$)—COOH | —COCH$_2$Ph |
| 1-48 | —COCH(NH$_2$)CH$_2$—S—CH$_2$—COOCH$_2$CH$_3$ | —COCH(NH$_2$)CH$_2$—S—CH$_2$—COOCH$_2$CH$_3$ |
| 1-49 | —COCH$_2$NHCH$_2$—S—CH$_2$CH$_2$—COOH | —COCH$_2$CH$_2$COOH |

TABLE 4

| | | |
|---|---|---|
| 1-50 | [structure: acetyl-CH$_2$-S-CH$_2$-phenyl-CH$_2$-S-CH$_2$-COOH] | —COCH$_2$CH$_2$COOH |

TABLE 4-continued

| | | |
|---|---|---|
| 1-51 | [Structure: acetyl-CH₂-S-(3,5-di-t-Bu-4-OH-phenyl)] | —COCH₂CH₂COOH |
| 1-52 | [Structure: acetyl-CH₂-S-(3,5-di-t-Bu-4-OH-phenyl)] | [Structure: acetyl-CH₂-S-(3,5-dimethyl-4-OH-phenyl)] |
| 1-53 | [Structure: acetyl-CH₂-S-(3,5-di-t-Bu-4-OH-phenyl)] | —COCH₂—NH₂ |
| 1-54 | —COCH₂—NHCONH₂ | —COCH₂—NHCONH₂ |
| 1-55 | —COCH₂CH₂—NHCONH₂ | —COCH₂CH₂—NHCONH₂ |
| 1-56 | —COCH₂—NHCONHCH₃ | —COCH₂—NHCONHCH₃ |
| 1-57 | —COCH₂CH₂CH₂—NHCONH₂ | —COCH₂CH₂CH₂—NHCONH₂ |
| 1-58 | —COCH₂CH₂—NHCONHCH₂CH₂CH₃ | —COCH₂CH₂—NHCONHCH₂CH₂CH₃ |
| 1-59 | —COCH₂—NHCONHCH₂-c-Hexyl | —COCH₂—NHCONHCH₂-c-Hexyl |
| 1-60 | —COCH₂—NHCONHNH₂ | —COCH₂—NHCONHNH₂ |
| 1-61 | —COCH₂—NHCONHOH | —COCH₂—NHCONHOH |
| 1-62 | —COCH₂—NHCONH—CH₂—COOBu$^t$ | —COCH₂—NHCONH—CH₂—COOBu$^t$ |
| 1-63 | —COCH₂—NHCONH—CH₂—COOH | —COCH₂—NHCONH—CH₂—COOH |
| 1-64 | —COCH₂—NHCONH—CH(CH₃)—COOBu$^t$ | —COCH₂—NHCONH—CH(CH₃)—COOBu$^t$ |
| 1-65 | —COCH₂—NHCONH—CH(CH₃)—COOH | —COCH₂—NHCONH—CH(CH₃)—COOH |
| 1-66 | —COCH₂—NHCONH—CH(i-Pr)—COOBu$^t$ | —COCH₂—NHCONH—CH(i-Pr)—COOBu$^t$ |

TABLE 5

| | | |
|---|---|---|
| 1-67 | —COCH₂—NHCONH—CH(i-Pr)—COOH | —COCH₂—NHCONH—CH(i-Pr)—COOH |
| 1-68 | —COCH₂—NHCONH—CH(s-Bu)—COOCH₂CH₃ | —COCH₂—NHCONH—CH(s-Bu)—COOCH₂CH₃ |
| 1-69 | —COCH₂—NHCONH—CH(s-Bu)—COOH | —COCH₂—NHCONH—CH(s-Bu)—COOH |
| 1-70 | —COCH₂—NHCONH—CH(i-Bu)—COOBu$^t$ | —COCH₂—NHCONH—CH(i-Bu)—COOBu$^t$ |
| 1-71 | —COCH₂—NHCONH—CH(i-Bu)—COOH | —COCH₂—NHCONH—CH(i-Bu)—COOH |
| 1-72 | —COCH₂—NHCONH—CH(CH₂CH₂—S—CH₃)—COOEt | —COCH₂—NHCONH—CH(CH₂CH₂—S—CH₃)—COOEt |
| 1-73 | —COCH₂—NHCONH—CH(CH₂CH₂—S—CH₃)—COOBu$^t$ | —COCH₂—NHCONH—CH(CH₂CH₂—S—CH₃)—COOBu$^t$ |
| 1-74 | —COCH₂—NHCONH—CH(CH₂CH₂—S—CH₃)—COOH | —COCH₂—NHCONH—CH(CH₂CH₂—S—CH₃)—COOH |
| 1-75 | —COCH₂—NHCONH—CH(CH₂Ph)—COOCH₃ | —COCH₂—NHCONH—CH(CH₂Ph)—COOCH₃ |
| 1-76 | —COCH₂—NHCONH—CH(CH₂Ph)—COOH | —COCH₂—NHCONH—CH(CH₂Ph)—COOH |
| 1-77 | —COCH₂—NHCONH—CH(4-hydroxyphenylmethyl)—COOCH₃ | —COCH₂—NHCONH—CH(4-hydroxyphenylmethyl)—COOCH₃ |
| 1-78 | —COCH₂—NHCONH—CH(4-hydroxyphenylmethyl)—COOH | —COCH₂—NHCONH—CH(4-hydroxyphenylmethyl)—COOH |
| 1-79 | —COCH₂—NHCONH—CH(CH₂CONH₂)—CONH₂ | —COCH₂—NHCONH—CH(CH₂CONH₂)—CONH₂ |
| 1-80 | —COCH₂—NHCONH—CH(CH₂CONH₂)—COOH | —COCH₂—NHCONH—CH(CH₂CONH₂)—COOH |

TABLE 6

| | | |
|---|---|---|
| 1-81 | —COCH₂—NHCONH—CH(CH₂CH₂CONH₂)—COOCH₂CH₃ | —COCH₂—NHCONH—CH(CH₂CH₂CONH₂)—COOCH₂CH₃ |
| 1-82 | —COCH₂—NHCONH—CH(CH₂CH₂CONH₂)—COOH | —COCH₂—NHCONH—CH(CH₂CH₂CONH₂)—COOH |
| 1-83 | —COCH₂—NHCONH—CH(CH₂OH)—COOBu$^t$ | —COCH₂—NHCONH—CH(CH₂OH)—COOBu$^t$ |
| 1-84 | —COCH₂—NHCONH—CH(CH₂OH)—COOH | —COCH₂—NHCONH—CH(CH₂OH)—COOH |
| 1-85 | —COCH₂—NHCONH—CH(CH(CH₃)OH)—COOBu$^t$ | —COCH₂—NHCONH—CH(CH(CH₃)OH)—COOBu$^t$ |
| 1-86 | —COCH₂—NHCONH—CH(CH(CH₃)OH)—COOH | —COCH₂—NHCONH—CH(CH(CH₃)OH)—COOH |
| 1-87 | —COCH₂—NHCONH—CH(CH₂CH₂CH₂CH₂NHCO₂t-Bu)—COOBu$^t$ | —COCH₂—NHCONH—CH(CH₂CH₂CH₂CH₂NHCO₂t-Bu)—COOBu$^t$ |
| 1-88 | —COCH₂—NHCONH—CH(CH₂CH₂CH₂CH₂NH₂)—COOH | —COCH₂—NHCONH—CH(CH₂CH₂CH₂CH₂NH₂)—COOH |
| 1-89 | —COCH₂—NHCONH—CH(CH₂CH₂CH₂CH(NH₂)—COOH | —COCH₂—NHCONH—CH(CH₂CH₂CH₂CH(NH₂)—COOH |
| 1-90 | —COCH₂—NHCONH—CH[CH₂CH₂CH₂NH(C=NH)NH₂]—COOH | —COCH₂—NHCONH—CH[CH₂CH₂CH₂NH(C=NH)NH₂]—COOH |
| 1-91 | —COCH₂—NHCONH—CH(CH₂COOBu$^t$)—COOBu$^t$ | —COCH₂—NHCONH—CH(CH₂COOBu$^t$)—COOBu$^t$ |
| 1-92 | —COCH₂—NHCONH—CH(CH₂COOH)—COOH | —COCH₂—NHCONH—CH(CH₂COOH)—COOH |
| 1-93 | —COCH₂—NHCONH—CH(CH₂CH₂COOBu$^t$)—COOBu$^t$ | —COCH₂—NHCONH—CH(CH₂CH₂COOBu$^t$)—COOBu$^t$ |

TABLE 7

| | | |
|---|---|---|
| 1-94 | —COCH$_2$—NHCONH—CH(CH$_2$CH$_2$COOH)—COOH | —COCH$_2$—NHCONH—CH(CH$_2$CH$_2$COOH)—COOH |
| 1-95 | —COCH$_2$—NHCONH—CH(CH$_2$SMe)—COOBu$^t$ | —COCH$_2$—NHCONH—CH(CH$_2$SMe)—COOBu$^t$ |
| 1-96 | —COCH$_2$—NHCONH—CH(CH$_2$SMe)—COOH | —COCH$_2$—NHCONH—CH(CH$_2$SMe)—COOH |
| 1-97 | —COCH$_2$—NHCONH—CH(CH$_2$S-Hexyl)—COOBu$^t$ | —COCH$_2$—NHCONH—CH(CH$_2$S-Hexyl)—COOBu$^t$ |
| 1-98 | —COCH$_2$—NHCONH—CH(CH$_2$S-Hexyl)—COOH | —COCH$_2$—NHCONH—CH(CH$_2$S-Hexyl)—COOH |
| 1-99 | [structure with pyrrole side chain] | [structure with pyrrole side chain] |
| 1-100 | [structure with imidazole side chain] | [structure with imidazole side chain] |
| 1-101 | [structure with proline] | [structure with proline] |
| 1-102 | —COCH$_2$CH$_2$—NHCONH—CH$_2$—COOBu$^t$ | —COCH$_2$CH$_2$—NHCONH—CH$_2$—COOBu$^t$ |
| 1-103 | —COCH$_2$CH$_2$—NHCONH—CH$_2$—COOH | —COCH$_2$CH$_2$—NHCONH—CH$_2$—COOH |
| 1-104 | —COCH$_2$CH$_2$—NHCONH—CH(CH$_3$)—COOBu$^t$ | —COCH$_2$CH$_2$—NHCONH—CH(CH$_3$)—COOBu$^t$ |
| 1-105 | —COCH$_2$CH$_2$—NHCONH—CH(CH$_3$)—COOH | —COCH$_2$CH$_2$—NHCONH—CH(CH$_3$)—COOH |
| 1-106 | —COCH$_2$CH$_2$—NHCONH—CH(i-Pr)—COOBu$^t$ | —COCH$_2$CH$_2$—NHCONH—CH(i-Pr)—COOBu$^t$ |
| 1-107 | —COCH$_2$CH$_2$—NHCONH—CH(i-Pr)—COOH | —COCH$_2$CH$_2$—NHCONH—CH(i-Pr)—COOH |

TABLE 8

| | | |
|---|---|---|
| 1-108 | —COCH$_2$CH$_2$—NHCONH—CH(s-Bu)—COOBu$^t$ | —COCH$_2$CH$_2$—NHCONH—CH(s-Bu)—COOBu$^t$ |
| 1-109 | —COCH$_2$CH$_2$—NHCONH—CH(s-Bu)—COOH | —COCH$_2$CH$_2$—NHCONH—CH(s-Bu)—COOH |
| 1-110 | —COCH$_2$CH$_2$—NHCONH—CH(i-Bu)—COOBu$^t$ | —COCH$_2$CH$_2$—NHCONH—CH(i-Bu)—COOBu$^t$ |
| 1-111 | —COCH$_2$CH$_2$—NHCONH—CH(i-Bu)—COOH | —COCH$_2$CH$_2$—NHCONH—CH(i-Bu)—COOH |
| 1-112 | —COCH$_2$CH$_2$—NHCONH—CH(CH$_2$CH$_2$—S—CH$_3$)—COOEt | —COCH$_2$CH$_2$—NHCONH—CH(CH$_2$CH$_2$—S—CH$_3$)—COOEt |
| 1-113 | —COCH$_2$CH$_2$—NHCONH—CH(CH$_2$CH$_2$—S—CH$_3$)—COOBu$^t$ | —COCH$_2$CH$_2$—NHCONH—CH(CH$_2$CH$_2$—S—CH$_3$)—COOBu$^t$ |
| 1-114 | —COCH$_2$CH$_2$—NHCONH—CH(CH$_2$CH$_2$—S—CH$_3$)—COOH | —COCH$_2$CH$_2$—NHCONH—CH(CH$_2$CH$_2$—S—CH$_3$)—COOH |
| 1-115 | —COCH$_2$CH$_2$—NHCONH—CH(CH$_2$Ph)—COOBu$^t$ | —COCH$_2$CH$_2$—NHCONH—CH(CH$_2$Ph)—COOBu$^t$ |
| 1-116 | —COCH$_2$CH$_2$—NHCONH—CH(CH$_2$Ph)—COOH | —COCH$_2$CH$_2$—NHCONH—CH(CH$_2$Ph)—COOH |
| 1-117 | —COCH$_2$CH$_2$—NHCONH—CH(4-hydroxyphenylmethyl)—COOBu$^t$ | —COCH$_2$CH$_2$—NHCONH—CH(4-hydroxyphenylmethyl)—COOBu$^t$ |
| 1-118 | —COCH$_2$CH$_2$—NHCONH—CH(4-hydroxyphenylmethyl)—COOH | —COCH$_2$CH$_2$—NHCONH—CH(4-hydroxyphenylmethyl)—COOH |
| 1-119 | —COCH$_2$CH$_2$—NHCONH—CH(CH$_2$CONH$_2$)—COOBu$^t$ | —COCH$_2$H$_2$—NHCONH—CH(CH$_2$CONH$_2$)—COOBu$^t$ |

TABLE 9

| | | |
|---|---|---|
| 1-120 | —COCH$_2$CH$_2$—NHCONH—CH(CH$_2$CONH$_2$)—COOH | —COCH$_2$CH$_2$—NHCONH—CH(CH$_2$CONH$_2$)—COOH |
| 1-121 | —COCH$_2$CH$_2$—NHCONH—CH(CH$_2$CH$_2$CONH$_2$)—COOBu$^t$ | —COCH$_2$CH$_2$—NHCONH—CH(CH$_2$CH$_2$CONH$_2$)—COOBu$^t$ |
| 1-122 | —COCH$_2$CH$_2$—NHCONH—CH(CH$_2$CH$_2$CONH$_2$)—COOH | —COCH$_2$CH$_2$—NHCONH—CH(CH$_2$CH$_2$CONH$_2$)—COOH |
| 1-123 | —COCH$_2$CH$_2$—NHCONH—CH(CH$_2$OH)—COOBu$^t$ | —COCH$_2$CH$_2$—NHCONH—CH(CH$_2$OH)—COOBu$^t$ |
| 1-124 | —COCH$_2$CH$_2$—NHCONH—CH(CH$_2$OH)—COOH | —COCH$_2$CH$_2$—NHCONH—CH(CH$_2$OH)—COOH |
| 1-125 | —COCH$_2$CH$_2$—NHCONH—CH(CH(CH$_3$)OH)—CONH$_2$ | —COCH$_2$CH$_2$—NHCONH—CH(CH(CH$_3$)OH)—CONH$_2$ |
| 1-126 | —COCH$_2$CH$_2$—NHCONH—CH(CH(CH$_3$)OH)—COOH | —COCH$_2$CH$_2$—NHCONH—CH(CH(CH$_3$)OH)—COOH |
| 1-127 | —COCH$_2$CH$_2$—NHCONH—CH(CH$_2$CH$_2$CH$_2$CH$_2$NHCO$_2$t-Bu)—COOBu$^t$ | —COCH$_2$CH$_2$—NHCONH—CH(CH$_2$CH$_2$CH$_2$CH$_2$NHCO$_2$t-Bu)—COOBu$^t$ |
| 1-128 | —COCH$_2$CH$_2$—NHCONH—CH(CH$_2$CH$_2$CH$_2$CH$_2$NH$_2$)—COOH | —COCH$_2$CH$_2$—NHCONH—CH(CH$_2$CH$_2$CH$_2$CH$_2$NH$_2$)—COOH |
| 1-129 | —COCH$_2$CH$_2$—NHCONH—CH(CH$_2$CH$_2$CH$_2$CH(NH$_2$)—COOH | —COCH$_2$CH$_2$—NHCONH—CH(CH$_2$CH$_2$CH$_2$CH(NH$_2$)—COOH |
| 1-130 | —COCH$_2$CH$_2$—NHCONH—CH(CH$_2$CH$_2$CH$_2$NH(C=NH)NH$_2$)—COOH | —COCH$_2$CH$_2$—NHCONH—CH(CH$_2$CH$_2$CH$_2$NH(C=NH)NH$_2$)—COOH |
| 1-131 | —COCH$_2$CH$_2$—NHCONH—CH(CH$_2$COOBu$^t$)—COOBu$^t$ | —COCH$_2$CH$_2$—NHCONH—CH(CH$_2$COOBu$^t$)—COOBu$^t$ |

TABLE 10

| | 45 | 46 |
|---|---|---|
| 1-132 | —COCH₂CH₂—NHCONH—CH(CH₂COOH)—COOH | —COCH₂CH₂—NHCONH—CH(CH₂COOH)—COOH |
| 1-133 | —COCH₂CH₂—NHCONH—CH(CH₂CH₂COOBuᵗ)—COOBuᵗ | —COCH₂CH₂—NHCONH—CH(CH₂CH₂COOBuᵗ)—COOBuᵗ |
| 1-134 | —COCH₂CH₂—NHCONH—CH(CH₂CH₂COOH)—COOH | —COCH₂CH₂—NHCONH—CH(CH₂CH₂COOH)—COOH |
| 1-135 | —COCH₂CH₂—NHCONH—CH(CH₂SMe)—COOBuᵗ | —COCH₂CH₂—NHCONH—CH(CH₂SMe)—COOBuᵗ |
| 1-136 | —COCH₂CH₂—NHCONH—CH(CH₂SMe)—COOH | —COCH₂CH₂—NHCONH—CH(CH₂SMe)—COOH |
| 1-137 | —COCH₂CH₂—NHCONH—CH(CH₂S-Hexyl)—COOBuᵗ | —COCH₂CH₂—NHCONH—CH(CH₂S-Hexyl)—COOBuᵗ |
| 1-138 | —COCH₂CH₂—NHCONH—CH(CH₂S-Hexyl)—COOH | —COCH₂CH₂—NHCONH—CH(CH₂S-Hexyl)—COOH |
| 1-139 | [structure: —CO—CH₂—NH—CO—NH—CH(COOH)—CH₂—(3-pyrrolyl)] | [structure: —CO—CH₂—NH—CO—NH—CH(COOH)—CH₂—(3-pyrrolyl)] |
| 1-140 | [structure: —CO—CH₂—CH₂—NH—CO—NH—CH(COOH)—CH₂—(imidazolyl)] | [structure: —CO—CH₂—CH₂—NH—CO—NH—CH(COOH)—CH₂—(imidazolyl)] |
| 1-141 | [structure: —CO—CH₂—CH₂—NH—CO—(prolyl-COOH)] | [structure: —CO—CH₂—CH₂—NH—CO—(prolyl-COOH)] |
| 1-142 | —COCH₂CH₂CH₂—NHCONH—CH₂—COOBuᵗ | —COCH₂CH₂CH₂—NHCONH—CH₂—COOBuᵗ |
| 1-143 | —COCH₂CH₂CH₂—NHCONH—CH₂—COOH | —COCH₂CH₂CH₂—NHCONH—CH₂—COOH |
| 1-144 | —COCH₂CH₂CH₂—NHCONH—CH(CH₃)—COOBuᵗ | —COCH₂CH₂CH₂—NHCONH—CH(CH₃)—COOBuᵗ |

TABLE 11

| | 45 | 46 |
|---|---|---|
| 1-145 | —COCH₂CH₂CH₂—NHCONH—CH(CH₃)—COOH | —COCH₂CH₂CH₂—NHCONH—CH(CH₃)—COOH |
| 1-146 | —COCH₂CH₂CH₂—NHCONH—CH(i-Pr)—COOBuᵗ | —COCH₂CH₂CH₂—NHCONH—CH(i-Pr)—COOBuᵗ |
| 1-147 | —COCH₂CH₂CH₂—NHCONH—CH(i-Pr)—COOH | —COCH₂CH₂CH₂—NHCONH—CH(i-Pr)—COOH |
| 1-148 | —COCH₂CH₂CH₂—NHCONH—CH(s-Bu)—COOBuᵗ | —COCH₂CH₂CH₂—NHCONH—CH(s-Bu)—COOBuᵗ |
| 1-149 | —COCH₂CH₂CH₂—NHCONH—CH(s-Bu)—COOH | —COCH₂CH₂CH₂—NHCONH—CH(s-Bu)—COOH |
| 1-150 | —COCH₂CH₂CH₂—NHCONH—CH(i-Bu)—COOBuᵗ | —COCH₂CH₂CH₂—NHCONH—CH(i-Bu)—COOBuᵗ |
| 1-151 | —COCH₂CH₂CH₂—NHCONH—CH(i-Bu)—COOH | —COCH₂CH₂CH₂—NHCONH—CH(i-Bu)—COOH |
| 1-152 | —COCH₂CH₂CH₂—NHCONH—CH(CH₂CH₂—S—CH₃)—COOEt | —COCH₂CH₂CH₂—NHCONH—CH(CH₂CH₂—S—CH₃)—COOEt |
| 1-153 | —COCH₂CH₂CH₂—NHCONH—CH(CH₂CH₂—S—CH₃)—COOBuᵗ | —COCH₂CH₂CH₂—NHCONH—CH(CH₂CH₂—S—CH₃)—COOBuᵗ |
| 1-154 | —COCH₂CH₂CH₂—NHCONH—CH(CH₂CH₂—S—CH₃)—COOH | —COCH₂CH₂CH₂—NHCONH—CH(CH₂CH₂—S—CH₃)—COOH |
| 1-155 | —COCH₂CH₂CH₂—NHCONH—CH(CH₂Ph)—COOBuᵗ | —COCH₂CH₂CH₂—NHCONH—CH(CH₂Ph)—COOBuᵗ |
| 1-156 | —COCH₂CH₂CH₂—NHCONH—CH(CH₂Ph)—COOH | —COCH₂CH₂CH₂—NHCONH—CH(CH₂Ph)—COOH |

TABLE 12

| | 45 | 46 |
|---|---|---|
| 1-157 | —COCH₂CH₂CH₂—NHCONH—CH(4-hydroxyphenylmethyl)—COOBuᵗ | —COCH₂CH₂CH₂—NHCONH—CH(4-hydroxyphenylmethyl)—COOBuᵗ |
| 1-158 | —COCH₂CH₂CH₂—NHCONH—CH(4-hydroxyphenylmethyl)—COOH | —COCH₂CH₂CH₂—NHCONH—CH(4-hydroxyphenylmethyl)—COOH |
| 1-159 | —COCH₂CH₂CH₂—NHCONH—CH(CH₂CONH₂)—COOBuᵗ | —COCH₂CH₂CH₂—NHCONH—CH(CH₂CONH₂)—COOBuᵗ |
| 1-160 | —COCH₂CH₂CH₂—NHCONH—CH(CH₂CONH₂)—COOH | —COCH₂CH₂CH₂—NHCONH—CH(CH₂CONH₂)—COOH |
| 1-161 | —COCH₂CH₂CH₂—NHCONH—CH(CH₂CH₂CONH₂)—COOBuᵗ | —COCH₂CH₂CH₂—NHCONH—CH(CH₂CH₂CONH₂)—COOBuᵗ |
| 1-162 | —COCH₂CH₂CH₂—NHCONH—CH(CH₂CH₂CONH₂)—COOH | —COCH₂CH₂CH₂—NHCONH—CH(CH₂CH₂CONH₂)—COOH |
| 1-163 | —COCH₂CH₂CH₂—NHCONH—CH(CH₂OH)—COOBuᵗ | —COCH₂CH₂CH₂—NHCONH—CH(CH₂OH)—COOBuᵗ |
| 1-164 | —COCH₂CH₂CH₂—NHCONH—CH(CH₂OH)—COOH | —COCH₂CH₂CH₂—NHCONH—CH(CH₂OH)—COOH |
| 1-165 | —COCH₂CH₂CH₂—NHCONH—CH(CH(CH₃)OH)—COOBuᵗ | —COCH₂CH₂CH₂—NHCONH—CH(CH(CH₃)OH)—COOBuᵗ |
| 1-166 | —COCH₂CH₂CH₂—NHCONH—CH(CH(CH₃)OH)—COOH | —COCH₂CH₂CH₂—NHCONH—CH(CH(CH₃)OH)—COOH |
| 1-167 | —COCH₂CH₂CH₂—NHCONH—CH(CH₂CH₂CH₂CH₂NHCO₂t-Bu)—COOBuᵗ | —COCH₂CH₂CH₂—NHCONH—CH(CH₂CH₂CH₂CH₂NHCO₂t-Bu)—COOBuᵗ |

TABLE 13

| | | |
|---|---|---|
| 1-168 | —COCH₂CH₂CH₂—NHCONH—CH(CH₂CH₂CH₂CH₂NH₂)—COOH | —COCH₂CH₂CH₂—NHCONH—CH(CH₂CH₂CH₂CH₂NH₂)—COOH |
| 1-169 | —COCH₂CH₂CH₂—NHCONH—CH₂CH₂CH₂CH₂CH(NH₂)—COOH | —COCH₂CH₂CH₂—NHCONH—CH₂CH₂CH₂CH₂CH(NH₂)—COOH |
| 1-170 | —COCH₂CH₂CH₂—NHCONH—CH(CH₂CH₂CH₂NH(C=NH)NH₂)—COOH | —COCH₂CH₂CH₂—NHCONH—CH(CH₂CH₂CH₂NH(C=NH)NH₂)—COOH |
| 1-171 | —COCH₂CH₂CH₂—NHCONH—CH(CH₂COOBuᵗ)—COOBuᵗ | —COCH₂CH₂CH₂—NHCONH—CH(CH₂COOBuᵗ)—COOBuᵗ |
| 1-172 | —COCH₂CH₂CH₂—NHCONH—CH(CH₂COOH)—COOH | —COCH₂CH₂CH₂—NHCONH—CH(CH₂COOH)—COOH |
| 1-173 | —COCH₂CH₂CH₂—NHCONH—CH(CH₂CH₂COOBuᵗ)—COOBuᵗ | —COCH₂CH₂CH₂—NHCONH—CH(CH₂CH₂COOBuᵗ)—COOBuᵗ |
| 1-174 | —COCH₂CH₂CH₂—NHCONH—CH(CH₂CH₂COOH)—COOH | —COCH₂CH₂CH₂—NHCONH—CH(CH₂CH₂COOH)—COOH |
| 1-175 | —COCH₂CH₂CH₂—NHCONH—CH(CH₂SMe)—COOBuᵗ | —COCH₂CH₂CH₂—NHCONH—CH(CH₂SMe)—COOBuᵗ |
| 1-176 | —COCH₂CH₂CH₂—NHCONH—CH(CH₂SMe)—COOH | —COCH₂CH₂CH₂—NHCONH—CH(CH₂SMe)—COOH |
| 1-177 | —COCH₂CH₂CH₂—NHCONH—CH(CH₂SBu)—COOBuᵗ | —COCH₂CH₂CH₂—NHCONH—CH(CH₂SBu)—COOBuᵗ |
| 1-178 | —COCH₂CH₂CH₂—NHCONH—CH(CH₂S-Hexyl)—COOH | —COCH₂CH₂CH₂—NHCONH—CH(CH₂S-Hexyl)—COOH |

TABLE 14

| | | |
|---|---|---|
| 1-179 | —COCH₂—NHCONH—CH(CH₂-(3-pyrrolyl))—COOH | —COCH₂—NHCONH—CH(CH₂-(3-pyrrolyl))—COOH |
| 1-180 | —COCH₂CH₂CH₂—NHCONH—CH(CH₂-(5-imidazolyl))—COOH | —COCH₂CH₂CH₂—NHCONH—CH(CH₂-(5-imidazolyl))—COOH |
| 1-181 | —COCH₂CH₂CH₂—NHCO—(prolyl)—COOH | —COCH₂CH₂CH₂—NHCO—(prolyl)—COOH |
| 1-182 | —COCH₂CH₂CH₂—NHCO—(prolyl)—COOH | —COCH₃ |
| 1-183 | —COCH₂CH₂CH₂—NHCO—(prolyl)—COOH | —COCH₂CH₂COOH |
| 1-184 | —COCH₂—NHCONH—CH₂CH₂—COOBuᵗ | —COCH₂—NHCONH—CH₂CH₂—COOBuᵗ |
| 1-185 | —COCH₂—NHCONH—CH₂CH₂—COOH | —COCH₂—NHCONH—CH₂CH₂—COOH |
| 1-186 | —COCH₂—NHCONH—CH₂CH₂CH₂—COOBuᵗ | —COCH₂—NHCONH—CH₂CH₂CH₂—COOBuᵗ |
| 1-187 | —COCH₂—NHCONH—CH₂CH₂CH₂—COOH | —COCH₂—NHCONH—CH₂CH₂CH₂—COOH |
| 1-188 | —COCH₂CH₂—NHCONH—CH₂CH₂—COOBuᵗ | —COCH₂CH₂—NHCONH—CH₂CH₂—COOBuᵗ |
| 1-189 | —COCH₂CH₂—NHCONH—CH₂CH₂—COOH | —COCH₂CH₂—NHCONH—CH₂CH₂—COOH |
| 1-190 | —COCH₂CH₂—NHCONH—CH₂CH₂CH₂—COOBuᵗ | —COCH₂CH₂—NHCONH—CH₂CH₂CH₂—COOBuᵗ |
| 1-191 | —COCH₂CH₂—NHCONH—CH₂CH₂CH₂—COOH | —COCH₂CH₂—NHCONH—CH₂CH₂CH₂—COOH |
| 1-192 | —COCH₂CH₂CH₂—NHCONH—CH₂CH₂—COOBuᵗ | —COCH₂CH₂CH₂—NHCONH—CH₂CH₂—COOBuᵗ |
| 1-193 | —COCH₂CH₂CH₂—NHCONH—CH₂CH₂—COOH | —COCH₂CH₂CH₂—NHCONH—CH₂CH₂—COOH |

TABLE 15

| | | |
|---|---|---|
| 1-194 | —COCH$_2$CH$_2$CH$_2$—NHCONH—CH$_2$CH$_2$CH$_2$—COOBu$^t$ | —COCH$_2$CH$_2$CH$_2$—NHCONH—CH$_2$CH$_2$CH$_2$—COOBu$^t$ |
| 1-195 | —COCH$_2$CH$_2$CH$_2$—NHCONH—CH$_2$CH$_2$CH$_2$—COOH | —COCH$_2$CH$_2$CH$_2$—NHCONH—CH$_2$CH$_2$CH$_2$—COOH |
| 1-196 | —COCH$_2$CH$_2$CH$_2$—NHCONH—CH$_2$CH$_2$CH$_2$—COOH | —COCH$_2$CH$_2$CH$_2$—NHCONH—CH(CH$_2$CH$_2$SCH$_3$)—COOH |
| 1-197 | —COCH$_2$CH$_2$CH$_2$—NHCONH—CH$_2$CH$_2$CH$_2$—CONHCH$_3$ | —COCH$_2$CH$_2$CH$_2$—NHCONH—CH(CH$_2$CH$_2$CH$_3$)—CONHCH$_3$ |
| 1-198 | —COCH$_2$—NHCONH$_2$ | H |
| 1-199 | —COCH$_2$CH$_2$—NHCONH$_2$ | H |
| 1-200 | —COCH$_2$—NHCONHCH$_3$ | H |
| 1-201 | —COCH$_2$CH$_2$CH$_2$—NHCONH$_2$ | H |
| 1-202 | —COCH$_2$CH$_2$CH$_2$—NHCONHCH$_2$CH$_3$ | H |
| 1-203 | —COCH$_2$—NHCONHCH$_2$-c-Hexyl | H |
| 1-204 | —COCH$_2$—NHCONHNH$_2$ | H |
| 1-205 | —COCH$_2$—NHCONHOH | H |
| 1-206 | —COCH$_2$—NHCONH—CH$_2$—COOBu$^t$ | H |
| 1-207 | —COCH$_2$—NHCONH—CH$_2$—COOH | H |
| 1-208 | —COCH$_2$—NHCONH—CH(CH$_3$)—COOBu$^t$ | H |
| 1-209 | —COCH$_2$—NHCONH—CH(CH$_3$)—COOH | H |
| 1-210 | —COCH$_2$—NHCONH—CH(i-Pr)—COOBu$^t$ | H |

TABLE 16

| | | |
|---|---|---|
| 1-211 | —COCH$_2$—NHCONH—CH(i-Pr)—COOH | H |
| 1-212 | —COCH$_2$—NHCONH—CH(s-Bu)—COOBu$^t$ | H |
| 1-213 | —COCH$_2$—NHCONH—CH(s-Bu)—COOH | H |
| 1-214 | —COCH$_2$—NHCONH—CH(i-Bu)—COOBu$^t$ | H |
| 1-215 | —COCH$_2$—NHCONH—CH(i-Bu)—COOH | H |
| 1-216 | —COCH$_2$—NHCONH—CH(CH$_2$CH$_2$—S—CH$_3$)—COOEt | H |
| 1-217 | —COCH$_2$—NHCONH—CH(CH$_2$CH$_2$—S—CH$_3$)—COOBu$^t$ | H |
| 1-218 | —COCH$_2$—NHCONH—CH(CH$_2$CH$_2$—S—CH$_3$)—COOH | H |
| 1-219 | —COCH$_2$—NHCONH—CH(CH$_2$Ph)—COOBu$^t$ | H |
| 1-220 | —COCH$_2$—NHCONH—CH(CH$_2$Ph)—COOH | H |
| 1-221 | —COCH$_2$—NHCONH—CH(4-hydroxyphenylmethyl)—COOBu$^t$ | H |
| 1-222 | —COCH$_2$—NHCONH—CH(4-hydroxyphenylmethyl)—COOH | H |
| 1-223 | —COCH$_2$—NHCONH—CH(CH$_2$CONH$_2$)—COOBu$^t$ | H |
| 1-224 | —COCH$_2$—NHCONH—CH(CH$_2$CONH$_2$)—COOH | H |
| 1-225 | —COCH$_2$—NHCONH—CH(CH$_2$CH$_2$CONH$_2$)—COOBu$^t$ | H |

TABLE 17

| | | |
|---|---|---|
| 1-226 | —COCH$_2$—NHCONH—CH(CH$_2$CH$_2$CONH$_2$)—COOH | H |
| 1-227 | —COCH$_2$—NHCONH—CH(CH$_2$OH)—COOBu$^t$ | H |
| 1-228 | —COCH$_2$—NHCONH—CH(CH$_2$OH)—COOH | H |
| 1-229 | —COCH$_2$—NHCONH—CH(CH(CH$_3$)OH)—COOBu$^t$ | H |
| 1-230 | —COCH$_2$—NHCONH—CH(CH(CH$_3$)OH)—COOH | H |
| 1-231 | —COCH$_2$—NHCONH—CH(CH$_2$CH$_2$CH$_2$CH$_2$NHCO$_2$t-Bu)—COOBu$^t$ | H |
| 1-232 | —COCH$_2$—NHCONH—CH(CH$_2$CH$_2$CH$_2$CH$_2$NH$_2$)—COOH | H |
| 1-233 | —COCH$_2$—NHCONH—CH$_2$CH$_2$CH$_2$CH$_2$CH(NH$_2$)—COOH | H |
| 1-234 | —COCH$_2$—NHCONH—CH(CH$_2$CH$_2$CH$_2$NH(C=NH)NH$_2$)—COOH | H |
| 1-235 | —COCH$_2$—NHCONH—CH(CH$_2$COOBu$^t$)—COOBu$^t$ | H |
| 1-236 | —COCH$_2$—NHCONH—CH(CH$_2$COOH)—COOH | H |
| 1-237 | —COCH$_2$—NHCONH—CH(CH$_2$CH$_2$COOBu$^t$)—COOBu$^t$ | H |
| 1-238 | —COCH$_2$—NHCONH—CH(CH$_2$CH$_2$COOH)—COOH | H |
| 1-239 | —COCH$_2$—NHCONH—CH(CH$_2$SMe)—COOBu$^t$ | H |

TABLE 18

| | | |
|---|---|---|
| 1-240 | —COCH$_2$—NHCONH—CH(CH$_2$SMe)—COOH | H |
| 1-241 | —COCH$_2$—NHCONH—CH(CH$_2$S-Hexyl)—COOBu$^t$ | H |
| 1-242 | —COCH$_2$—NHCONH—CH(CH$_2$S-Hexyl)—COOH | H |
| 1-243 | 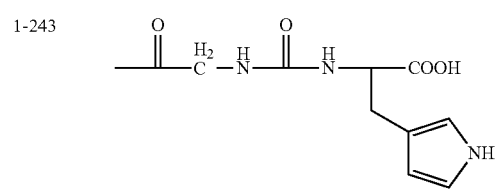 | H |

TABLE 18-continued

| | | |
|---|---|---|
| 1-244 | 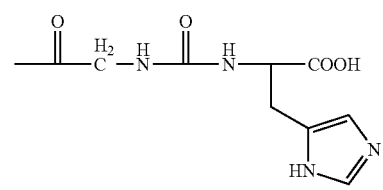 [SMILES: CC(=O)CNC(=O)NC(Cc1cnc[nH]1)C(=O)O] | H |
| 1-245 | 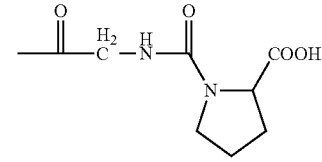 | H |
| 1-246 | —COCH$_2$CH$_2$—NHCONH—CH$_2$—COOBu$^t$ | H |
| 1-247 | —COCH$_2$CH$_2$—NHCONH—CH$_2$—COOH | H |
| 1-248 | —COCH$_2$CH$_2$—NHCONH—CH(CH$_3$)—COOBu$^t$ | H |
| 1-249 | —COCH$_2$CH$_2$—NHCONH—CH(CH$_3$)—COOH | H |
| 1-250 | —COCH$_2$CH$_2$—NHCONH—CH(i-Pr)—COOBu$^t$ | H |
| 1-251 | —COCH$_2$CH$_2$—NHCONH—CH(i-Pr)—COOH | H |
| 1-252 | —COCH$_2$CH$_2$—NHCONH—CH(s-Bu)—COOBu$^t$ | H |
| 1-253 | —COCH$_2$CH$_2$—NHCONH—CH(s-Bu)—COOH | H |

TABLE 19

| | | |
|---|---|---|
| 1-254 | —COCH$_2$CH$_2$—NHCONH—CH(i-Bu)—COOBu$^t$ | H |
| 1-255 | —COCH$_2$CH$_2$—NHCONH—CH(i-Bu)—COOH | H |
| 1-256 | —COCH$_2$CH$_2$—NHCONH—CH(CH$_2$CH$_2$—S—CH$_3$)—COOEt | H |
| 1-257 | —COCH$_2$CH$_2$—NHCONH—CH(CH$_2$CH$_2$—S—CH$_3$)—COOBu$^t$ | H |
| 1-258 | —COCH$_2$CH$_2$—NHCONH—CH(CH$_2$CH$_2$—S—CH$_3$)—COOH | H |
| 1-259 | —COCH$_2$CH$_2$—NHCONH—CH(CH$_2$Ph)—COOBu$^t$ | H |
| 1-260 | —COCH$_2$CH$_2$—NHCONH—CH(CH$_2$Ph)—COOH | H |
| 1-261 | —COCH$_2$CH$_2$—NHCONH—CH(4-hydroxyphenylmethyl)—COOBu$^t$ | H |
| 1-262 | —COCH$_2$CH$_2$—NHCONH—CH(4-hydroxyphenylmethyl)—COOH | H |
| 1-263 | —COCH$_2$CH$_2$—NHCONH—CH(CH$_2$CONH$_2$)—COOBu$^t$ | H |
| 1-264 | —COCH$_2$CH$_2$—NHCONH—CH(CH$_2$CONH$_2$)—COOH | H |
| 1-265 | —COCH$_2$CH$_2$—NHCONH—CH(CH$_2$CH$_2$CONH$_2$)—COOBu$^t$ | H |

TABLE 20

| | | |
|---|---|---|
| 1-266 | —COCH$_2$CH$_2$—NHCONH—CH(CH$_2$CH$_2$CONH$_2$)—COOH | H |
| 1-267 | —COCH$_2$CH$_2$—NHCONH—CH(CH$_2$OH)—COOBu$^t$ | H |
| 1-268 | —COCH$_2$CH$_2$—NHCONH—CH(CH$_2$OH)—COOH | H |
| 1-269 | —COCH$_2$CH$_2$—NHCONH—CH(CH(CH$_3$)OH)—COOBu$^t$ | H |
| 1-270 | —COCH$_2$CH$_2$—NHCONH—CH(CH(CH$_3$)OH)—COOH | H |
| 1-271 | —COCH$_2$CH$_2$—NHCONH—CH(CH$_2$CH$_2$CH$_2$CH$_2$NHCO$_2$t-Bu)—COOBu$^t$ | H |
| 1-272 | —COCH$_2$CH$_2$—NHCONH—CH(CH$_2$CH$_2$CH$_2$CH$_2$NH$_2$)—COOH | H |
| 1-273 | —COCH$_2$CH$_2$—NHCONH—CH(CH$_2$CH$_2$CH$_2$CH(NH$_2$))—COOH | H |
| 1-274 | —COCH$_2$CH$_2$—NHCONH—CH(CH$_2$CH$_2$CH$_2$NH(C=NH)NH$_2$)—COOH | H |
| 1-275 | —COCH$_2$CH$_2$—NHCONH—CH(CH$_2$COOBu$^t$)—COOBu$^t$ | H |
| 1-276 | —COCH$_2$CH$_2$—NHCONH—CH(CH$_2$COOH)—COOH | H |
| 1-277 | —COCH$_2$CH$_2$—NHCONH—CH(CH$_2$CH$_2$COOBu$^t$)—COOBu$^t$ | H |

TABLE 21

| | | |
|---|---|---|
| 1-278 | —COCH$_2$CH$_2$—NHCONH—CH(CH$_2$CH$_2$COOH)—COOH | H |
| 1-279 | —COCH$_2$CH$_2$—NHCONH—CH(CH$_2$SMe)—COOBu$^t$ | H |
| 1-280 | —COCH$_2$CH$_2$—NHCONH—CH(CH$_2$SMe)—COOH | H |
| 1-281 | —COCH$_2$CH$_2$—NHCONH—CH(CH$_2$S-Hexyl)—COOBu$^t$ | H |
| 1-282 | —COCH$_2$CH$_2$—NHCONH—CH(CH$_2$S-Hexyl)—COOH | H |
| 1-283 | [structure: —CO—CH$_2$—CH$_2$—NH—CO—NH—CH(CH$_2$-(1H-pyrrol-3-yl))—COOH] | H |
| 1-284 | [structure: —CO—CH$_2$—CH$_2$—NH—CO—NH—CH(CH$_2$-(1H-imidazol-4-yl))—COOH] | H |
| 1-285 | [structure: —CO—CH$_2$—CH$_2$—NH—CO—N(pyrrolidine-2-COOH)] | H |
| 1-286 | —COCH$_2$CH$_2$CH$_2$—NHCONH—CH$_2$—COOBu$^t$ | H |
| 1-287 | —COCH$_2$CH$_2$CH$_2$—NHCONH—CH$_2$—COOH | H |
| 1-288 | —COCH$_2$CH$_2$CH$_2$—NHCONH—CH(CH$_3$)—COOBu$^t$ | H |
| 1-289 | —COCH$_2$CH$_2$CH$_2$—NHCONH—CH(CH$_3$)—COOH | H |

TABLE 22

| | | |
|---|---|---|
| 1-290 | —COCH$_2$CH$_2$CH$_2$—NHCONH—CH(i-Pr)—COOBu$^t$ | H |
| 1-291 | —COCH$_2$CH$_2$CH$_2$—NHCONH—CH(i-Pr)—COOH | H |
| 1-292 | —COCH$_2$CH$_2$CH$_2$—NHCONH—CH(s-Bu)—COOBu$^t$ | H |
| 1-293 | —COCH$_2$CH$_2$CH$_2$—NHCONH—CH(s-Bu)—COOH | H |
| 1-294 | —COCH$_2$CH$_2$CH$_2$—NHCONH—CH(i-Bu)—COOBu$^t$ | H |
| 1-295 | —COCH$_2$CH$_2$CH$_2$—NHCONH—CH(i-Bu)—COOH | H |
| 1-296 | —COCH$_2$CH$_2$CH$_2$—NHCONH—CH(CH$_2$CH$_2$—S—CH$_3$)—COOEt | H |
| 1-297 | —COCH$_2$CH$_2$CH$_2$—NHCONH—CH(CH$_2$CH$_2$—S—CH$_3$)—COOBu$^t$ | H |
| 1-298 | —COCH$_2$CH$_2$CH$_2$—NHCONH—CH(CH$_2$CH$_2$—S—CH$_3$)—COOH | H |
| 1-299 | —COCH$_2$CH$_2$CH$_2$—NHCONH—CH(CH$_2$Ph)—COOBu$^t$ | H |
| 1-300 | —COCH$_2$CH$_2$CH$_2$—NHCONH—CH(CH$_2$Ph)—COOH | H |
| 1-301 | —COCH$_2$CH$_2$CH$_2$—NHCONH—CH(4-hydroxyphenylmethyl)—COOBu$^t$ | H |

TABLE 23

| | | |
|---|---|---|
| 1-302 | —COCH$_2$CH$_2$CH$_2$—NHCONH—CH(4-hydroxyphenylmethyl)—COOH | H |
| 1-303 | —COCH$_2$CH$_2$CH$_2$—NHCONH—CH(CH$_2$CONH$_2$)—COOBu$^t$ | H |
| 1-304 | —COCH$_2$CH$_2$CH$_2$—NHCONH—CH(CH$_2$CONH$_2$)—COOH | H |
| 1-305 | —COCH$_2$CH$_2$CH$_2$—NHCONH—CH(CH$_2$CH$_2$CONH$_2$)—COOBu$^t$ | H |
| 1-306 | —COCH$_2$CH$_2$CH$_2$—NHCONH—CH(CH$_2$CH$_2$CONH$_2$)—COOH | H |
| 1-307 | —COCH$_2$CH$_2$CH$_2$—NHCONH—CH(CH$_2$OH)—COOBu$^t$ | H |
| 1-308 | —COCH$_2$CH$_2$CH$_2$—NHCONH—CH(CH$_2$OH)—COOH | H |
| 1-309 | —COCH$_2$CH$_2$CH$_2$—NHCONH—CH(CH(CH$_3$)OH)—COOBu$^t$ | H |
| 1-310 | —COCH$_2$CH$_2$CH$_2$—NHCONH—CH(CH(CH$_3$)OH)—COOH | H |
| 1-311 | —COCH$_2$CH$_2$CH$_2$—NHCONH—CH(CH$_2$CH$_2$CH$_2$CH$_2$NHCO$_2$t-Bu)—COOBu$^t$ | H |
| 1-312 | —COCH$_2$CH$_2$CH$_2$—NHCONH—CH(CH$_2$CH$_2$CH$_2$CH$_2$NH$_2$)—COOH | H |

TABLE 24

| | | |
|---|---|---|
| 1-313 | —COCH$_2$CH$_2$CH$_2$—NHCONH—CH$_2$CH$_2$CH$_2$CH$_2$CH(NH$_2$)—COOH | H |
| 1-314 | —COCH$_2$CH$_2$CH$_2$—NHCONH—CH(CH$_2$CH$_2$CH$_2$NH(C=NH)NH$_2$)—COOH | H |
| 1-315 | —COCH$_2$CH$_2$CH$_2$—NHCONH—CH(CH$_2$COOBu$^t$)—COOBu$^t$ | H |
| 1-316 | —COCH$_2$CH$_2$CH$_2$—NHCONH—CH(CH$_2$COOH)—COOH | H |
| 1-317 | —COCH$_2$CH$_2$CH$_2$—NHCONH—CH(CH$_2$CH$_2$COOBu$^t$)—COOBu$^t$ | H |
| 1-318 | —COCH$_2$CH$_2$CH$_2$—NHCONH—CH(CH$_2$CH$_2$COOH)—COOH | H |
| 1-319 | —COCH$_2$CH$_2$CH$_2$—NHCONH—CH(CH$_2$SMe)—COOBu$^t$ | H |
| 1-320 | —COCH$_2$CH$_2$CH$_2$—NHCONH—CH(CH$_2$SMe)—COOH | H |
| 1-321 | —COCH$_2$CH$_2$CH$_2$—NHCONH—CH(CH$_2$S-Hexyl)—COOBu$^t$ | H |
| 1-322 | —COCH$_2$CH$_2$CH$_2$—NHCONH—CH(CH$_2$S-Hexyl)—COOH | H |
| 1-323 | [structure: —C(=O)—CH$_2$—NH—C(=O)—NH—CH(COOH)—CH$_2$-(1H-pyrrol-3-yl)] | H |

TABLE 25

| | | |
|---|---|---|
| 1-324 | [structure: —C(=O)—CH$_2$CH$_2$CH$_2$—NH—C(=O)—NH—CH(COOH)—CH$_2$-(1H-imidazol-4-yl)] | H |
| 1-325 | [structure: —C(=O)—CH$_2$CH$_2$CH$_2$—NH—C(=O)—N(pyrrolidine-2-COOH)] | H |
| 1-326 | —COCH$_2$CH$_2$CH$_2$—NHCONH—CH(CH$_2$SMe)—COOH | —COCH$_2$CH$_2$CH$_2$—NHCONH—CH(CH$_3$)—COOHH |
| 1-327 | —COCH$_2$CH$_2$CH$_2$—NHCONH—CH(CH$_2$SMe)—COOH | —COCH$_2$CH$_2$CH$_2$—NHCONH—CH(CH$_2$CH$_2$SMe)—COOHH |
| 1-328 | —COCH$_2$—NHCONH—CH$_2$CH$_2$—COOBu$^t$ | H |
| 1-329 | —COCH$_2$—NHCONH—CH$_2$CH$_2$—COOH | H |
| 1-330 | —COCH$_2$—NHCONH—CH$_2$CH$_2$CH$_2$—COOBu$^t$ | H |
| 1-331 | —COCH$_2$—NHCONH—CH$_2$CH$_2$CH$_2$—COOH | H |
| 1-332 | —COCH$_2$CH$_2$—NHCONH—CH$_2$CH$_2$—COOBu$^t$ | H |
| 1-333 | —COCH$_2$CH$_2$—NHCONH—CH$_2$CH$_2$—COOH | H |
| 1-334 | —COCH$_2$CH$_2$—NHCONH—CH$_2$CH$_2$CH$_2$—COOBu$^t$ | H |
| 1-335 | —COCH$_2$CH$_2$—NHCONH—CH$_2$CH$_2$CH$_2$—COOH | H |
| 1-336 | —COCH$_2$CH$_2$CH$_2$—NHCONH—CH$_2$CH$_2$—COOBu$^t$ | H |
| 1-337 | —COCH$_2$CH$_2$CH$_2$—NHCONH—CH$_2$CH$_2$—COOH | H |
| 1-338 | —COCH$_2$CH$_2$CH$_2$—NHCONH—CH$_2$CH$_2$CH$_2$—COOBu$^t$ | H |

TABLE 26

| | | |
|---|---|---|
| 1-339 | —COCH$_2$CH$_2$CH$_2$—NHCONH—CH$_2$CH$_2$CH$_2$—COOH | H |
| 1-340 | —COCH$_2$CH$_2$CH$_2$—NHCONH—CH$_2$CH$_2$CH$_2$—COOH | —COCH$_2$CH$_2$CH$_2$—NHCONH—CH$_2$CH$_2$OH |
| 1-341 | —COCH$_2$CH$_2$CH$_2$—NHCONH—CH$_2$CH$_2$CH$_2$—COOH | —COCH$_3$ |
| 1-342 | —COCH$_2$—NHCON(CH$_3$)—CH$_2$—COOH | —COCH$_2$—NHCON(CH$_3$)—CH$_2$—COOH |
| 1-343 | —COCH$_2$—N(CH$_3$)CONH—CH$_2$—COOH | —COCH$_2$—N(CH$_3$)CONH—CH$_2$—COOH |
| 1-344 | —COCH(CH$_3$)—NHCONH—CH$_2$—COOH | —COCH(CH$_3$)—NHCONH—CH$_2$—COOH |
| 1-345 | —COCH(CH$_2$CH$_2$SCH$_3$)—NHCONH—CH$_2$—COOH | —COCH(CH$_2$CH$_2$SCH$_3$)—NHCONH—CH$_2$—COOH |
| 1-346 | —COCH(CH$_3$)—NHCONH—CH(i-Bu)—COOH | —COCH(CH$_3$)—NHCONH—CH(i-Bu)—COOH |
| 1-347 | —COCH(4-Aminobutyl)—NHCONH—CH(4-Aminobutyl)—COOH | —COCH(4-Aminobutyl)—NHCONH—CH(4-Aminobutyl)—COOH |
| 1-348 | —COCH$_2$CH$_2$—NHCON(CH$_3$)—CH$_2$CH$_2$CH$_2$—COOH | —COCH$_2$CH$_2$—NHCON(CH$_3$)—CH$_2$CH$_2$CH$_2$—COOH |
| 1-349 | —COCH$_2$CH$_2$—NHCONH—CH$_2$CH$_2$NHCOCH$_2$Ph | —COCH$_2$CH$_2$—NHCONH—CH$_2$CH$_2$NHCOCH$_2$Ph |
| 1-350 | —COCH$_2$CH$_2$—NHCONH—CH$_2$CH$_2$NHCO(p-NH$_2$Ph) | —COCH$_2$CH$_2$—NHCONH—CH$_2$CH$_2$NHCO(p-NH$_2$Ph) |
| 1-351 | —COCH$_2$CH$_2$—NHCONH—CH$_2$CH$_2$NHCO(o-COOHPh) | —COCH$_2$CH$_2$—NHCONH—CH$_2$CH$_2$NHCO(o-COOHPh) |

TABLE 27

| | |
|---|---|
| 1-352 | —COCH₂CH₂—NHCONH—CH₂CH₂—S—CH₂CH₂—NHCOCH₂Ph |
| 1-353 | —COCH₂—NHCONH—(CH₂)₇—COOEt |
| 1-354 | —COCH₂—NHCONH—(CH₂)₇—COOH |
| 1-355 | —COCH₂—N(CH₃)—(CH₂)₆NHCONH—CH₂—COOH |
| 1-356 | —CONH—CH₂CONHCH₂NHCONHCH₂CH₂N(CH₃)(Ph) |
| 1-357 | —COCH₂—NHCONH—(CH₂)₃—CONH-(3-Pyridyl) |
| 1-358 | —COCH₂—NHCONH—CH₂CH₂—NHCOCH₂COOH |
| 1-359 | —COCH₂—NHCONH—CH₂CH₂—OH |
| 1-360 | —COCH₂—NHCONH—CH₂CH₂—OH |
| 1-361 | —CONH—CH₂CONHCH₂CH₂CH₂CH₂C(COOH)NHCONHCH₂CH₂N(CH₃)(Ph) |

TABLE 28

| # | 59 | 60 |
|---|---|---|
| 1-366 | —COCH₂CH₂—NHCO-imidazol-1-yl (structure) | —COCH₂CH₂—NHCO-imidazol-1-yl (structure) |
| 1-367 | —COCH₂CH₂CH₂—NHCO-imidazol-1-yl (structure) | —COCH₂CH₂CH₂—NHCO-imidazol-1-yl (structure) |
| 1-368 | —COCH(CH$_3$)—NHCOImidazol-1-yl | —COCH(CH$_3$)—NHCOImidazol-1-yl |
| 1-369 | —COCH$_2$—NHCOImidazol-1-yl | H |
| 1-370 | —COCH$_2$CH$_2$—NHCOImidazol-1-yl | H |
| 1-371 | —COCH(CH$_2$CH$_2$CH$_2$NH$_2$)—NH—CONH—CH(CH$_2$CH$_2$CH$_2$CH$_2$NH$_2$)—COOH | —COCH(CH$_2$CH$_2$CH$_2$NH$_2$)—NH—CONH—CH(CH$_2$CH$_2$CH$_2$CH$_2$NH$_2$)—COOH |
| 1-372 | —COCH$_2$CH$_2$CH$_2$—NHCONH—CH$_2$CH$_2$CH$_2$CH(NH$_2$)—COOH | —COCH$_2$CH$_2$CH$_2$—NHCONH—CH$_2$CH$_2$CH$_2$CH(NH$_2$)—COOH |
| 1-373 | —COCH$_2$CH$_2$—NHCONH—CH$_2$CH$_2$CH$_2$CH(NH$_2$)—COOH | —COCH$_2$CH$_2$—NHCONH—CH$_2$CH$_2$CH$_2$CH(NH$_2$)—COOH |
| 1-374 | —COCH$_2$—NHCONH—CH(CH$_2$CH$_2$CH$_2$NH$_2$)—COOH | —COCH$_2$—NHCONH—CH(CH$_2$CH$_2$CH$_2$NH$_2$)—COOH |
| 1-375 | —COCH$_2$—NHCONH—CH$_2$CH$_2$CH$_2$CH(NH$_2$)—COOH | —COCH$_2$—NHCONH—CH$_2$CH$_2$CH$_2$CH(NH$_2$)—COOH |
| 1-376 | —COCH$_2$CH$_2$—NHCONH—CH$_2$CH$_2$CH$_2$CH(NHCOCH$_3$)—COOH | —COCH$_2$CH$_2$—NHCONH—CH$_2$CH$_2$CH$_2$CH(NHCOCH$_3$)—COOH |
| 1-377 | —COCH$_2$CH$_2$CH$_2$—NHCONH—CH$_2$CH$_2$CH$_2$CH$_2$(NHCOCH$_3$)—COOH | —COCH$_2$CH$_2$CH$_2$—NHCONH—CH$_2$CH$_2$CH$_2$CH$_2$(NHCOCH$_3$)—COOH |
| 1-378 | —COCH$_2$—NHCONH—CH$_2$CH(i-Bu)CH$_2$—COOH | —COCH$_2$—NHCONH—CH$_2$CH(i-Bu)CH$_2$—COOH |

TABLE 29

| # | 59 | 60 |
|---|---|---|
| 1-379 | —COCH$_2$CH$_2$—NHCONH—CH$_2$CH(i-Bu)CH$_2$—COOH | —COCH$_2$CH$_2$—NHCONH—CH$_2$CH(i-Bu)CH$_2$—COOH |
| 1-380 | —COCH$_2$CH$_2$CH$_2$—NHCONH—CH$_2$CH(i-Bu)CH$_2$—COOH | —COCH$_2$CH$_2$CH$_2$—NHCONH—CH$_2$CH(i-Bu)CH$_2$—COOH |
| 1-381 | —COCH$_2$CH(i-Bu)CH$_2$—NHCONH—CH$_2$—COOH | —COCH$_2$CH(i-Bu)CH$_2$—NHCONH—CH$_2$—COOH |
| 1-382 | —COCH$_2$CH(i-Bu)CH$_2$—NHCONH—CH$_2$CH$_2$—COOH | —COCH$_2$CH(i-Bu)CH$_2$—NHCONH—CH$_2$CH$_2$—COOH |
| 1-383 | —COCH$_2$CH(i-Bu)CH$_2$—NHCONH—CH$_2$CH$_2$CH$_2$—COOH | —COCH$_2$CH(i-Bu)CH$_2$—NHCONH—CH$_2$CH$_2$CH$_2$—COOH |
| 1-384 | —COCH$_2$CH(i-Bu)CH$_2$—NHCONH—CH$_2$CH(i-Bu)CH$_2$—COOH | —COCH$_2$CH(i-Bu)CH$_2$—NHCONH—CH$_2$CH(i-Bu)CH$_2$—COOH |
| 1-385 | —COCH$_2$—NHCONH—CH$_2$C(CH$_2$CH$_2$CH$_2$CH$_2$CH$_2$)CH$_2$—COOH | —COCH$_2$—NHCONH—CH$_2$C(CH$_2$CH$_2$CH$_2$CH$_2$CH$_2$)CH$_2$—COOH |
| 1-386 | —COCH$_2$CH$_2$—NHCONH—CH$_2$C(CH$_2$CH$_2$CH$_2$CH$_2$CH$_2$)CH$_2$—COOH | —COCH$_2$CH$_2$—NHCONH—CH$_2$C(CH$_2$CH$_2$CH$_2$CH$_2$CH$_2$)CH$_2$—COOH |
| 1-387 | —COCH$_2$CH$_2$CH$_2$—NHCONH—CH$_2$C(CH$_2$CH$_2$CH$_2$CH$_2$CH$_2$)CH$_2$—COOH | —COCH$_2$CH$_2$CH$_2$—NHCONH—CH$_2$C(CH$_2$CH$_2$CH$_2$CH$_2$CH$_2$)CH$_2$—COOH |
| 1-388 | —COCH$_2$C(CH$_2$CH$_2$CH$_2$CH$_2$CH$_2$)CH$_2$—NHCONH—CH$_2$C(CH$_2$CH$_2$CH$_2$CH$_2$CH$_2$)CH$_2$—COOH | —COCH$_2$C(CH$_2$CH$_2$CH$_2$CH$_2$CH$_2$)CH$_2$—NHCONH—CH$_2$C(CH$_2$CH$_2$CH$_2$CH$_2$CH$_2$)CH$_2$—COOH |
| 1-389 | —COCH$_2$—NH—CO—NH—CH(bicyclic-methyl)—CH$_2$CH$_2$—COOH (structure) | —COCH$_2$—NH—CO—NH—CH(bicyclic-methyl)—CH$_2$CH$_2$—COOH (structure) |

TABLE 30

| # | 59 | 60 |
|---|---|---|
| 1-390 | —COCH$_2$—NH—CO—NH—CH(bicyclic-ethyl)—CH$_2$CH$_2$—COOH (structure) | —COCH$_2$—NH—CO—NH—CH(bicyclic-ethyl)—CH$_2$CH$_2$—COOH (structure) |

TABLE 30-continued
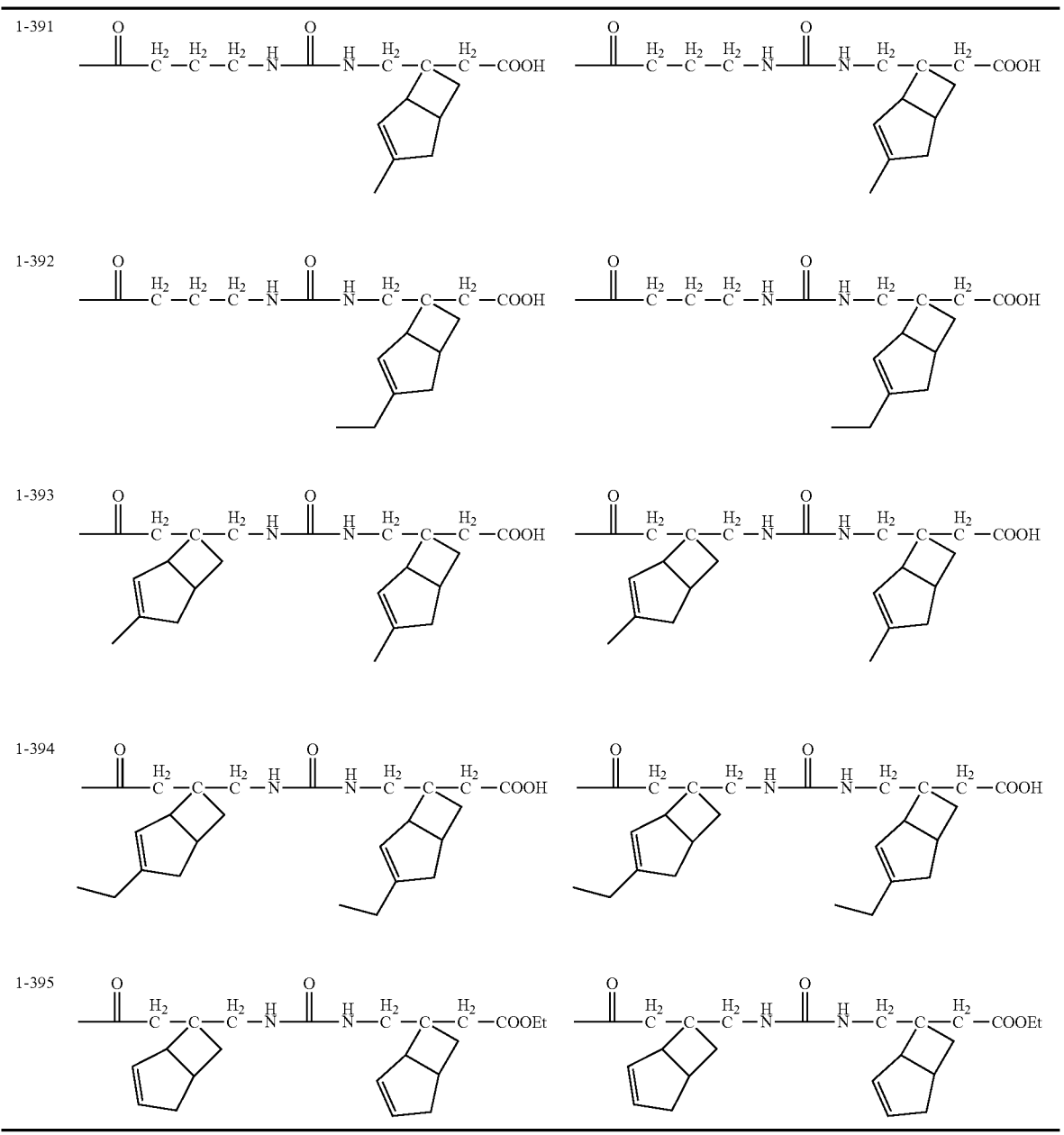
(B) Compound of the formula described below wherein the $R^1$ and $R^2$ are shown in Tables 31 to 37.
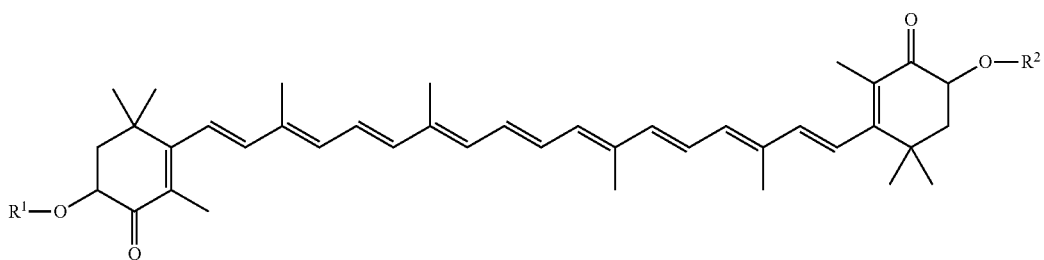

TABLE 31

| Exemplified Compound No. | R$^1$ | R$^2$ |
|---|---|---|
| 2-1 | —COCH$_2$CH$_2$—CO—NH—CH$_2$CH$_2$—SO$_3$H | —COCH$_2$CH$_2$—CO—NH—CH$_2$CH$_2$—SO$_3$H |
| 2-2 | —COCH$_2$CH$_2$—CO—N(CH$_3$)—CH$_2$CH$_2$—SO$_3$H | —COCH$_2$CH$_2$—CO—N(CH$_3$)—CH$_2$CH$_2$—SO$_3$H |
| 2-3 | —COCH$_2$CH$_2$CH$_2$—CO—NH—CH$_2$CH$_2$—SO$_3$H | —COCH$_2$CH$_2$CH$_2$—CO—NH—CH$_2$CH$_2$—SO$_3$H |
| 2-4 | —COCH$_2$CH$_2$CH$_2$CH$_2$—CO—NH—CH$_2$CH$_2$—SO$_3$H | —COCH$_2$CH$_2$CH$_2$CH$_2$—CO—NH—CH$_2$CH$_2$—SO$_3$H |
| 2-5 | —COCH$_2$CH$_2$CH$_2$CH$_2$CH$_2$CH$_2$—CO—NH—CH$_2$CH$_2$—SO$_3$H | —COCH$_2$CH$_2$CH$_2$CH$_2$CH$_2$CH$_2$—CO—NH—CH$_2$CH$_2$—SO$_3$H |
| 2-6 | —CO(CH$_2$)$_8$—CO—NH—CH$_2$CH$_2$—SO$_3$H | —CO(CH$_2$)$_8$—CO—NH—CH$_2$CH$_2$—SO$_3$H |
| 2-7 | —COCH$_2$CH(CH$_3$)—CO—NH—CH$_2$CH$_2$—SO$_3$H | —COCH$_2$CH(CH$_3$)—CO—NH—CH$_2$CH$_2$—SO$_3$H |
| 2-8 | —COCH=CH—CO—NH—CH$_2$CH$_2$—SO$_3$H | —COCH=CH—CO—NH—CH$_2$CH$_2$—SO$_3$H |
| 2-9 | —COC≡C—CO—NH—CH$_2$CH$_2$—SO$_3$H | —COC≡C—CO—NH—CH$_2$CH$_2$—SO$_3$H |
| 2-10 | —CONH—CH$_2$CH$_2$—SO$_3$H | —CONH—CH$_2$CH$_2$—SO$_3$H |
| 2-11 | —COCH$_2$—NHCONH—CH$_2$CH$_2$—SO$_3$H | —COCH$_2$—NHCONH—CH$_2$CH$_2$—SO$_3$H |
| 2-12 | —COCH$_2$CH$_2$—NHCONH—CH$_2$CH$_2$—SO$_3$H | —COCH$_2$CH$_2$—NHCONH—CH$_2$CH$_2$—SO$_3$H |
| 2-13 | —COCH$_2$CH$_2$CH$_2$—NHCONH—CH$_2$CH$_2$—SO$_3$H | —COCH$_2$CH$_2$CH$_2$—NHCONH—CH$_2$CH$_2$—SO$_3$H |
| 2-14 | —COCH$_2$—NHCONH—CH$_2$—PO$_3$H | —COCH$_2$—NHCONH—CH$_2$—PO$_3$H |

TABLE 32

| | | |
|---|---|---|
| 2-15 | —COCH$_2$CH$_2$—NHCONH—CH$_2$CH$_2$—NH—SO$_3$H | —COCH$_2$CH$_2$—NHCONH—CH$_2$CH$_2$—NH—SO$_3$H |
| 2-16 | —COCH$_2$CH$_2$—CO—NH—CH$_2$CH$_2$—SO$_3$H | H |
| 2-17 | —COCH$_2$CH$_2$—CO—N(CH$_3$)—CH$_2$CH$_2$—SO$_3$H | H |
| 2-18 | —COCH$_2$CH$_2$CH$_2$—CO—NH—CH$_2$CH$_2$—SO$_3$H | H |
| 2-19 | —COCH$_2$CH$_2$CH$_2$CH$_2$—CO—NH—CH$_2$CH$_2$—SO$_3$H | H |
| 2-20 | —COCH$_2$CH$_2$CH$_2$CH$_2$CH$_2$CH$_2$—CO—NH—CH$_2$CH$_2$—SO$_3$H | H |
| 2-21 | —CO(CH$_2$)$_8$—CO—NH—CH$_2$CH$_2$—SO$_3$H | H |
| 2-22 | —COCH$_2$CH(CH$_3$)—CO—NH—CH$_2$CH$_2$—SO$_3$H | H |
| 2-23 | —COCH=CH—CO—NH—CH$_2$CH$_2$—SO$_3$H | H |
| 2-24 | —COC≡C—CO—NH—CH$_2$CH$_2$—SO$_3$H | H |
| 2-25 | —CONH—CH$_2$CH$_2$—SO$_3$H | H |
| 2-26 | —COCH$_2$—NHCONH—CH$_2$CH$_2$—SO$_3$H | H |
| 2-27 | —COCH$_2$CH$_2$—NHCONH—CH$_2$CH$_2$—SO$_3$H | H |
| 2-28 | —COCH$_2$CH$_2$CH$_2$—NHCONH—CH$_2$CH$_2$—SO$_3$H | H |
| 2-29 | —COCH$_2$—NHCONH—CH$_2$—PO$_3$H | H |

TABLE 33

| | | |
|---|---|---|
| 2-30 | —COCH$_2$CH$_2$—NHCONH—CH$_2$CH$_2$—NH—SO$_3$H | H |
| 2-31 | —CON(CH$_3$)—CH$_2$CH$_2$—SO$_3$H | H |
| 2-32 | —COCH$_2$NH—SO$_3$H | —COCH$_2$CH$_2$NH—SO$_3$H |
| 2-33 | —COCH$_2$CH$_2$NH—SO$_3$H | —COCH$_2$CH$_2$NH—SO$_3$H |
| 2-34 | —COCH$_2$CH$_2$CH$_2$NH—SO$_3$H | —COCH$_2$CH$_2$NH—SO$_3$H |
| 2-35 | —CONH—CH(CH$_3$)—CONH—CH$_2$CH$_2$—SO$_3$H | —CONH—CH(CH$_3$)—CONH—CH$_2$CH$_2$—SO$_3$H |
| 2-36 | —CONH—CH(i-Pr)—CONH—CH$_2$CH$_2$—SO$_3$H | —CONH—CH(i-Pr)—CONH—CH$_2$CH$_2$—SO$_3$H |
| 2-37 | —CONH—CH(s-Bu)—CONH—CH$_2$CH$_2$—SO$_3$H | —CONH—CH(s-Bu)—CONH—CH$_2$CH$_2$—SO$_3$H |
| 2-38 | —CONH—CH(i-Bu)—CONH—CH$_2$CH$_2$—SO$_3$H | —CONH—CH(i-Bu)—CONH—CH$_2$CH$_2$—SO$_3$H |
| 2-39 | —CONH—CH(CH$_2$—S—CH$_3$)—CONH—CH$_2$CH$_2$—SO$_3$H | —CONH—CH(CH$_2$—S—CH$_3$)—CONH—CH$_2$CH$_2$—SO$_3$H |
| 2-40 | —CONH—CH(CH$_2$Ph)—CONH—CH$_2$CH$_2$—SO$_3$H | —CONH—CH(CH$_2$Ph)—CONH—CH$_2$CH$_2$—SO$_3$H |
| 2-41 | —CONH—CH(4-hydroxyphenylmethyl)—CONH—CH$_2$CH$_2$—SO$_3$H | —CONH—CH(4-hydroxyphenylmethyl)—CONH—CH$_2$CH$_2$—SO$_3$H |
| 2-42 | —CONH—CH(CH$_2$CONH$_2$)—CONH—CH$_2$CH$_2$—SO$_3$H | —CONH—CH(CH$_2$CONH$_2$)—CONN—CH$_2$CH$_2$—SO$_3$H |

TABLE 34

| | | |
|---|---|---|
| 2-43 | —CONH—CH(CH$_2$CH$_2$CONH$_2$)—CONH—CH$_2$CH$_2$—SO$_3$H | —CONH—CH(CH$_2$CH$_2$CONH$_2$)—CONH—CH$_2$CH$_2$—SO$_3$H |
| 2-44 | —CONH—CH(CH$_2$OH)—CONH—CH$_2$CH$_2$—SO$_3$H | —CONH—CH(CH$_2$OH)—CONH—CH$_2$CH$_2$—SO$_3$H |
| 2-45 | —CONH—CH(CH(CH$_3$)OH)—CONH—CH$_2$CH$_2$—SO$_3$H | —CONH—CH(CH(CH$_3$)OH)—CONH—CH$_2$CH$_2$—SO$_3$H |
| 2-46 | —CONH—CH(CH$_2$CH$_2$CH$_2$CH$_2$NH$_2$)—CONH—CH$_2$CH$_2$—SO$_3$H | —CONH—CH(CH$_2$CH$_2$CH$_2$CH$_2$NH$_2$)—CONH—CH$_2$CH$_2$—SO$_3$H |
| 2-47 | —CONH—CH$_2$CH$_2$CH$_2$CH$_2$CH(NH$_2$)—CONH—CH$_2$CH$_2$—SO$_3$H | —CONH—CH$_2$CH$_2$CH$_2$CH$_2$CH(NH$_2$)—CONH—CH$_2$CH$_2$—SO$_3$H |
| 2-48 | —CONH—CH(CH$_2$CH$_2$CH$_2$—NH(C=NH)NH$_2$)—CONH—CH$_2$CH$_2$—SO$_3$H | —CONH—CH(CH$_2$CH$_2$CH$_2$—NH(C=NH)NH$_2$)—CONH—CH$_2$CH$_2$—SO$_3$H |
| 2-49 | —CONH—CH(CH$_2$COOH)—CONH—CH$_2$CH$_2$—SO$_3$H | —CONH—CH(CH$_2$COOH)—CONH—CH$_2$CH$_2$—SO$_3$H |
| 2-50 | —CONH—CH(CH$_2$CH$_2$COOH)—CONH—CH$_2$CH$_2$—SO$_3$H | —CONH—CH(CH$_2$CH$_2$COOH)—CONH—CH$_2$CH$_2$—SO$_3$H |
| 2-51 | —CONH—CH(CH$_2$SMe)—CONH—CH$_2$CH$_2$—SO$_3$H | —CONH—CH(CH$_2$SMe)—CONH—CH$_2$CH$_2$—SO$_3$H |
| 2-52 | —CONH—CH(CH$_2$S-Hexyl)—CONH—CH$_2$CH$_2$—SO$_3$H | —CONH—CH(CH$_2$S-Hexyl)—CONH—CH$_2$CH$_2$—SO$_3$H |

TABLE 34-continued

| | 65 | 66 |
|---|---|---|
| 2-53 | 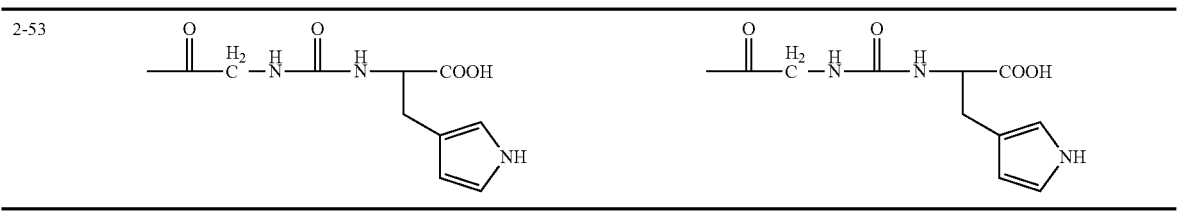 | |

TABLE 35

| | 65 | 66 |
|---|---|---|
| 2-54 | 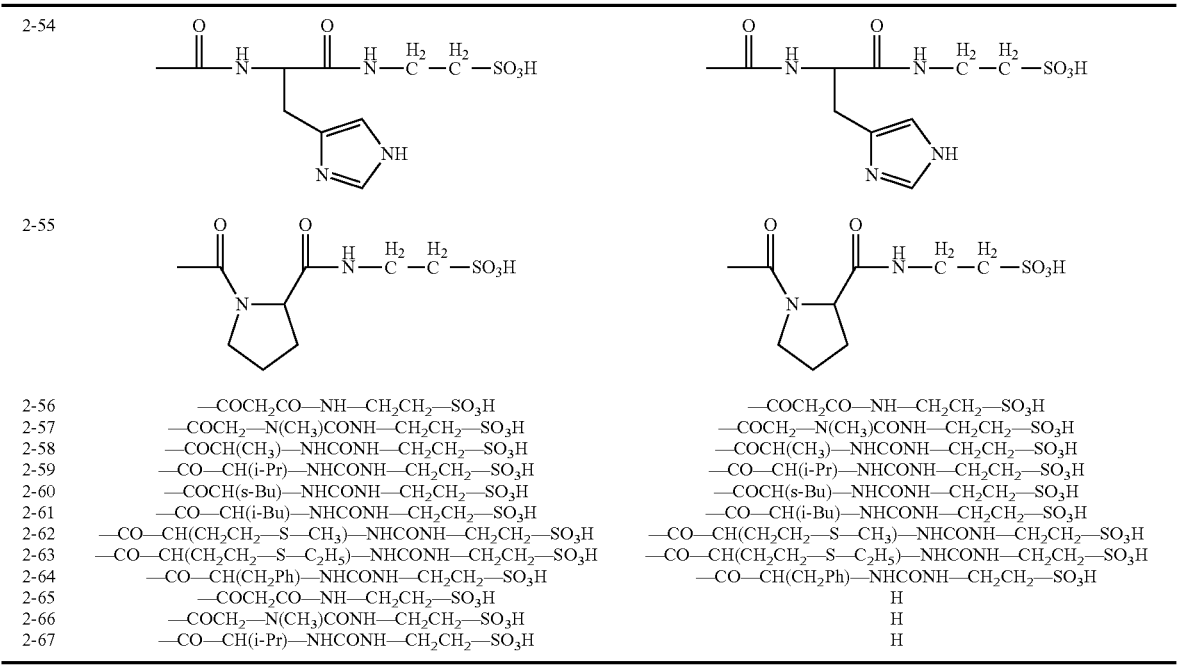 | |
| 2-55 | | |
| 2-56 | —COCH$_2$CO—NH—CH$_2$CH$_2$—SO$_3$H | —COCH$_2$CO—NH—CH$_2$CH$_2$—SO$_3$H |
| 2-57 | —COCH$_2$—N(CH$_3$)CONH—CH$_2$CH$_2$—SO$_3$H | —COCH$_2$—N(CH$_3$)CONH—CH$_2$CH$_2$—SO$_3$H |
| 2-58 | —COCH(CH$_3$)—NHCONH—CH$_2$CH$_2$—SO$_3$H | —COCH(CH$_3$)—NHCONH—CH$_2$CH$_2$—SO$_3$H |
| 2-59 | —CO—CH(i-Pr)—NHCONH—CH$_2$CH$_2$—SO$_3$H | —CO—CH(i-Pr)—NHCONH—CH$_2$CH$_2$—SO$_3$H |
| 2-60 | —COCH(s-Bu)—NHCONH—CH$_2$CH$_2$—SO$_3$H | —COCH(s-Bu)—NHCONH—CH$_2$CH$_2$—SO$_3$H |
| 2-61 | —CO—CH(i-Bu)—NHCONH—CH$_2$CH$_2$—SO$_3$H | —CO—CH(i-Bu)—NHCONH—CH$_2$CH$_2$—SO$_3$H |
| 2-62 | —CO—CH(CH$_2$CH$_2$—S—CH$_3$)—NHCONH—CH$_2$CH$_2$—SO$_3$H | —CO—CH(CH$_2$CH$_2$—S—CH$_3$)—NHCONH—CH$_2$CH$_2$—SO$_3$H |
| 2-63 | —CO—CH(CH$_2$CH$_2$—S—C$_2$H$_5$)—NHCONH—CH$_2$CH$_2$—SO$_3$H | —CO—CH(CH$_2$CH$_2$—S—C$_2$H$_5$)—NHCONH—CH$_2$CH$_2$—SO$_3$H |
| 2-64 | —CO—CH(CH$_2$Ph)—NHCONH—CH$_2$CH$_2$—SO$_3$H | —CO—CH(CH$_2$Ph)—NHCONH—CH$_2$CH$_2$—SO$_3$H |
| 2-65 | —COCH$_2$CO—NH—CH$_2$CH$_2$—SO$_3$H | H |
| 2-66 | —COCH$_2$—N(CH$_3$)CONH—CH$_2$CH$_2$—SO$_3$H | H |
| 2-67 | —CO—CH(i-Pr)—NHCONH—CH$_2$CH$_2$—SO$_3$H | H |

TABLE 36

| 2-68 | —COCH(s-Bu)—NHCONH—CH$_2$CH$_2$—SO$_3$H | H |
|---|---|---|
| 2-69 | —CO—CH(i-Bu)—NHCONH—CH$_2$CH$_2$—SO$_3$H | H |
| 2-70 | —CO—CH(CH$_2$CH$_2$—S—CH$_3$)—NHCONH—CH$_2$CH$_2$—SO$_3$H | H |
| 2-71 | —CO—CH(CH$_2$CH$_2$—S—C$_2$H$_5$)—NHCONH—CH$_2$CH$_2$—SO$_3$H | H |
| 2-72 | —CO—CH(CH$_2$Ph)—NHCONH—CH$_2$CH$_2$—SO$_3$H | H |
| 2-73 | —CO—CH(i-Pr)—NHCONH—CH$_3$CH$_2$CH$_2$—SO$_3$H | —CO—CH(i-Pr)—NHCONH—CH$_3$CH$_2$CH$_2$—SO$_3$H |
| 2-74 | —COCH(s-Bu)—NHCONH—CH$_3$CH$_2$CH$_2$—SO$_3$H | —COCH(s-Bu)—NHCONH—CH$_3$CH$_2$CH$_2$—SO$_3$H |
| 2-75 | —CO—CH(i-Bu)—NHCONH—CH$_3$CH$_2$CH$_2$—SO$_3$H | —CO—CH(i-Bu)—NHCONH—CH$_3$CH$_2$CH$_2$—SO$_3$H |
| 2-76 | —CO—CH(CH$_2$CH$_2$—S—CH$_3$)—NHCONH—CH$_3$CH$_2$CH$_2$—SO$_3$H | —CO—CH(CH$_2$CH$_2$—S—CH$_3$)—NHCONH—CH$_3$CH$_2$CH$_2$—SO$_3$H |
| 2-77 | —CO—CH(CH$_2$CH$_2$—S—CH$_3$)—NHCONH—CH$_3$CH$_2$CH$_2$—SO$_3$H | —CO—CH(CH$_2$CH$_2$—S—CH$_3$)—NHCONH—CH$_3$CH$_2$CH$_2$—SO$_3$H |
| 2-78 | —CO—CH(CH$_2$Ph)—NHCONH—CH$_3$CH$_2$CH$_2$—SO$_3$H | —CO—CH(CH$_2$Ph)—NHCONH—CH$_3$CH$_2$CH$_2$—SO$_3$H |
| 2-79 | —COCH$_2$CO—NH—CH$_3$CH$_2$CH$_2$—SO$_3$H | H |
| 2-80 | —COCH$_2$—NHCONH—CH$_3$CH$_2$CH$_2$—SO$_3$H | H |

TABLE 37

| 2-81 | —CO—CH(i-Pr)—NHCONH—CH$_3$CH$_2$CH$_2$—SO$_3$H | H |
|---|---|---|
| 2-82 | —COCH(s-Bu)—NHCONH—CH$_3$CH$_2$CH$_2$—SO$_3$H | H |
| 2-83 | —CO—CH(i-Bu)—NHCONH—CH$_3$CH$_2$CH$_2$—SO$_3$H | H |
| 2-84 | —CO—CH(CH$_2$CH$_2$—S—CH$_3$)—NHCONH—CH$_3$CH$_2$CH$_2$—SO$_3$H | H |
| 2-85 | —CO—CH(CH$_2$CH$_2$—S—C$_2$H$_5$)—NHCONH—CH$_3$CH$_2$CH$_2$—SO$_3$H | H |
| 2-86 | —CO—CH(CH$_2$Ph)—NHCONH—CH$_3$CH$_2$CH$_2$—SO$_3$H | H |

(C) Compound of the formula described below wherein the $R^1$ and $R^2$ are shown in Tables 38 to 42.

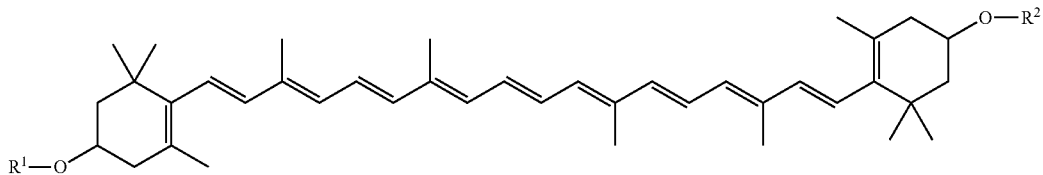

TABLE 38

| Exemplified Compound No. | $R^1$ | $R^2$ |
|---|---|---|
| 3-1 | —COCH$_2$—S—CH$_2$—COOH | —COCH$_2$—S—CH$_2$—COOH |
| 3-2 | —COCH$_2$—S(O)—CH$_2$—COOH | —COCH$_2$—S(O)—CH$_2$—COOH |
| 3-3 | —COCH$_2$—S(O)$_2$—CH$_2$—COOH | —COCH$_2$—S(O)$_2$—CH$_2$—COOH |
| 3-4 | —COCH$_2$—NHCONH$_2$ | —COCH$_2$—NHCONH$_2$ |
| 3-5 | —COCH$_2$CH$_2$—NHCONH$_2$ | —COCH$_2$CH$_2$—NHCONH$_2$ |
| 3-6 | —COCH$_2$CH$_2$CH$_2$—NHCONH$_2$ | —COCH$_2$CH$_2$CH$_2$—NHCONH$_2$ |
| 3-7 | —COCH$_2$—NHCONH—CH$_2$—COOH | —COCH$_2$—NHCONH—CH$_2$—COOH |
| 3-8 | —COCH$_2$—NHCONH—CH(CH$_3$)—COOH | —COCH$_2$—NHCONH—CH(CH$_3$)—COOH |
| 3-9 | —COCH$_2$—NHCONH—CH(i-Pr)—COOH | —COCH$_2$—NHCONH—CH(i-Pr)—COOH |
| 3-10 | —COCH$_2$—NHCONH—CH(s-Bu)—COOH | —COCH$_2$—NHCONH—CH(s-Bu)—COOH |
| 3-11 | —COCH$_2$—NHCONH—CH(i-Bu)—COOH | —COCH$_2$—NHCONH—CH(i-Bu)—COOH |
| 3-12 | —COCH$_2$—NHCONH—CH(CH$_2$CH$_2$—S—CH$_3$)—COOEt | —COCH$_2$—NHCONH—CH(CH$_2$CH$_2$—S—CH$_3$)—COOEt |
| 3-13 | —COCH$_2$—NHCONH—CH(CH$_2$CH$_2$—S—CH$_3$)—COOH | —COCH$_2$—NHCONH—CH(CH$_2$CH$_2$—S—CH$_3$)—COOH |
| 3-14 | —COCH$_2$—NHCONH—CH(CH$_2$Ph)—COOH | —COCH$_2$—NHCONH—CH(CH$_2$Ph)—COOH |
| 3-15 | —COCH$_2$CH$_2$—NHCONH—CH$_2$—COOH | —COCH$_2$CH$_2$—NHCONH—CH$_2$—COOH |
| 3-16 | —COCH$_2$CH$_2$—NHCONH—CH(CH$_3$)—COOH | —COCH$_2$CH$_2$—NHCONH—CH(CH$_3$)—COOH |

TABLE 39

| | | |
|---|---|---|
| 3-17 | —COCH$_2$CH$_2$—NHCONH—CH(i-Pr)—COOH | —COCH$_2$CH$_2$—NHCONH—CH(i-Pr)—COOH |
| 3-18 | —COCH$_2$CH$_2$—NHCONH—CH(s-Bu)—COOH | —COCH$_2$CH$_2$—NHCONH—CH(s-Bu)—COOH |
| 3-19 | —COCH$_2$CH$_2$—NHCONH—CH(i-Bu)—COOH | —COCH$_2$CH$_2$—NHCONH—CH(i-Bu)—COOH |
| 3-20 | —COCH$_2$CH$_2$—NHCONH—CH(CH$_2$CH$_2$—S—CH$_3$)—COOEt | —COCH$_2$CH$_2$—NHCONH—CH(CH$_2$CH$_2$—S—CH$_2$)—COOEt |
| 3-21 | —COCH$_2$CH$_2$—NHCONH—CH(CH$_2$CH$_2$—S—CH$_3$)—COOH | —COCH$_2$CH$_2$—NHCONH—CH(CH$_2$CH$_2$—S—CH$_3$)—COOH |
| 3-22 | —COCH$_2$CH$_2$—NHCONH—CH(CH$_2$Ph)—COOH | —COCH$_2$CH$_2$—NHCONH—CH(CH$_2$Ph)—COOH |
| 3-23 | —COCH$_2$CH$_2$CH$_2$—NHCONH—CH$_2$—COOH | —COCH$_2$CH$_2$CH$_2$—NHCONH—CH$_2$—COOH |
| 3-24 | —COCH$_2$CH$_2$CH$_2$—NHCONH—CH(CH$_3$)—COOH | —COCH$_2$CH$_2$CH$_2$—NHCONH—CH(CH$_3$)—COOH |
| 3-25 | —COCH$_2$CH$_2$CH$_2$—NHCONH—CH(i-Pr)—COOH | —COCH$_2$CH$_2$CH$_2$—NHCONH—CH(i-Pr)—COOH |
| 3-26 | —COCH$_2$CH$_2$CH$_2$—NHCONH—CH(s-Bu)—COOH | —COCH$_2$CH$_2$CH$_2$—NHCONH—CH(s-Bu)—COOH |
| 3-27 | —COCH$_2$CH$_2$CH$_2$—NHCONH—CH(i-Bu)—COOH | —COCH$_2$CH$_2$CH$_2$—NHCONH—CH(i-Bu)—COOH |
| 3-28 | —COCH$_2$CH$_2$CH$_2$—NHCONH—CH(CH$_2$CH$_2$—S—CH$_3$)—COOEt | —COCH$_2$CH$_2$CH$_2$—NHCONH—CH(CH$_2$CH$_2$—S—CH$_3$)—COOEt |

TABLE 40

| | | |
|---|---|---|
| 3-29 | —COCH$_2$CH$_2$CH$_2$—NHCONH—CH(CH$_2$CH$_2$—S—CH$_3$)—COOH | —COCH$_2$CH$_2$CH$_2$—NHCONH—CH(CH$_2$CH$_2$—S—CH$_3$)—COOH |
| 3-30 | —COCH$_2$CH$_2$CH$_2$—NHCONH—CH(CH$_2$Ph)—COOH | —COCH$_2$CH$_2$CH$_2$—NHCONH—CH(CH$_2$Ph)—COOH |
| 3-31 | —COCH$_2$CH$_2$—CO—NH—CH$_2$CH$_2$—SO$_3$H | —COCH$_2$CH$_2$—CO—NH—CH$_2$CH$_2$—SO$_3$H |
| 3-32 | —COCH$_2$CH$_2$—CO—N(CH$_3$)—CH$_2$CH$_2$—SO$_3$H | —COCH$_2$CH$_2$—CO—N(CH$_3$)—CH$_2$CH$_2$—SO$_3$H |
| 3-33 | —COCH$_2$CH$_2$CH$_2$—CO—NH—CH$_2$CH$_2$—SO$_3$H | —COCH$_2$CH$_2$CH$_2$—CO—NH—CH$_2$CH$_2$—SO$_3$H |
| 3-34 | —COCH$_2$CH$_2$CH$_2$CH$_2$—CO—NH—CH$_2$CH$_2$—SO$_3$H | —COCH$_2$CH$_2$CH$_2$CH$_2$—CO—NH—CH$_2$CH$_2$—SO$_3$H |
| 3-35 | —COCH$_2$CH$_2$CH$_2$CH$_2$CH$_2$CH$_2$—CO—NH—CH$_2$CH$_2$—SO$_3$H | —COCH$_2$CH$_2$CH$_2$CH$_2$CH$_2$CH$_2$—CO—NH—CH$_2$CH$_2$—SO$_3$H |
| 3-36 | —CO(CH$_2$)$_8$—CO—NH—CH$_2$CH$_2$—SO$_3$H | —CO(CH$_2$)$_8$—CO—NH—CH$_2$CH$_2$—SO$_3$H |
| 3-37 | —COCH$_2$CH(CH$_3$)—CO—NH—CH$_2$CH$_2$—SO$_3$H | —COCH$_2$CH(CH$_3$)—CO—NH—CH$_2$CH$_2$—SO$_3$H |
| 3-38 | —COCH═CH—CO—NH—CH$_2$CH$_2$—SO$_3$H | —COCH═CH—CO—NH—CH$_2$CH$_2$—SO$_3$H |
| 3-39 | —COC≡C—CO—NH—CH$_2$CH$_2$—SO$_3$H | —COC≡C—CO—NH—CH$_2$CH$_2$—SO$_3$H |
| 3-40 | —CONH—CH$_2$CH$_2$—SO$_3$H | —CONH—CH$_2$CH$_2$—SO$_3$H |
| 3-41 | —COCH$_2$—NHCONH—CH$_2$CH$_2$—SO$_3$H | —COCH$_2$—NHCONH—CH$_2$CH$_2$—SO$_3$H |
| 3-42 | —COCH$_2$CH$_2$—NHCONH—CH$_2$CH$_2$—SO$_3$H | —COCH$_2$CH$_2$—NHCONH—CH$_2$CH$_2$—SO$_3$H |
| 3-43 | —COCH$_2$CH$_2$CH$_2$—NHCONH—CH$_2$CH$_2$—SO$_3$H | —COCH$_2$CH$_2$CH$_2$—NHCONH—CH$_2$CH$_2$—SO$_3$H |

TABLE 41

| | | |
|---|---|---|
| 3-44 | —COCH$_2$—NHCONH—CH$_2$—PO$_3$H | —COCH$_2$—NHCONH—CH$_2$—PO$_3$H |
| 3-45 | —COCH$_2$CH$_2$—NHCONH—CH$_2$CH$_2$—NH—SO$_3$H | —COCH$_2$CH$_2$—NHCONH—CH$_2$CH$_2$—NH—SO$_3$H |
| 3-46 | —CONH—CH(CH$_3$)—CONH—CH$_2$CH$_2$—SO$_3$H | —CONH—CH(CH$_3$)—CONH—CH$_2$CH$_2$—SO$_3$H |
| 3-47 | —CONH—CH(i-Pr)—CONH—CH$_2$CH$_2$—SO$_3$H | —CONH—CH(i-Pr)—CONH—CH$_2$CH$_2$—SO$_3$H |
| 3-48 | —CONH—CH(s-Bu)—CONH—CH$_2$CH$_2$—SO$_3$H | —CONH—CH(s-Bu)—CONH—CH$_2$CH$_2$—SO$_3$H |
| 3-49 | —CONH—CH(i-Bu)—CONH—CH$_2$CH$_2$—SO$_3$H | —CONH—CH(i-Bu)—CONH—CH$_2$CH$_2$—SO$_3$H |
| 3-50 | —CONH—CH(CH$_2$CH$_2$—S—CH$_3$)—CONH—CH$_2$CH$_2$—SO$_3$H | —CONH—CH(CH$_2$CH$_2$—S—CH$_3$)—CONH—CH$_2$CH$_2$—SO$_3$H |
| 3-51 | —CONH—CH(CH$_2$Ph)—CONH—CH$_2$CH$_2$—SO$_3$H | —CONH—CH(CH$_2$Ph)—CONH—CH$_2$CH$_2$—SO$_3$H |
| 3-52 | —CONH—CH(4-hydroxyphenylmethyl)—CONH—CH$_2$CH$_2$—SO$_3$H | —CONH—CH(4-hydroxyphenylmethyl)—CONH—CH$_2$CH$_2$—SO$_3$H |
| 3-53 | —CONH—CH(CH$_2$CONH$_2$)—CONH—CH$_2$CH$_2$—SO$_3$H | —CONH—CH(CH$_2$CONH$_2$)—CONN—CH$_2$CH$_2$—SO$_3$H |
| 3-54 | —CONH—CH(CH$_2$CH$_2$CONH$_2$)—CONH—CH$_2$CH$_2$—SO$_3$H | —CONH—CH(CH$_2$CH$_2$CONH$_2$)—CONH—CH$_2$CH$_2$—SO$_3$H |
| 3-55 | —CONH—CH(CH$_2$OH)—CONH—CH$_2$CH$_2$—SO$_3$H | —CONH—CH(CH$_2$OH)—CONH—CH$_2$CH$_2$—SO$_3$H |

TABLE 42

| | | |
|---|---|---|
| 3-56 | —CONH—CH(CH(CH$_3$)OH)—CONH—CH$_2$CH$_2$—SO$_3$H | —CONH—CH(CH(CH$_3$)OH)—CONH—CH$_2$CH$_2$—SO$_3$H |
| 3-57 | —CONH—CH(CH$_2$CH$_2$CH$_2$CH$_2$NH$_2$)—CONH—CH$_2$CH$_2$—SO$_3$H | —CONH—CH(CH$_2$CH$_2$CH$_2$CH$_2$NH$_2$)—CONH—CH$_2$CH$_2$—SO$_3$H |
| 3-58 | —CONH—CH(CH$_2$CH$_2$CH$_2$CH(NH$_2$)—CONH—CH$_2$CH$_2$—SO$_3$H | —CONH—CH(CH$_2$CH$_2$CH$_2$CH(NH$_2$)—CONH—CH$_2$CH$_2$—SO$_3$H |
| 3-59 | —CONH—CH(CH$_2$CH$_2$CH$_2$—NH(C=NH)NH$_2$)—CONH—CH$_2$CH$_2$—SO$_3$H | —CONH—CH(CH$_2$CH$_2$CH$_2$—NH(C=NH)NH$_2$)—CONH—CH$_2$CH$_2$—SO$_3$H |
| 3-60 | —CONH—CH(CH$_2$COOH)—CONH—CH$_2$CH$_2$—SO$_3$H | —CONH—CH(CH$_2$COOH)—CONH—CH$_2$CH$_2$—SO$_3$H |
| 3-61 | —CONH—CH(CH$_2$CH$_2$COOH)—CONH—CH$_2$CH$_2$—SO$_3$H | —CONH—CH(CH$_2$CH$_2$COOH)—CONH—CH$_2$CH$_2$—SO$_3$H |
| 3-62 | —CONH—CH(CH$_2$SMe)—CONH—CH$_2$CH$_2$—SO$_3$H | —CONH—CH(CH$_2$SMe)—CONH—CH$_2$CH$_2$—SO$_3$H |
| 3-63 | —CONH—CH(CH$_2$S-Hexyl)-CONH—CH$_2$CH$_2$—SO$_3$H | —CONH—CH(CH$_2$S-Hexyl)-CONH—CH$_2$CH$_2$—SO$_3$H |
| 3-64 | [structure: pyrrole-containing dipeptide with COOH] | [structure: pyrrole-containing dipeptide with COOH] |
| 3-65 | [structure: imidazole-containing dipeptide with SO$_3$H] | [structure: imidazole-containing dipeptide with SO$_3$H] |
| 3-66 | [structure: proline-containing amide with SO$_3$H] | [structure: proline-containing amide with SO$_3$H] |
| 3-67 | —COCH$_2$CO—NH—CH$_2$CH$_2$—SO$_3$H | —COCH$_2$CH$_2$CH$_2$—CO—NH—CH$_2$CH$_2$—SO$_3$H |

In the above-mentioned Tables 1 to 42, "Me" represents a methyl group, "Et" represents an ethyl group, "i-Pr" represents an isopropyl group, "i-Bu" represents an isobutyl group, "s-Bu" represents a secondary-butyl group, "t-Bu" and "Bu$^t$" represent a tert-butyl group and "Ph" represents a phenyl group.

In the above-mentioned Tables 1 to 42, the compound (I) of the present invention is preferably the compound of exemplified compound No. 1-1, 1-2, 1-3, 1-35, 1-48, 1-51, 1-54, 1-57, 1-62, 1-63, 1-65, 1-67, 1-74, 1-76, 1-80, 1-82, 1-84, 1-86, 1-88, 1-89, 1-90, 1-100, 1-101, 1-102, 1-103, 1-129, 1-130, 1-132, 1-134, 1-140, 1-142, 1-143, 1-145, 1-147, 1-149, 1-151, 1-152, 1-153, 1-154, 1-160, 1-162, 1-164, 1-166, 1-169, 1-170, 1-172, 1-174, 1-185, 1-187, 1-189, 1-191, 1-193, 1-195, 1-196, 1-201, 1-206, 1-233, 1-365, 1-366, 1-367, 1-372, 1-373, 1-375, 1-378, 1-379, 1-380, 1-384, 1-385, 1-386, 1-387, 1-388, 1-390, 1-392, 1-394, 2-1, 2-10, 2-11, 2-12, 2-13, 2-58, 2-62 or 3-40, and more preferably the compound of exemplified compound No. 1-1, 1-2, 1-3, 1-54, 1-57, 1-62, 1-63, 1-65, 1-67, 1-74, 1-76, 1-80, 1-82, 1-84, 1-86, 1-88, 1-89, 1-90, 1-100, 1-101, 1-102, 1-103, 1-129, 1-130, 1-132, 1-134, 1-142, 1-143, 1-145, 1-154, 1-160, 1-162, 1-166, 1-169, 1-170, 1-172, 1-174, 1-185, 1-187, 1-189, 1-191, 1-193, 1-195, 1-196, 1-206, 1-365, 1-366, 1-367, 1-372, 1-373, 1-375, 1-378, 1-384, 1-385, 1-388, 1-390, 1-392, 1-394, 2-1, 2-10, 2-11, 2-12, 2-13, 2-58 or 2-62.

Even more preferably, the compound (I) of the present invention is the compound of exemplified compound No. 1-1: 4-{18-[4-carboxymethylthioacetoxy-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyloxycarbonylmethylthioacetic acid, the compound of exemplified compound No. 1-2:(4-{18-[4-carboxymethylsulfinylacetoxy)-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyloxycarbonylmethylsulfinyl)acetic acid, the compound of exemplified compound No. 1-102: 3-[2-(4-(18-{4-[3-(3-t-butoxycarbonylmethyl-ureido)propionyloxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonyl)ethyl]ureidoacetic acid t-butyl ester, the compound of exemplified compound No. 1-103: 3-{2-[4-(18-{4-[3-(3-carboxymethylureido)propionyloxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonyl]ethyl}ureidoacetic acid, the compound of exemplified compound No. 2-1: 2-[3-(4-[18-[4-{3-(2-sulfoethylaminocarbonyl)propionyloxy}-2,6,6-trimethyl-3-oxocyclohexa-1-enyl]-3,7,12,16-tetramethyloctadeca-1,3,5,7,9,11,13,15,17-nonaenyl]-3,5,5-trimethyl-2-oxocyclohexa-3-enyloxycarbonyl)propionylamino]ethanesulfonic acid, the compound of exemplified compound No. 2-10: 2-(3,5,5-trimethyl-2-oxo-4-{3,7,12,16-tetramethyl-18-[2,6,6-trimethyl-3-oxo-4-(2-sulfoethylcarbamoyloxy)cyclohexa-1-enyl]octadeca-1,3,5,7,9,11,13,15,17-nonaenyl}cyclohexa-3-enyloxycarbonylamino)ethanesulfonic acid, the compound of exemplified compound No. 1-62: 3-[4-(18-{4-[3-t-butoxycarbonylmethylureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]-ureidoacetic acid t-butyl ester, the compound of exemplified compound No. 1-63: 3-[4-(18-{4-(3-carboxymethylureidoacetoxy)-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureidoacetic acid, the compound of exemplified compound No. 1-365: imidazol-1-ylcarbonylaminoacetic acid 4-[18-(4-{imidazol-1-ylcarbonylaminoacetoxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester, the compound of exemplified compound No. 1-366: 3-(imidazol-1-ylcarbonylamino)propionic acid 4-[18-(4-{3-(imidazol-1-ylcarbonylamino)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester, the compound of exemplified compound No. 1-367: 4-(imidazol-1-ylcarbonylamino)butyric acid 4-[18-(4-{4-(imidazol-1-ylcarbonylamino)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester, the compound of exemplified compound No. 2-11: 2-[3-{4-(18-[4-(3-[2-sulfoethyl]ureidoacetoxy)-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonylmethyl}-ureido]ethanesulfonic acid, the compound of exemplified compound No. 2-12: 2-[3-(2-{4-[18-(4-{3-[3-(2-sulfoethyl)ureido]propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)-ureido]ethanesulfonic acid, the compound of exemplified compound No. 2-13: 2-[3-(3-{4-[18-(4-{4-[3-(2-sulfoethyl)ureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)-ureido]ethanesulfonic acid, the compound of exemplified compound No. 2-58: 2-[3-(1-{4-[18-{4-[2-(3-(2-sulfoethyl)ureido)propionyloxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonyl}ethyl)-ureido]ethanesulfonic acid, the compound of exemplified compound No. 2-62: 2-[3-(1-{4-(18-{4-[2-(3-(2-sulfoethyl)ureido)-4-methylthiobutyryloxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonyl}-3-methylthiopropyl) ureido]ethanesulfonic acid, the compound of exemplified compound No. 1-185: 3-{3-[4-(18-{4-[3-(2-carboxyethyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]-ureido}propionic acid, the compound of exemplified compound No. 1-187: 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid, the compound of exemplified compound No. 1-193: 3-[3-(3-{4-[18-(4-{4-[3-(2-carboxyethyl)ureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)ureido]propionic acid, the compound of exemplified compound No. 1-195: 4-[3-(3-{4-[18-(4-{4-[3-(3-carboxypropyl)ureido]-butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)ureido]butyric acid, the compound of exemplified compound No. 1-65: 2-{3-[4-(18-{4-[3-(1-carboxyethyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]-ureido}propionic acid, the compound of exemplified compound No. 1-76: 3-phenyl-2-{3-[4-(18-{4-[3-(2-phenyl-1-carboxyethyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl] ureido}propionic acid, the compound of exemplified compound No. 1-74: 4-methylthio-2-{3-[4-(18-{4-[3-(3-methylthio-1-carboxypropyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}butyric acid, the compound of exemplified compound No. 1-88: 6-amino-2-{3-[4-(18-{4-[3-(5-amino-1-carboxypentyl)-ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}hexanoic acid, the compound of exemplified compound No. 1-89: 2-amino-6-{3-[4-(18-{4-[3-(5-amino-5-carboxypentyl)-ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}hexanoic acid, the compound of exemplified compound No. 1-375: 2-amino-5-{3-[4-(18-{4-[3-(4-amino-4-carboxybutyl)-ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}pentanoic acid, the compound of exemplified compound No. 1-90: 5-guanidyl-2-{3-[4-(18-{4-[3-(1-carboxy-4-guanidyl-butyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}pentanoic acid, the compound of exemplified compound No. 1-189: 3-[3-(2-{4-[18-(4-{3-[3-(2-carboxyethyl)ureido]-propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]propionic acid, the compound of exemplified compound No. 1-191: 4-[3-(2-{4-[18-(4-{3-[3-(3-carboxypropyl)ureido]propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]butyric acid, the compound of exemplified compound No. 1-143: 3-(3-{4-[18-(4-{4-[3-carboxymethylureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}-propyl)ureidoacetic acid, the compound of exemplified compound No. 1-134: 4-carboxy-4-(3-<2-{4-[18-(4-{3-(3-[1,3-dicarboxypropyl]ureido)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl>ureido)butyric acid, the compound of exemplified compound No. 1-132: 3-carboxy-3-(3-<2-{4-[18-(4-{3-(3-[1,2-dicarboxyethyl]ureido)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl>ureido)propionic acid, the compound of exemplified compound No. 1-129: 2-amino-6-(3-<2-{4-[18-(4-{3-(3-[5-amino-5-carboxypentyl]ureido)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl>ureido)hexanoic acid, the compound of exemplified compound No. 1-174: 4-carboxy-4-(3-<3-{4-[18-(4-{4-(3-[1,3-dicarboxypropyl]ureido)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl>ureido)butyric acid, the compound of exemplified compound No. 1-172: 3-carboxy-3-(3-<3-{4-[18-(4-{4-(3-[1,2-dicarboxyethyl]ureido)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl>ureido)propionic acid, the compound of exemplified compound No. 1-169: 2-amino-6-(3-<3-{4-[18-(4-{4-(3-[5-amino-5-carboxypentyl]ureido)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl>ureido)hexanoic acid, the compound of exemplified compound No. 1-373: 2-amino-5-(3-<2-{4-[18-(4-{3-(3-[4-amino-4-carboxybutyl]ureido)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl>ureido)pentanoic acid, the compound of exemplified compound No. 1-372: 2-amino-5-(3-<3-{4-[18-(4-{4-(3-[4-amino-4-carboxybutyl]ureido)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl>ureido)pentanoic acid, 2Na salt of the compound of exemplified compound No. 1-187: 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid disodium salt, dilysine salt of the compound of exemplified compound No. 1-187: 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid dilysine salt, the compound of exemplified compound No. 1-378: 3-isobutyl-4-(3-{4-[18-(4-[3-(2-isobutyl-3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid, the compound of exemplified compound No. 1-385: 1-(3-{4-[18-(4-[3-(1-carboxymethyl-cyclohexylmethyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureidomethyl)cyclohexylacetic acid, 2Na salt of the compound of exemplified compound No. 2-12: 2-[3-(2-{4-[18-(4-{3-[3-(2-sulfoethyl)ureido]propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]ethanesulfonic acid disodium salt, dilysine salt of the compound of exemplified compound No. 2-12: 2-[3-(2-{4-[18-(4-{3-[3-(2-sulfoethyl)ureido]propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]ethanesulfonic acid dilysine salt, the compound of exemplified compound No. 1-384: 3-isobutyl-4-[3-{2-isobutyl-3-[4-(18-[4-{3-isobutyl-4-[3-(2-isobutyl-3-carboxypropyl)ureido]butyryloxy}-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonyl]-propyl}ureido]butyric acid, the compound of exemplified compound No. 1-388: 1-(3-[1-{4-(18-[4-{1-(3-[1-carboxymethyl-cyclohexylmethyl]ureidomethyl)cyclohexylacetoxy}-2,6,6-trimethyl-3-oxocyclohexa-1-enyl]-3,7,12,16-tetramethyloctadeca-1,3,5,7,9, 11,13,15,17-nonaenyl)-3,5,5-trimethyl-2-oxocyclohexa-3-enyloxycarbonylmethyl}-cyclohexylmethyl]ureidomethyl)cyclohexylacetic acid, the compound of exemplified compound No. 1-390: 6-(3-{4-(18-[4-{3-(6-carboxymethyl-3-ethylbicyclo[3,2,0]hepta-3-en-6-ylmethyl)ureidomethylacetoxy}-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonylmethyl}ureidomethyl)-3-ethylbicyclo[3,2,0]hepta-3-en-6-ylacetic acid, the compound of exemplified compound No. 1-392: 6-(3-[3-{4-(18-[4-[4-{3-(6-carboxymethyl-3-ethylbicyclo[3,2,0]hepta-3-en-6-ylmethyl)-ureido}butyryloxy]-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonyl}propyl}ureidomethyl)-3-ethylbicyclo[3,2,0]hepta-3-en-6-ylacetic acid or the compound of exemplified compound No. 1-394: 6-(3-[6-{4-(18-[4-[6-{3-(6-carboxymethyl-3-ethylbicyclo[3,2,0]hepta-3-en-6-ylmethyl)ureidomethyl}-3-ethylbicyclo[3,2,0]hepta-3-en-6-ylacetoxy]-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonylmethyl}-3-ethylbicyclo[3,2,0]hepta-3-en-6-ylmethyl]ureidomethyl)-3-ethylbicyclo[3,2,0]hepta-3-en-6-ylacetic acid.

Most preferably, the compound (I) of the present invention is the compounds of exemplified compound No. 1-63, 1-74, 1-89, 1-90, 1-103, 1-129, 1-132, 1-134, 1-143, 1-169, 1-172, 1-174, 1-185, 1-187, 1-189, 1-191, 1-193, 1-195, 1-372, 1-373, 1-375, 1-378, 1-385, 2-1, 2-10, 2-11, 2-12, 2-13, 2-58 or 2-62.

The compound of the present invention having the general formula (I) can be produced in accordance with any methods of <Method A> to <Method G> shown below.

<Method A>

This method for removing the protective groups is performed by a known method in organic chemistry, namely, (a) a method for reacting the compound (I') with an acid in an inert solvent or (b) a method for reacting the compound (I') with a base in an inert solvent.

When the protective group of a carboxyl group is a triphenylmethyl group or a $C_1$-$C_6$ alkyl group, the protective group can be removed by using (a) a method for reacting the compound (I') with an acid.

The solvent to be used is not particularly limited, as long as it is inert to the present reaction, but it may be, for example, an aliphatic hydrocarbon such as hexane, heptane, ligroin and petroleum ether; an aromatic hydrocarbon such as benzene, toluene and xylene; a halogenated hydrocarbon such as chloroform, methylene chloride, 1,2-dichloroethane and carbon tetrachloride; an ether such as diethyl ether, diisopropyl ether, tetrahydrofuran, dioxane, dimethoxyethane and diethylene glycol dimethyl ether; an amide such as dimethylformamide, dimethylacetoamide and hexamethylphosphoric triamide; an alcohol such as methanol, ethanol and propanol; an organic acid such as trifluoroacetic acid, acetic acid and propionic acid; water; or a mixed solvent of these solvents, and it is preferably a halogenated hydrocarbon, an ether, an alcohol, an amide, water or a mixed solvent of these solvents, more preferably a halogenated hydrocarbon, an alcohol, an ether, water or a mixed solvent of these solvents and most preferably a halogenated hydrocarbon, water, methanol, ethanol, dioxane, tetrahydrofuran or a mixed solvent of water and these organic solvents (when the protective group is a $C_1$-$C_6$ alkyl group).

The acid to be used is not particularly limited, as long as it is used in an ordinary reaction as an acid, but it may be, for example, an, inorganic acid such as hydrochloric acid, hydrobromic acid, sulfuric acid, perchloric acid and phosphoric acid; an organic acid such as acetic acid, formic acid, oxalic acid, methanesulfonic acid, p-toluenesulfonic acid, camphorsulfonic acid, trifluoroacetic acid and trifluo-

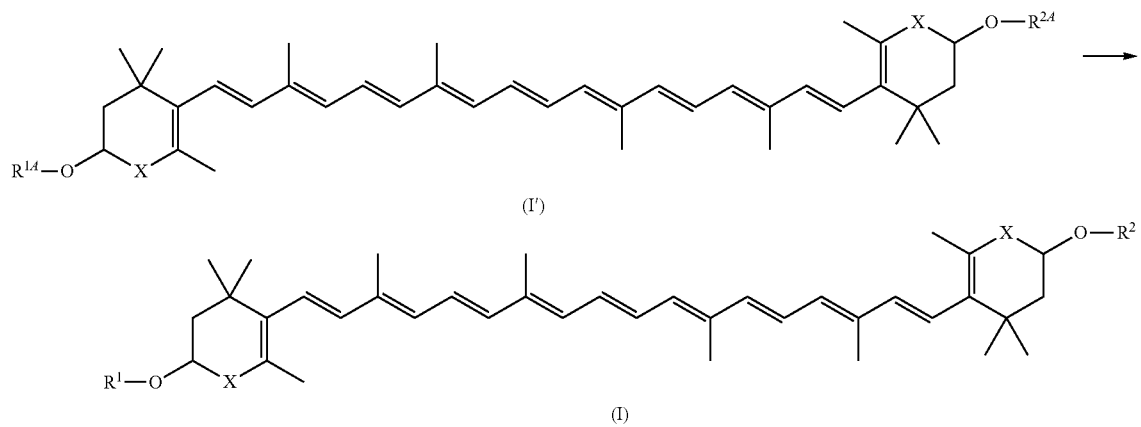

wherein $R^1$ and $R^2$ represent the same meanings as those described above, and $R^{1A}$ and $R^{2A}$ represent those in which the hydroxy group, the primary amino group, the secondary amino group or the carboxyl group in the groups A, D, E and G contained in $R^1$ and $R^2$ are protected.

Method A is a method for producing the compound having the general formula (I) and it is achieved by removing the protective group of the compound having a general formula (I').

romethanesulfonic acid; a Lewis acid such as zinc chloride, tin tetrachloride, boron trichloride, boron trifluoride and boron tribromide; or an acidic ion exchange resin and it is preferably an inorganic acid or an organic acid, and most preferably hydrochloric acid, acetic acid or trifluoroacetic acid.

The reaction temperature varies, depending on the raw material compounds, the acid, the solvent and so on, but it is usually −20° C. to 150° C. and preferably 10° C. to 100° C.

The reaction time varies, depending on the raw material compounds, the solvent, the reaction temperature and so on, but it is usually 30 minutes to 10 days and preferably 2 hours to 5 days.

When the protective group is a $C_1$-$C_6$ alkyl group, the protective group can be removed by using (b) a method of reacting the compound (I') with a base.

The solvent to be used is not particularly limited, as long as it is inert to the present reaction, but it may be those used in the above-mentioned "reaction (a)", and it is preferably a halogenated hydrocarbon, an ether, an alcohol, an amide, water or a mixed solvent of these solvents, more preferably water, an alcohol, an ether or a mixed solvent with water and most preferably water, methanol, ethanol, dioxane, tetrahydrofuran or a mixed solvent of water and these organic solvents.

The base to be used is not particularly limited, as long as it is used as a base in an ordinary reaction and it does not have influence on other moieties of the compound, but it may be an alkali metal carbonic acid salt such as lithium carbonate, sodium carbonate and potassium carbonate; an alkali metal hydrogen carbonic acid salt such as lithium hydrogen carbonate, sodium hydrogen carbonate and potassium hydrogen carbonate; an alkali metal hydroxide such as lithium hydroxide, sodium hydroxide and potassium hydroxide; a metal alkoxide such as lithium methoxide, sodium methoxide, sodium ethoxide and potassium t-butoxide; ammonia such as ammonia water and conc. ammonia-methanol; or an organic amine such as ethylamine, propylamine, isopropylamine, triethylamine, n-butylamine, dibutylamine, tributylamine, N,N-diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2]octane (DABCO) and 1,8-diazabicyclo[5.4.0]-7-undecene (DBU), and it is preferably an alkali metal hydroxide, an alkali metal carbonic acid salt or an organic amine and most preferably lithium hydroxide, sodium hydroxide, potassium hydroxide, potassium carbonate, propylamine or butylamine.

The reaction temperature and the reaction time are similar to those applied to the above-mentioned "reaction (a)".

When the protective group of the primary and the secondary amino groups is a t-butoxycarbonyl group, the protective group can be removed by using a method of reacting the compound (I') with an acid.

The solvent to be used is not particularly limited, as long as it is inert to the present reaction, but it may be an aliphatic hydrocarbon such as hexane, heptane, ligroin and petroleum ether; an aromatic hydrocarbon such as benzene, toluene and xylene; a halogenated hydrocarbon such as chloroform, methylene chloride, 1,2-dichloroethane and carbon tetrachloride; an ether such as diethyl ether, diisopropyl ether, tetrahydrofuran, dioxane, dimethoxyethane and diethylene glycol dimethyl ether; an amide such as dimethylformamide, dimethylacetoamide and hexamethylphosphoric triamide; an alcohol such as methanol, ethanol and propanol; an organic acid such as trifluoroacetic acid, acetic acid and propionic acid; water; or a mixed solvent of these solvents, and it is preferably a halogenated hydrocarbon, an ether, an alcohol, an amide, water or a mixed solvent of these solvents, more preferably a halogenated hydrocarbon, an alcohol or an ether and most preferably a halogenated hydrocarbon, methanol, ethanol, dioxane, tetrahydrofuran or a mixed solvent of these organic solvents.

The acid to be used is not particularly limited, as long as it is used in an ordinary reaction as an acid, but it may be an inorganic acid such as hydrochloric acid, hydrobromic acid, sulfuric acid, perchloric acid and phosphoric acid; an organic acid such as acetic acid, formic acid, oxalic acid, methanesulfonic acid, p-toluenesulfonic acid, camphorsulfonic acid, trifluoroacetic acid and trifluoromethanesulfonic acid; a Lewis acid such as zinc chloride, tin tetrachloride, boron trichloride, boron trifluoride and boron tribromide; or an acidic ion exchange resin, and it is preferably an inorganic acid or an organic acid and most preferably hydrochloric acid, acetic acid or trifluoroacetic acid.

The reaction temperature varies, depending on the raw material compounds, the acid, the solvent and so on, but it is usually −20° C. to 150° C. and preferably 0° C. to 80° C.

The reaction time varies, depending on the raw material compounds, the acid, the solvent, the reaction temperature and so on, but it is usually 30 minutes to 3 days and preferably 1 hour to 2 days.

When the protective group of the hydroxy group is a $C_1$-$C_6$ alkylacyl group, the protective group can be removed by applying the deprotection reaction of the carboxy group described above.

<Method B>

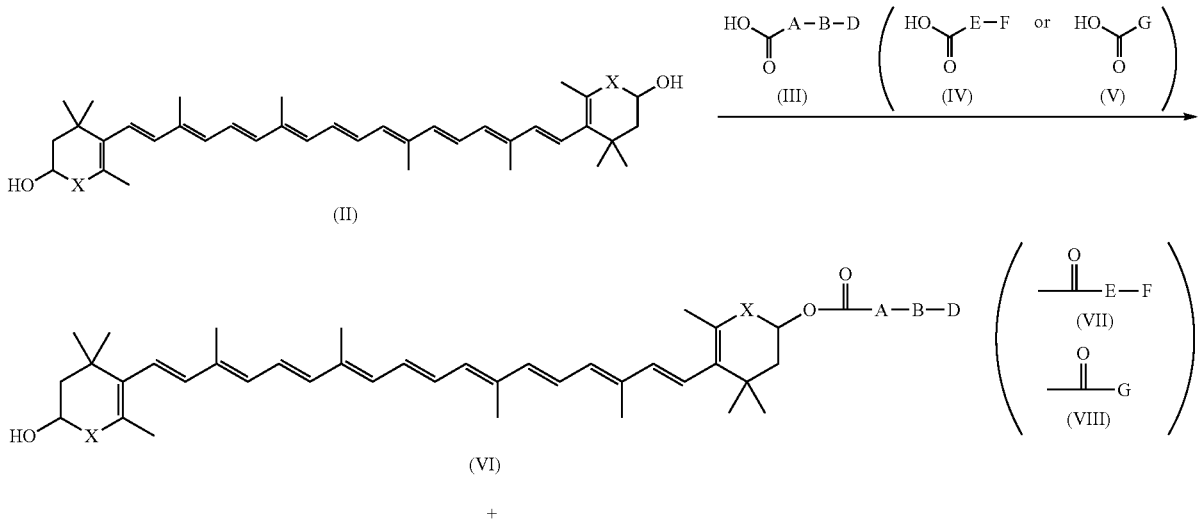

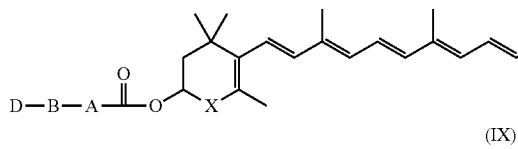
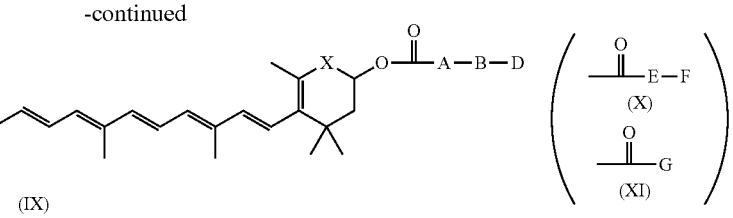

(IX)        (XI)

wherein X, A, B, D, E, F and G represent the same meanings as those described above, provided that the hydroxy group and the amino group in A, D, E and G are protected and the carboxy group may be protected or not.

Method B is a method for producing a compound having general formulae (VI) to (VIII) or/and general formulae (IX) to (XI) and it is achieved by dehydration condensation of a compound having a general formula (II) and a compound having general formulae (III) to on.

(a) Acid Halide Method

An acid halide method is performed by reacting a compound having general formulae (III) to (V) with a halogenating agent (for example, it may be thionyl chloride, thionyl bromide, oxalyl chloride, oxalyl dichloride, phosphorus oxychloride, phosphorus trichloride or phosphorus pentachloride and it is preferably oxalyl dichloride) in an inert solvent and by reacting the obtained acid halide or the acid addition salt thereof with a compound (II) in an inert solvent in the presence or the absence of a base (preferably in the presence).

The base to be used is, for example, an alkali metal carbonic acid salt such as lithium carbonate, sodium carbonate and potassium carbonate; an alkali metal hydrogen carbonic acid salt such as lithium hydrogen carbonate, sodium hydrogen carbonate and potassium hydrogen carbonate; an alkali metal hydride such as lithium hydride, sodium hydride and potassium hydride; an alkali metal hydroxide such as lithium hydroxide, sodium hydroxide and potassium hydroxide; an alkali metal alkoxide such as lithium methoxide, sodium methoxide, sodium ethoxide and potassium t-butoxide; or an organic amine such as triethylamine, tributylamine, N,N-diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) and 1,8-diazabicyclo[5.4.0]-7-undecene (DBU) and it is preferably an organic amine and most preferably triethylamine, 4-(N,N-dimethylamino)pyridine or N,N-diisopropylethylamine.

The solvent to be used is not particularly limited, as long as it is inert to the present reaction, but it may be, for example, an aliphatic hydrocarbon such as hexane, heptane, ligroin and petroleum ether; an aromatic hydrocarbon such as benzene, toluene and xylene; a halogenated hydrocarbon such as methylene chloride, chloroform, 1,2-dichloroethane and carbon tetrachloride; an ether such as diethyl ether, diisopropyl ether, tetrahydrofuran, dioxane, dimethoxyethane and diethylene glycol dimethyl ether; a ketone such as acetone; an amide such as formamide, dimethylformamide, dimethylacetoamide and hexamethylphosphoric acid triamide; a sulfoxide such as dimethyl sulfoxide; or sulfolane, and it is preferably a halogenated hydrocarbon, an ether or an amide and most preferably methylene chloride, chloroform, tetrahydrofuran, dioxane or dimethylformamide.

The reaction temperature varies, depending on the raw material compounds, the halogenating agent and so on, but it is usually −20° C. to 150° C. in the reaction of the halogenating agent with a compound having general formulae (III) to (V) and also in the reaction of an acid halides with the compound (II) and preferably −10° C. to 100° C. in the reaction of the halogenating agent with the compound having general formulae (III) to (V) and −20° C. to 100° C. in the reaction of the acid halide with the compound (II).

The reaction time varies, depending on the raw material compounds, the halogenating agent, the reaction temperature and so on, but it is usually 30 minutes to 80 hours and preferably 1 hour to 48 hours in the reaction of the halogenating agent with the compound having the formulae (III) to (V) and also in the reaction of the acid halide with the compound (II).

(b) Active Ester Method

An active ester method is performed by reacting a compound having the general formulae (III) to (V) with an active esterifying agent in an inert solvent and by reacting the obtained active ester with the compound (II) in the presence or the absence of a base (preferably in the presence) in an inert solvent. In addition, the active ester method is also performed by adding an active esterifying agent and a base in the presence of the compound having the general formulae (III) to (V) and the compound having the formula (II).

The active esterifying agent to be used may be, for example, an N-hydroxy compound such as N-hydroxysuccinimide, 1-hydroxybenzotriazole and N-hydroxy-5-norbornen-2,3-dicarboxyimide; a disulfide compound such as dipyridyl disulfide; a carbodiimide such as N,N'-diisopropylcarbodiimide, dicyclohexylcarbodiimide, 1-ethyl-3-(3-di-methylaminopropyl)carbodiimide hydrochloride and bis-(trimethylsilyl)carbodiimide; 1,1'-carbonylbis-1H-imidazole; 4-(4,6-dimethoxy-1,3,5-triazin-2-yl)-4-methylmorpholinium chloride (DMTMM), diphenylphosphoric acid azide, hexafluorophosphoric acid benzotriazol-1-yloxy-tris(dimethylamino)phosphonium or triphenylphopshine and it is preferably N,N'-diisopropylcarbodiimide, dicyclohexylcarbodiimide, 1-ethyl-3-(3-dimethylaminopropyl)carbodiimide hydrochloride, 4-(4,6-dimethoxy-1,3,5-triazin-2-yl)-4-methylmorpholinium chloride (DMTMM), diphenyl phosphoric acid azide or 1,1'-carbonylbis-1H-imidazole and most preferably N,N'-diisopropylcarbodiimide, 1-ethyl-3-(3-dimethylaminopropyl)-carbodiimide hydrochloride, 4-(4,6-dimethoxy-1,3,5-triazin-2-yl)-4-methylmorpholinium chloride (DMTMM) or 1,1'-carbonylbis-1H-imidazole.

The solvent to be used is not particularly limited, as long as it is inert to the present reaction, but it may be, for example, an aliphatic hydrocarbon such as hexane, heptane, ligroin and petroleum ether; an aromatic hydrocarbon such as benzene, toluene and xylene; a halogenated hydrocarbon such as methylene chloride, 1,2-dichloroethane and carbon tetrachloride; an ether such as diethyl ether, diisopropyl ether, tetrahydrofuran, dioxane, dimethoxyethane and diethylene glycol dimethyl ether; a ketone such as acetone; an amide such as formamide, dimethylformamide, dimethylacetoamide and hexamethylphosphoric triamide; a sulfoxide such as dimethyl sulfoxide; or sulfolane, and it is preferably a halogenated hydrocarbon, an ether or an amide and most preferably methylene chloride, 1,2-dichloroethane, dioxane, tetrahydrofuran or dimethylformamide.

The base to be used is, for example, a base similar to those used in the above-mentioned "(a) acid halide method", and it is preferably an organic amine and most preferably triethylamine, N,N-diisopropylethylamine or 4-(N,N-dimethylamino)pyridine.

The reaction temperature varies, depending on the raw material compounds, the base, the active esterifying agent and so on, but it is usually −70° C. to 150° C. and preferably −10° C. to 100° C. in the active esterification reaction, and -20° C. to 100° C. and preferably 0° C. to 50° C. in a reaction of the active ester with the compound (II).

The reaction time varies, depending on the raw material compounds, the base, an active esterifying agent, the reaction temperature and so on, but, in the active esterification reaction and also the reaction of the active ester with the compound (II), it is usually 30 minutes to 10 days and preferably 1 hour to 48 hours.

(c) Mixed Acid Anhydride Method

A mixed acid anhydride method is performed by reacting a compound having the general formulae (III) to (V) with a mixed acid anhydride reagent in the presence or the absence of a base (preferably in the presence) in an inert solvent and by reacting the obtained mixed acid anhydride with a compound (II) in an inert solvent.

The base to be used may be, for example, an alkali metal carbonic acid salt such as lithium carbonate, sodium carbonate and potassium carbonate; an alkali metal hydrogen carbonic acid salt such as lithium hydrogen carbonate, sodium hydrogen carbonate and potassium hydrogen carbonate; an alkali metal hydride such as lithium hydride, sodium hydride and potassium hydride; an alkali metal hydroxide such as lithium hydroxide, sodium hydroxide and potassium hydroxide; an alkali metal alkoxide such as lithium methoxide, sodium methoxide, sodium ethoxide and potassium t-butoxide; or an organic amine such as triethylamine, tributylamine, N,N-diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) and 1,8-diazabicyclo[5.4.0]-7-undecene (DBU), and it is preferably an organic amine and most preferably triethylamine, N,N-diisopropylethylamine or 4-(N,N-dimethylamino)pyridine.

The mixed acid anhydride reagent to be used is, for example, a $C_1$-$C_6$ alkyl haloformate such as ethyl chloroformate and isobutyl chloroformate; a $C_1$-$C_6$ alkanoyl halide such as pivaloyl chloride; or a di-$C_1$-$C_6$ alkyl or di-$C_6$-$C_{14}$ aryl cyanophosphoric acid such as diethyl cyanophosphonate and diphenyl cyanophosphonate, and it is preferably isobutyl chloroformate, di-$C_1$-$C_4$ alkyl cyanophosphoric acid or diphenyl cyanophosphoric acid and most preferably isobutyl chloroformate or diethyl cyanophosphonate.

The inert solvent to be used in production of the mixed acid anhydride is not particularly limited, as long as it does not inhibit the reaction and dissolves a starting substance to some degree, but it may be, for example, an aliphatic hydrocarbon such as hexane, heptane, ligroin and petroleum ether; an aromatic hydrocarbon such as benzene, toluene and xylene; a halogenated hydrocarbon such as methylene chloride, 1,2-dichloroethane and carbon tetrachloride; an ether such as diethyl ether, diisopropyl ether, tetrahydrofuran, dioxane, dimethoxyethane and diethylene glycol dimethyl ether; a ketone such as acetone; an amide such as formamide, dimethylformamide, dimethylacetoamide and hexamethylphosphoric triamide; a sulfoxide such as dimethyl sulfoxide; or sulfolane, and it is preferably a halogenated hydrocarbon, an ether or an amide and most preferably methylene chloride, tetrahydrofuran or dimethylformamide.

The reaction temperature in the production of the mixed acid anhydride varies, depending on the raw material compounds, the base, the mixed acid anhydride agent and so on, but it is usually −50° C. to 100° C. and preferably −20° C. to 60° C.

The reaction time in the production of the mixed acid anhydride varies, depending on the raw material compounds, the base, the mixed acid anhydride reagent, the reaction temperature and so on, but it is usually 30 minutes to 1 week and preferably 1 hour to 3 days.

The reaction of the mixed acid anhydride with the compound (II) is performed in the presence or the absence of a base (preferably in the presence) in an inert solvent, and the base and the inert solvent to be used are similar to those used in the reaction of producing the above-mentioned mixed acid anhydride.

The reaction temperature of the mixed acid anhydride with the compound (II) varies, depending on the raw material compounds, the base and so on, but it is usually from −30° C. to 100° C. and preferably 0° C. to 80° C.

The reaction time of the mixed acid anhydride with the compound (II) varies, depending on the raw material compounds, the base, the reaction temperature and so on, but it is usually 5 minutes to 24 hours and preferably 30 minutes to 16 hours.

In addition, when a di-$C_1$-$C_6$ alkyl cyanophosphoric acid or di-$C_6$-$C_{14}$ aryl cyanophosphoric acid is used in the present Method B reaction, the compound (II) and the compound having the formulae (III) to (V) can be also reacted directly in the presence of a base.

After completion of the Method B reaction, the objective compound in the each reaction is collected from the reaction solution in accordance with an ordinary method. For example, the reaction solution is suitably neutralized or when an insoluble substance is present, the insoluble substance is suitably removed by filtration; water and an organic solvent immiscible with water such as ethyl acetate or methylene chloride are added thereto; an organic layer containing the objective compound is isolated, washed with, for example, water, dried over anhydrous magnesium sulfate, anhydrous sodium sulfate, anhydrous sodium hydrogen carbonate and so on; and the solvent is distilled off, whereby to obtain the objective compound of the each reaction. In addition, if necessary, in accordance with an ordinary method (for example, recrystallization, silica gel column chromatography and so on), the objective compound can be further purified (or the reaction mixture can be directly purified).

<Method C>

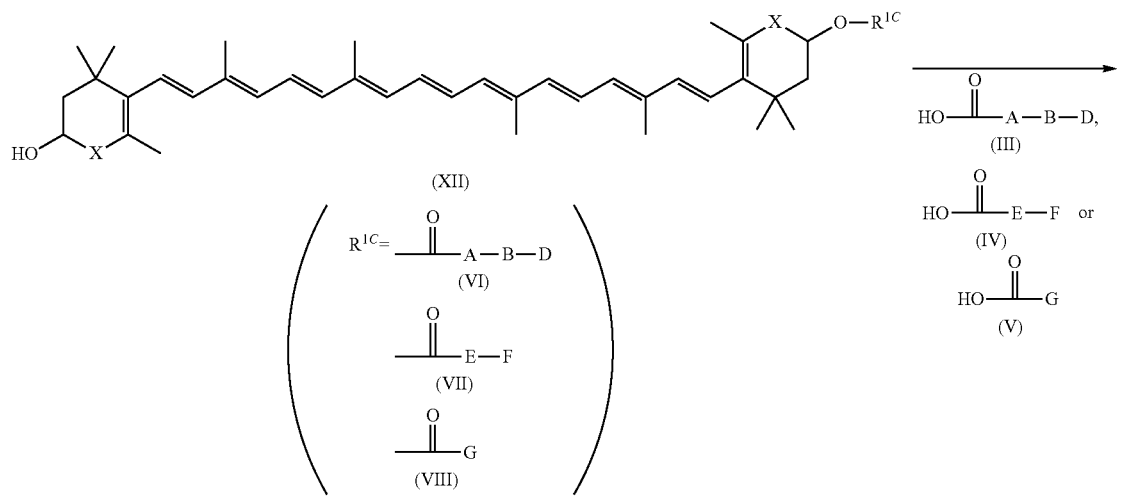

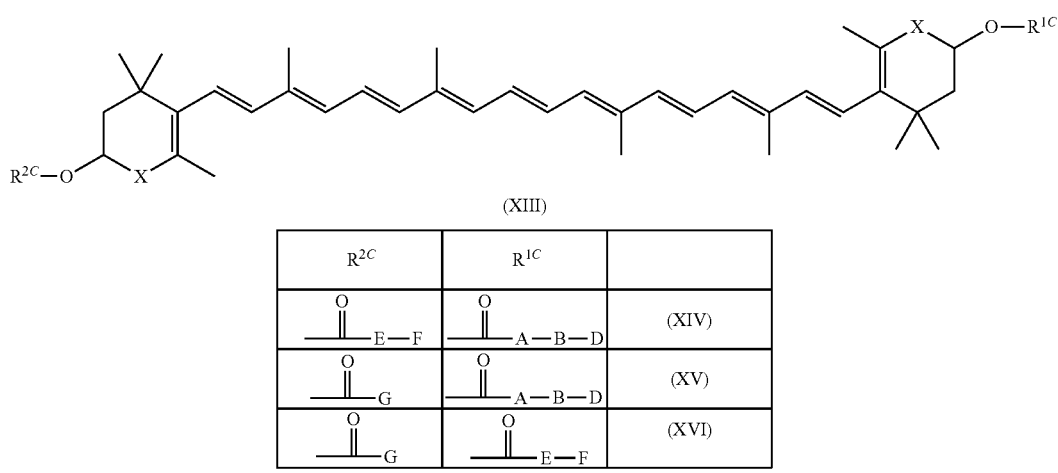

| $R^{2C}$ | $R^{1C}$ | |
|---|---|---|
| ─C(=O)─E─F | ─C(=O)─A─B─D | (XIV) |
| ─C(=O)─G | ─C(=O)─A─B─D | (XV) |
| ─C(=O)─G | ─C(=O)─E─F | (XVI) | wherein X, A, B, D, E, F and G represent the same meanings as those described above, and $R^{1C}$ and $R^{2C}$ are different and represent the group of —CO-A-B-D, the group of —CO-E-F or the group of —CO-G. However, the hydroxy group and the amino group in A, D, E and G are protected and the carboxy group may not be protected.

Method C is a method for producing compounds having general formulae (XIV) to (XVI) (compounds of formula (I) wherein $R^1$ and $R^2$ are different), and it is achieved by dehydration condensation of a compound having a general formula (XII) and a compound having general formulae (III) to (V). However, as represented by the general formula (XIII), $R^{1C}$ and $R^{2C}$ in the compounds are in the different combination.

The present reaction is performed similarly to the Method B described before.

<Method D>

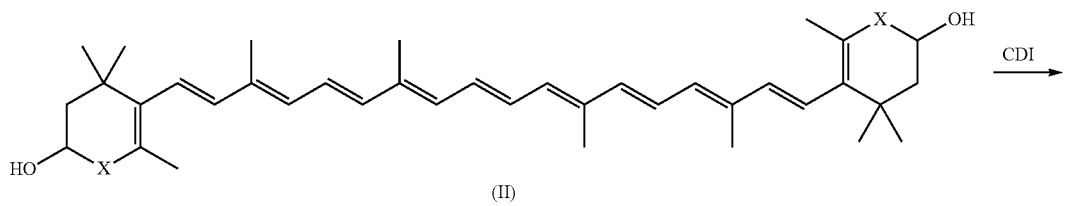

-continued

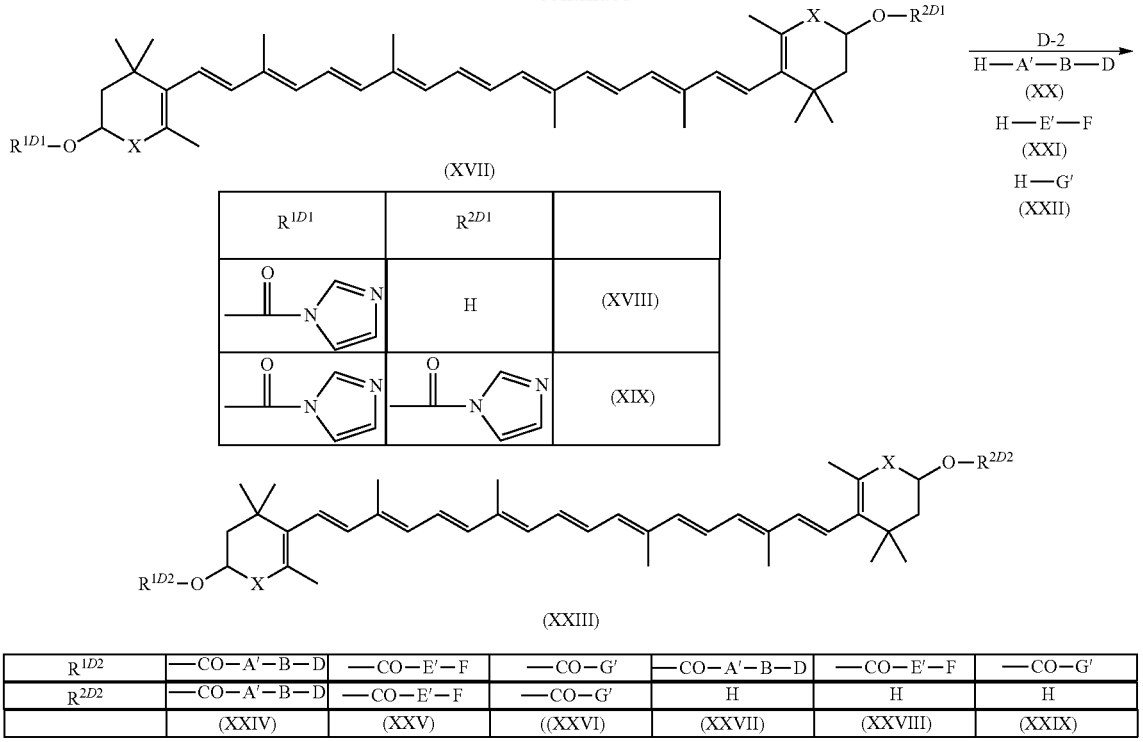

(XVII)

| $R^{1D1}$ | $R^{2D1}$ | |
|---|---|---|
| ![imidazole-carbonyl] | H | (XVIII) |
| ![imidazole-carbonyl] | ![imidazole-carbonyl] | (XIX) |

(XXIII)

| $R^{1D2}$ | —CO—A'—B—D | —CO—E'—F | —CO—G' | —CO—A'—B—D | —CO—E'—F | —CO—G' |
|---|---|---|---|---|---|---|
| $R^{2D2}$ | —CO—A'—B—D | —CO—E'—F | —CO—G' | H | H | H |
| | (XXIV) | (XXV) | ((XXVI) | (XXVII) | (XXVIII) | (XXIX) | wherein X, B, D, and F represent the same meanings as those described above; CDI represents 1,1'-carbonylbis-1H-imidazole; $R^{1D1}$ represents an imidazol-1-ylcarbonyl group; $R^{2D1}$ represents an imidazol-1-ylcarbonyl group or a hydrogen atom; $R^{1D2}$ represents a group of —CO-A'-B-D wherein A' is A described above in which the moiety bound to the carbonyl group is an oxygen atom or a primary or secondary amino group, a group of —CO-E'-F wherein E' is E described above in which the moiety bound to a carbonyl group is an oxygen atom or a primary or secondary amino group, or a group of —CO-G' wherein G' is G described above in which the moiety bound to a carbonyl group is an oxygen atom or a primary or secondary amino group; and $R^{2D2}$ represents the same meaning as $R^{1D2}$ or a hydrogen atom. However, the hydroxy group and the amino group in A, D, E and G are protected, and the carboxy group may not be protected.

Method D is a method for producing compounds having general formulae (XXIV) to (XXIX).

The first step is a step for producing a compound having a general formula (XVII) [(XVIII) to (XIX)]. This step is achieved by reacting a compound having formula (II) with 1,1'-carbonylbis-1H-imidazole.

The present reaction is performed similarly to the (b) active ester method in the above-mentioned Method B. A base may be absent in the present reaction.

The second step is a step for producing a compound having a general formula (XXIII) [(XXIV) and (XXIX)]. This step is achieved by reacting a compound having a general formula (XVII) with a compound having general formulae (XX) to (XXII).

When the compounds having the general formulae (XX), (XXI) and (XXII) have a carboxy group, a hydroxyl group or a sulfo group in this step, these compounds may be previously reacted with chlorotrimethylsilane in the presence of a base to silylate these groups and this step may be performed without isolating the silylated compounds.

The present reaction is performed similarly to the (b) active ester method in the above-mentioned Method B.

The solvent to be used is not particularly limited as long as it is inert to the present reaction, but it may be, for example, an aliphatic hydrocarbon such as hexane, heptane, ligroin and petroleum ether; an aromatic hydrocarbon such as benzene, toluene and xylene; a halogenated hydrocarbon such as methylene chloride, 1,2-dichloroethane and carbon tetrachloride; an ether such as diethyl ether, diisopropyl ether, tetrahydrofuran, dioxane, dimethoxyethane and diethylene glycol dimethyl ether; a ketone such as acetone; an amide such as formamide, dimethylformamide, dimethylacetoamide and hexamethylphosphoric triamide; a sulfoxide such as dimethyl sulfoxide; or sulfolane, and it is preferably a halogenated hydrocarbon, an ether or an amide and most preferably methylene chloride, 1,2-dichloroethane, dioxane, tetrahydrofuran or dimethylformamide.

The base to be used is, for example, a base similar to those used in the Method B described before, and it is preferably an organic amine and most preferably 4-(N,N-dimethylamino)pyridine, triethylamine or N,N-diisopropylethylamine.

The reaction temperature varies, depending on the raw material compounds, the compounds having the formulae (II) and (XVII) and so on, but it is usually −70° C. to 150° C. and preferably −10° C. to 100° C. in the reaction of the first step, and it is −20° C. to 100° C. and preferably 0° C. to 50° C. in the reaction of the second step.

The reaction time varies, depending on the raw material compounds, the compounds having the general formulae (II) and (XVII), the reaction temperature and so on, but it is usually 30 minutes to 10 days and preferably 1 hour to 48 hours.

<Method E>

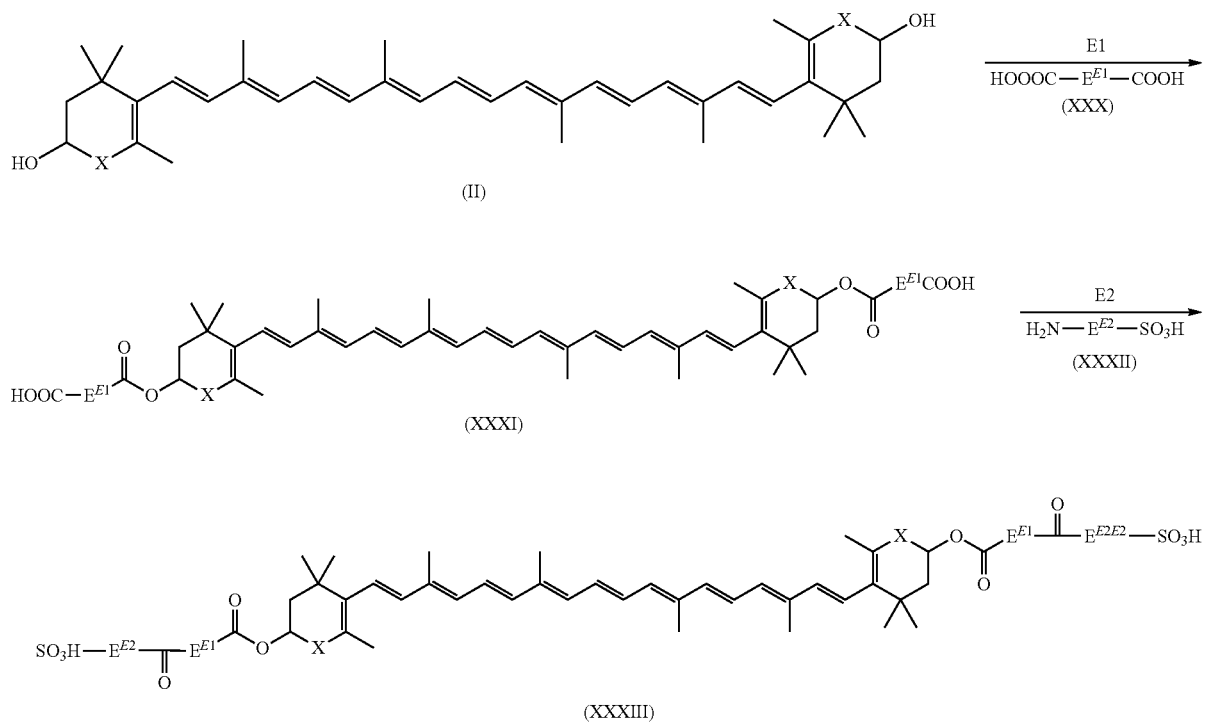

wherein X represents the same meaning as those described above and $E^{E1}$ and $E^{E2}$ are groups to form E together with —CONH— in the general formula (XXXIII). However, the hydroxy group and the amino group in $E^{E1}$ and $E^{E2}$ are protected and the carboxy group may not be protected.

Method E is a method for producing a compound having a general formula (XXXIII).

The first step is a step for producing a compound having a general formula (XXXI). This step is achieved by reacting a compound having a general formula (II) with a compound having a general formula (XXX).

The present reaction is performed similarly to Method B described before.

The second step is a step for producing a compound having a general formula (XXXIII). This step is achieved by reacting a compound having a general formula (XXXI) with a compound having a general formula (XXXII).

The present reaction is performed similarly to Method B described before. The sulfo group in the general formula (XXXII) may be reacted with chlorotrimethylsilane in the presence of a base in this step to silylate this group, and this step may be performed without isolating the silylated compound.

Meanwhile, this Method E can be also applied to a method for producing a compound having an amide group in A, D, E or G. The reaction is achieved in a similar method to Method B described before.

<Method F>
Method F-1

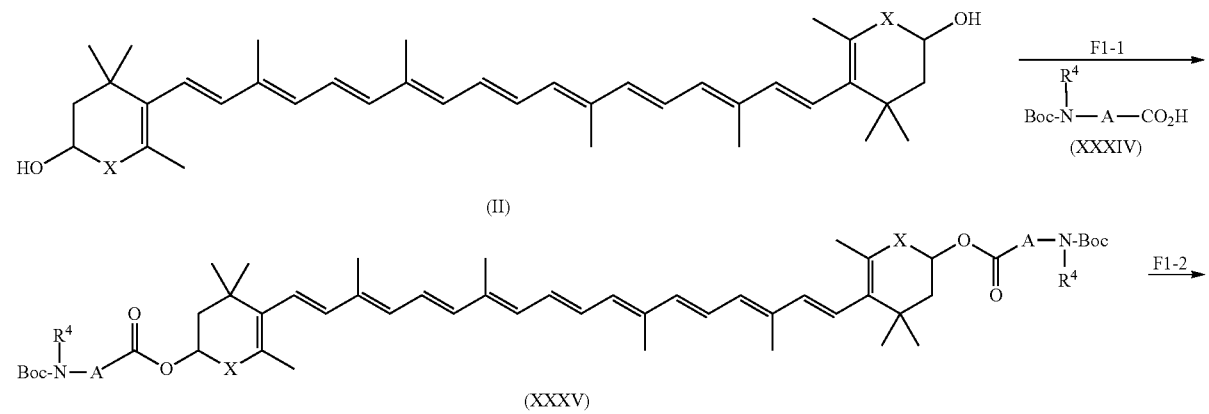

-continued

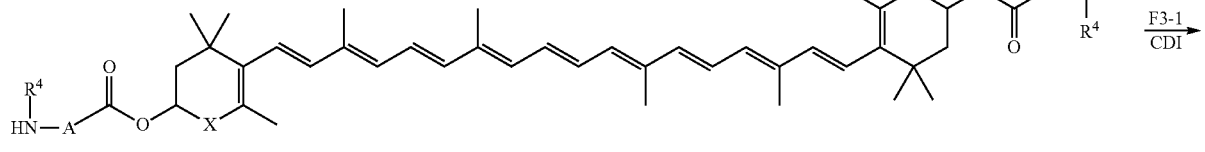

(XXXVI)

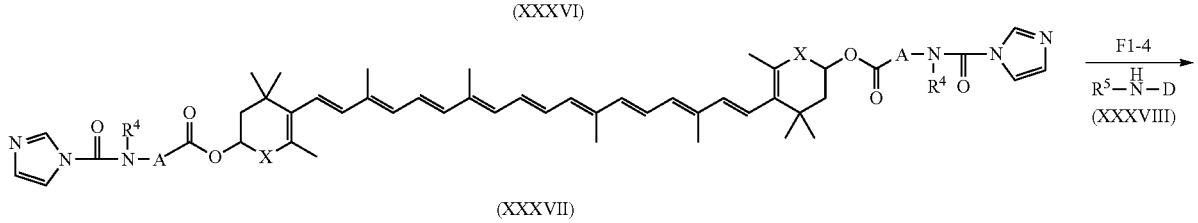

(XXXVII)

wherein X, A, D, R⁴ and R⁵ represent the same meanings as those described above, CDI represents 1,1'-carbonylbis-1H-imidazole and Boc represents a t-butoxycarbonyl group. However, the hydroxy group and the amino group in A and D are protected and the carboxy group may not be protected.

Method F (Method F-1) is a method for producing a compound having a general formula (XXXIX), which is a compound having the general formula (I) or (I') wherein B is a ureido group.

The first step is a step for producing a compound having a general formula (XXXV). This step is achieved by reacting a compound having the general formula (II) with a compound having a general formula (XXXIV).

The present reaction is performed similarly to Method B described before.

The second step is a step for producing a compound having a general formula (XXXVI). This step is achieved by removing a t-butoxycarbonyl group which is a protective group for the amino group in the compound having a general formula (XXXV).

The present reaction is performed similarly to Method A described before.

The third step is a step for producing a compound having a general formula (XXXVII). This step is achieved by reacting a compound having a general formula (XXXVI) with 1,1'-carbonylbis-1H-imidazole.

The present reaction is performed similarly to the (b) active ester method in Method B described before.

The fourth step is a step for producing a compound having a general formula (XXXIX). This step is achieved by reacting a compound having a general formula (XXXVII) with a compound having a general formula (XXXVIII).

When a compound having a general formula (XXXVIII) has a carboxy group, a hydroxyl group or a sulfo group in this step, these compounds may be previously reacted with chlorotrimethylsilane in the presence of a base to silylate these groups, and this step may be performed without isolating the silylated compound.

The present reaction is performed similarly to the second step of Method D described before.

Method F-2

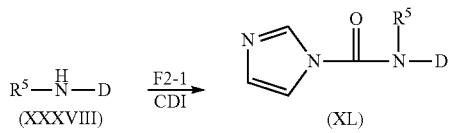

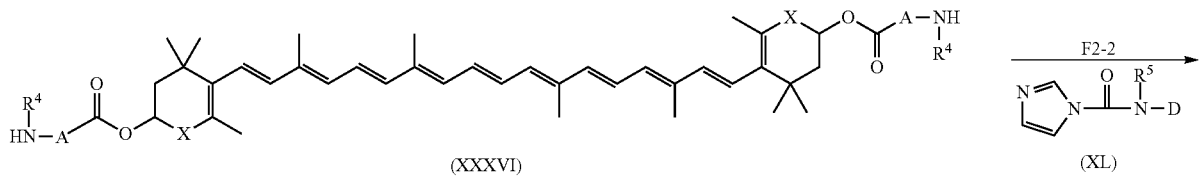

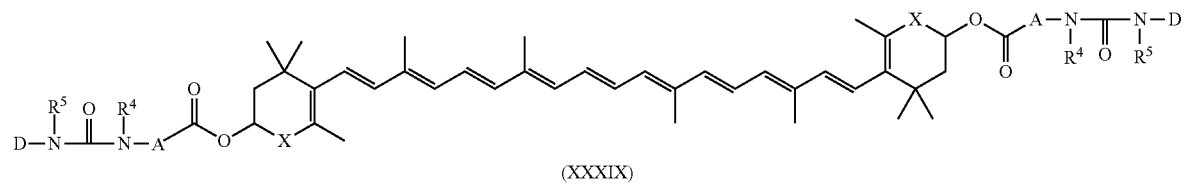

(XXXIX)

wherein X, A, D, $R^4$ and $R^5$ represent the same meanings as those described above and CDI represents 1,1'-carbonylbis-1H-imidazole. However, the hydroxy group and the amino group in A and D are protected and the carboxy group may not be protected.

Method F (Method F-2) is a method for producing a compound having a general formula (XXXIX).

The first step is a process for producing a compound having a general formula (XL). This step is achieved by reacting a compound having a general formula (XXXVIII) with 1,1'-carbonylbis-1H-imidazole.

The present reaction is performed similarly to the (b) active ester method in Method B described before.

The second step is a step for producing a compound having a general formula (XXXIX). This step is achieved by reacting a compound having a general formula (XXXVI) with a compound having a general formula (XL).

The present reaction is performed similarly to the second step of Method D described before.

Method F-3

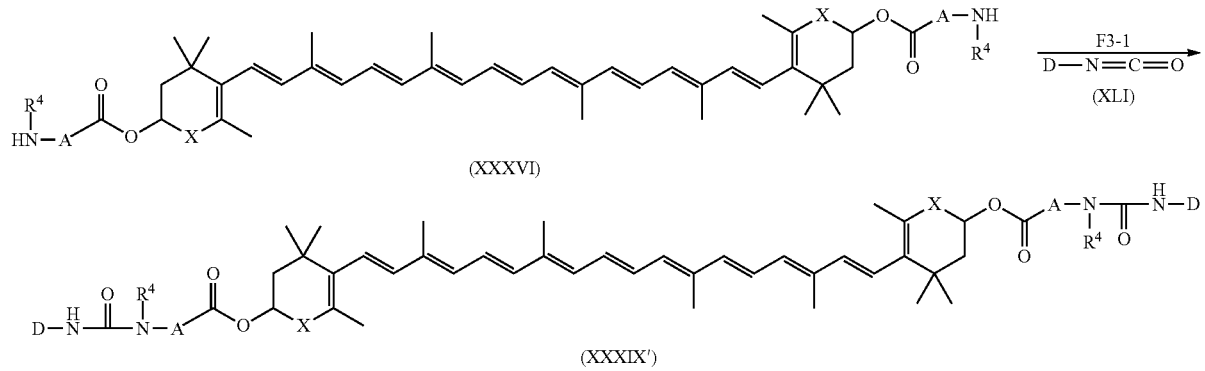

wherein X, A, D and $R^3$ represent the same meanings as those described above. However, the hydroxy group and the amino group in A and D are protected and the carboxyl group may not be protected.

Method F (Method F-3) is a method for producing a compound having a general formula (XXXIX') (the compound wherein $R^5$ is a hydrogen atom).

The reaction is performed by reacting a compound having a general formula (XXXVI) with a compound having a general formula (XLI) in an inert solvent.

The solvent to be used is not particularly limited, as long as it is inert to the present reaction, but it may be, for example, an aliphatic hydrocarbon such as hexane, heptane, ligroin and petroleum ether; an aromatic hydrocarbon such as benzene, toluene and xylene; a halogenated hydrocarbon such as methylene chloride, 1,2-dichloroethane and carbon tetrachloride; an ether such as diethyl ether, diisopropyl ether, tetrahydrofuran, dioxane, dimethoxyethane and diethylene glycol dimethyl ether; a ketone such as acetone; an amide such as formamide, dimethylformamide, dimethylacetoamide and hexamethylphosphoric triamide; a sulfoxide such as dimethyl sulfoxide; or sulfolane, and it is preferably a halogenated hydrocarbon, an ether or amide and most preferably methylene chloride, 1,2-dichloroethane, dioxane, tetrahydrofuran or dimethylformamide.

A base is not necessary, but it may be used to promote the reaction. For example, the base is a base similar to those used in the above-mentioned "(a) acid halide method", and it is preferably an organic amine and most preferably triethylamine, 4-(N,N-dimethyl-amino)pyridine or N,N-diisopropylethylamine.

The reaction temperature varies, depending on the raw material compounds, the solvent, the base and so on, but it is usually −70° C. to 150° C. and preferably −10° C. to 100° C.

The reaction time varies, depending on the raw material compounds, the solvent, the base, the reaction temperature and so on, but it is usually 30 minutes to 3 days and preferably 1 hour to 48 hours.

<Method G>

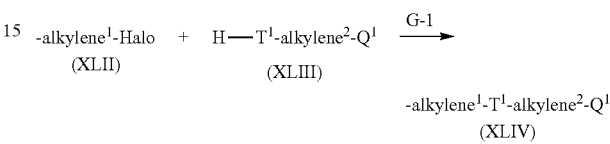

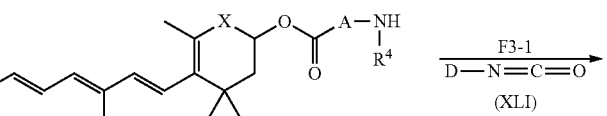

-continued

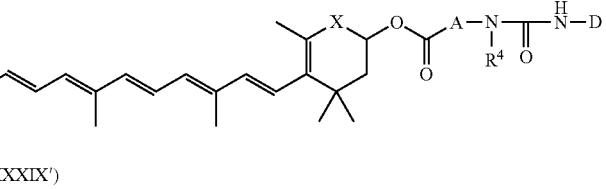

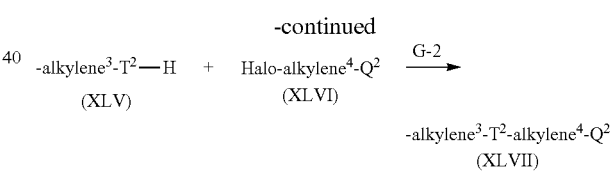

wherein "Halo" represents a halogen atom, $T^1$-H and $T^2$-H represent, an amino group, a hydroxyl group, a sulfhydryl group, a carbamoyl group and so on, bound to an alkylene group and $Q^1$ and $Q^2$ represent the group of —CO-A-B-D, the group —CO-E-F or the group —CO-G described before as -alkylene$^1$-$T^1$-alkylene$^2$-$Q^1$ and -alkylene$^3$-$T^2$-alkylene$^4$-$Q^2$, respectively. However, a group having an active hydrogen atom such as a hydroxy group, an amino group and a carboxy group in the alkylene$^1$, alkylene$^2$, alkylene$^3$, alkylene$^4$, $Q^1$ and $Q^2$ is protected.

Method G is a method for producing a compound having the general formula (I) or a compound having the general formula (I') by reacting a halogenated alkyl compound having a general formula (XLII) or a halogenated alkyl compound having a general formula (XLVI) with a compound having a general formula (XLIII) or formula (XLV) which has an active hydrogen atom such as an amino group, a hydroxyl group, a sulfhydryl group, a carbamoyl group and so on.

Steps G-1 and G-2 are steps for producing compounds (XLIV) and (XLVII) having substituents -alkylene$^1$-$T^1$- alkylene²-Q¹ and -alkylene³-T²-alkylene⁴-Q², and they are achieved by reacting a compound (XLII) or compound (XLVI) with a compound (XLIII) or (XLV) in the presence of a base in an inert solvent.

The base to be used is not particularly limited, as long as it is used in ordinary organic reactions as a base, but it may be, for example, an alkali metal carbonic acid salt such as lithium carbonate, sodium carbonate, potassium carbonate and cesium carbonate; an alkali metal hydrogen carbonic acid salt such as lithium hydrogen carbonate, sodium hydrogen carbonate and potassium hydrogen carbonate; an alkali metal hydride such as lithium hydride, sodium hydride and potassium hydride; an alkali metal hydroxide such as lithium hydroxide, sodium hydroxide and potassium hydroxide; an alkali metal alkoxide such as lithium methoxide, sodium methoxide, sodium ethoxide and potassium t-butoxide; or an organic amine such as triethylamine, tributylamine, 4-(N,N-dimethylamino)pyridine, N,N-diisopropylethylamine, N-methylmorpholine, pyridine, N,N-dimethylaniline, N,N-diethylaniline, 1,5-diazabicyclo-[4.3.0]non-5-ene, 1,4-diazabicyclo[2.2.2]octane (DABCO) and 1,8-diazabicyclo [5.4.0]-7-undecene (DBU), and it is preferably 4-(N,N-dimethylamino)pyridine, N,N-diisopropylethylamine, alkali metal hydride or an alkali metal carbonic acid salt and most preferably 4-(N,N-dimethylamino)pyridine, N,N-diisopropylethylamine, sodium hydride, potassium carbonate or cesium carbonate.

The solvent to be used is not particularly limited, as long as it is inert to the present reaction, but it may be, for example, an aliphatic hydrocarbon such as hexane, heptane, ligroin and petroleum ether; an aromatic hydrocarbon such as benzene, toluene and xylene; a halogenated hydrocarbon such as chloroform, methylene chloride, 1,2-dichloroethane and carbon tetrachloride; an ester such as methyl acetate, ethyl acetate, propyl acetate, butyl acetate and diethyl carbonate; a ketone such as acetone and methyl ethyl ketone; an ether such as diethyl ether, diisopropyl ether, tetrahydrofuran, dioxane, dimethoxyethane and diethylene glycol dimethyl ether; an amide such as formamide, dimethylformamide, dimethylacetoamide and hexamethylphosphoric triamide; or a mixed solvent of these solvents, and it is preferably a halogenated hydrocarbon, an ether or an amide and most preferably methylene chloride, dioxane, tetrahydrofuran, dimethylformamide or dimethylacetoamide.

The reaction temperature varies, depending on the raw material compounds, the base to be used, the solvent and so on, but it is usually −20° C. to the boiling point temperature of a solvent and preferably 0° C. to 100° C.

The reaction time varies, depending on the raw material compounds, the base to be used, the solvent, the reaction temperature and so on, but it is usually 30 minutes to 5 days and preferably 1 hour to 3 days.

When an amino group is present in the structure of the compound having the general formula (I), a production intermediate thereof and so on in the above-mentioned production method, a triphenylmethyl group or a Boc group can bind suitably as a protective group, and further the protective group can be removed suitably from these protected groups. These can be carried out in accordance with a well-known method in the technology of organic synthetic chemistry, for example, that is, the method of T. W. Greene, (Protective Groups in Organic Synthesis), JohnWiley & Sons; and of J. F. W. Mcomie, (Protective Groups in Organic Synthesis), Plenum Press.

For example, when the amino group is protected with a triphenylmethyl group, the protection is performed by reacting a compound to be protected with triphenylmethyl chloride or triphenylmethyl bromide usually at 0° C. to the boiling point temperature of a solvent (preferably 0° C. to 70° C.) for 1 hour to 5 days (preferably 2 hours to 2 days) in the presence of triethylamine or N,N-diisopropylethylamine in dimethylformamide, tetrahydrofuran, methylene chloride or a mixed solvent thereof.

When the amino group is protected with a Boc group, the protection is performed by reacting a compound to be protected with di-t-butyl-di-carbonate in an inert solvent.

The solvent to be used is not particularly limited, as long as it is inert to the present reaction, but it may be, for example, an aliphatic hydrocarbon such as hexane, heptane, ligroin and petroleum ether; an aromatic hydrocarbon such as benzene, toluene and xylene; a halogenated hydrocarbon such as chloroform, methylene chloride, 1,2-dichloroethane and carbon tetrachloride; an ester such as methyl acetate, ethyl acetate, propyl acetate, butyl acetate and diethyl carbonate; a ketone such as acetone and methyl ethyl ketone; an ether such as diethyl ether, diisopropyl ether, tetrahydrofuran, dioxane, dimethoxyethane and diethylene glycol dimethyl ether; an amide such as formamide, dimethylformamide, dimethylacetoamide and hexamethylphosphoric triamide; or a mixed solvent of these solvents, and it is preferably a halogenated hydrocarbon or an ether and most preferably chloroform, methylene chloride, 1,2-dichloroethane, diethyl ether, tetrahydrofuran or dioxane.

The reaction temperature varies, depending on the raw material compounds, the solvent and so on, but it is usually 0° C. to the boiling point temperature of a solvent and preferably 0° C. to 70° C.

The reaction time varies, depending on the raw material compounds, the solvent, the reaction temperature and so on, but it is usually from 1 hour to 5 days and preferably from 2 hours to 2 days.

Removal of a Boc group is performed similarly to Method A described before by reacting with an acid.

Further, when a carboxy group is present in the structure of the compound having the general formula (I), a production intermediate thereof and so on in the above-mentioned production method, the carboxy group can be suitably converted to a $C_1$-$C_6$ alkoxycarbonyl group, and further the $C_1$-$C_6$ alkoxycarbonyl group can be reconverted suitably to a carboxy group. Conversion to a carboxy group from the $C_1$-$C_6$ alkoxycarbonyl group is performed similarly to Method A described before, and conversion to a $C_1$-$C_6$ alkoxycarbonyl group from the carboxy group is performed similarly to Method B described before.

Furthermore, when a hydroxy group is present in the structure of the compound having the general formula (I), a production intermediate thereof and so on in the above-mentioned production method, the hydroxy group can be protected if desired, and the protective group for the hydroxyl group can be suitably removed if necessary. Protection of the hydroxy group and removal of the protective group are performed in accordance with, for example, the description of the literatures related to the protective group described below.

The literatures related to the protective group are as described below.

Literatures: PROTECTIVE GROUPS IN ORGANIC SYNTHESIS, Theodora W. Greene & Peter G. M. Wuts, JOHN WILEY & SONS, INC., PROTECTING GROUPS IN ORGANIC SYNTHESIS, James R. Hanson, Sheffield Academic Press, Blackwell Science, and PROTECTIVE GROUPS IN ORGANIC CHEMISTRY, J. F. W. McOmie, PLENUM PRESS.

In addition, the production method described above is also performed in accordance with, for example, the method in the literatures described below.

Literatures: FORMATION OF C—C BONDS, Jean Mathieu & Jean Weill-Raynal, Preface by D. H. R. Barton, Georg Thieme Publishers.

ORGANIC SYNTHESES, Henry Gilman, Editor-in-Chief, JOHN WILEY & SONS, INC.

ORGANIC REACTIONS, Roger Adams, Editor-in-Chief, JOHN WILEY & SONS, INC.

REAGENTS FOR ORGANIC SYNTHESIS, Louis F. Fieser and Mary Fieser, JOHN WILEY & SONS, INC.

THE CHEMISTRY OF FUNCTIONAL GROUPS, Saul Patai, INTERSCIENCE PUBLISHERS, a division of JOHN WILEY & SONS, INC.

COMPREHENSIVE ORGANIC TRANSFORMATIONS, Richard C. Larock, VCH Publishers, Inc.,

COMPREHENSIVE ORGANIC CHEMISTRY, Sir Derek Barton, F. R. S. and W. David Ollis, F. R. S., PERGAMON PRESS.

COMPREHENSIVE ORGANIC SYNTHESIS, Barry M, Trost, PERGAMON PRESS, and

COMPREHENSIVE ORGANIC FUNCTIONAL GROUP TRANSFORMATIONS, Alan R. Katritzky, F R S, Otto Meth-Cohn, Charles W. Rees, F R S, PERGAMON PRESS.

The compound (I) of the present invention may have one or more kinds of crystal form or noncrystalline form. As a method for producing different crystal forms, they can be produced by a method to obtain a crystal polymorphism in an active ingredient of a medicine. Examples of the method for producing the crystal forms include a method to dissolve the compound (I) of the present invention in a solvent and to precipitate the compound (I) by adding a poor solvent; a method to precipitate the compound (I) by distill the solvent off; a method to precipitate the compound (I) by lowering temperature and so on, and these methods may be combined. The crystal of the compound (I) of the present invention can be precipitated selectively and easily by adding a desired seed crystal. The noncrystalline form can be produced by using a method to obtain a noncrystalline form in an active ingredient of a medicine. For example, examples of the method for producing a noncrystalline form include a method to enhance the precipitation speed at the time to produce the crystal form described above, a method to add a crystallization inhibitor such as a polymer at the time to dissolve, a method to melt using a biaxial extruder by adding a melting point depressant and so on.

The therapeutic agent of the present invention is explained below. Meanwhile, a medicine is explained as a therapeutic agent in the present invention, but the therapeutic agent includes the meanings of an improvement agent and a preventive agent, unless specifically stated.

The carotenoid derivative of the present invention has a unique chemical structure, and for that reason, it has excellent water solubility, has higher bioincorporation than a nature-producing, free form carotenoid or a carotenoid derivative of a fatty acid ester and is useful as an active ingredient of a medicine in a warm-blooded animal including human. When a free form carotenoid such as astaxanthin is an active substance, the acyl group binding to the oxygen molecule at the position 3 in the 6-membered cycles at both ends of the molecule is cleaved by esterase and so on, and the resulting free form acts in a case where the carotenoid exhibits the activity in a living body. In addition, the carotenoid represented by the general formula (I) of the present invention itself or the compound in which the urea bond moiety, the amide bond moiety or the ester bond moiety is cleaved in the molecular structure, may exhibit the pharmacological activity.

Meanwhile, a free form carotenoid has high crystallinity, and it is difficult to perform significant improvement for solubility to water by using a method usually used for improving solubility of a poor-soluble drug such as formation of a solid dispersion using a polymer, addition of a solubilizer and so on. For that reason, it becomes important to improve solubility to water in order to be easily bioincorporated.

The carotenoid derivative of the present invention has effects on a disease where an active oxygen is involved and of which curative effect is confirmed by a free form carotenoid. Examples of the disease where an active oxygen is involved that can be improved or prevented include, for example, hyperlipidemia, obesity, impaired glucose tolerance, hypertension, insulin resistance, a metabolic syndrome, fatty liver disease, diabetes, diabetic complication (for example, retinopathy, nephropathy, neuropathy, cataract, coronary artery disease, brain infarction and so on), steatohepatitis, non-alcoholic steatohepatitis (NASH), Type C hepatitis, arteriosclerosis, gestational diabetes, polycystic ovary syndrome, a cardiovascular disease (for example, an ischemic cardiac disease or myocardial infarction), heart failure, atherosclerosis, vascular insufficiency, cell damage caused by an ischemic cardiac disease (for example, brain damage caused by apoplexy and so on), gout, an inflammatory disease (for example, osteoarthritis, pain, fever, rheumatoid arthritis, inflammatory bowel disease, acne, sunburn, psoriasis, eczema, an allergic disease, atopic dermatitis, asthma, GI ulcer, cachexia, an autoimmune disease, pancreatitis and so on), stomach ulcer, cancer, osteoporosis, cataract, glaucoma, age-related macular degeneration, dry eye, eyestrain, Alzheimer's disease, depression, bipolar disorder, schizophrenia, chronic fatigue, disuse muscle atrophy, amyotrophic lateral sclerosis, amyotrophy, sarcopenia, cachexia, uric acid suppression action, hair growth promotion action, wound improvement and improvement after surgery. In addition, the therapeutic agent of the present invention can be also used as, for example, a preservative for an organ or a preservative for cultured skin, cartilage and so on.

Preferably, the therapeutic agent of the present invention is a preventive agent and/or a therapeutic agent for dry eye, eyestrain, cataract, glaucoma, age-related macular degeneration, steatohepatitis, non-alcoholic steatohepatitis, insulin resistance, diabetes, diabetic complication, hypertension, hyperlipidemia, heart failure, Alzheimer's disease, atopic dermatitis, sarcopenia and cancer.

Most preferably, the therapeutic agent of the present invention is for dry eye, non-alcoholic steatohepatitis, heart failure and atopic dermatitis.

Further, the carotenoid derivative of the present invention may be blended with other active ingredients in combination. The effect of the other active ingredient may be selected, depending on the properties of the other active ingredient such as complementary action to each other, synergistic effect, reduction of side effects of the other active ingredients and so on. Examples of the other active ingredient include a RXR activating agent, a sulfonyl urea agent, an α-glucosidase inhibitor, an insulin formulation, an aldose reductase inhibitor, a biguanide agent, a DPP-IV inhibitor, a GLP-1-related compound, a statin compound, a squalene synthesis inhibitor, a fibrate-based compound, a LDL catabolism accelerator, an angiotensin converting enzyme inhibitor, an angiotensin II antagonist, a renin inhibitor, a calcium antagonist, an aldosterone receptor antagonist, a diuretic, a secretase inhibitor, an antitumor agent, a preventive agent and/or therapeutic agent for diabetes, a preventive agent and/or therapeutic agent for diabetic complication, a steroid and a non-steroidal anti-inflammatory drug. Preferably, examples of the other active ingredient that is used in combination include a statin compound, an angiotensin converting enzyme inhibitor, an angiotensin II antagonist, a renin inhibitor, a calcium antagonist, an aldosterone receptor antagonist, a diuretic, an antitumor agent, a preventive agent and/or therapeutic agent for diabetes, and a therapeutic agent for diabetic complication, a steroid and a non-steroidal anti-inflammatory drug.

In combination with a steroid, it is possible to suppress or prevent amyotrophy that is a long-term dosing disorder of a steroid. In combination with NSAIDs (non-steroidal anti-inflammatory drug), it is possible to suppress or prevent a gastrointestinal tract disorder of NSAIDs.

When the carotenoid derivative of the present invention is used as the therapeutic agent or preventive agent mentioned above, the carotenoid derivative itself or as, for example, a tablet, a capsule, a granule, a powder, a syrup and so on, which are prepared by mixing suitably with a pharmaceutically acceptable medical additive such as an excipient, a disintegrator, a binder and so on, is orally administered. Alternatively, the carotenoid derivative of the present invention can be parenterally administered as an injection, an eye drop, a suppository, a percutaneous absorption formulation, and so on. The carotenoid derivative of the present invention is different from an existing carotenoid or carotenoid derivative having insufficient solubility to water and it is also effective for a disease for which treatment administration in a liquid form such as an eye drop and an injection is required.

These formulations are produced by a well-known method using additives such as a excipient (for example, it may be an organic excipient including a sugar derivative such as lactose, sucrose, glucose, mannitol and sorbitol; a starch derivative such as corn starch, potato starch, a starch and dextrin; a cellulose derivative such as a crystalline cellulose; acacia; dextran; and pullulan; or an inorganic excipient including a silicic acid salt derivative such as light anhydrous silicic acid, synthesized aluminum silicate, calcium silicate and magnesium aluminometasilicate; a phosphoric acid salt such as calcium hydrogen phosphate; a carbonic acid salt such as calcium carbonate; a sulfuric acid salt such as calcium sulfate; and so on), a lubricant (for example, it may be a stearic acid metal salt such as stearic acid, calcium stearate and magnesium stearate; talc; colloidal silica; Veegum; a wax such as a Gay wax; boric acid; adipic acid; a sulfuric acid salt such as sodium sulfate; glycol; fumaric acid; sodium benzoate; an amino acid such as DL leucine; peptide; sodium salt of a fatty acid; a lauryl sulfuric acid salt such as sodium lauryl sulfate and magnesium lauryl sulfate; a silicic acid such as anhydrous silicic acid and silicic acid hydrate; or the above-mentioned starch derivative), a binder (for example, it may be hydroxypropyl cellulose, hydroxypropylmethyl cellulose, polyvinylpyrrolidone, macrogol or a compound similar to the above-mentioned excipient), a disintegrator (for example, it may be a cellulose derivative such as low substituted hydroxypropyl cellulose, carboxymethyl cellulose, calcium carboxymethyl cellulose and internally cross-linked sodium carboxymethyl cellulose; a chemically modified starch/cellulose such as carboxymethyl starch and sodium carboxymethyl starch; or cross-linked polyvinylpyrrolidone), a stabilizer (it may be a paraoxybenzoate ester such as methyl paraben and propyl paraben; an alcohol such as chlorobutanol, benzyl alcohol and phenylethyl alcohol; benzalkonium chloride; a phenol such as phenol and cresol; thimerosal; dehydroacetic acid; sorbic acid; and so on), a corrective (for example, it may be a sweetener, an acidulant, a perfume and so on, which are usually used), a diluent and so on.

A liquid formulation such as a syrup, a drinkable formulation, a suspension, an eye drop, an injection and so on can be formulated by an ordinary method in the presence of a pH regulator, a buffer agent, a solubilizing agent, a suspending agent, a tonicity agent, a stabilizing agent, a preservative and so on, if necessary. Examples of the pH regulator may include, for example, hydrochloric acid, sodium hydroxide, potassium hydroxide, triethanolamine and so on. Examples of the buffering material may include, for example, sodium phosphate, sodium acetate, sodium borate, sodium citrate, sodium aspartate and so on. Examples of the suspending agent may include, for example, polysorbate 80, methyl cellulose, hydroxyethyl cellulose, sodium carboxymethyl cellulose, polyoxyethylene sorbitan monolaurate, gum arabic, powder tragacanth, polyvinylpyrrolidone, glycerin monostearate and so on. Examples of the solubilizing agent may include, for example, polysorbate 80, hydrogenated polyoxyethylene castor oil, nicotinic acid amide, polyoxyethylene sorbitan monolaurate, macrogol, castor oil fatty acid ethyl ester, vaseline, glycerin, propylene glycol and so on. Examples of the stabilizing agent may include, for example, sodium sulfite, sodium metabisulfite, sodium citrate, sodium edetate, monoethanolamine and so on. Examples of the preservative may include, for example, methyl p-hydroxybenzoate, ethyl p-hydroxybenzoate, sodium benzoate, sorbic acid, phenol, cresol, chlorocresol, benzalkonium chloride, paraben and so on.

To the compound (I) of the present invention, it is preferable to add, for example, an anti-oxidant, a colorant and so on. The anti-oxidant includes, for example, sodium nitrite, ascorbic acid, sodium ascorbate, L-ascorbyl stearate, ascorbyl palmitate, sodium hydrogen sulfite, alpha-thioglycerin, erythorbic acid, cysteine hydrochloride, citric acid, tocopherol acetate, potassium dichloroisocyanurate, dibutylhydroxytoluene, sodium thioglycolate, sodium thiomalate, vitamin E, tocopherol, d-δ-tocopherol, tocotrienol, palmitic acid, ascorbic acid glucoside, sodium pyrosulfite, butylhydroxyanisole, 1,3-butyleneglycol, benzotriazole, pentaerythrityl-tetrakis[3-(3,5-di-t-butyl-4-hydroxyphenyl)propionate], propyl gallate or 2-mercaptobenzimidazole and preferably tocopherol, tocopherol acetate, tocotrienol, ascorbyl palmitate or ascorbic acid glucoside. A colorant may be mixed in a tablet or may be added to a gelatin layer for a sugar-coated tablet or capsule.

The dose of the carotenoid derivative of the present invention is different, depending on symptoms, age, administration route and so on, but it is, for example, 0.001 to 500 mg/kg body weight and preferably 0.01 to 50 mg/kg body weight per one oral administration. In intravenous administration, the dose of the carotenoid derivative of the present invention is 0.001 to 50 mg/kg body weight and preferably 0.05 to 10 mg/kg body weight per one administration. The concentration of the carotenoid derivative in intravenous administration may be suitably selected among a concentration of 0.00001 to 1.0% by using an ordinary method based on dose and administered amount of the liquid formulation.

The concentration of the carotenoid derivative for ocular administration is adjusted within a concentration of 0.00001 to 5.0% and (the carotenoid derivative) is dropped by one to several drops per one administration. The dropping number per day may be set up at a frequency of once to ten times, depending on the intended effects. The concentration of the carotenoid derivative is preferably 0.001 to 1.0%.

In addition to application as a medicine, the carotenoid derivative of the present invention can be used as an improver of final redyeing or productivity or a viability improver at the time of fertilization by feeding the carotenoid derivative to animals, or a protective agent for an organ at the time of transplantation.

EXAMPLES

Hereinafter, Examples, Reference Examples, Test Examples and Formulation Examples are shown and the present invention will be further explained in detail, but the scope of the present invention is not limited thereto.

Example (1) (Exemplified Compound No. 2-1)

2-[3-(4-[18-[4-{3-(2-sulfoethylaminocarbonyl)-propionyloxy}-2,6,6-trimethyl-3-oxocyclohexa-1-enyl]-3,7,12,16-tetramethyloctadeca-1,3,5,7,9,11,13,15,17-nonaenyl]-3,5,5-trimethyl-2-oxocyclohexa-3-enyloxycarbonyl)propionylamino]ethanesulfonic acid To a mixture of 6-(3-carboxypropionyloxy)-3-[18-[4-(3-carboxypropionyloxy)-2,6,6-trimethyl-3-oxo-1-cyclohexenyl]-3,7,12,16-tetramethyloctadeca-1,3,5,7,9,11,13,15,17-nonaenyl]-2,4,4-trimethyl-2-cyclohexen-1-one (6.11 g), taurine (3.82 g) and N-hydroxy-5-norbornene-2,3-dicarboximide (2.75 g), anhydrous dimethylformamide (70 ml) and subsequently N,N-diisopropylethylamine (19.86 g) were added and the reaction vessel was substituted by argon. To the mixture, 1-ethyl-3-(3-dimethylaminopropyl) carbodiimide hydrochloride (6.11 g) was added and the mixture was stirred for 4 days at room temperature. n-Hexane (300 ml) was added and the n-hexane layer was removed by decantation, and further n-hexane (300 ml) was added to the residue and the similar operation was performed. The residue was purified by silica gel column chromatography (eluent; methylene chloride: methanol=3:1 to 2:1) and a crystal was obtained from an ethyl acetate-n-hexane solution. The obtained crystal was washed with methanol to obtain the title compound (0.751 g) as a reddish black powder.

$^1$H-NMR ($\delta$, ppm) (DMSO-d$_6$): 1.19 (s, 6H), 1.33 (s, 6H), 1.81 (s, 6H), 1.97-2.00 (m, 16H), 2.36-2.38 (m, 4H), 2.51-2.59 (m, 8H), 3.18-3.33 (m, 4H, overlapping with the peak of water), 5.40-5.44 (dd, 2H), 6.28-6.76 (m, 14H), 7.82 (t, 2H)

Example (2) (Exemplified Compound No. 1-2)

4-{18-[4-carboxymethylsulfinylacetoxy-2,6,6-trimethyl-3-oxocyclohexa-1-enyl]-3,7,12,16-tetramethyl-octadeca-1,3,5,7,9,11,13,15,17-nonaenyl}-3,5,5-trimethyl-2-oxocyclohexa-3-enyloxycarbonylmethylsulfinyl-acetic acid Production Method A To a solution of astaxanthin (3.00 g), 2,2'-sulfinyl diatetic acid (8.35 g), N,N-diisopropylethylamine (17.1 mL), 4-(N,N-dimethylamino)pyridine (1.23 g) and methylene chloride (90 mL), N,N'-diisopropylcarbodiimide (7.8 mL) was added and the reaction solution was stirred for 3 hours. Completion of the reaction was confirmed by HPLC and the solution of methylene chloride and N,N-diisopropylethylamine was concentrated under reduced pressure. The obtained residue was purified by silica gel column chromatography (eluent; methylene chloride: methanol=2:1 to 1:2). The residue was purified again twice by silica gel column chromatography (eluent; methylene chloride: methanol=2:1 to 1:9). The purified product was dissolved in methylene chloride (20 mL) and 1 N hydrochloric acid (20 mL) was added thereto. The methylene chloride layer was separated and washed twice with a saturated saline solution, and the precipitated reddish black solid was collected by filtration and dried to obtain the title compound (38 mg) as a reddish black powder.

$^1$H-NMR 400 MHz (DMSO-d$_6$) :$\delta$ 6.79-6.29 (14H, m), 5.55-5.50 (2H, m), 4.24-3.86 (8H, m), 2.07-2.03 (4H, m), 2.01 (6H, s), 1.97 (6H, s), 1.83 (6H, s), 1.35 (6H, s), 1.21 (6H, s)

Mass spectrum: −ESI, m/z=891.34 (M$^-$)

Production Method B

To a solution of 6-hydroxy-3-(18-[4-hydroxy-2,6,6-trimethyl-3-oxo-1-cyclohexenyl]-3,7,12,16-tetramethyloctadeca-1,3,5,7,9,11,13,15,17-nonaenyl)-2,4,4-trimethyl-2-cyclohexen-1-one (astaxanthin) (1.50 g), 2,2'-sulfinyl diacetic acid (4.18 g), N,N-diisopropylethylamine (8.5 mL), 4-(N,N-dimethylamino)pyridine (0.61 g) and methylene chloride (45 mL), N,N'-diisopropylcarbodiimide (3.9 mL) was dropped and the reaction solution was stirred for 3 hours. Completion of the reaction was confirmed by HPLC and then methylene chloride (10 mL), AQUALIC HL415 (NIPPON SHOKUBAI CO., LTD., 5 mL) and AQUALIC AS (NIPPON SHOKUBAI CO., LTD., 5 g) were sequentially added. The reaction mixture was stirred for 15 minutes and filtered. The filtrate was concentrated under reduced pressure and the residue was dried under reduced pressure at 40° C. The obtained residue was purified by silica gel column chromatography (eluent; methylene chloride:methanol=2:1 to 1:4) to obtain the title compound (110 mg) as a reddish black powder.

$^1$H-NMR 400 MHz (DMSO-d$_6$): $\delta$ 6.78-6.29 (14H, m), 5.51 (2H, dd), 4.24 (2H, t), 3.85 (2H, d), 3.75 (2H, t), 3.54-3.50 (2H, m), 2.09-2.06 (4H, m), 2.00 (6H, s), 1.97 (6H, s), 1.83 (6H, s), 1.35 (6H, s), 1.21 (6H, s)

Mass spectrum: −ESI, m/z=891.4426 (M−H$^-$)

Example (3) (Exemplified Compound No. 1-1)

4-{18-[4-carboxymethylthioacetoxy-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyloxycarbonylmethylthioacetic acid The reaction vessel was substituted by argon, 6-hydroxy-3-(18-[4-hydroxy-2,6,6-trimethyl-3-oxo-1-cyclohexenyl]-3,7,12,16-tetramethyloctadeca-1,3,5,7,9,11,13,15,17-nonaenyl)-2,4,4-trimethyl-2-cyclohexene-1-one (astaxanthin, 2.00 g), 2,2'-thiodiacetic acid (5.03 g), N,N-diisopropylethylamine (8.66 g), 4-(N,N-dimethylamino)pyridine (0.82 g) and methylene chloride (60 mL) were mixed and the reaction solution was stirred for 18 hours at room temperature. 1-Ethyl-3-(3-dimethyl-aminopropyl)carbodiimide hydrochloride (6.42 g) was added to the reaction solution and the reaction solution was stirred further for 1.5 hours. Completion of the reaction was confirmed by high performance liquid chromatography (HPLC) and polyacrylic acid (AQUALIC HL415 (NIPPON SHOKUBAI CO., LTD.), 60 mL) was added to the reaction solution. The reaction solution was stirred for 10 minutes and further polyacrylic acid (AQUALIC AS (NIPPON SHOKUBAI CO., LTD.), 10 g) was added thereto. Solidification of polyacrylic acid was confirmed, and the organic layer was isolated by decantation and filtration, dried over anhydrous $Na_2SO_4$ and concentrated under reduced pressure. The residue was purified by reverse phase (ODS) column chromatography (10% $CH_2Cl_2$-MeOH:water=8:2 to 9:1) once and purified by the chromatography (10% $CH_2Cl_2$-MeOH:water=8:2 to 19:1) twice, and the fractions containing the product were dried under reduced pressure. To the purified product, $CH_2Cl_2$ (50 mL) and 1N—HCl (50 mL) were added and the $CH_2Cl_2$ layer was separated. The $CH_2Cl_2$ layer was dried over anhydrous $Na_2SO_4$ and concentrated under reduced pressure. The residue was purified by reverse phase (ODS) column chromatography (10% $CH_2Cl_2$-MeOH:water=8:2 to 9:1) and the fractions containing the product were dried under reduced pressure to obtain the title compound (90 mg) as a reddish black powder.

$^1$H-NMR 400 MHz ($CDCl_3$): δ 6.69-6.18 (14H, m), 5.58 (2H, dd), 3.62-3.47 (8H, m), 2.15-2.03 (4H, m), 2.00 (6H, s), 1.99 (6H, s), 1.92 (6H, s), 1.36 (6H, s), 1.24 (6H, s)

Mass spectrum: −ESI, m/z=859.54 (M−H$^-$)

Example (4) (Exemplified Compound No. 2-10)

2-(3,5,5-trimethyl-2-oxo-4-{3,7,12,16-tetramethyl-18-[2,6,6-trimethyl-3-oxo-4-(2-sulfoethylcarbamoyloxy)-cyclohexa-1-enyl]octadeca-1,3,5,7,9,11,13,15,17-nonaenyl}cyclohexa-3-enyloxycarbonylamino) ethanesulfonic acid A solution of imidazol-1-ylcarboxylic acid 4-[18-{4-(imidazol-1-ylcarbonyloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester (the compound in Reference Example 2, 5.73 g) in dry N,N-dimethylformamide (25 ml) was substituted by nitrogen, taurine (13.82 g), N,N-diisopropylethylamine (22.0 g), N-hydroxy-5-norbornen-2,3-dicarboxyimide (11.71 g) and N,N-dimethyl-4-aminopyridine (1.3 g) were added thereto, further dry N,N-dimethylformamide (25 ml) was added thereto and the reaction solution was stirred for 6 hours at room temperature. To the reaction solution, taurine (4.03 g), N-hydroxy-5-norbornen-2,3-dicarboxyimide (7.45 g) and N,N-dimethyl-4-aminopyridine (1.5 g) were added and the reaction solution was heated and stirred for 7.5 hours on the oil bath of 40° C. The reaction solution was further stirred for 20 hours at room temperature. N,N-Dimethylformamide was distilled off under reduced pressure, and the obtained residue was purified by silica gel column chromatography (eluent; methylene chloride:methanol=7:3) and further purified by the silica gel chromatography (eluent; methylene chloride:methanol=3:1) to obtain the title compound (1.57 g) as a reddish black solid.

$^1$H-NMR (δ, ppm) (DMSO-$d_6$): 1.18 (s, 6H), 1.33 (s, 6H), 1.81 (s, 6H), 1.92-2.05 (m, 16H), 2.61 (t, 4H), 3.29-3.32 (m, 4H), 5.27 (dd, 2H), 6.28-6.76 (m, 14H), 7.11 (t, 2H)

Example (5) [Sodium Salt of Compound in Example (4) (Exemplified Compound No. 2-10)]

2-(3,5,5-trimethyl-2-oxo-4-{3,7,12,16-tetramethyl-18-[2,6,6-trimethyl-3-oxo-4-(2-sulfoethylcarbamoyloxy)-cyclohexa-1-enyl]-octadeca-1,3,5,7,9,11,13,15,17-nonaenyl}cyclohexa-3-enyloxycarbonylamino)ethanesulfonic acid disodium salt 2-(3,5,5-trimethyl-2-oxo-4-{3,7,12,16-tetramethyl-18-[2,6,6-trimethyl-3-oxo-4-(2-sulfoethylcarbamoyloxy)-cyclo-hexa-1-enyl]-octadeca-1,3,5,7,9,11,13,15,17-nonaenyl}cyclohexa-3-enyloxycarbonylamino) ethanesulfonic acid (the compound in Example (4), 0.6 g) was dissolved in dry methanol (12 mL), a solution of 28% sodium methoxide in methanol (265 μL) was added thereto and the reaction solution was stirred for 1.5 hours at room temperature. Anhyrdrous methanol (12 ml) was further added, and the reaction solution was stirred for 0.5 hour at room temperature. The reaction solution was added to hexane (500 mL) and the reaction solution was stirred for 15 minutes. A precipitate was collected by filtration to obtain the title compound (0.579 g) as a reddish brown solid.

$^1$H-NMR (δ, ppm) (DMSO-$d_6$): 7.12 (t, 2H), 6.79-6.28 (m, 14H), 5.27 (dd, 2H), 3.30-3.24 (m, 4H), 2.59 (t, 4H), 2.04-1.89 (m, 16H), 1.81 (s, 6H), 1.33 (s, 6H), 1.18 (s, 6H)

Mass spectrum: Fab-MS, m/z=897 (M−H$^-$)

Example (6) (Exemplified Compound No. 1-102)

3-[2-(4-(18-{4-[3-(3-t-butoxycarbonylmethylureido)-propionyloxy]-2,6,6-trimethyl-3-oxocyclo-hexa-1-enyl}-3,7,12,16-tetramethyloctadeca-1,3,5,7,9,11,13,15,17-nonaenyl)-3,5,5-trimethyl-2-oxocyclohexa-3-enyloxy-carbonyl)ethyl]ureidoacetic acid t-butyl ester To a solution of 3-amino-propionic acid 4-{18-[4-(3-aminopropionyloxy)-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyl ester dihydrochloride (the compound in Reference Example 4, 2 g), N-(imidazol-1-ylcarbonyl)glycine t-butyl ester (the compound in Reference Example 1, 2.77 g) and dry N,N-dimethylformamide (60 mL), N,N-diisopropylethylamine (2.1 mL) was added and the reaction solution was stirred for 15 hours at room temperature. N,N-dimethylformamide and N,N-diisopropylethyl amine were distilled off under reduced pressure, and the obtained residue was purified by silica gel column chromatography (eluent; methylene chloride:ethyl acetate=7:3 to 0:10), and the solvent was distilled under reduced pressure. The residue was dissolved in methylene chloride (30 mL), 1 N hydrochloric acid was added thereto and the layer was separated. The organic layer was washed with water (30 mL) and subsequently saturated saline solution (30 mL) twice, dried over anhydrous sodium sulfate, concentrated under reduced pressure and dried under reduced pressure. Further similar operations were repeated twice to obtain the title compound (180 mg) as a reddish black powder.

$^1$H-NMR 400 MHz (DMSO-$d_6$): δ 6.79-6.23 (18H, m), 5.45 (2H, dd), 3.66-3.64 (4H, m), 3.32-3.23 (4H, m), 2.04-2.02 (4H, m), 2.01 (6H, s), 1.97 (6H, s), 1.82 (6H, s), 1.41 (18H, s), 1.34 (6H, s), 1.20 (6H, s)

Mass spectrum: +ESI, m/z 1053.28 (M+H$^+$), 1075.60 (M+Na$^+$)

Example (7) (Exemplified Compound No. 1-365)

Imidazol-1-ylcarbonylaminoacetic acid 4-{18-(4-imidazol-1-ylcarbonylaminoacetoxy-2,6,6-trimethyl-3-oxocyclohexa-1-enyl)-3,7,12,16-tetramethyloctadeca-1,3,5,7,9,11,13,15,17-nonaenyl}-3,5,5-trimethyl-2-oxocyclohexa-3-enyl ester To methylene chloride (513 mL), 1,1'-carbonyldiimidazole (21.2 g) was added and the reaction solution was stirred for 30 minutes under ice cooling. To this, aminoacetic acid 4-{18-[4-aminoacetoxy-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyl ester dihydrochloride (the compound in Reference Example 6, 20.5 g) was added and the reaction solution was returned to room temperature. The reaction solution was stirred for 3 hours, water (500 mL) was added and the layers were separated. To the organic layer, water (500 mL) was added and the organic layer was separated. Further, the organic layer was washed with water (500 mL) and a saturated saline solution (400 mL), dried over anhydrous sodium sulfate concentrated under reduced pressure and dried under reduced pressure to obtain 24.0 g of a reddish black powder.

$^1$H-NMR (δ, ppm) (DMSO-$d_6$): 9.13 (t, 2H), 8.28 (s, 2H), 7.71 (m, 2H), 7.07 (s, 2H), 6.79-6.29 (m, 14H), 5.50 (dd, 2H), 4.22-4.08 (m, 4H), 2.10-2.03 (m, 4H), 2.00 (s, 6H), 1.97 (s, 6H), 1.83 (s, 6H), 1.35 (s, 6H), 1.20 (s, 6H)

Mass spectrum: m/z=898.72 (M$^+$)

Example (8) (Exemplified Compound No. 1-187)

4-(3-{4-[18-(4-[3-(3-carboxylpropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid 4-Aminobutyric acid (1.4 g) was suspended in methylene chloride (15 mL), triethylamine (1.9 mL) was added thereto and the reaction solution was stirred under ice cooling. To the reaction solution, a solution of chlorotrimethylsilane (1.7 mL) in methylene chloride (15 mL) was dropped over a period of 5 minutes. The reaction solution was returned to room temperature and stirred for 3 hours. Imidazol-1-ylcarbonylaminoacetic acid 4-[18-(4-imidazol-1-ylcarbonylaminoacetoxy-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (7), 3.0 g) was added to the mixture under ice cooling and the mixture was stirred for 22 hours at room temperature. The reaction solution was purified by silica gel column chromatography (MeOH:CH$_2$Cl$_2$=1:2), by reverse phase (ODS) column chromatography (MeOH:water=8:2 to 19:1) and further by silica gel column chromatography (MeOH:CH$_2$Cl$_2$=1:2), and dried under reduced pressure to obtain the title compound (147 mg) as a reddish black powder.

$^1$H-NMR (δ, ppm) (DMSO-$d_6$): 6.79-6.23 (m, 18H), 5.44 (dd, 2H), 3.93-3.80 (m, 4H), 3.02-2.98 (m, 4H), 2.19 (t, 4H), 2.03 (s, 4H), 2.00 (s, 6H), 1.97 (s, 6H), 1.82 (s, 6H), 1.63-1.56 (m, 6H), 1.34 (s, 6H), 1.20 (s, 6H)

Mass spectrum: +ESI, m/z=969.50 (M+H$^+$)

Example (9) (Exemplified Compound No. 1-63)

3-[4-(18-{4-(3-carboxymethylureidoacetoxy)-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]-ureidoacetic acid Glycine (1.03 g) was suspended in methylene chloride (15 mL), triethylamine (1.9 mL) was added thereto and the reaction solution was stirred under ice cooling. To the reaction solution, a mixed solution of chlorotrimethylsilane (1.7 mL) and methylene chloride (15 mL) was dropped over a period of 10 minutes under ice cooling and the reaction solution was returned to room temperature. The reaction solution was stirred for 2 hours and imidazol-1-ylcarbonylaminoacetic acid 4-{18-(4-imidazol-1-ylcarbonylaminoacetoxy-2,6,6-trimethyl-3-oxocyclohexa-1-enyl)-3,7,12,16-tetramethyloctadeca-1,3,5,7,9,11,13,15,17-nonaenyl}-3,5,5-trimethyl-2-oxocyclohexa-3-enyl ester (the compound in Example (7), 3.0 g) was added thereto. The reaction solution was stirred for 18 hours, and THF (40 mL) and water (5 mL) were added to the reaction solution and concentrated under reduced pressure. 5% Aqueous acetic acid solution (100 mL) was added to the solution and filtered to obtain a reddish black powder. To the obtained powder, methanol (100 mL) and ethyl acetate (200 mL) were added, concentrated under reduced pressure to about 100 mL and kept for 15 hours at no higher than −18° C. The reaction solution was filtered to obtain a reddish black powder. The powder was dissolved in methanol (20 mL) and methylene chloride (10 mL), the solution was dropped to ethyl acetate (500 mL) and the precipitated solid was filtered to obtain a reddish black powder. The obtained powder was dissolved in methanol (1.2 L) at 60° C., the solution was dropped to 2% aqueous acetic acid solution (1 L). The precipitated solid was collected by filtration and dried under vacuum to obtain the title compound (558 g) as a reddish black powder.

$^1$H-NMR (δ, ppm) (DMSO-$d_6$): 6.78-6.28 (m, 18H), 5.44 (dd, 2H), 3.96-3.84 (m, 4H), 3.72 (d, 4H), 2.03 (s, 4H), 2.00 (s, 6H), 1.97 (s, 6H), 1.82 (s, 6H), 1.34 (s, 6H), 1.20 (s, 6H)

Mass spectrum: +ESI, m/z=913.36 (M+H$^+$)

Example (10) (Exemplified Compound No. 1-185)

3-(3-{4-[18-(4-[3-(2-carboxyethyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)propionic acid β-Alanine (1.22 g) was suspended in methylene chloride (15 mL), triethylamine (1.9 mL) was added thereto and the reaction solution was stirred under ice cooling. To the reaction solution, a mixed solution of chlorotrimethylsilane (1.7 mL) and methylene chloride (15 mL) was dropped over a period of 5 minutes under ice cooling and the reaction solution was returned to room temperature. The reaction solution was stirred for 2 hours and imidazol-1-ylcarbonylaminoacetic acid 4-{18-(4-imidazol-1-ylcarbonylaminoacetoxy-2,6,6-trimethyl-3-oxocyclohexa-1-enyl)-3,7,12,16-tetramethyloctadeca-1,3,5,7,9,11,13,15,17-nonaenyl}-3,5,5-trimethyl-2-oxocyclohexa-3-enyl ester (the compound in Example (7), 3.0 g)) was added thereto. The reaction solution was stirred for 16 hours, THF (40 mL) and water (5 mL) were added thereto and the solution was concentrated under reduced pressure. The residue was dissolved in MeOH (100 mL) at 50° C., 5% aqueous acetic acid solution (35 mL) was added thereto and the solution was left for 1.5 hours at −20° C. The precipitated solid was collected by filtration to obtain a reddish black powder. The obtained powder was purified by reverse phase (ODS) column chromatography (MeOH:water=7:3 to 19:1) and dried under vacuum to obtain the title compound (560 mg) as a reddish black powder.

NMR (δ, ppm) (DMSO-$d_6$): 12.2 (brs, 2H), 6.79-6.22 (m, 18H), 5.44 (dd, 2H), 3.93-3.81 (m, 4H), 3.20 (q, 4H), 2.35 (t, 4H), 2.06-2.03 (m, 4H), 2.00 (s, 6H), 1.97 (s, 6H), 1.82 (s, 6H), 1.34 (s, 6H), 1.20 (s, 6H)

Mass spectrum: +ESI, m/z=941.51 (M+H$^+$)

Example (11) (Exemplified No. Compound No. 2-11)

2-[3-{4-(18-[4-(3-[2-sulfoethyl]ureidoacetoxy)-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonylmethyl}ureido]ethanesulfonic acid Taurine (2.55 g) was suspended in methylene chloride (15 mL), N,N-diisopropylethylamine (3.6 mL) was added thereto and a solution of chlorotrimethylsilane (2.5 mL) in methylene chloride (15 mL) was dropped over a period of 5 minutes under ice cooling. The reaction solution was returned to room temperature and stirred for 3 hours. Imidazol-1-ylcarbonylaminoacetic acid 4-{18-(4-imidazol-1-ylcarbonylaminoacetoxy-2,6,6-trimethyl-3-oxocyclohexa-1-enyl)-3,7,12,16-tetramethyloctadeca-1,3,5,7,9,11,13,15,17-nonaenyl}-3,5,5-trimethyl-2-oxocyclohexa-3-enyl ester (the compound in Example (7), 3.0 g) was added to the reaction solution and the solution was stirred for 1 hour (the reaction solution A). In another vessel, taurine (0.88 g), methylene chloride (5 mL) and N,N-diisopropylethylamine (1.2 mL) were added, a solution of chlorotrimethylsilane (0.85 mL) in methylene chloride (5 mL) was dropped thereto over a period of 5 minutes under ice cooling and the reaction solution was returned to room temperature (the reaction solution B). The reaction solution B was dropped to the reaction solution A over 5 minutes and stirred for 1 hour, and THF (40 mL) and water (10 mL) were added thereto. The reaction solution was concentrated under reduced pressure, and the residue was dissolved in 5% aqueous acetic acid solution (600 mL) and purified by reverse phase (ODS) column chromatography (MeOH:water=0:1 to 3:1) and by the chromatography (MeOH:water=1:1 to 3:1), and dried under vacuum to obtain a reddish black powder. To the obtained powder, ethyl acetate (150 mL) was added and the solution was stirred for 17 hours. The powder was collected by filtration to obtain the title compound (189 mg) as a reddish black powder.

NMR (δ, ppm) (DMSO-$d_6$): 6.78-6.23 (m, 18H), 5.44 (dd, 2H), 3.90-3.78 (m, 4H), 3.28 (t, 4H), 2.54-2.49 (m, 4H), 2.07-2.02 (m, 4H), 2.00 (s, 6H), 1.97 (s, 6H), 1.82 (s, 6H), 1.34 (s, 6H), 1.20 (s, 6H).

Mass spectrum: −ESI, m/z=1011.51 (M−H$^-$)

Example (12) (Exemplified Compound No. 1-366)

3-(Imidazol-1-ylcarbonylamino)propionic acid 4-[18-(4-{3-(imidazol-1-ylcarbonylamino)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester To a mixed solution of methylene chloride (200 mL) and N,N-dimethylformamide (200 mL), 1,1′-carbonyldiimidazole (20 g) was added under ice cooling and the reaction solution was stirred for 20 minutes. Then, to the solution, 3-aminopropionic acid 4-{18-[4-(3-aminopropionyloxy)-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyl ester dihydrochloride (the compound in Reference Example (4), 20 g) was added. The reaction solution was stirred for 2 hours at room temperature, methylene chloride (200 mL) and water (400 mL) were added thereto and the layers were separated. The organic layer was washed with water (400 mL) twice and with saturated saline solution (400 mL), dried over anhydrous sodium sulfate and concentrated under reduced pressure. The residue was dissolved in ethyl acetate (500 mL), the resulting solution was dropped to n-hexane (1 L) and the crystals were generated. The precipitate was filtered to obtain the title compound (19.21 g) as a reddish black powder.

NMR (δ, ppm) (DMSO-$d_6$): 8.63 (t, 2H), 8.24 (m, 2H), 7.67-7.66 (m, 2H), 7.04-7.03 (m, 2H), 6.79-6.28 (m, 14H), 5.46 (dd, 2H), 3.53 (q, 4H), 2.73 (t, 4H), 2.01-1.97 (m, 16H), 1.82 (s, 10H), 1.33 (s, 6H), 1.18 (s, 6H)

Mass spectrum: −ESI, m/z=925.17 (M−H$^-$)

Example (13) (Exemplified Compound No. 1-103)

3-{2-[4-(18-{4-[3-(3-carboxylmethylureido)-propionyloxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxy-carbonyl]ethyl}ureidoacetic acid Glycine (9.7 g) was suspended in methylene chloride (40 mL), triethylamine (18 mL) was added thereto and the reaction solution was stirred under ice cooling. A solution of chlorotrimethylsilane (16 mL) in methylene chloride (40 mL) was dropped over a period of for 15 minutes to the solution and the reaction solution was returned to room temperature. The reaction solution was stirred for 2 hours and 3-(imidazol-1-ylcarbonylamino)propionic acid 4-[18-(4-{3-(imidazol-1-ylcarbonylamino)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (12), 4.0 g) was added thereto. The reaction solution was stirred for 1 hour and concentrated under reduced pressure. To the residue, methanol (200 mL), water (200 mL) and strong acidic cation exchange resin (RCP160M, manufactured by Mitsubishi Chemical Corporation, 20 mL) were added in this order and the reaction solution was stirred for 40 minutes. The reaction solution was filtered using a filtration aid (celite) and a reddish black solid attached to the celite was eluted with methanol (1.5 L). The eluted solution was concentrated under reduced pressure, the residue was dissolved in methanol (800 mL) and a 5% aqueous acetic acid solution (200 mL) was dropped thereto. This solution was purified by reverse phase silica gel (RP-18) column chromatography (MeOH:5% aqueous acetic acid solution=4:1 to acetone:water=7:3) to obtain the title compound (400 mg) as a reddish black powder.

NMR (δ, ppm) (DMSO-$d_6$): 6.79-6.23 (m, 18H), 5.45 (dd, 2H), 3.69 (d, 4H), 3.33-3.25 (m, 4H), 2.53-2.49 (m, 4H), 2.09-2.02 (m, 4H), 2.00 (s, 6H), 1.97 (s, 6H), 1.82 (s, 6H), 1.34 (s, 6H), 1.20 (s, 6H)

Mass spectrum: +ESI, m/z=941.58 (M+H$^+$)

Example (14) (Exemplified Compound No. 1-189)

3-[3-(2-{4-[18-(4-{3-[3-(2-carboxyethyl)-ureido]propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]propionic acid β-Alanine (8.7 g) was suspended in methylene chloride (30 mL), triethylamine (14 mL) was added thereto and the reaction solution was stirred under ice cooling. A solution of chlorotrimethylsilane (12 mL) in methylene chloride (30 mL) was dropped to the solution over a period of for 15 minutes and the reaction solution was returned to room temperature. The reaction solution was stirred for 3 hours and 3-(imidazol-1-ylcarbonylamino)propionic acid 4-[18-(4-{3-(imidazol-1-ylcarbonylamino)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound of Example (12), 3.0 g) was added thereto. The reaction solution was stirred for 2 hours and concentrated under reduced pressure. To the residue, methanol (200 mL), water (200 mL) and strong acidic cation exchange resin (RCP160M, manufactured by Mitsubishi Chemical Corporation, 20 mL) were added in this order and the reaction solution was stirred for 30 minutes. The mixed solution was filtered using a filtration aid (celite) and a reddish black solid attached to the celite was eluted with methanol (1 L). The eluted solution was concentrated under reduced pressure to approximately 850 mL, a 5% aqueous acetic acid solution was added thereto and the mixture was purified by reverse phase silica gel (RP-18) column chromatography (MeOH:5% aqueous acetic acid solution=4:1 to acetone:water=7:3) to obtain the title compound (397 mg) as a reddish black powder.

NMR (δ, ppm) (DMSO-$d_6$): 12.2 (s, 2H), 6.79-6.28 (m, 14H), 6.05 (t, 4H), 5.44 (dd, 2H), 3.29-3.16 (m, 8H), 2.51-2.47 (m, 4H), 2.34 (t, 4H), 2.18-2.03 (m, 4H), 2.00 (s, 6H), 1.97 (s, 6H), 1.82 (s, 6H), 1.34 (s, 6H), 1.20 (s, 6H).

Mass spectrum: +ESI, m/z=969.65 (M+H$^+$)

Example (15) (Exemplified Compound No. 1-191)

4-[3-(2-{4-[18-(4-{3-[3-(3-carboxypropyl)-ureido]propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]butyric acid γ-Aminobutyric acid (10.0 g) was suspended in methylene chloride (30 mL), triethylamine (14 mL) was added thereto and the reaction solution was stirred under ice cooling. A solution of chlorotrimethylsilane (12 mL) in methylene chloride (30 mL) was dropped to the solution over a period of 10 minutes and the reaction solution was returned to room temperature. The reaction solution was stirred for 3 hours, 3-(imidazol-1-ylcarbonylamino)propionic acid 4-[18-(4-{3-(imidazol-1-ylcarbonylamino)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (12), 3.0 g) was added thereto. The mixture was stirred for 20 hours and concentrated under reduced pressure. To the residue, water (1.5 L) and methylene chloride (400 mL) were added and the layers were separated. The obtained aqueous layer was extracted twice with methylene chloride (400 mL). Then, the organic layer was combined, washed with a saturated saline solution (600 mL), dried over anhydrous sodium sulfate, concentrated under reduced pressure and dried in vacuum. The residue was dissolved in methanol (425 mL) and water (75 mL) and purified by reverse phase silica gel (RP-18) column chromatography (methanol:water=17:3 to acetone:water=7:3) to obtain the title compound (790 mg) as a reddish black powder.

NMR (δ, ppm) (DMSO-$d_6$): 6.82-6.28 (m, 16H), 6.06 (t, 4H), 5.90 (t, 4H), 5.44 (dd, 2H), 3.31-3.22 (m, 4H), 2.98 (q, 4H), 2.52-2.49 (m, 4H), 2.19 (t, 4H), 2.03-1.97 (m, 16H), 1.82 (s, 6H), 1.66-1.49 (m, 6H), 1.34 (s, 6H), 1.20 (s, 6H)

Mass spectrum: +ESI, m/z=997.81 (M+H$^+$)

Example (16) (Exemplified Compound No. 2-12)

2-[3-(2-{4-[18-(4-{3-[3-(2-sulfoethyl)-ureido]propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]ethanesulfonic acid Taurine (11.4 g) was suspended in methylene chloride (28 mL), triethylamine (13 mL) was added thereto and the reaction solution was stirred under ice cooling. A solution of chlorotrimethylsilane (11 mL) and methylene chloride (28 mL) was dropped to the solution over a period of 10 minutes under ice cooling and the reaction solution was returned to room temperature. The reaction solution was stirred for 2 hours and 3-(imidazol-1-ylcarbonylamino)propionic acid 4-[18-(4-{3-(imidazol-1-ylcarbonylamino)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (12), 2.8 g) was added thereto. The reaction solution was stirred for 1 hour and then kept in a freezer. After for 15 hours, the reaction solution was returned to room temperature and concentrated under reduced pressure. To the residue, methanol (200 mL) and strong acidic cation exchange resin (RCP160M, manufactured by Mitsubishi Chemical Corporation, 20 mL) were added, and the reaction solution was stirred for 1 hour and filtered with celite (Celite 545, manufactured by Wako Pure Chemical Industries, Ltd.). The filtrate was purified by reverse phase silica gel (RP-18) column chromatography (MeOH:5% aqueous acetic acid solution=1:1 to MeOH:water=2:3) to obtain the title compound (1.3 g) as a reddish black powder.

NMR (δ, ppm) (DMSO-$d_6$): 6.79-6.28 (m, 18H), 5.54 (dd, 2H), 3.28-3.23 (q, 8H), 3.14-3.07 (m, 4H), 2.53-2.48 (m, 4H), 2.08-2.03 (m, 4H), 1.97 (s, 6H), 1.91 (s, 6H), 1.82 (s, 6H), 1.34 (s, 6H), 1.20 (s, 6H).

Mass spectrum: −ESI, m/z=1039.85 (M−H$^-$)

Example (17) (Exemplified Compound No. 1-367)

4-(Imidazol-1-ylcarbonylamino)butyric acid 4-[18-(4-{4-(imidazol-1-ylcarbonylamino)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester To a solution of methylene chloride (250 mL) and N,N-dimethylformamide (250 mL), 1,1'-carbonyldiimidazole (24.1 g) was added and the reaction solution was stirred for 15 minutes under ice cooling. To the solution, 4-aminobutyric acid 4-{18-[4-(4-aminobutyryloxy)-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyl ester dihydrochloride (the compound in Reference Example (8), 25 g) was added and the reaction solution was returned to room temperature. The reaction solution was stirred for 2.5 hours, methylene chloride (250 mL) and water (500 mL) were added thereto and the layers were separated. The organic layer was washed twice with water (500 mL) and with a saturated saline solution (500 mL), and dried over anhydrous sodium sulfate. The organic layer was concentrated under reduced pressure at room temperature to about 200 mL and the resulting solution was dropped to n-hexane (4 L). The precipitated solid was collected by filtration to obtain a reddish black powder. This was dissolved in ethyl acetate (1.5 L), and n-hexane (1 L) was dropped thereto while stirring. The precipitate was collected by filtration to obtain the title compound (18.5 g) as a reddish black powder.

NMR (δ, ppm) (DMSO-d$_6$): 8.54 (t, 2H), 8.24 (s, 2H), 7.67 (s, 2H), 7.03 (s, 2H), 6.78-6.28 (m, 14H), 5.43 (t, 2H), 3.35-3.30 (m, 4H), 2.51-2.47 (m, 4H), 2.00-1.97 (m, 16H), 1.91-1.82 (m, 10H), 1.33 (s, 6H), 1.18 (s, 6H).

Mass spectrum: +ESI, m/z=955.31 (M+H$^+$)

Example (18) (Exemplified Compound No. 1-143)

3-(3-{4-[18-(4-{4-[3-carboxymethylureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)ureidoacetic acid Glycine (7.1 g) was suspended in methylene chloride (30 mL), triethylamine (13 mL) was added thereto and the reaction solution was stirred under ice cooling. A solution of chlorotrimethylsilane (12 mL) in methylene chloride (30 mL) was dropped to the solution over a period of 10 minutes and the reaction solution was returned to room temperature. The reaction solution was stirred for 2.5 hours and 4-(imidazol-1-ylcarbonylamino)butyric acid 4-[18-(4-{4-(imidazol-1-ylcarbonylamino)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (17), 3.0 g) was added thereto. The reaction solution was stirred for 2.5 hours and kept in a refrigerator. The reaction solution was concentrated under reduced pressure at 25° C., to the residue, methanol (100 mL), water (100 mL) and strong acidic cation exchange resin (RCP160M, manufactured by Mitsubishi Chemical Corporation, 40 mL) were added in this order and the mixture was stirred for 1.5 hours. The mixed solution was filtered using a filtration aid (celite) and a reddish black solid attached to celite was eluted with methanol (800 mL). The eluted solution was concentrated under reduced pressure to precipitate crystals and cooled to −11° C., and water (300 mL) was dropped thereto. The precipitated reddish black solid was collected by filtration and dried in vacuum. This solid was purified by reverse phase silica gel (RP-18) column chromatography (MeOH:water=7:3 to 19:1) and the obtained reddish black solid was dissolved in methanol (30 mL). To the reaction solution, water (30 mL) was dropped over a period of 5 minutes and to the mixture, strong acidic cation exchange resin (RCP160M, manufactured by Mitsubishi Chemical Corporation, 6 mL) was added and the mixture was filtered using celite (Celite 545, manufactured by Wako Pure Chemical Industries, Ltd.). The celite to which the title compound was attached was eluted with methanol (100 mL) and water (50 mL) was dropped thereto. The precipitated solid was collected by filtration and dried to obtain the title compound (277 mg) as a reddish black powder.

NMR (δ, ppm) (DMSO-d$_6$): 6.78-6.23 (m, 18H), 6.04 (t, 2H), 5.43 (dd, 2H), 3.66 (d, 2H), 3.04 (q, 4H), 2.38 (t, 4H), 2.06-2.03 (m, 4H), 2.00 (s, 6H), 1.97 (s, 6H), 1.82 (s, 6H), 1.72-1.64 (m, 4H), 1.33 (s, 6H), 1.19 (s, 6H).

Mass spectrum: +ESI, m/z=969.70 (M+H$^+$)

Example (19) (Exemplified Compound No. 1-193)

3-[3-(3-{4-[18-(4-{4-[3-(2-carboxyethyl)-ureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)ureido]propionic acid β-Alanine (8.4 g) was suspended in methylene chloride (30 mL), triethylamine (13 mL) was added thereto and the reaction solution was stirred under ice cooling. A solution of chlorotrimethylsilane (12 mL) in methylene chloride (30 mL) was dropped to the solution over a period of 10 minutes and the reaction solution was returned to room temperature. The reaction solution was stirred for 2 hours and 4-(imidazol-1-ylcarbonylamino)butyric acid 4-[18-(4-{4-(imidazol-1-ylcarbonylamino)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (17), 3.0 g) was added thereto. The mixture was stirred for 20 hours and concentrated under reduced pressure. To the residue, methanol (150 mL), water (150 mL) and strong acidic cation exchange resin (RCP160M, manufactured by Mitsubishi Chemical Corporation, 30 mL) were added in this order and the reaction solution was stirred for 45 minutes. The mixed solution was filtered using a filtration aid (celite) and a reddish black solid attached to the celite was eluted with methanol (1 L). The eluted solution was concentrated under reduced pressure, and kept in a refrigerator for 2 days. The precipitated reddish black solid was purified by reverse phase silica gel (RP-18) column chromatography (MeOH:water=19:1) to obtain the title compound (413 mg) as a reddish black powder.

NMR (δ, ppm) (DMSO-d$_6$): 6.78-6.28 (m, 16H), 6.04 (t, 2H), 5.86 (m, 2H), 5.43 (dd, 2H), 3.18 (q, 4H), 3.03 (q, 4H), 2.39-2.31 (m, 8H), 2.03 (s, 4H), 2.00 (s, 6H), 1.97 (s, 6H), 1.82 (s, 6H), 1.66 (quint, 4H), 1.34 (s, 6H), 1.19 (s, 6H)

Mass spectrum: +ESI, m/z=997.80 (M+H$^+$)

Example (20) (Exemplified Compound No. 1-195)

4-[3-(3-{4-[18-(4-{4-[3-(3-carboxypropyl)-ureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)ureido]butyric acid γ-Aminobutyric acid (9.7 g) was suspended in methylene chloride (30 mL), triethylamine (13 mL) was added thereto under ice cooling and the reaction solution was stirred. A solution of chlorotrimethylsilane (12 mL) in methylene chloride (30 mL) was dropped to the solution over a period of 5 minutes and the reaction solution was returned to room temperature. The reaction solution was stirred for 22.5 hours and 4-(imidazol-1-ylcarbonylamino)butyric acid 4-[18-(4-{4-(imidazol-1-ylcarbonylamino)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (17), 3.0 g) was added thereto. The mixture was stirred for 21.5 hours and concentrated under reduced pressure. To the residue, methanol (150 mL), water (150 mL) and strong acidic cation exchange resin (RCP160M, manufactured by Mitsubishi Chemical Corporation, 30 mL) were added in this order and the reaction solution was stirred for 25 minutes. The mixed solution was filtered using a filtration aid (celite) and a reddish black solid attached to Celite was eluted with methanol (1 L). The eluted solution was concentrated under reduced pressure and kept in a refrigerator. The precipitated reddish black solid was purified by reverse phase silica gel (RP-18) column chromatography (MeOH: water=19:1) and by the chromatography (acetone:water=3:2 to 7:3) to obtain the title compound (1.0 g) as a reddish black powder.

NMR (δ, ppm) (DMSO-$d_6$): 6.78-6.28 (m, 14H), 5.90-5.84 (m, 4H), 5.43 (dd, 2H), 3.05-2.96 (m, 8H), 2.39-2.33 (m, 4H), 2.19 (t, 4H), 2.02 (s, 4H), 2.00 (s, 6H), 1.97 (s, 6H), 1.82 (s, 6H), 1.70-1.55 (m, 8H), 1.33 (s, 6H), 1.19 (s, 6H)

Mass spectrum: +ESI, m/z=1025.44 (M+H$^+$)

Example (21) (Exemplified Compound No. 2-13)

2-[3-(3-{4-[18-(4-{4-[3-(2-sulfoethyl)-ureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)ureido]ethanesulfonic acid Taurine (11.8 g) was suspended in 30 mL methylene chloride, triethylamine (13 mL) was added thereto and the reaction solution was stirred under ice cooling. A solution of chlorotrimethylsilane (12 mL) in methylene chloride (30 mL) was dropped to the solution over a period of 12 minutes and the reaction solution was returned to room temperature. The reaction solution was stirred for 2 hours and 4-(imidazol-1-ylcarbonylamino)butyric acid 4-[18-(4-{4-(imidazol-1-ylcarbonylamino)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyl ester (the compound in Example (17), 3.0 g) was added thereto. The reaction solution was stirred for 17 hours and concentrated under reduced pressure. To the residue, methanol (200 mL) was added, the mixed solution was filtered using a filtration aid (celite) and the filtrate was purified by reverse phase silica gel (RP-18) column chromatography (MeOH:5% aqueous acetic acid solution=7:3 to MeOH:water=7:3) and by the chromatography (MeOH:5% aqueous acetic acid solution=1:1 to MeOH:water=7:3) to obtain a reddish black solid. To this, methanol (100 mL) and strong acidic cation exchange resin (RCP160M, manufactured by Mitsubishi Chemical Corporation, 10 mL) were added, and the reaction solution was stirred for 1 hour and filtered using celite (Celite 545, manufactured by Wako Pure Chemical Industries, Ltd.). The filtrate was purified by reverse phase silica gel (RP-18) column chromatography (MeOH:water=7:3 to MeOH:water=4:1) to obtain the title compound (460 mg) as a reddish black powder.

NMR (δ, ppm) (DMSO-$d_6$): 6.78-6.28 (m, 18H), 5.43 (dd, 2H), 3.26 (t, 4H), 3.01 (t, 4H), 2.54-2.48 (m, 4H), 2.37 (t, 4H), 2.03-2.02 (m, 4H), 2.00 (s, 6H), 1.97 (s, 6H), 1.82 (s, 6H), 1.66 (quint, 4H), 1.34 (s, 6H), 1.19 (s, 6H).

Mass spectrum: −ESI, m/z=1067.67 (M−H$^−$)

Example (22) (Exemplified Compound No. 1-187 (2Na Salt of Compound in Example (8)))

4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid disodium salt To 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido) butyric acid (the compound in Example (8), 730 mg) and sodium 2-ethylhexanoate (250 mg), methanol (15 mL) was added and the reaction solution was stirred for 2 hours. To the reaction solution, ethyl acetate (60 mL) was dropped and the solution was concentrated under reduced pressure to around 30 mL. The precipitated solid was filtered, ethyl acetate (100 mL) was added thereto and the reaction solution was stirred for 7.5 hours. The solid was collected by filtration and dried under vacuum to obtain the title compound (680 mg) as a reddish black powder.

NMR (δ, ppm) (CD$_3$OD): 6.77-6.29 (m, 14H), 5.57 (dd, 2H), 4.05-3.93 (m, 4H), 3.17-3.12 (m, 4H), 2.22 (t, 4H), 2.15-1.99 (m, 16H), 1.89 (s, 6H), 1.81-1.73 (m, 4H), 1.37 (s, 6H), 1.25 (s, 6H).

Mass spectrum: +ESI, m/z=1013.66 (M+H$^+$); 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid disodium salt, m/z=991.52 (M+H$^+$); 4-(3-{4-[18-(4-[3-(3-carboxypropyl)-ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid sodium salt, m/z=969.42 (M+H$^+$); 4-(3-{4-[18-(4-[3-(3-carboxypropyl-) ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid Example (23) (Exemplified Compound No. 1-187 (Dilysine Salt of Compound in Example (8)))

4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid dilysine salt To 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido) butyric acid (the compound in Example (8), 6.5 g) and L-(+)-lysine (1.96 g), methanol (163 mL) was added and the reaction solution was stirred for 2 hours. The reaction solution was filtered and the obtained solid was dried under vacuum to obtain the title compound (3.99 g) as a reddish black powder.

NMR (δ, ppm) (CD$_3$OD): 6.77-6.29 (m, 14H), 5.57 (dd, 2H), 4.05-3.93 (m, 4H), 3.53 (t, 2H), 3.17-3.13 (m, 4H), 2.92 (t, 4H), 2.22 (t, 4H), 2.09-2.00 (m, 16H), 1.88 (s, 6H), 1.85-1.49 (m, 22H), 1.37 (s, 6H), 1.25 (s, 6H).

Mass spectrum: −ESI, m/z=967.60 (M−H$^−$); 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid Example (24) (Exemplified Compound No. 1-378)

3-isobutyl-4-(3-{4-[18-(4-[3-(2-isobutyl-3-carboxy-propyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid 4-Amino-3-isopropylbutyric acid (16.0 g) was suspended in methylene chloride (30 mL), triethylamine (14 mL) was added thereto and the reaction solution was stirred under ice cooling. To the reaction solution, a solution of chlorotrimethylsilane (12.7 mL) and methylene chloride (30 mL) was dropped over a period of 10 minutes and the reaction solution was returned to room temperature. The reaction solution was stirred for 3.5 hours, imidazol-1-ylcarbonylaminoacetic acid 4-{18-(4-imidazol-1-ylcarbonylaminoacetoxy-2,6,6-trimethyl-3-oxocyclohexa-1-enyl)-3,7,12,16-tetramethyloctadeca-1,3,5,7,9,11,13,15,17-nonaenyl}-3,5,5-trimethyl-2-oxocyclohexa-3-enyl ester (the compound in Example (7), 3 g) was added thereto under ice cooling and the solution was returned to room temperature. 20 Hours after, methylene chloride (140 mL) and a 5% aqueous acetic acid solution (200 mL) were added to the reaction solution and the layers were separated. The organic layer was washed with water (200 mL) twice and with a saturated saline solution (200 mL), dried over anhydrous sodium sulfate, concentrated under reduced pressure and dried in vacuum. The residue was dissolved in methanol (425 mL), water (75 mL) was dropped thereto and this was purified by reverse phase silica gel (RP-18) column chromatography (methanol: 5% aqueous acetic acid solution=17:3 to acetone:water=4:1) to obtain the title compound (1.4 g) as a reddish black powder.

NMR (δ, ppm) (DMSO-d$_6$): 12.0 (brs, 2H), 6.79-6.20 (m, 18H), 5.44 (dd, 2H), 3.94-3.81 (m, 4H), 3.10-2.86 (m, 4H), 2.24-2.19 (m, 4H), 2.05-2.03 (m, 4H), 2.00 (s, 6H), 1.97 (s, 6H), 1.93-1.87 (m, 4H), 1.82 (s, 6H), 1.68-1.60 (m, 2H), 1.34 (s, 6H), 1.20 (s, 6H), 1.17-1.00 (m, 4H), 0.86-0.83 (t, 12H)

Mass spectrum: −±ESI, m/z=1081.50 (M±H$^-$)

Example (25) (Exemplified Compound No. 1-385)

1-(3-{4-[18-(4-[3-(1-carboxymethylcyclo-hexylmethyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureidomethyl)cyclohexylacetic acid 1-Aminomethylcyclohexylacetic acid (17.2 g) was suspended in methylene chloride (30 mL), N,N-diisopropylethylamine (17.5 mL) was added thereto and the reaction solution was stirred under ice cooling. A solution of chlorotrimethylsilane (12.7 mL) and methylene chloride (30 mL) was dropped to the solution over a period of 5 minutes and the reaction solution was returned to room temperature. The reaction solution was stirred for 2 hours, imidazol-1-ylcarbonylaminoacetic acid 4-{18-(4-imidazol-1-ylcarbonylaminoacetoxy-2,6,6-trimethyl-3-oxocyclohexa-1-enyl)-3,7,12,16-tetramethyloctadeca-1,3,5,7,9,11,13,15,17-nonaenyl}-3,5,5-trimethyl-2-oxocyclohexa-3-enyl ester (the compound in Example (7), 3 g) was added thereto under ice cooling and the mixture was stirred for 16 hours at room temperature. To the reaction solution, methylene chloride (140 mL) and a 5% aqueous acetic acid solution (200 mL) were added and the layers were separated. The organic layer was washed with water (200 mL) and with a saturated saline solution (200 mL), dried over anhydrous sodium sulfate, concentrated under reduced pressure and dried in vacuum. The residue was dissolved in methanol (350 mL) and water (150 mL) was dropped thereto. This was purified by reverse phase silica gel (RP-18) column chromatography (acetone:water=7:3 to acetone:water=3:1) and further by the chromatography (acetone:water=3:2 to 3:1) to obtain the title compound (84 mg) as a reddish black powder.

NMR (δ, ppm) (DMSO-d$_6$): 6.82-6.28 (m, 18H), 5.44 (dd, 2H), 3.95-3.83 (m, 4H), 3.15-3.04 (m, 4H), 2.13 (s, 4H), 2.06-2.02 (m, 4H), 2.00 (s, 6H), 1.97 (s, 6H), 1.82 (s, 6H), 1.55-1.23 (m, 26H), 1.19 (s, 6H)

Mass spectrum: −ESI, m/z=1105.54 (M+H$^+$)

Reference Example (1)

N-(imidazol-1-ylcarbonyl)glycine t-butyl ester

To a mixture of 1,1'-carbonyldiimidazole (9.15 g) and dry tetrahydrofuran (100 ml), glycine t-butyl ester hydrochloride (6.1 g) was added and the reaction solution was stirred overnight. The solvent was distilled off under reduced pressure, ethyl acetate and water were added to the residue and the organic layer was separated. The organic layer was washed with water twice and with a saturated saline solution, and dried over anhydrous sodium sulfate. The solvent was distilled off to obtain the titled compound (6.72 g) as white crystals.

$^1$H-NMR (δ, ppm) (DMSO-d$_6$): 1.43 (s, 9H), 3.92 (d, 2H), 7.06 (dd, 1H), 7.69 (dd, 1H), 8.26 (dd, 1H), 8.95 (t, 1H)

Reference Example (2)

Imidazol-1-ylcarboxylic acid 4-[18-{4-(imidazol-1-ylcarbonyloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester To a mixture of 6-hydroxy-3-(18-[4-hydroxy-2,6,6-trimethyl-3-oxo-1-cyclohexenyl]-3,7,12,16-tetramethyloctadeca-1,3,5,7,9,11,13,15,17-nonaenyl)-2,4,4-trimethyl-2-cyclohexene-1-one (astaxanthin, 5.97 g) and 1,1'-carbonyldiimidazole (4.87 g), anhydrous methylene chloride (150 ml) was added. The reaction solution was substituted by argon and then stirred for 2 days at room temperature. To the reaction solution, methylene chloride (100 ml) and water (300 ml) were added, substituted by argon and stirred for 3 hours at the same temperature. The methylene chloride layer was separated, washed with water twice and with saturated saline solution, and dried over anhydrous sodium sulfate. The methylene chloride was distilled off under reduced pressure to obtain the title compound (7.99 g) as a reddish black powder.

$^1$H-NMR (δ, ppm) (CDCl$_3$): 1.30 (s, 6H), 1.41 (s, 6H), 1.94 (s, 6H), 2.00 (s, 6H), 2.02 (s, 6H), 2.21-2.26 (m, 4H), 5.65 (dd, 2H), 6.21-6.70 (m, 14H), 7.09 (d, 2H), 7.48 (s, 2H), 8.18 (s, 2H)

Reference Example (3)

N-t-butoxycarbonylaminoacetic acid 4-[18-{4-(N-t-butoxycarbonylaminoacetoxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester To 6-hydroxy-3-(18-[4-hydroxy-2,6,6-trimethyl-3-oxo-1-cyclohexenyl]-3,7,12,16-tetramethyloctadeca-1,3,5,7,9,11, 13,15,17-nonaenyl)-2,4,4-trimethyl-2-cyclohexene-1-one (astaxanthin, 5.97 g), N-t-butoxycarbonyl glycine (10.51 g) and 4-(N,N-dimethylamino)pyridine (14.66 g), anhydrous methylene chloride (300 ml) was added, the reaction solution was substituted by argon and N,N'-diisopropylcarbodiimide (15.13 g) was added thereto. The reaction solution was heated and stirred for 3 days on the oil bath of 35° C. The reaction solution was purified by silica gel column chromatography (eluent; methylene chloride:ethyl acetate=10:1 to 5:1) to obtain the title compound (6.01 g) as a reddish black powder.

$^1$H-NMR (δ, ppm) (DMSO-$d_6$): 1.20 (s, 6H), 1.34 (s, 6H), 1.39 (s, 18H), 1.82 (s, 6H), 1.97-2.00 (m, 16H), 3.77 (dd, 4H), 5.46 (dd, 2H), 6.28-6.76 (m, 14H), 7.29 (t, 2H)

Reference Example (4)

3-Aminopropionic acid 4-[18-{4-(3-aminopropionyloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester dihydrochloride To a solution of 3-N-t-butoxycarbonylaminopropionic acid 4-[18-{4-(3-N-t-butoxycarbonylaminopropionyloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester (the compound in Reference Example (5), 6.00 g) and dioxane (60 mL), a 4 N hydrogen chloride/dioxane solution (60 mL) was dropped over a period of 10 minutes and the reaction solution was stirred for 30 minutes at room temperature. Completion of the reaction was confirmed, and the solution was concentrated under reduced pressure and dried in vacuum. To the concentrated residue, methanol (60 mL) and methylene chloride (120 mL) were added, the residue was dissolved and the reaction solution was concentrated under reduced pressure to about 30 mL. After the concentration, diethyl ether (120 mL) was slowly dropped to the solution while the reaction solution was stirred and the precipitate was collected by filtration. This was dissolved in methanol (60 mL) and methylene chloride (60 mL) and concentrated under reduced pressure, and the concentrated solution was dropped to diethyl ether (40 mL). The precipitated solid was collected by filtration and dried to obtain the title compound (2.38 g) as a reddish black powder.

$^1$H-NMR 400 MHz (DMSO-$d_6$): δ 8.04 (6H, s), 6.79-6.29 (14H, m), 5.47 (2H, dd), 3.06 (4H, m), 2.80 (4H, t), 2.06-2.03 (4H, m), 2.01 (6H, s), 1.97 (6H, s), 1.83 (6H, s), 1.35 (6H, s), 1.21 (6H, s)

Mass spectrum: +ESI, m/z=739.54 (M+H$^+$)

Reference Example (5)

3-N-t-butoxycarbonylaminopropionic acid 4-[18-{4-(3-N-t-butoxycarbonylaminopropionyloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester The reaction vessel was substituted by argon, to a mixture of astaxanthin (6.00 g), N-(t-butoxycarbonyl)-β-alanine (9.50 g), methylene chloride (180 mL) and 4-(N,N-dimethylamino)pyridine (6.10 g), N,N'-diisopropylcarbodiimide (7.8 mL) was added and the reaction solution was stirred for 1 hour at room temperature. The insoluble substance was filtered off and the filtrate was concentrated under reduced pressure. The residue was purified by silica gel column chromatography (methylene chloride:ethyl acetate=1:0 to 1:1) and dried under vacuum to obtain the title compound (7.41 g) as a reddish black powder.

$^1$H-NMR 400 MHz (CDCl$_3$):δ6.69-6.19 (14H, m), 5.57 (2H, dd), 5.44 (2H, brs), 3.49 (4H, m), 2.64 (4H, m), 2.12-2.02 (4H, 1H), 2.00 (6H, s), 1.99 (6H, s), 1.91 (6H, s), 1.45 (18H, s), 1.36 (6H, s), 1.24 (6H, s)

Mass spectrum: +ESI, m/z=938.61 (M+H$^+$), 961.56 (M+Na$^+$)

Reference Example (6)

Aminoacetic acid 4-{18-[4-aminoacetoxy-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyl ester dihydrochloride In methylene chloride (28 mL), N-t-butoxycarbonylaminoacetic acid 4-{18-[4-tert-butoxy-carbonylaminoacetoxy-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyl ester (the compound in Reference Example (3), 5.50 g) was dissolved, a mixed solution of 4 N hydrogen chloride/dioxane (14 mL) and methylene chloride (28 mL) was dropped thereto over a period of 10 minutes under ice cooling and the reaction solution was stirred for 1.5 hours at room temperature. Further, a mixed solution of 4 N hydrogen chloride/dioxane (14 mL) and methylene chloride (56 mL) was dropped to the solution over a period of 10 minutes. The reaction solution was stirred for 3.5 hours. Hexane (112 mL) was added to the reaction solution, and the precipitated solid was collected by filtration and dried to obtain the title compound (4.68 g) as a reddish black powder.

$^1$H-NMR (δ, ppm) (DMSO-$d_6$): 8.51 (s, 6H), 6.79-6.30 (m, 14H), 5.55 (dd, 2H), 3.94 (d, 4H), 2.08-2.05 (m, 4H), 2.01 (s, 6H), 1.97 (s, 6H), 1.84 (s, 6H), 1.37 (s, 6H), 1.22 (s, 6H)

Mass spectrum: +ESI, m/z=711.50 (M+H$^+$); glycine diester of astaxanthin

Reference Example (7)

4-N-t-butoxycarbonylaminobutyric acid 4-[18-{4-(4-N-t-butoxycarbonylaminobutyryloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester To a mixture of astaxanthin (20 g), N-(t-butoxycarbonyl)-γ-aminobutyric acid (34.1 g), methylene chloride (500 mL) and 4-(N,N-dimethylamino)pyridine (40.9 g), N,N'-diisopropylcarbodiimide (51.6 mL) was dropped over a period of 5 minutes and the reaction solution was stirred for 2 hours at room temperature. The reaction solution was ice-cooled, 1 N hydrochloric acid was added thereto to pH 4, the mixture was filtered using a filtration aid (celite) and the layers were separated. The organic layer was washed with a saturated saline solution, dried over anhydrous sodium sulfate, filtered and concentrated under reduced pressure. The residue was purified by silica gel column chromatography (CH$_2$Cl$_2$:ethyl acetate=5:1) and the eluent was concentrated under reduced pressure to around 200 mL. The concentrated solution was dropped to hexane (3 L) and the precipitated reddish black powder was collected by filtration and dried under reduced pressure to obtain the title compound (29.2 g).

NMR (δ, ppm) (DMSO-$d_6$): 6.88-6.28 (m, 16H), 5.43 (dd, 2H), 2.97 (q, 4H), 2.37 (t, 4H), 2.04-2.02 (m, 4H), 2.00 (s, 6H), 1.97 (s, 6H), 1.81 (s, 6H), 1.71-1.64 (m, 4H), 1.38 (s, 18H), 1.33 (s, 6H), 1.19 (s, 6H)

Mass spectrum: +ESI, m/z=967.26 (M+H$^+$)

Reference Example (8)

4-Aminobutyric acid 4-[18-{4-(4-aminobutyryloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester dihydrochloride In methylene chloride (290 mL), 4-N-t-butoxycarbonylaminobutyric acid 4-[18-{4-(4-N-t-butoxycarbonylaminobutyryloxy)-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyl ester (the compound in Reference Example 7, 29 g) was dissolved and a mixed solution of 4 N hydrogen chloride/dioxane (145 mL) and methylene chloride (290 mL) was dropped thereto over a period of 35 minutes under ice cooling. The reaction solution was stirred for 2.5 hours and hexane (810 mL) was added thereto. After the precipitated solid was confirmed, it was collected by filtration to obtain the title compound (25.3 g) as a reddish black powder.

NMR (δ, ppm) (DMSO-$d_6$): 7.95 (s, 6H), 6.79-6.29 (m, 14H), 5.45 (dd, 2H), 2.91-2.83 (m, 4H), 2.58-2.47 (m, 4H), 2.09-2.02 (m, 4H), 2.01 (s, 6H), 1.97 (s, 6H), 1.90-1.82 (m, 10H), 1.34 (s, 6H), 1.20 (s, 6H)

Mass spectrum: +ESI, m/z=767.80 (M+H$^+$); 4-aminobutyric acid 4-{18-[4-(4-aminobutyryloxy)-2,6,6-trimethyl-3-oxocyclohexa-1-enyl]-3,7,12,16-tetramethyloctadeca-1,3,5,7,9,11,13,15,17-nonaenyl}-3,5,5-trimethyl-2-oxocyclohexa-3-enyl ester Test Example (1)

Test for Confirmation of Water Solubility (Distribution to Water/Methylene Chloride)

To each of the samples (1 mg) in Table 43, water (5 mL) and methylene chloride (5 mL) were added and the mixture was shaken, which was called the group of Solution A. A 28% sodium methoxide/methanol solution (463 μL (2.33 mmol)) was dissolved in water (10 mL), and the aqueous solution (1 mL) was collected and dissolved in water (100 mL), which was called Solution B. To each of the group of Solution A, Solution B (1 mL) was added and shaken. The solution was left at room temperature, each of the aqueous layer and of the organic layer were measured by HPLC and the ratio of the compound in the aqueous layer was shown in Table 4.

HPLC conditions were as follows:
chromatograph (HITACHI LaChrom Elite D-2000), column (SHISEIDO CAPCELL PAK C18 (3 μm particle diameter, 4.6 mm×150 mm)), detection temperature (40° C.), detection wavelength (474 nm), flow rate (1.0 mL/min) and mobile phase set up (% A=0.025% TFA/water, % B=0.025% TFA/acetonitrile); 70% A/30% B (at the start), 50% B gradient until 2.5 minutes, 98% B gradient until 4.2 minutes and the ratio (98% B) maintained until 15 minutes. The ratio in the aqueous layer was calculated from the following equation.

Ratio in aqueous layer [%]=[peak area of a compound in aqueous layer/(peak area of a compound in aqueous layer+peak area of a compound in organic layer)]×100

Astaxanthin manufactured by Sigma-Aldrich Co. LLC. was used and astaxanthin disuccinic acid ester was produced by the method described in Example 10 of a pamphlet in WO 2003/066583 A.

TABLE 43

| | Compound | Ratio of aqueous layer [%] |
|---|---|---|
| (A) | Astaxanthin | 0.0 |
| (B) | Astaxanthin disuccinate ester | 43.8 |
| (C) | Compound in Example (1) | 99.7 |
| (D) | Compound in Example (2) | 90.8 |
| (E) | Compound in Example (4) | 100.0 |
| (F) | Compound in Example (8) | 100.0 |
| (G) | Compound in Example (9) | 98.3 |
| (H) | Compound in Example (10) | 100.0 |

Astaxanthin (A) was not detected in the aqueous layer at all and has extremely low solubility in water. The dissolution ratio of the compound (B) (reference compound) in the aqueous layer was 43.8%. In contrast, the compounds (C) to (H) of the present invention have extremely higher dissolution ratios in the aqueous layer compared to the reference compound and are extremely excellent in water solubility.

Test Example (2)

Test for Oral Absorption in Mouse

Each of the compound in Example 8, astaxanthin (free form) and an extract from Haematococcus algae (AstaReal L10, manufactured by Fuji Chemical Industries Co., Ltd., oil containing 10% astaxanthin extracted from Haematococcus algae) was diluted with 33% dimethyl sulfoxide, 60% polyethylene glycol and 0.03% aqueous carboxymethyl cellulose solution and prepared to have a concentration of 5 mg/ml as a conversion to astaxanthin free form. The prepared sample was administered to a Wistar rat fasted one night (male, 9 to 13 weeks old, 250 to 300 g of body weight, 2 or 4 animals per group) by oral gavage in an amount of astaxanthin (50 mg) per 1 kg of body weight. Then, the blood was collected at the time points of 3 hours, 6 hours and 24 hours and the blood plasma was isolated. To the obtained blood plasma (0.1 ml), acetone in an amount of 6 folds and hexane in an amount of 50 folds were added, and the solution was stirred well and centrifuged to obtain a hexane layer. The hexane layer was dried under reduced pressure and dissolved in acetone (0.1 ml). The obtained acetone solution (0.05 mL) was analyzed by high performance liquid chromatography (HPLC) under the following conditions and the blood concentration was measured.

HPLC conditions:

Column (YMC-Carotenoid), mobile phase (methanol:t-butyl methyl ether:1% aqueous phosphoric acid=81:15:4 (V:V:V)), elution (linear gradient), detection wavelength (470 nm), flow rate (1.0 ml/min) and column temperature (25° C.)

Results which compared the absorbability of the compound in Example 8 with that of commercially available AstaReal L10 oil in rats (average value) are shown in Table 44 and FIG. 1.

TABLE 44

| Blood plasma concentration [ng/ml] | Compound in Example (8) | AstaReal L10 oil | Astaxanthin (free form) |
|---|---|---|---|
| 3 hour | 49.6 ± 2.3 | 13.5 ± 7.1 | 1.6 ± 0.5 |
| 6 hour | 43.3 ± 18.2 | 15.9 ± 7.4 | 0.9 ± 0.7 |
| 24 hour | 4.1 ± 5.8 | 0.2 ± 0.4 | 1.0 ± 0.6 |
| AUC | 640.4 | 209.3 | 23.3 |

It was confirmed that the compound in Example (8) had higher maximum blood concentration and AUC of astaxanthin in the blood plasma compared to astaxanthin (free form) and to the extract from Haematococcus algae and had higher oral absorbability.

Test Example (3)

Test for Anti-Inflammation in a Cell

RAW264.7 cells (mouse monocyte cell, ATCC) in RPMI 1640 medium were dispensed into a 12 well micro-plate. These cells were cultured for 48 hours in 5% $CO_2$ at 37° C. After the medium replacement, an aqueous solution of the sample was added to the medium and the cell was cultured for 24 hours. The medium was then replaced, LPS (1 ng/mL) was added thereto and the cell was cultured for 2 hours.

Figure 2:
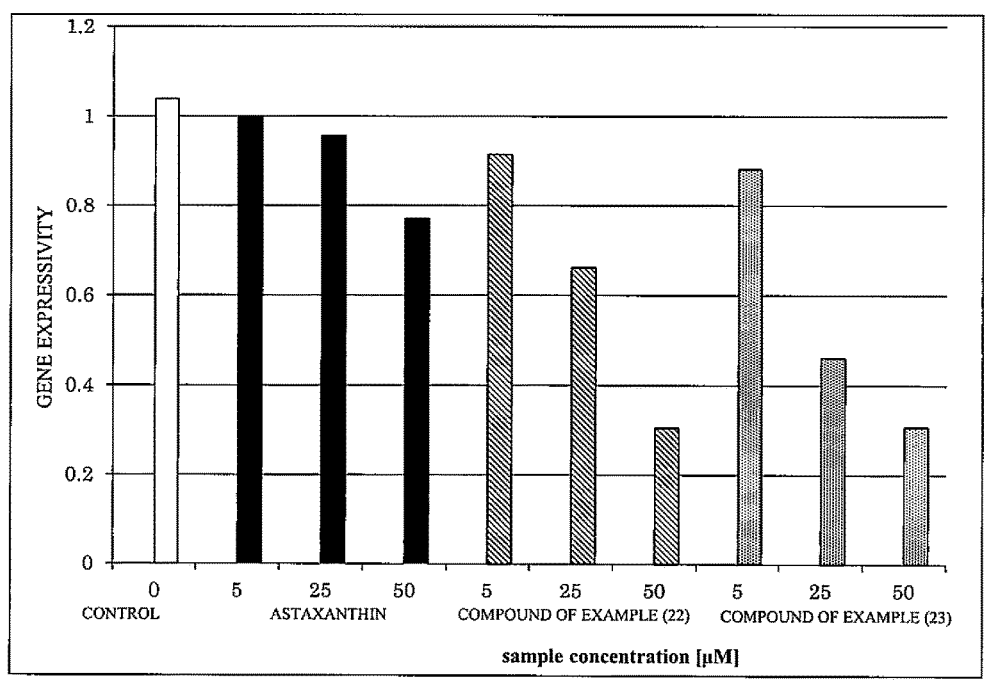
FIG. 2 shows the gene expressivity of IL-1β when LPS was added to RAW264.7 cells in Test example (3).

Then, the medium was removed and the RAW264.7 cells were washed with physiological phosphate buffer solution (PBS). This operation was performed 3 times. Then, Total RNA was extracted using RNeasy Mini Kit (QIAGEN Inc.), and the production amount of IL-1β mRNA which is an inflammatory cytokine, was measured by a quantitative RT-PCR method using PRISM 7000 (Applied Biosystem). The results of IL-1β gene expressivity relative to the control are shown in Table 6 and FIG. 2.

TABLE 45

| Sample | Sample concentration [μM] | IL-1β Gene expressivity |
|---|---|---|
| Control | — | 1.04 |
| Astaxanthin (free form) | 5 | 1.00 |
|  | 25 | 0.96 |
|  | 50 | 0.77 |
| Compound in Example (22) | 5 | 0.92 |
|  | 25 | 0.66 |
|  | 50 | 0.31 |
| Compound in Example (23) | 5 | 0.88 |

Each of the samples suppressed expression of IL-1β gene, a marker for inflammation in a concentration-dependent manner. It was confirmed that the compounds in Examples (22) and (23) of the present invention suppressed IL-1β gene expression superiorly to astaxanthin and that they were excellent in anti-inflammatory effects.

Test Example (4)

Test for Anti-Inflammation in Rats

Figure 3:
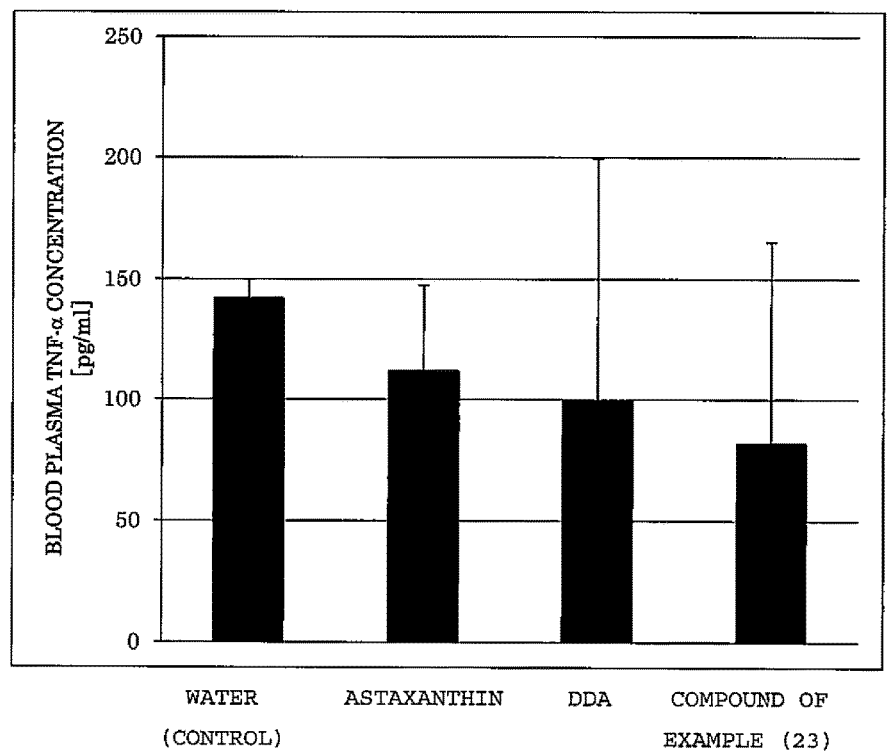
FIG. 3 shows the blood plasma concentration of TNF-α when LPS was injected into the abdominal cavity of the rat in Test example (4).
Figure 4:
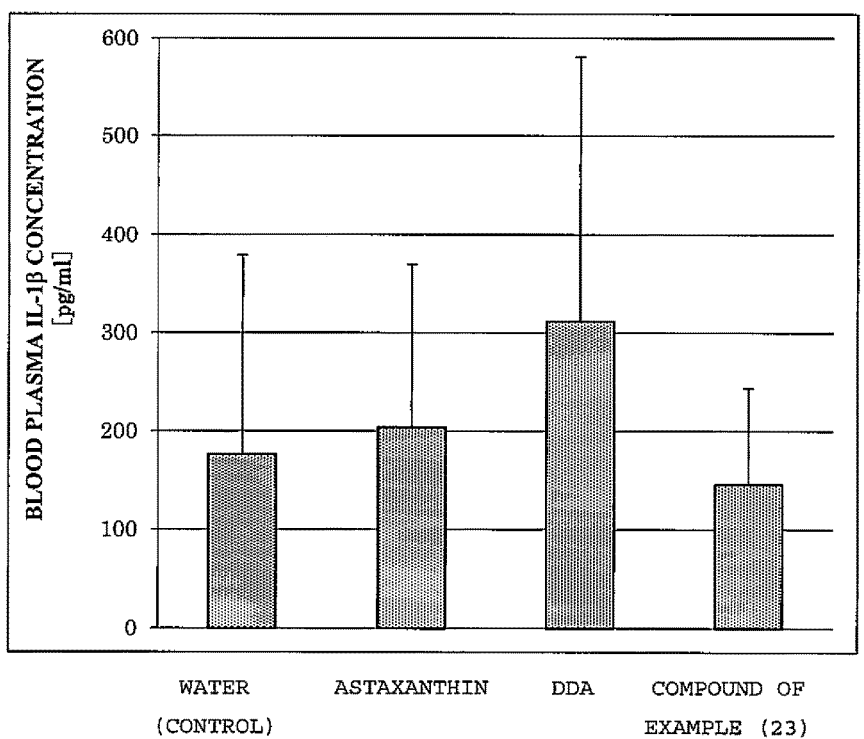
FIG. 4 shows the blood plasma concentration of IL-1β when LPS was injected into the abdominal cavity of the rat in Test example (4).

Six week-old Wistar rats (purchased from Sankyo Labo Service Corporation, 200-250 g body weight) were acclimatized for 1 week with free access to food under a 12/12-hr light-dark cycle. An aqueous solution of 4 mg/kg LPS (lipopolysaccharide, derived from *Escherichia coli* and manufactured by Wako Pure Chemical Industries, Ltd.) was injected intraperitoneally and then an aqueous solution of the sample was injected intraperitoneally. After 9 hours, the whole blood was collected from the ventral aorta and centrifuged for 10 minutes at 10,000 rpm, and the blood plasma was collected. The blood plasma TNF-α concentration was measured using a kit for measuring TNF-α (Rat TNF-alpha Quantikine ELISA Kit RTA00, manufactured by R&D Systems Inc.) and the blood plasma IL-1β concentration was measured using a kit for measuring IL-1β (Rat IL-1b/IL1F2 Quantikine ELISA Kit, manufactured by R&D Systems Inc.). The 3 to 4 animals per group were used. The blood plasma TNF-α concentration is shown in Table 46 and FIG. 3 and the blood plasma IL-1β concentration is shown in Table 46 and FIG. 4.

TABLE 46

TNF-α concentration and IL-1β concentration in blood plasma

| Sample | TNF-α concentration [pg/ml] | IL-1β concentration [pg/ml] |
|---|---|---|
| Water (Control) | 142.1 ± 7.7 | 177.1 ± 201.8 |
| Astaxanthin | 112.0 ± 35.6 | 203.9 ± 165.3 |
| Disodium Disuccinate Astaxanthin (DDA) | 99.6 ± 99.9 | 311.7 ± 269.1 |
| Compound in Example (23) | 81.8 ± 83.5 | 146.3 ± 98.0 |

It was confirmed that the compound in Example (23) suppressed generation of TNF-α and of IL-1β more effectively than astaxanthin and disodium disuccinate astaxanthin and that it was excellent in anti-inflammatory effects.

Preparation Example (1)

Tablet

In the ratio of the compound in Example 4 (17.5 weight parts), lactose (67.6 weight parts), low substituted hydroxypropyl cellulose (20 weight parts), hydroxypropyl cellulose (2.5 weight parts), crystalline cellulose (10 weight parts), yellow iron sesquioxide (0.0002 weight parts) and magnesium stearate (1 weight part), they are weighed, mixed and tableted under the conditions of 240 mg tablet weight, 7 N set up hardness and 8.5 mm tablet diameter using a rotary tableting machine.

Preparation Example (2)

Tablet

Lactose (100.5 weight parts) is fluidized in a fluidized-bed granulating machine and an aqueous solution containing the compound in Example 4 (17.5 weight parts) and hydroxypropyl cellulose (3.9 weight parts) is sprayed to obtain granules. The granules (65 weight parts), crystalline cellulose (15.0 weight parts), sodium croscarmellose (19.5 weight parts) and magnesium stearate (0.5 weight parts) are mixed, compressed and molded under the conditions of 200 mg tablet weight, 7 N set up hardness and 7 mm tablet diameter using a rotary tableting machine.

Preparation Example (3)

Eye Drop

An eye drop containing 0.00175% of the compound in Example (8), 0.05% polysorbate 80, 0.05% sodium edetate, 0.1% sodium hydrogen phosphate hydrate, 0.5% glycerin, an appropriate amount of hydrochloric acid/sodium hydroxide to adjust pH to 6.5 to 7.0 and the remainder of water is prepared.

Preparation Example (4)

Injection

The compound in Example (23) (36 mg) is added to a phosphate buffer Solution (pH 7.0) to obtain a mixture (1 ml of the total amount) and the mixture is dispensed into a 2 mL glass ampule, sealed and sterilized to prepare an ampule soluble at time of use.

Preparation Example (5)

Injection

Sterilized water is added to the compound in Example (23) (36 mg), sodium chloride (90 mg) and polysorbate (an appropriate amount) to obtain a solution (10 ml of the total amount) and to prepare an injection.

The invention claimed is:
1. A carotenoid derivative having a general formula (I):

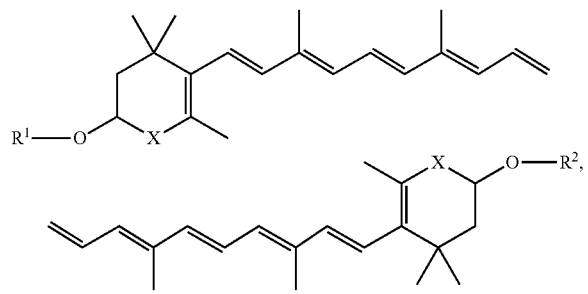

wherein:
represents a carbonyl group or a methylene group;
at least one of $R^1$ and $R^2$ in the general formula (I) is —CO-A-B-D and the other is —CO-A-B-D or a hydrogen atom;
A is —CH$_2$—, —CH(CH$_3$)—, —CH(C$_2$H$_5$)—, —CH(n-C$_3$H$_7$)—, —CH(i-C$_3$H$_7$)—, —CH(n-C$_4$H$_9$)—, —CH(i-C$_4$H$_9$)—, —CH(s-C$_4$H$_9$)—, —CH$_2$CH$_2$—, —CH$_2$CH$_2$CH$_2$—, —CH$_2$CH(CH$_3$)—, —CH$_2$CH$_2$CH$_2$CH$_2$—, —CH(CH$_3$)CH$_2$CH$_2$—, —CH$_2$CH(CH$_3$)CH$_2$—, —CH$_2$CH(i-C$_4$H$_9$)CH$_2$—, —CH$_2$C(CH$_2$CH$_2$CH$_2$CH$_2$CH$_2$)CH$_2$—, —CH$_2$CH$_2$CH$_2$CH$_2$CH$_2$—, —CH(CH$_3$)CH$_2$CH$_2$CH$_2$—, —CH$_2$CH(CH$_3$)CH$_2$CH$_2$—, —CH$_2$CH(CH$_3$)CH(CH$_3$)—, —CH$_2$CH$_2$CH$_2$CH$_2$CH$_2$CH$_2$—, —CH(CH$_3$)CH$_2$CH$_2$CH$_2$CH$_2$—, —CH(C$_2$H$_5$)CH$_2$CH$_2$CH$_2$—, —CH(CH$_3$)CH(CH$_3$)CH$_2$CH$_2$—, —CH(CH$_3$)CH(CH$_3$)CH(CH$_3$)—,
—CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$CH$_2$—,
—CH(CH(CH$_3$)$_2$)CH$_2$CH$_2$CH$_2$CH$_2$CH$_2$CH$_2$—,
-6—CH$_2$-3-ethylbicyclo[3,2,0]hepta-3ene-6-yl-CH$_2$—, —CH(CH$_2$SCH$_3$)—, —CH(CH$_2$CH$_2$SCH$_3$)—, —CH(CH$_2$Phenyl)-, —CH[CH$_2$(4-hydroxyphenyl)]-, —CH[CH$_2$(4-imidazolyl)]-, —CH(CH$_2$CONH$_2$), —CH(CH$_2$CH$_2$CONH$_2$)—, —CH(CH$_2$OH)—, —CH[CHOH(CH$_3$]—, —CH(CH$_2$CH$_2$CH$_2$NH$_2$)—, —CH(CH$_2$CH$_2$CH$_2$CH$_2$NH$_2$)—, —CH[CH$_2$CH$_2$CH$_2$NHC(=NH)NH$_2$]—, —CH(CH$_2$CO$_2$H)—, —CH(CH$_2$CO$_2$Bu$^t$)—, —CH(CH$_2$CH$_2$CO$_2$H)—, —CH(CH$_2$CH$_2$CO$_2$Bu$^t$)—, —CH(NH$_2$)CH$_2$—, —CH(COOH)—, —CH(COOH)CH$_2$—, —CH(CH$_2$SCH$_3$)CH$_2$—, —CH(CH$_2$S-n-hexyl)-, —CH(CH$_2$-2-imidazolyl)-, —CH$_2$NHCH$_2$—, —CH$_2$CH$_2$NHCH$_2$CH$_2$—, —CH$_2$CH$_2$N(CH$_3$)CH$_2$CH$_2$—, —CH$_2$CH$_2$N(i-C$_3$H$_7$)CH$_2$CH$_2$—, —CH$_2$CH$_2$N(4-Methoxyphenyl)CH$_2$CH$_2$—, —CH$_2$CH$_2$N(CH$_2$Ph)CH$_2$CH$_2$—, —CH$_2$CH$_2$N(n-C$_4$H$_9$)CH$_2$CH$_2$CH$_2$—, —CH$_2$CH$_2$N(n-C$_4$H$_9$)CH$_2$CH$_2$CH$_2$CH$_2$, —CH$_2$CH(OH)CH$_2$NHCH$_2$—, —CH$_2$NHCH$_2$CH$_2$—, —CH$_2$CH$_2$NHCH$_2$CH$_2$CH$_2$—, —CH$_2$CH$_2$NHCH$_2$CH$_2$CH$_2$CH$_2$CH$_2$—, —CH$_2$N(CH$_3$)CH$_2$CH$_2$—, —CH$_2$CH$_2$N(CH$_3$)CH$_2$CH$_2$CH$_2$—, —CH$_2$N(C$_2$H$_5$)CH$_2$CH$_2$—, —CH$_2$CH$_2$N(C$_2$H$_5$)CH$_2$CH$_2$—, —CH$_2$CH$_2$N(C$_2$H$_5$)CH$_2$CH$_2$CH$_2$—, —CH$_2$N(C$_2$H$_5$)CH$_2$CH$_2$CH$_2$CH$_2$-, —CH$_2$N(i-C$_3$H$_7$)CH$_2$CH$_2$CH$_2$CH$_2$—, —CH$_2$N(CH$_3$)CH$_2$NHCH$_2$—, —CH$_2$N(Ph)CH$_2$CH$_2$-, —CH$_2$N(4—Cl-Ph)CH$_2$—, —CH$_2$N(4-Cl-3-CH$_3$-Ph)CH$_2$—, —CH$_2$N(CH$_2$Ph)CH$_2$CH$_2$—, —CH$_2$CH$_2$N(CH$_2$Ph)CH$_2$—, —CH$_2$CH$_2$SCH$_2$CH$_2$—, —CH$_2$CH$_2$SCH$_2$—, —CH$_2$CH(OH)CH$_2$SCH$_2$CH$_2$—, —CH$_2$CH$_2$S(O)$_2$CH$_2$CH$_2$—, —CH$_2$COCH$_2$—, —CH$_2$CH$_2$COCH$_2$CH$_2$—, —NH—, —N(CH$_3$)—, —N(CH$_2$CH$_3$)—, —N(CH$_2$CH$_2$CH$_3$)—, —N(CH$_2$CH$_2$Ph)-, —N(i-C$_3$H$_7$)—N(CH$_2$CH$_2$CH$_2$CH$_3$)—, —N(i-C$_4$H$_9$)—, N(s-C$_4$H$_9$)—, —N(Ph)-, —N(3-Bromo-Ph)-, —N(3-Nitro-Ph)-, —N(4-Ethyl-Ph)-, —N(4-Butyl-Ph)-, —N(4-Chloro-Ph)-, —N(3-Chloro-Ph)-, —N(2-Chloro-Ph)-, —N(4-Fluoro-Ph)-, —N(4-Benzyl-Ph)-, —N(2,4-Dichloro-Ph)-, —N(4-Trifluoromethyl-Ph)-, —N(4-Hydroxy-Ph)-, —N(4-Cyano-Ph)-, —N(4-Ph-Ph)-, —N(4CHO-Ph)-, —N(4-Carbamoyl-Ph)-, —N(4-Amino-Ph)-, —N(3-(N,N-Dimethylamino)-Ph)-, —N(4-Me-Ph-Ph)-, —N(4-Benzyloxy-Ph)-, —N(4-Ethoxycarbonyl-Ph)-, —N(4-Carboxy-Ph)-, —N(3-Carboxy-Ph)-, —N(2-Carboxy-Ph)-, —N(CH$_2$Ph)-, —N(4-Carboxyphenylmethyl)- ,

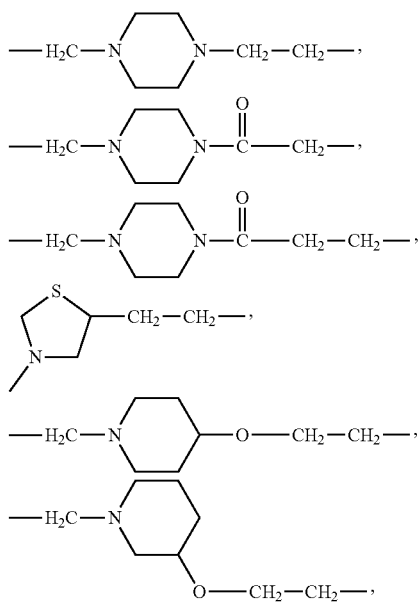

-continued

—H₂C—N(piperidine)—CH₂—CH₂—O—CH₂—CH₂—,

—H₂C—N(piperidine)—C(=O)—NH—CH₂—CH₂—,

—H₂C—H₂C—N(piperidine)—NH—C(=O)—O—CH₂—CH₂—,

—H₂C—HC(OH)—H₂C—N(piperidine)—CH₂—C(=O)—NH—CH₂—CH₂—,

—NHCH₂CONHCH₂CH₂—, —N(CH₃)CH₂CONHCH₂CH₂—, —N(CH₂Ph)CH₂CONHCH₂CH₂—, —NHCH₂CON(CH₃)CH₂CH₂—, —NHCH₂CH₂SCH₂CH₂—, —CH₂CH₂CONHCH₂CH₂—, —CH₂COCH₂SCH₂—, —CH(CH₂CH₂SCH₃)CONHCH₂CH₂—, —CH₂CH₂CH₂CH₂CH(NH₂)—, —NHCH₂CH₂CH₂CH₂CH(COOH)—, —NHCH₂CH₂CH₂CH(COOH)—, —NHCH₂CH₂CH(COOC₂H₅)— or —NHCH₂CH₂CH₂CH(COOC₂H₅)—;

B is —NHCONH—, —N(CH₃)CONH—, —NHCON(CH₃)—, —N(CH₃)CON(CH₃)—, —N(C₂H₅)CONH—, —N(n-C₃H₇)CONH—, —N(i-C₃H₇)CONH—, —N(n-C₄H₉)CONH—, —N(n-C₆H₁₃)CONH—, —N(n-C₄H₉)CON(CH₃)—, —N(Ph)CONH—, —NHCON(4-Chlorophenyl)-, —NHCON(CH₂Phenyl)-, —N(i-C₃H₇)CON(4-Methoxyphenyl)-, —N(4-Chlorophenyl)CON(4-Methoxyphenyl)- or a group of formula:

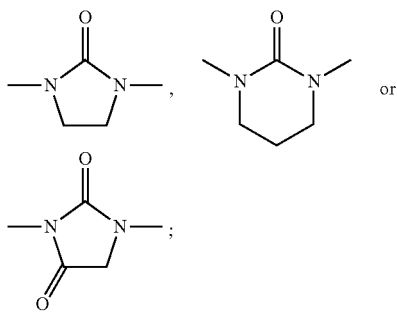

and

D is —CH₂COOH, —CH₂CH₂COOH, —CH₂CH₂CH₂COOH, —CH₂CH(i-C₄H₉)CH₂COOH, —CH₂CH(i-C₄H₉)CH₂CONHCH₂CH(i-C₄H₉)CH₂COOH, —CH₂C(CH₂CH₂CH₂CH₂CH₂)CH₂COOH, —CH₂C(CH₂CH₂CH₂CH₂CH₂)CH₂CONHCH₂C(CH₂CH₂CH₂CH₂CH₂)CH₂COOH, —CH(CH₂SCH₃)COOH, —CH(CH₂CH₂SCH₃)COOH, —CH(CH₂Phenyl)COOH, —CH[CH₂(4-hydroxyphenyl)]COOH, —CH[CH₂(4-imidazolyl)]COOH, —CH(CH₂CONH₂)COOH, —CH(CH₂CH₂CONH₂)COOH, —CH(CH₂OH)COOH, —CH[CHOH(CH₃)]COOH, —CH(CH₂CH₂CH₂NH₂)COOH, —CH(CH₂CH₂CH₂CH₂NH₂)COOH, —CH[CH₂CH₂CH₂NHC(=NH)NH₂]COOH, —CH(CH₂CO₂H)COOH, —CH(CH₂CO₂Buᵗ)COOH, —CH(CH₂CH₂CO₂H)COOH, —CH(CH₂CH₂CO₂Buᵗ)COOH, —CH₂CH₂CH₂CH(NH₂)COOH, —CH₂CH₂CH₂CH₂CH(NH₂)COOH, —CH(COOH)CH₃, —CH₂CONHCH₂COOH, —CH₂CONHCH(CH₂CH₂SCH₃)COOH, —CH₂CONHCH[CH₂(4-imidazolyl)]COOH, —CH₂CONHCH(CH₂CONH₂)COOH, —CH₂CONHCH(CH₂CH₂CONH₂)COOH, —CH₂CH₂CONHCH₂COOH, —CH₂CH₂CONHCH(CH₂CH₂SCH₃)COOH, —CH₂CH₂CONHCH[CH₂(4-imidazolyl)]COOH, —CH₂CH₂CONHCH(CH₂CONH₂)COOH, —CH₂CH₂CONHCH(CH₂CH₂CONH₂)COOH, —CH₂CH₂CH₂CONHCH₂COOH, CH₂CH₂CH₂CONHCH(CH₂CH₂SCH₃)COOH, —CH₂CH₂CH₂CONHCH[CH₂(4-imidazolyl)]COOH, —CH₂CH₂CH₂CONHCH(CH₂CONH₂)COOH, —CH₂CH₂CH₂CONHCH (CH₂CH₂CONH₂)COOH, -6-CH₂-3-ethylbicyclo-[3,2,0]hepta-3-en-6-yl-CH₂COOH or a group of a formula described below, formed together with a moiety of —NH— in B:

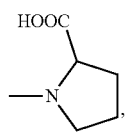

or a pharmaceutically acceptable salt thereof.

2. The carotenoid derivative according to claim 1, or a pharmaceutically acceptable salt thereof, wherein:

$R^1$ and $R^2$ in the general formula (I) are same and each is —CO-A-B-D;

A is —CH₂—, —CH(CH₃)—, —CH(C₂H₅)—, —CH(n-C₃H₇)—, —CH(i-C₃H₇)—, —CH(n-C₄H₉)—, —CH(i-C₄H₉)—, —CH(s-C₄H₉)—, —CH₂CH₂—, —CH₂CH₂CH₂—, —CH₂CH(CH₃)—, —CH₂CH₂CH₂CH₂—, —CH(CH₃)CH₂CH₂—, —CH₂CH(CH₃)CH₂—, —CH₂CH(i-C₄H₉)CH₂—, —CH₂C(CH₂CH₂CH₂CH₂CH₂)CH₂—, —CH₂CH₂CH₂CH₂CH₂—, —CH(CH₃)CH₂CH₂CH₂—, —CH₂CH(CH₃)CH₂CH₂—, —CH₂CH(CH₃)CH(CH₃)—, —CH₂CH₂CH₂CH₂CH₂C₂—, —CH(CH₃)CH₂CH₂CH₂CH₂—, —CH(C₂H₅)CH₂CH₂CH₂—, —CH(CH₃)CH(CH₃)CH₂CH₂—, —CH(CH₃)CH(CH₃)CH(CH₃)—, —CH₂CH₂CH₂CH₂CH₂CH₂CH₂—, —CH(CH₂SCH₃)—, —CH(CH₂CH₂SCH₃)—, —CH(CH₂Phenyl)-, —CH[CH₂(4-hydroxyphenyl)]-, —CH[CH₂(4-imidazolyl)]-, —CH(CH₂CONH₂)—, —CH(CH₂CH₂CONH₂)—, —CH(CH₂OH)—, —CH[CHOH(CH₃)]—, —CH(CH₂CH₂CH₂NH₂)—, —CH(CH₂CH₂CH₂CH₂NH₂)—, —CH[CH₂CH₂CH₂NHC(=NH)NH₂]—, —CH(CH₂CO₂H)—, —CH(CH₂CH₂CO₂H)—, —CH₂NHCH₂—, —CH₂CH₂NHCH₂CH₂—, —CH₂CH₂N(CH₃)CH₂CH₂—, —CH₂CH₂N(i-C₃H₇)CH₂CH₂—, —CH₂CH₂N(4-Methoxyphenyl)CH₂CH₂—, —CH₂CH₂N(CH₂Ph)CH₂CH₂—, —CH₂CH₂N(n-C₄H₉)CH₂CH₂CH₂—, —CH₂CH₂N(n-C₄H₉)CH₂CH₂CH₂—, —CH₂NHCH₂CH₂—, —CH₂CH₂NHCH₂CH₂CH₂—, —CH₂CH₂NHCH₂CH₂CH₂CH₂CH₂—, —CH₂N(CH₃)CH₂CH₂—, —CH₂CH₂N(CH₃)CH₂CH₂—, —CH₂N(C₂H₅)CH₂CH₂—, —CH₂CH₂N(C₂H₅)

CH₂CH₂—, —CH₂CH₂N(C₂H₅)CH₂CH₂CH₂—, —CH₂N(C₂H₅)CH₂CH₂CH₂CH₂—, —CH₂N(i-C₃H₇)CH₂CH₂CH₂CH₂—, —CH₂N(CH₃)CH₂NHCH₂—, —CH₂N(Ph)CH₂CH₂—, —CH₂N(4-Cl-Ph)CH₂CH₂—, —CH₂N(4-Cl-3-CH₃-Ph)CH₂CH₂—, —CH₂N(CH₂Ph)CH₂CH₂—, —CH₂CH₂N (CH₂Ph)CH₂CH₂—, —CH₂CH₂SCH₂CH₂—, —CH₂CH₂SCH₂—, —CH₂CH₂S(O)₂CH₂CH₂—, —CH₂COCH₂—, —CH₂CH₂COCH₂CH₂—, —NH—, —N(CH₃)—, —N(CH₂CH₃)—, —N(CH₂CH₂CH₃)—, —N(CH₂CH₂Ph)-, —N(i-C₃H₇)—, —N(CH₂CH₂CH₂CH₃)—, —N(i-C₄H₉)—, —N(s-C₄H₉)—, —N(Ph)-, —N(3-Bromo-Ph)-, —N(3-Nitro-Ph)-, —N(4-Ethyl-Ph)-, —N(4-Butyl-Ph)-, —N(4-Chloro-Ph)-, —N(3-Chloro-Ph)-, —N(2-Chloro-Ph)-, —N(4-Fluoro-Ph)-, —N(4-Benzyl-Ph)-, —N(2,4-Dichioro-Ph)-, —N(4-Trifluoromethyl-Ph)-, —N(4-Hydroxy-Ph)-, —N(4-Cyano-Ph)-, —N(4-Ph-Ph)-, —N(4-CHO-Ph)-, —N(4-Carbamoyl-Ph)-, —N(4-Amino-Ph)-, —N(4-Me-Ph-Ph)-, —N(4-Benzyloxy-Ph)-, —N(4-Carboxy-Ph)-, —N(3-Carboxy-Ph)-, —N(2-Carboxy-Ph)-, —N(CH₂Ph)-, —N(4-Carboxyphenylmethyl),

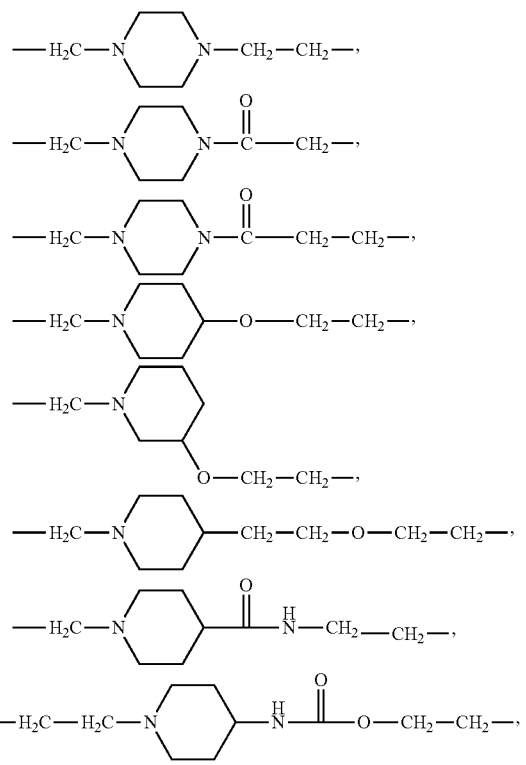

—NHCH₂CONHCH₂CH₂—, —N(CH₃)CH₂CONHCH₂CH₂—, —N(CH₂Ph)CH₂CONHCH₂CH₂—, —NHCH₂CON(CH₃)CH₂CH₂—, —NHCH₂CH₂SCH₂CH₂—, —CH₂CH₂CONHCH₂CH₂—, —CH₂COCH₂SCH₂—, —CH(CH₂CH₂SCH₃)CONHCH₂CH₂—, —NHCH₂CH₂CH₂CH₂CH(COOH)—, or —NHCH₂CH₂CH₂CH(COOH)—;

B is —NHCONH—, —N(CH₃)CONH—, —NHCON(CH₃)—, —N(CH₃)CON(CH₃)—, —N(C₂H₅)CONH—, —N(n-C₃H₇)CONH—, —N(i-C₃H₇)CONH—, —N(n-C₄H₉)CONH—, —N(n-C₆H₁₃)CONH—, —N(n-C₄H₉)CON(CH₃)—, or a group of a formula:

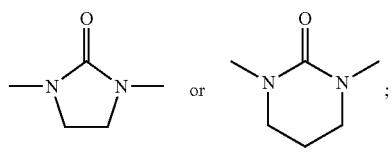

and

D is a —CH₂COOH, —CH₂CH₂COOH, —CH₂CH₂CH₂COOH, —CH₂CH(i-C₄H₉)CH₂COOH, —CH₂CH(i-C₄H₉)CH₂CONHCH₂CH(i-C₄H₉)CH₂COOH, —CH₂C(CH₂CH₂CH₂CH₂CH₂)CH₂COOH, —CH₂C(CH₂CH₂CH₂CH₂CH₂)CH₂CONHCH₂C (CH₂CH₂CH₂CH₂CH₂)CH₂COOH, —CH(CH₂SCH₃)COOH, —CH(CH₂CH₂SCH₃)COOH, —CH(CH₂Phenyl)COOH, —CH[CH₂(4-hydroxyphenyl)]COOH, —CH[CH₂(4-imidazolyl)]COOH, —CH(CH₂CONH₂)COOH, —CH(CH₂CH₂CONH₂)COOH, —CH(CH₂OH)COOH, —CH[CHOH(CH₃)]COOH, —CH(CH₂CH₂CH₂NH₂)COOH, —CH(CH₂CH₂CH₂CH₂NH₂) COOH, —CH[CH₂CH₂CH₂NHC(=NH)NH₂]COOH, —CH(CH₂CO₂H)COOH, —CH(CH₂CH₂CO₂H)COOH, —CH₂CH₂CH₂CH(NH₂)COOH, —CH₂CH₂CH₂CH₂CH(NH₂) COOH, —CH(COOH)CH₃, —CH₂CONHCH₂COOH, —CH₂CONHCH(CH₂CH₂SCH₃)COOH, —CH₂CONHCH[CH₂(4-imidazolyl)]COOH, —CH₂CONHCH(CH₂CONH₂)COOH, —CH₂CONHCH(CH₂CH₂CONH₂)COOH, —CH₂CH₂CONHCH₂COOH, —CH₂CH₂CONHCH(CH₂CH₂SCH₃)COOH, —CH₂CH₂CONHCH[CH₂(4-imidazolyl)]COOH, —CH₂CH₂CONHCH(CH₂CONH₂)COOH, —CH₂CH₂CONHCH(CH₂CH₂CONH₂)COOH, —CH₂CH₂CH₂CONHCH₂COOH, —CH₂CH₂CH₂CONHCH(CH₂CH₂SCH₃)COOH, —CH₂CH₂CH₂CONHCH[CH₂(4-imidazolyl)]COOH, —CH₂CH₂CH₂CONHCH(CH₂CONH₂)COOH or —CH₂CH₂CH₂CONHCH(CH₂CH₂CONH₂)COOH.

3. The carotenoid derivative according to claim 1, or a pharmaceutically acceptable salt thereof, wherein:

R¹ and R² in the general formula (I) are same and each is —CO-A-B-D;

A is —CH₂—, —CH(CH₃)—, —CH(C₂H₅)—, —CH(n-C₃H₇)—, —CH(i-C₃H₇)—, —CH(n-C₄H₉)—, —CH(i-C₄H₉)—, —CH(s-C₄H₉)—, —CH₂CH₂—, —CH₂CH₂CH₂—, —CH₂CH(CH₃)—, —CH₂CH₂CH₂CH₂—, —CH₂CH(i-C₄H₉)CH₂—, —CH₂C(CH₂CH₂CH₂CH₂CH₂)CH₂—, —CH(CH₂SCH₃)—, —CH(CH₂CH₂SCH₃)—, —CH(CH₂Phenyl)—, —CH[CH₂(4-hydroxyphenyl)]-, —CH[CH₂(4-imidazolyl)]-, —CH(CH₂CONH₂)—, —CH(CH₂CH₂CONH₂)—, —CH(CH₂OH)—, —CH[CHOH(CH₃)]—, —CH(CH₂CH₂CH₂NH₂)—, —CH(CH₂CH₂CH₂CH₂NH₂)—, —CH[CH₂CH₂CH₂NHC(=NH)NH₂]—, —CH(CH₂CO₂H)—, —CH(CH₂CH₂CO₂H)—, —CH₂NHCH₂—, —CH₂CH₂NHCH₂CH₂—, —CH₂CH₂N(CH₃)CH₂CH₂—, —CH₂CH₂N(i-C₃H₇) CH₂CH₂—, —CH₂CH₂N(4-Methoxyphenyl)CH₂CH₂—, —CH₂CH₂N(CH₂Ph)CH₂CH₂—, —CH₂CH₂N(n-C₄H₉)CH₂CH₂CH₂—, —CH₂CH₂N(n-C₄H₉)CH₂CH₂CH₂CH₂—, —CH₂NHCH₂CH₂—, —CH₂CH₂NHCH₂CH₂CH₂, —CH₂N(CH₃)CH₂CH₂—, —CH₂CH₂N(CH₃)CH₂CH₂CH₂—, —CH₂N (C₂H₅)CH₂CH₂—, —CH₂CH₂N(C₂H₅)

$CH_2CH_2$—, —$CH_2CH_2N(C_2H_5)CH_2CH_2CH_2$—, —$CH_2N(C_2H_5)$ $CH_2CH_2CH_2CH_2$—, —$CH_2N(i-C_3H_7)CH_2CH_2CH_2CH_2$—, —$CH_2N(CH_3)CH_2NHCH_2$—, —$CH_2N(Ph)$ $CH_2CH_2$—, —$CH_2N(4-Cl-Ph)CH_2CH_2$—, —$CH_2N(4-Cl-3-CH_3-Ph)CH_2CH_2$—, —$CH_2N(CH_2Ph)$ $CH_2CH_2$—, —$CH_2CH_2N(CH_2Ph)CH_2CH_2$—, —$CH_2CH_2SCH_2CH_2$—, —$CH_2CH_2SCH_2$—, —$CH_2CH_2S(O)_2CH_2CH_2$—, —$CH_2COCH_2$—, —$CH_2CH_2COCH_2CH_2$—, —NH—, —$N(CH_3)$—, —$N(CH_2CH_3)$—, —$N(CH_2CH_2CH_3)$—, —$N(CH_2CH_2Ph)$—, —$N(i-C_3H_7)$, —$N(CH_2CH_2CH_2CH_3)$—, —$N(i-C_4H_9)$—, —N(Ph)-, —N(3-Nitro-Ph)-, —N(4-Ethyl-Ph)-, —N(4-Butyl-Ph)-, —N(4-Chloro-Ph)-, —N(3-Chloro-Ph)-, —N(2-Chloro-Ph)-, —N(4-Fluoro-Ph)-, —N(4-Benzyl-Ph)-, —N(2,4-Dichloro-Ph)-, —N(4-Trifluoromethyl-Ph)-, —N(4-Hydroxy-Ph)-, —N(4-Cyano-Ph)-, —N(4-Ph-Ph)-, —N(4-CHO-Ph)-, —N(4-Carbamoyl-Ph)-, —N(4-Amino-Ph)-, —N(4-Me-Ph-Ph)-, —N(4-Benzyloxy-Ph)-, —N(4-Carboxy-Ph)-, —N(3-Carboxy-Ph)-, —N(2-Carboxy-Ph)-, —$N(CH_2Ph)$-, —N(4-Carboxyphenylmethyl)-,

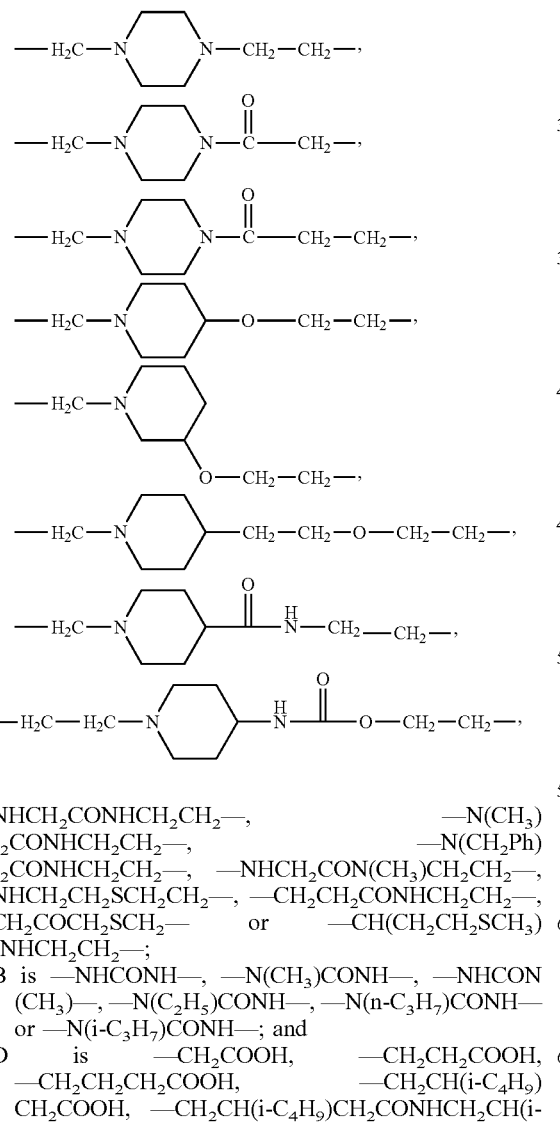

—$NHCH_2CONHCH_2CH_2$—, —$N(CH_3)CH_2CONHCH_2CH_2$—, —$N(CH_2Ph)CH_2CONHCH_2CH_2$—, —$NHCH_2CON(CH_3)CH_2CH_2$—, —$NHCH_2CH_2SCH_2CH_2$—, —$CH_2CH_2CONHCH_2CH_2$—, —$CH_2COCH_2SCH_2$— or —$CH(CH_2CH_2SCH_3)CONHCH_2CH_2$—;

B is —NHCONH—, —$N(CH_3)CONH$—, —$NHCON(CH_3)$—, —$N(C_2H_5)CONH$—, —$N(n-C_3H_7)CONH$— or —$N(i-C_3H_7)CONH$—; and D is —$CH_2COOH$, —$CH_2CH_2COOH$, —$CH_2CH_2CH_2COOH$, —$CH_2CH(i-C_4H_9)CH_2COOH$, —$CH_2CH(i-C_4H_9)CH_2CONHCH_2CH(i-C_4H_9)CH_2COOH$, —$CH_2C(CH_2CH_2CH_2CH_2CH_2)CH_2COOH$, —$CH_2C(CH_2CH_2CH_2CH_2CH_2)CH_2CONHCH_2C$ $(CH_2CH_2CH_2CH_2CH_2)CH_2COOH$, —$CH(CH_2SCH_3)COOH$, —$CH(CH_2CH_2SCH_3)$ COOH, —$CH(CH_2Phenyl)COOH$, —$CH[CH_2(4-hydroxyphenyl)]COOH$, —$CH[CH_2(4-imidazolyl)]COOH$, —$CH(CH_2CONH_2)COOH$, —$CH(CH_2CH_2CONH_2)COOH$, —$CH(CH_2OH)COOH$, —$CH[CHOH(CH_3)]COOH$, —$CH(CH_2CH_2CH_2NH_2)COOH$, —$CH(CH_2CH_2CH_2CH_2NH_2)$ COOH, —$CH[CH_2CH_2CH_2NHC(=NH)NH_2]COOH$, —$CH(CH_2CO_2H)COOH$, —$CH_2CONHCH_2COOH$, —$CH_2CONHCH(CH_2CH_2SCH_3)$ COOH, —$CH_2CONHCH[CH_2(4-imidazolyl)]COOH$, —$CH_2CONHCH(CH_2CONH_2)COOH$, —$CH_2CONHCH(CH_2CH_2CONH_2)COOH$, —$CH_2CH_2CONHCH_2COOH$, —$CH_2CH_2CONHCH(CH_2CH_2SCH_3)COOH$, —$CH_2CH_2CONHCH[CH_2(4-imidazolyl)]COOH$, —$CH_2CH_2CONHCH(CH_2CONH_2)COOH$, —$CH_2CH_2CONHCH(CH_2CH_2CONH_2)COOH$, —$CH_2CH_2CH_2CONHCH_2COOH$, —$CH_2CH_2CH_2CONHCH(CH_2CH_2SCH_3)COOH$, —$CH_2CH_2CH_2CONHCH[CH_2(4-imidazolyl)]COOH$, —$CH_2CH_2CH_2CONHCH(CH_2CONH_2)COOH$ or —$CH_2CH_2CH_2CONHCH(CH_2CH_2CONH_2)COOH$ 4. The carotenoid derivative according to claim 1, or a pharmaceutically acceptable salt thereof, wherein:

X in the general formula (I) is a carbonyl group;

$R^1$ and $R^2$ in the general formula (I) are same and each is —CO-A-B-D;

A is —$CH_2$—, —$CH(CH_3)$—, —$CH(C_2H_5)$—, —$CH(i-C_3H_7)$—, —$CH(n-C_4H_9)$—, —$CH(i-C_4H_9)$—, —$CH_2CH_2$—, —$CH_2CH_2CH_2$—, —$CH_2CH(i-C_4H_9)CH_2$—, —$CH_2C(CH_2CH_2CH_2CH_2CH_2)CH_2$—, —$CH(CH_2SCH_3)$—, —$CH(CH_2CH_2SCH_3)$—, —$CH(CH_2Phenyl)$—, —$CH[CH_2(4-hydroxyphenyl)]$—, —$CH[CH_2(4-imidazolyl)]$-, —$CH(CH_2CONH_2)$—, —$CH(CH_2CH_2CONH_2)$—, —$CH(CH_2OH)$—, —$CH[CHOH(CH_3)]$—, —$CH(CH_2CH_2CH_2NH_2)$—, —$CH(CH_2CH_2CH_2CH_2NH_2)$—, —$CH[CH_2CH_2CH_2NHC(=NH)NH_2]$—, —$CH(CH_2CO_2H)$—, —$CH(CH_2CH_2CO_2H)$—, —$CH(CH_2SCH_3)CH_2$—, —$CH_2NHCH_2$—, —$CH_2CH_2NHCH_2CH_2$—, —$CH_2CH_2N(CH_3)CH_2CH_2$—, —$CH_2CH_2N(4-Methoxyphenyl)CH_2CH_2$—, —$CH_2CH_2N(CH_2Ph)CH_2CH_2$—, —$CH_2NHCH_2CH_2$—, —$CH_2CH_2NHCH_2CH_2CH_2$—, —$CH_2N(CH_3)CH_2CH_2$—, —$CH_2CH_2N(CH_3)CH_2CH_2CH_2$—, —$CH_2N(C_2H_5)CH_2CH_2$—, —$CH_2CH_2N(C_2H_5)CH_2CH_2$—, —$CH_2CH_2N(C_2H_5)CH_2CH_2CH_2$—, —$CH_2N(CH_3)CH_2NHCH_2$—, —$CH_2N(Ph)CH_2CH_2$—, —$CH_2N(4-Cl-Ph)CH_2CH_2$—, —$CH_2N(4-Cl-3-CH_3-Ph)CH_2CH_2$—, —$CH_2N(CH_2Ph)CH_2CH_2$—, —$CH_2CH_2N(CH_2Ph)CH_2CH_2$—, —$CH_2CH_2SCH_2CH_2$—, —$CH_2CH_2SCH_2$—, —$CH_2CH_2S(O)_2CH_2CH_2$—, —$CH_2COCH_2$—, —$CH_2CH_2COCH_2CH_2$—, —NH—, —$N(CH_3)$—, —$N(CH_2CH_3)$—, —$N(CH_2CH_2CH_3)$—, —$N(CH_2CH_2Ph)$-, —N(Ph)-, —N(3-Nitro-Ph)-, —N(4-Ethyl-Ph)-, —N(4-Chloro-Ph)-, —N(3-Chloro-Ph)-, —N(2-Chloro-Ph)-, —N(4-Fluoro-Ph)-, —N(4-Benzyl-Ph)-, —N(2,4-Dichloro-Ph)-, —N(4-Trifluoromethyl-Ph)-, —N(4-Hydroxy-Ph)-, —N(4-Cyano-Ph)-, —N(4-Ph-Ph)-, —N(4-CHO-Ph)-, —N(4-Carbamoyl-Ph)-, —N(4-Amino-Ph)-, —N(4-Me-Ph-Ph)-, —N(4-Benzyloxy-Ph)-, —N(4-Carboxy-Ph)-, —N(3-Carboxy-Ph)-,   —N(2-Carboxy-Ph)-,
—N(CH$_2$Ph)-, —N(4-Carboxyphenylmethyl)-,

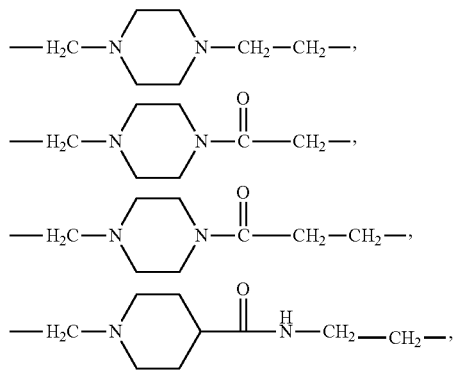

—NHCH$_2$CONHCH$_2$CH$_2$—, —N(CH$_3$)CH$_2$CONHCH$_2$CH$_2$—, —N(CH$_2$Ph)CH$_2$CONHCH$_2$CH$_2$—, —NHCH$_2$CON(CH$_3$)CH$_2$CH$_2$—, —NHCH$_2$CH$_2$SCH$_2$CH$_2$—, —CH$_2$CH$_2$CONHCH$_2$CH$_2$—, —CH$_2$COCH$_2$SCH$_2$— or —CH(CH$_2$CH$_2$SCH$_3$)CONHCH$_2$CH$_2$—;

B is —NHCONH—, —N(CH$_3$)CONH—, —NHCON(CH$_3$)— or —N(C$_2$H$_5$)CONH—; and

D is —CH$_2$COOH, —CH$_2$CH$_2$COOH, —CH$_2$CH$_2$CH$_2$COOH, —CH$_2$CH(i-C$_4$H$_9$)CH$_2$COOH, —CH$_2$CH(i-C$_4$H$_9$)CH$_2$CONHCH$_2$CH(i-C$_4$H$_9$)CH$_2$COOH, —CH$_2$C(CH$_2$CH$_2$CH$_2$CH$_2$CH$_2$)CH$_2$COOH, —CH$_2$C(CH$_2$CH$_2$CH$_2$CH$_2$CH$_2$)CH$_2$CONHCH$_2$C(CH$_2$CH$_2$CH$_2$CH$_2$CH$_2$)CH$_2$COOH, —CH(CH$_2$SCH$_3$)COOH, —CH(CH$_2$CH$_2$SCH$_3$)COOH, —CH(CH$_2$Phenyl)COOH, —CH[CH$_2$(4-hydroxyphenyl)]COOH, —CH[CH$_2$(4-imidazolyl)]COOH, —CH(CH$_2$CONH$_2$)COOH, —CH(CH$_2$CH$_2$CONH$_2$)COOH, —CH(CH$_2$OH)COOH, —CH[CHOH(CH$_3$)]COOH, —CH(CH$_2$CH$_2$CH$_2$NH$_2$)COOH, —CH(CH$_2$CH$_2$CH$_2$CH$_2$) COOH, —CH[CH$_2$CH$_2$CH$_2$NHC(=NH)NH$_2$]COOH, —CH(CH$_2$CO$_2$H)COOH, —CH(CH$_2$CH$_2$CO$_2$H)COOH, —CH(COOH)CH$_3$, —CH$_2$CONHCH$_2$COOH, —CH$_2$CONHCH(CH$_2$CH$_2$SCH$_3$)COOH, —CH$_2$CONHCH[CH$_2$(4-imidazolyl)]COOH, —CH$_2$CONHCH(CH$_2$CONH$_2$)COOH, —CH$_2$CONHCH(CH$_2$CH$_2$CONH$_2$) COOH, —CH$_2$CH$_2$CONHCH$_2$COOH, —CH$_2$CH$_2$CONHCH(CH$_2$CH$_2$SCH$_3$)COOH, —CH$_2$CH$_2$CONHCH[CH$_2$(4-imidazolyl)]COOH, —CH$_2$CH$_2$CONHCH(CH$_2$CONH$_2$)COOH, —CH$_2$CH$_2$CONHCH(CH$_2$CH$_2$CONH$_2$)COOH, —CH$_2$CH$_2$CH$_2$CONHCH$_2$COOH, —CH$_2$CH$_2$CH$_2$CONHCH(CH$_2$CH$_2$SCH$_3$)COOH, —CH$_2$CH$_2$CH$_2$CONHCH[CH$_2$(4-imidazolyl)]COOH, —CH$_2$CH$_2$CH$_2$CONHCH(CH$_2$CONH$_2$)COOH or —CH$_2$CH$_2$CH$_2$CONHCH (CH$_2$CH$_2$CONH$_2$)COOH.

5. The carotenoid derivative according to claim 1, or a pharmaceutically acceptable salt thereof, wherein the carotenoid derivative is selected from the group consisting of 3-{2-[4-(18-{4[3-(3-carboxymethylureido)propionyloxy]-2,6,6-trimethyl-3-oxocyclohexa-1-enyl}-3,7,12,16-tetramethyloctadeca-1,3,5,7,9,11,13,15,17-nonaenyl]-3,5,5-trimethyl-2-oxocyclohexa-3-enyloxycarbonyl]ethy}-ureidoacetic acid, 3-[4-(18-{4-(3-carboxymethylureidoacetoxy)-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]-ureidoacetic acid, 3-{3-[4-(18-{4[3-(2-carboxyethyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]-ureido}propionic acid, 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid, 3-[3-(3-{4-[18-(4{4-[3-(2-carboxyethyl)ureido]-butyryloxy}-2,6,6-trimethyl-3-oxocyclohexa-1-enyl)-3,7,12,16-tetratmethyloctadeca-1,3,5,7,9,11,13,15,17-nonaenyl]-3,5,5-trimethyl-2-oxocyclohexa-3-enyloxycarbonyl}propyl)ureido]propionic acid, 4-[3-(3{4-[18-(4-{4[3-(3-carboxypropyl)ureido]-butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)ureido]butyric acid, 2-{3-[4-(18-{4-[3-(1-carboxyethyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]-ureido}propionic acid, 3-phenyl-2-{3-[4-(18-{4-[3-(2-phenyl-1-carboxyethyl)-ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}propionic acid, 4-methylthio-2-{3-[4-(18-{4-[3-(3-methylthio-1-carboxypropyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}butyric acid, 6-amino-2-{3-[4-(18-{4-[3-(5-amino-1-carboxypentyl)-ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}hexanoic acid, 2-amino-6-{3-[4-(18-{4-[3-(5-amino-5-carboxypentyl)-ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}hexanoic acid, 2-amino-5-{3-[4-(18-{4-[3-(4-amino-4-carboxybutyl)-ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}pentanoic acid, 5-guanidyl-2-{3-[4-(18-{4-[3-(1-carboxy-4-guanidyl-butyl)ureidoacetoxy]-2,6,6-trimethyl-3-oxocyclohexa-1-enyl}-3,7,12,16-tetramethyloctadeca-1,3,5,7,9,11,13,15,17-nonaenyl)-3,5,5-trimethyl-2-oxocyclohexa-3-enyloxycarbonylmethyl]ureido}pentanoic acid, 3-[3-(2-{4-[18-(4-{3-[3-(2-carboxyethyl)ureido]-propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]propionic acid, 4-[3-(2-{4-[18-(4-{3-[3-(3-carboxypropyl)ureido]-propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]butyric acid, 3-(3-{4-[18-(4-{4-[3-carboxymethylureido]butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl)-ureidoacetic acid, 4-carboxy-4-(3-<2-{4-[18-(4-{3-(3-[1,3-dicarboxypropyl]-ureido)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl>ureido) butyric acid, 3-carboxy-3-(3-<2-{4-[18-(4-{3-(3-[1,2-dicarboxyethyl]-ureido)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl>ureido) propionic acid, 2-amino-6-(3-<2-{4-[18-(4{3-(3-[5-amino-5-carboxypentyl]ureido)propionyloxy}2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}-ethyl>ureido) hexanoic acid, 4-carboxy-4-(3-<3-{4-[18-(4-{4-(3-[1,3-dicarboxypropyl]-ureido)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxy-carbonyl}propyl>ureido) butyric acid, 3-carboxy-3-(3-<3-{4-[18-(4-{4-(3[1,2-dicarboxyethyl]ureido)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxy-carbonyl}propyl>ureido)propionic acid, 2-amino-6-(3-<3-{4-[18-(4-{4-(3-[5-amino-5-carboxypentyl]ureido)butyryloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}propyl>ureido) hexanoic acid, 2-amino-5-(3-<2-{4-[18(4-{3-(3-[4-amino-4-carboxybutyl]ureido)propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}-ethyl>ureido) pentanoic acid, 2-amino-5-(3-<3-{4-[18-(4-{4-(3-[4-amino-4-carboxybutyl]ureido)butyroxy}-2,6,6-rimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}-propyl>ureido) pentanoic acid, 3-isobutyl-4-(3-{4-[18-(4-[3-(2-isobutyl-3-carboxypropyl)-ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureido)butyric acid, 1-(3-{4-[18-(4-[3-(1-carboxymethylcyclohexylmethyl)-ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}ureidomethyl) cyclohexylacetic acid, 3-isobutyl-4-[3-{2-isobutyl-3-[4-(18-[4-{3-isobutyl-4-[3-(2-isobutyl-3-carboxylpropyl)ureido]butyryloxy}-2,6,6-trimethyl-3-oxocyclohexa-1-enyl]-3,7,12,16-tetramethyloctadeca-1,3,5,7,9,11,13,15,17-nonaenyl]-3,5,5-trimethyl-2-oxocyclohexa-3-enyloxycarbonyl] propyl}-ureido]butyric acid, 1-(3-[1-{4-(18-[4-{1-(3-[1-carboxymethylcyclohexylmethyl]-ureidomethyl)cyclohexylacetoxy}-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonylmethyl}cyclohexylmethyl]-ureidomethyl)cyclohexyacetic acid, 6-(3{4-(18-[4-{3-(6-carboxymethyl-3-ethylbicyclo[3,2,0]-hepta-3-en-6-ylmethyl)ureidomethylacetoxy}-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonylmethyl}ureidomethyl)-3-ethylbicyclo[3,2,0]hepta-3-en-6-ylacetic acid, 6-(3-[3-{4-(18-[4-[4-{3-(6-carboxymethyl-3-ethylbicyclo[3,2,0]hepta-3-en-6-ylmethy)ureido}-butyryloxy]-2,6,6-trimethyl-3-oxocyclohexa-1-enyl]-3,7,12,16-tetramethyloctadeca-1,3,5,7,9,11,13,15,17-nonaenyl)-3,5,5-trimethyl-2-oxocyclohexa-3-enyloxycarbonyl}propyl}ureidomethyl)-3-ethylbicyclo[3,2,0]hepta-3-en-6-ylacetic acid, and 6-(3-[6-{4-(18-[4-[6-{3-(6-carboxymethyl-3-ethylbicyclo[3,2,0]hepta-3-en-6-ylmethyl)ureidomethyl}-3-ethylbicyclo[3,2,0]hepta-3-en-6-ylacetoxy]-2,6,6-trimethyl-3-oxocyclohexa-1-enyl]-3,7,12,16-tetramethyloctadeca-1,3,5,7,9,11,13,15,17-nonaenyl-3,5,5-trimethyl-2-oxocyclohexa-3-enyloxycarbonylmethyl}-3-ethylbicyclo[3,2,0]hepta-3-en-6-ylmethyl]ureidomethyl)-3-ethylbicyclo[3,2,0]hepta-3-en-6-ylacetic acid.

6. The carotenoid derivative according to claim 1, or a pharmaceutically acceptable salt thereof, selected from the group consisting of 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid disodium salt, and 4-(3-{4-[18-(4-[3-(3-carboxypropyl)ureidoacetoxy]-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid dilysine salt.

7. The carotenoid derivative according to claim 1, or a pharmaceutically acceptable salt thereof, which is 4-(3-{4-[18-(4-[3-(3-carboxypropyl)ureidoacetoxy]-2,6,6-trimethyl-3-oxocyclohexa-1-enyl)-3,7,12,16-tetramethyloctadeca-,3,5,7,9,11,13,15,17-nonaenyl]-3,5,5-trimethyl-2-oxocyclohexa-3-enyloxycarbonylmethyl}-ureido)butyric acid.

8. The carotenoid derivative according to claim 1, or a pharmaceutically acceptable salt thereof, which is 4-(3-{4-[18-(4-[3-(3-carboxypropyl)ureideacetoxy]-2,6,6-trimethyl-3-oxocyclohexa.-1-enyl)-3,7,12,16-tetramethyloctadeca-1,3,5,7,9,11,13,15,17-nonaenyl]-3,5,5-trimethyl-2-oxocyclohexa-3-enyloxycarbonylmethyl}-ureido)butyric acid dilysine salt.

9. The carotenoid derivative according to claim 1, or a pharmaceutically acceptable salt thereof, which is 3-[3-(2-{4[18-(4-{3[3-(2-carboxyethy)ureido]-propionyloxy}-2,6,6-trimethyl-3-oxocyclohexa-1-enyl)-3,7,12,16-tetramethyloctadeca-1,3,5,7,9,11,13,15,17-nonaenyl]-3,5,5-trimethyl-2-oxocyclohexa-3-enyloxycarbonyl}ethyl)ureido]propionic acid or a pharmaceutically acceptable salt thereof.

10. A pharmaceutical composition, comprising the carotenoid derivative according to claim 1, or a pharmaceutically acceptable salt thereof, as an active ingredient.

11. The pharmaceutical composition according to claim 10, for treating hyperlipidemia, obesity, impaired glucose tolerance, hypertension, insulin resistance, a metabolic syndrome, fatty liver disease, diabetes, diabetic complication, steatohepatitis, non-alcoholic steatohepatitis, Type C hepatitis, arteriosclerosis, gestational diabetes, polycystic ovary syndrome, a cardiovascular disease, heart failure, atherosclerosis, vascular insufficiency, cell damage caused by an ischemic cardiac disease, gout, an inflammatory disease, stomach ulcer, cancer, osteoporosis, cataract, glaucoma, age-related macular degeneration, dry eye, eyestrain, Alzheimer's disease, depression, bipolar disorder, schizophrenia, chronic fatigue, disuse muscle atrophy, amyotrophic lateral sclerosis, amyotrophy, sarcopenia, cachexia, uric acid suppression action, hair growth promotion action, wound improvement, or improvement after surgery.

* * * * *

UNITED STATES PATENT AND TRADEMARK OFFICE
CERTIFICATE OF CORRECTION

PATENT NO. : 10,125,104 B2
APPLICATION NO. : 15/312111
DATED : November 13, 2018
INVENTOR(S) : Fujita et al.

Page 1 of 1

It is certified that error appears in the above-identified patent and that said Letters Patent is hereby corrected as shown below:

In the Claims

Column 132, Line 57, "3-oxocyclohexa-1-enyl)-3,7,12,16-tetramethyloctadeca-,3," should read --3-oxocyclohexa-1-enyl)-3,7,12,16-tetramethyloctadeca-1,3,--

Column 132, Line 63, "[18-(4-[3-(3-carboxypropyl)ureideacteoxy]-2,6,6-trimethyl-" should read --[18-(4-[3-(3-carboxypropyl)ureidoacteoxy]-2,6,6-trimethyl- --

Signed and Sealed this
Twenty-first Day of April, 2020

Andrei Iancu
*Director of the United States Patent and Trademark Office*